United States Patent
Metchik et al.

(10) Patent No.: US 11,612,485 B2
(45) Date of Patent: *Mar. 28, 2023

(54) NATIVE VALVE REPAIR DEVICES AND PROCEDURES

(71) Applicant: Edwards Lifesciences Corporation, Irvine, CA (US)

(72) Inventors: Asher L. Metchik, Rolling Hills Estates, CA (US); Gregory Scott Tyler, II, Costa Mesa, CA (US); Matthew T. Winston, Aliso Viejo, CA (US); Sergio Delgado, Irvine, CA (US); Lauren R. Freschauf, Mission Viejo, CA (US); Eric Robert Dixon, Villa Park, CA (US); Alexander J. Siegel, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 481 days.

This patent is subject to a terminal disclaimer.

(21) Appl. No.: 16/818,947

(22) Filed: Mar. 13, 2020

(65) Prior Publication Data
US 2020/0214832 A1 Jul. 9, 2020

Related U.S. Application Data

(63) Continuation of application No. 16/141,549, filed on Sep. 25, 2018, now Pat. No. 10,595,997, which is a
(Continued)

(51) Int. Cl.
*A61F 2/24* (2006.01)

(52) U.S. Cl.
CPC ............ *A61F 2/246* (2013.01); *A61F 2/2463* (2013.01); *A61F 2/2466* (2013.01);
(Continued)

(58) Field of Classification Search
CPC ...... A61F 2/246; A61F 2/2463; A61F 2/2466; A61F 2220/0016; A61F 2220/0025; A61F 2220/0075; A61F 2230/0013
(Continued)

(56) References Cited

U.S. PATENT DOCUMENTS 3,874,388 A 4/1975 King et al.
4,340,091 A 7/1982 Skelton et al.
(Continued)

FOREIGN PATENT DOCUMENTS

CN 1142351 A 2/1997
CN 106175845 A 12/2016
(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Suzette J Gherbi
(74) *Attorney, Agent, or Firm* — Thomas C. Richardson

(57) ABSTRACT

A system for implanting a repair device onto a native valve of a natural heart to repair the native valve of a patient during a non-open-heart procedure. The system includes a delivery catheter and a valve repair device. The valve repair device is disposed inside the delivery catheter. The valve repair device includes a pair of paddles and a pair of gripping members. The pair of paddles are movable between an open position and a closed position. The pair of paddles and the pair of gripping members are configured to secure the valve repair device to leaflets of the native valve. The pair of paddles are compressed inside the delivery catheter. Each paddle of the pair of paddles is configured to expand upon exiting the delivery catheter to increase the surface area of each paddle.

27 Claims, 73 Drawing Sheets

Related U.S. Application Data continuation of application No. 15/865,955, filed on Jan. 9, 2018, now Pat. No. 10,111,751.

(52) U.S. Cl.
CPC .............. *A61F 2220/0016* (2013.01); *A61F 2220/0025* (2013.01); *A61F 2220/0075* (2013.01); *A61F 2230/0013* (2013.01)

(58) Field of Classification Search
USPC ................................................ 623/2.1–2.19
See application file for complete search history.

(56) References Cited

U.S. PATENT DOCUMENTS

| | | | |
|---|---|---|---|
| 4,506,669 A | 3/1985 | Blake, III | |
| 4,590,937 A | 5/1986 | Deniega | |
| 4,693,248 A | 9/1987 | Failla | |
| 4,803,983 A | 2/1989 | Siegel | |
| 5,125,895 A | 6/1992 | Buchbinder et al. | |
| 5,171,252 A | 12/1992 | Friedland | |
| 5,195,962 A | 3/1993 | Martin et al. | |
| 5,292,326 A | 3/1994 | Green et al. | |
| 5,327,905 A | 7/1994 | Avitall | |
| 5,363,861 A | 11/1994 | Edwards et al. | |
| 5,370,685 A | 12/1994 | Stevens | |
| 5,389,077 A | 2/1995 | Melinyshyn et al. | |
| 5,411,552 A | 5/1995 | Andersen et al. | |
| 5,450,860 A | 9/1995 | O'Connor | |
| 5,456,674 A | 10/1995 | Bos et al. | |
| 5,474,057 A | 12/1995 | Makower et al. | |
| 5,478,353 A | 12/1995 | Yoon | |
| 5,487,746 A | 1/1996 | Yu et al. | |
| 5,565,004 A | 10/1996 | Christoudias | |
| 5,607,462 A | 3/1997 | Imran | |
| 5,609,598 A | 3/1997 | Laufer et al. | |
| 5,611,794 A | 3/1997 | Sauer et al. | |
| 5,626,607 A | 5/1997 | Malecki et al. | |
| 5,695,504 A | 12/1997 | Gifford, III et al. | |
| 5,716,417 A | 2/1998 | Girard et al. | |
| 5,727,569 A | 3/1998 | Benetti et al. | |
| 5,741,297 A | 4/1998 | Simon | |
| 5,782,746 A | 7/1998 | Wright | |
| 5,797,960 A | 8/1998 | Stevens et al. | |
| 5,836,311 A | 11/1998 | Borst et al. | |
| 5,843,076 A | 12/1998 | Webster, Jr. et al. | |
| 5,855,590 A | 1/1999 | Malecki et al. | |
| 5,885,271 A | 3/1999 | Hamilton et al. | |
| 5,888,247 A | 3/1999 | Benetti | |
| 5,891,017 A | 4/1999 | Swindle et al. | |
| 5,891,112 A | 4/1999 | Samson | |
| 5,894,843 A | 4/1999 | Benetti et al. | |
| 5,921,979 A | 7/1999 | Kovac et al. | |
| 5,944,738 A | 8/1999 | Amplatz et al. | |
| 5,957,835 A | 9/1999 | Anderson et al. | |
| 5,972,020 A | 10/1999 | Carpentier et al. | |
| 5,980,534 A | 11/1999 | Gimpelson | |
| 6,004,329 A | 12/1999 | Myers et al. | |
| 6,010,531 A | 1/2000 | Donlon et al. | |
| 6,017,358 A | 1/2000 | Yoon et al. | |
| 6,086,600 A | 7/2000 | Kortenbach | |
| 6,120,496 A | 9/2000 | Whayne et al. | |
| 6,132,370 A | 10/2000 | Furnish et al. | |
| 6,162,239 A | 12/2000 | Manhes | |
| 6,165,183 A | 12/2000 | Kuehn et al. | |
| 6,182,664 B1 | 2/2001 | Cosgrove | |
| 6,193,732 B1 | 2/2001 | Frantzen et al. | |
| 6,193,734 B1 | 2/2001 | Bolduc et al. | |
| 6,200,315 B1 | 3/2001 | Gaiser et al. | |
| 6,228,032 B1 | 5/2001 | Eaton et al. | |
| 6,241,743 B1 | 6/2001 | Levin et al. | |
| 6,269,819 B1 | 8/2001 | Oz et al. | |
| 6,269,829 B1 | 8/2001 | Chen et al. | |
| 6,312,447 B1 | 11/2001 | Grimes | |
| 6,461,366 B1 | 10/2002 | Seguin | |
| 6,468,285 B1 | 10/2002 | Hsu et al. | |
| 6,508,806 B1 | 1/2003 | Hoste | |
| 6,508,825 B1 | 1/2003 | Selmon et al. | |
| 6,530,933 B1 | 3/2003 | Yeung et al. | |
| 6,537,290 B2 | 3/2003 | Adams et al. | |
| 6,544,215 B1 | 4/2003 | Bencini et al. | |
| 6,626,930 B1 | 9/2003 | Allen et al. | |
| 6,629,534 B1 | 10/2003 | St. Goar et al. | |
| 6,719,767 B1 | 4/2004 | Kimblad | |
| 6,764,510 B2 | 7/2004 | Vidlund et al. | |
| 6,770,083 B2 | 8/2004 | Seguin | |
| 6,837,867 B2 | 1/2005 | Kortelling | |
| 6,855,137 B2 | 2/2005 | Bon | |
| 6,913,614 B2 | 7/2005 | Marino et al. | |
| 6,939,337 B2 | 9/2005 | Parker et al. | |
| 6,945,956 B2 | 9/2005 | Waldhauser et al. | |
| 7,048,754 B2 | 5/2006 | Martin et al. | |
| 7,101,395 B2 | 9/2006 | Tremulis et al. | |
| 7,125,421 B2 | 10/2006 | Tremulis et al. | |
| 7,288,097 B2 | 10/2007 | Seguin | |
| 7,371,210 B2 | 5/2008 | Brock et al. | |
| 7,464,712 B2 | 12/2008 | Oz et al. | |
| 7,509,959 B2 | 3/2009 | Oz et al. | |
| 7,569,062 B1 | 8/2009 | Kuehn et al. | |
| 7,618,449 B2 | 11/2009 | Tremulis et al. | |
| 7,682,369 B2 | 3/2010 | Seguin | |
| 7,731,706 B2 | 6/2010 | Potter | |
| 7,744,609 B2 | 6/2010 | Allen et al. | |
| 7,748,389 B2 | 7/2010 | Salahieh et al. | |
| 7,753,932 B2 | 7/2010 | Gingrich et al. | |
| 7,758,596 B2 | 7/2010 | Oz et al. | |
| 7,780,723 B2 | 8/2010 | Taylor | |
| 7,803,185 B2 | 9/2010 | Gabbay | |
| 7,811,296 B2 * | 10/2010 | Goldfarb | A61F 2/246 606/151 |
| 7,824,443 B2 | 11/2010 | Salahieh et al. | |
| 7,981,123 B2 | 7/2011 | Seguin | |
| 7,988,724 B2 | 8/2011 | Salahieh et al. | |
| 8,052,750 B2 | 11/2011 | Tuval et al. | |
| 8,070,805 B2 | 12/2011 | Vidlund et al. | |
| 8,096,985 B2 | 1/2012 | Legaspi et al. | |
| 8,104,149 B1 | 1/2012 | McGarity | |
| 8,133,239 B2 | 3/2012 | Oz et al. | |
| 8,147,542 B2 | 4/2012 | Maisano et al. | |
| 8,172,856 B2 | 5/2012 | Eigler et al. | |
| 8,206,437 B2 | 6/2012 | Bonhoeffer et al. | |
| 8,216,301 B2 | 7/2012 | Bonhoeffer et al. | |
| 8,303,653 B2 | 11/2012 | Bonhoeffer et al. | |
| 8,313,525 B2 | 11/2012 | Tuva et al. | |
| 8,348,995 B2 | 1/2013 | Tuval et al. | |
| 8,348,996 B2 | 1/2013 | Tuval et al. | |
| 8,414,643 B2 | 4/2013 | Tuval et al. | |
| 8,425,404 B2 | 4/2013 | Wilson et al. | |
| 8,449,599 B2 | 5/2013 | Chau et al. | |
| 8,449,606 B2 | 5/2013 | Eliasen et al. | |
| 8,460,368 B2 | 6/2013 | Taylor et al. | |
| 8,470,028 B2 | 6/2013 | Thornton et al. | |
| 8,480,730 B2 | 7/2013 | Maurer et al. | |
| 8,540,767 B2 | 9/2013 | Zhang | |
| 8,579,965 B2 | 11/2013 | Bonhoeffer et al. | |
| 8,585,756 B2 | 11/2013 | Bonhoeffer et al. | |
| 8,652,202 B2 | 2/2014 | Alon et al. | |
| 8,668,733 B2 | 3/2014 | Haug et al. | |
| 8,721,665 B2 | 5/2014 | Oz et al. | |
| 8,740,918 B2 | 6/2014 | Seguin | |
| 8,771,347 B2 | 7/2014 | DeBoer et al. | |
| 8,778,017 B2 | 7/2014 | Eliasen et al. | |
| 8,834,564 B2 | 9/2014 | Tuval et al. | |
| 8,840,663 B2 | 9/2014 | Salahieh et al. | |
| 8,876,894 B2 | 11/2014 | Tuval et al. | |
| 8,876,895 B2 | 11/2014 | Tuval et al. | |
| 8,945,177 B2 | 2/2015 | Dell et al. | |
| 9,034,032 B2 | 5/2015 | McLean et al. | |
| 9,198,757 B2 | 12/2015 | Schroeder et al. | |
| 9,220,507 B1 | 12/2015 | Patel et al. | |
| 9,259,317 B2 | 2/2016 | Wilson et al. | |
| 9,282,972 B1 | 3/2016 | Patel et al. | |
| 9,301,834 B2 | 4/2016 | Tuval et al. | |
| 9,308,360 B2 | 4/2016 | Bishop et al. | |

(56) References Cited

U.S. PATENT DOCUMENTS

| | | |
|---|---|---|
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1* | 3/2019 | Metchik ............... A61F 2/2466 |
| 10,238,494 B2 | 3/2019 | McNiven et al. |
| 10,238,495 B2 | 3/2019 | Marsot |
| 10,299,924 B2 | 5/2019 | Kizuka |
| 10,376,673 B2 | 8/2019 | Van Hoven et al. |
| 10,575,841 B1 | 3/2020 | Paulos |
| 10,595,997 B2* | 3/2020 | Metchik ............... A61F 2/246 |
| 10,918,482 B2* | 2/2021 | Delgado ............ A61B 17/3468 |
| 10,925,732 B2* | 2/2021 | Delgado ............ A61F 2/243 |
| 10,925,735 B2* | 2/2021 | Metchik ............... A61F 2/246 |
| 10,959,847 B2* | 3/2021 | Metchik ............... A61F 2/246 |
| 10,973,639 B2* | 4/2021 | Metchik ............... A61F 2/246 |
| 11,020,229 B2* | 6/2021 | Delgado ............ A61F 2/2442 |
| 11,039,925 B2* | 6/2021 | Metchik ............... A61F 2/246 |
| 11,179,240 B2* | 11/2021 | Delgado ............ A61F 2/24 |
| 11,259,927 B2* | 3/2022 | Metchik ............... A61F 2/246 |
| 11,298,228 B2* | 4/2022 | Metchik ............... A61F 2/2454 |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0125805 A1 | 7/2003 | Johnson et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1* | 4/2006 | Goldfarb ............ A61B 17/1285 606/215 |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | KETAi et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |

(56) References Cited

U.S. PATENT DOCUMENTS

| | | |
|---|---|---|
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0066693 A1 | 3/2014 | Goldfarb et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1* | 6/2016 | Wei .................. A61F 2/246 606/151 |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0245988 A1 | 8/2017 | Siegel et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0092661 A1 | 4/2018 | Prabhu |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1* | 10/2018 | Dixon ............. A61F 2/2436 |
| 2018/0296327 A1* | 10/2018 | Dixon ............. A61B 17/1227 |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1* | 2/2019 | Zeng ................. A61F 2/2445 |
| 2019/0060073 A1 | 2/2019 | Delgado et al. |
| 2019/0060074 A1 | 2/2019 | Delgado et al. |
| 2019/0060075 A1 | 2/2019 | Delgado |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0214832 A1* | 7/2020 | Metchik ............. A61F 2/246 |
| 2020/0237512 A1 | 7/2020 | McCann et al. |
| 2020/0337842 A1 | 10/2020 | Metchik et al. |
| 2020/0360054 A1 | 11/2020 | Walsh et al. |

(56) References Cited

U.S. PATENT DOCUMENTS

| | | |
|---|---|---|
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361422 A1 | 11/2021 | Gross et al. |
| 2021/0401434 A1 | 12/2021 | Tien et al. |
| 2022/0104819 A1* | 4/2022 | Wei .................. A61B 17/08 |
| 2022/0133327 A1 | 5/2022 | Zhang et al. |
| 2022/0142780 A1 | 5/2022 | Zhang et al. |
| 2022/0142781 A1 | 5/2022 | Zhang et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A1 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022052506 A1 | 3/2022 |
| WO | 2022068188 A1 | 4/2022 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Andersen et al., "Transluminal Implantation of Artificial Heart Valves. Description of a New Expandable Aortic Valve and Initial Results with implantation by Catheter Technique in Closed Chest Pigs" European Heart Journal, 1992, 13, 704-708.

Andersen, H.R. "History of Percutaneous Aortic Valve Prosthesis," Herz No. 34. pp. 343-346. 2009.

Batista, M.D. et al., "Partial Left Ventriculectomy to Treat End-Stage Heart Disease," The Society of Thoracic Surgeons, 1997, pp. 634-638.

Beall et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

D. Pavcnik: Development and initial Experimental Evaluation of a Prosthetic Aortic Valve for Transcatheter Placement; Cardiovascular Radiology (1992) 183, pp. 151-154.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Fucci et alL., "improved results with mitral valve repair using new surgical techniques", Eur J Cardiothorac Surg. 1995:Issue 9, vol. 11, pp. 621-626.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device that Opens Clogged Arteries Gets a Failing Grade in a New Study", The New York Times, http://www.nytimes.com/1991/01/03/health/device-that-opens-clogged-arteries-gets-a-faili . . . , pp. 1-2, wrriten Jan. 3, 199, web page access Jul. 29, 2009.

Lawrence, Jr., et al., "Percutaneous Endovascular Graft: Experimental Evaluation", Cardiovascular Radiology 163, pp. 357-360, May 1987.

Maisano et al., 'The edge-to-edge technique: a simplified method to correct mitral insufficiency', Eur J Cardiothorac Surg., vol. 13, Issue—3, pp. 240-245, Mar. 1998.

Porstmann et al., "Der Verschluß des Ductus Arteriosus Persistens Ohne Thorakotomie", Thoraxchirurgie Vaskuläre Chirurgie, Band 15, Heft 2, Stuttgart, Im Apr. 1967, pp. 199-203.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, vol. 13, No. 4, pp. 363-367, Dec. 1986.

Reul RM et al., "Mitral valve reconstruction for mitral insufficiency", Prog Cardiovasc Dis., vol. 39, Issue—6, May-Jun. 1997.

Rosch, M.D., Josef, "The Birth, Early Years and Future of Interventional Radiology," J Vasc Interv Radiol 2003; 14:841-853.

Ross, "Aortic Valve Surgery," At a meeting of the Council on Aug. 4, 1966. pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

(56) References Cited

OTHER PUBLICATIONS

Umaña et al., "'Bow-tie'mitral valve repair: an adjuvant technique for ischemic mitral regurgitation', Ann Thorac Surg., vol. 66, Issue—6, pp. 1640-1646, Nov. 1998.

Urban, M.D., Philip, "Coronary Artery Stenting," Editions Medecine et Hygiene, Geneve, 1991, pp. 5-47.

Watt et al., "Intravenous Adenosine in the Trealment ot Supraventricular Tachycardia: A Dose-Ranging Study and interaction with Dipyridamole", Br. J. Clin. Pharmac. 21, pp. 227-230, 1986.

Wheatlty, "Valve Prostheses," Operalive Surgery, 4th ed. pp. 415-424. 1986.

Praz et al., "Compassionate use of the PASCAL transcatheter mitral valve repair system for patients with severe mitral regurgitation: a multicentre, prospective, observational, first-in-man study," Lancet, vol. 390, pp. 773-780, 2017.

Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.

\* cited by examiner

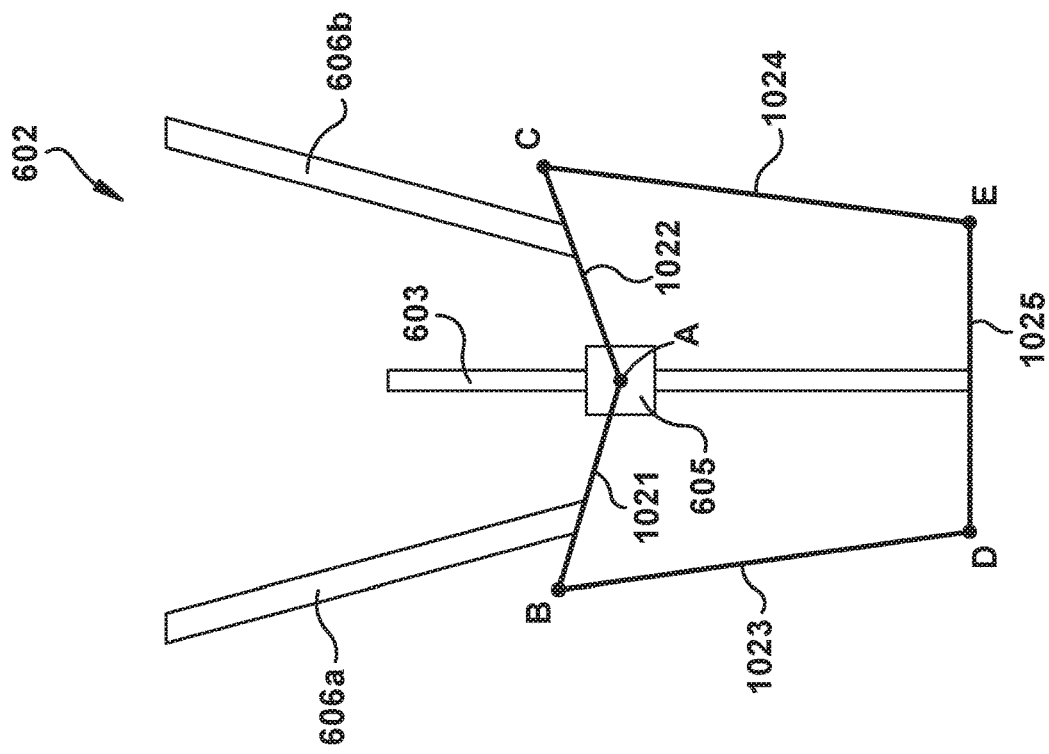
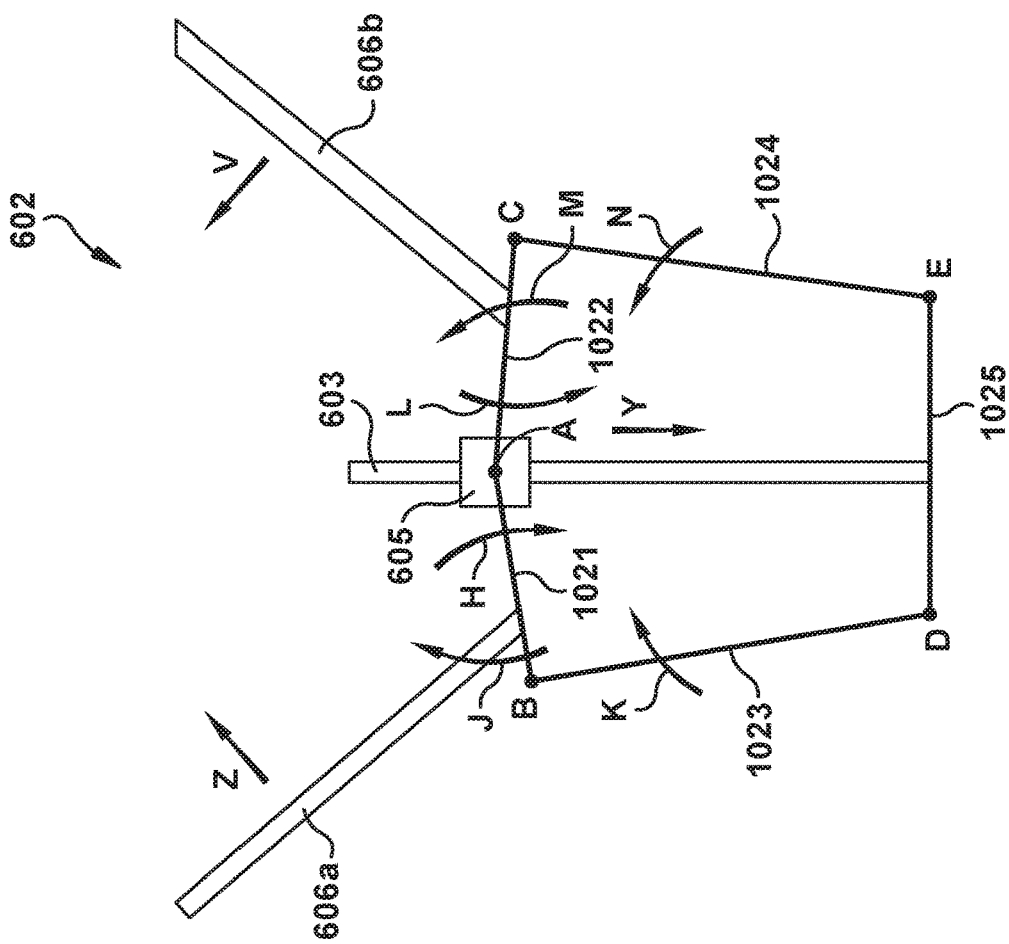
Figure 10A
Figure 10B

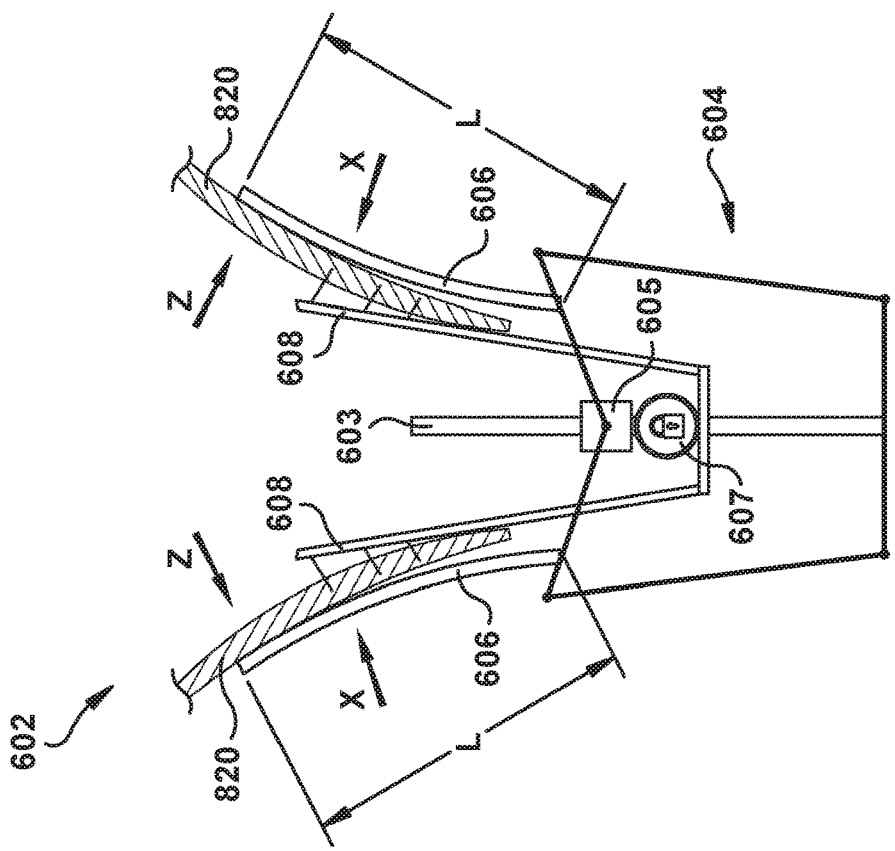
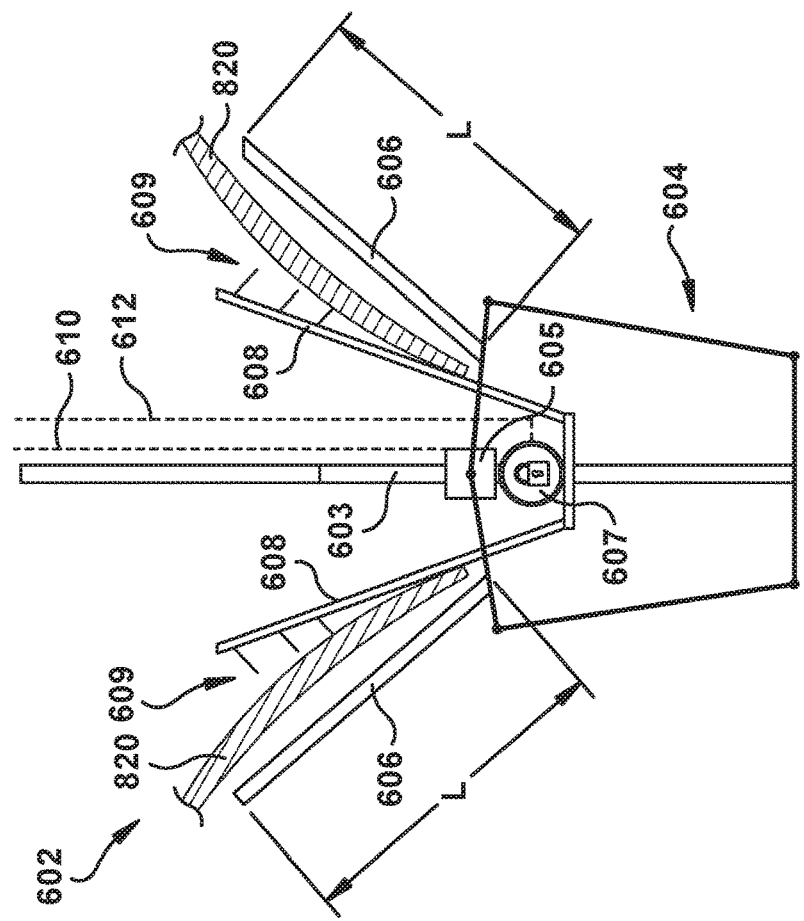

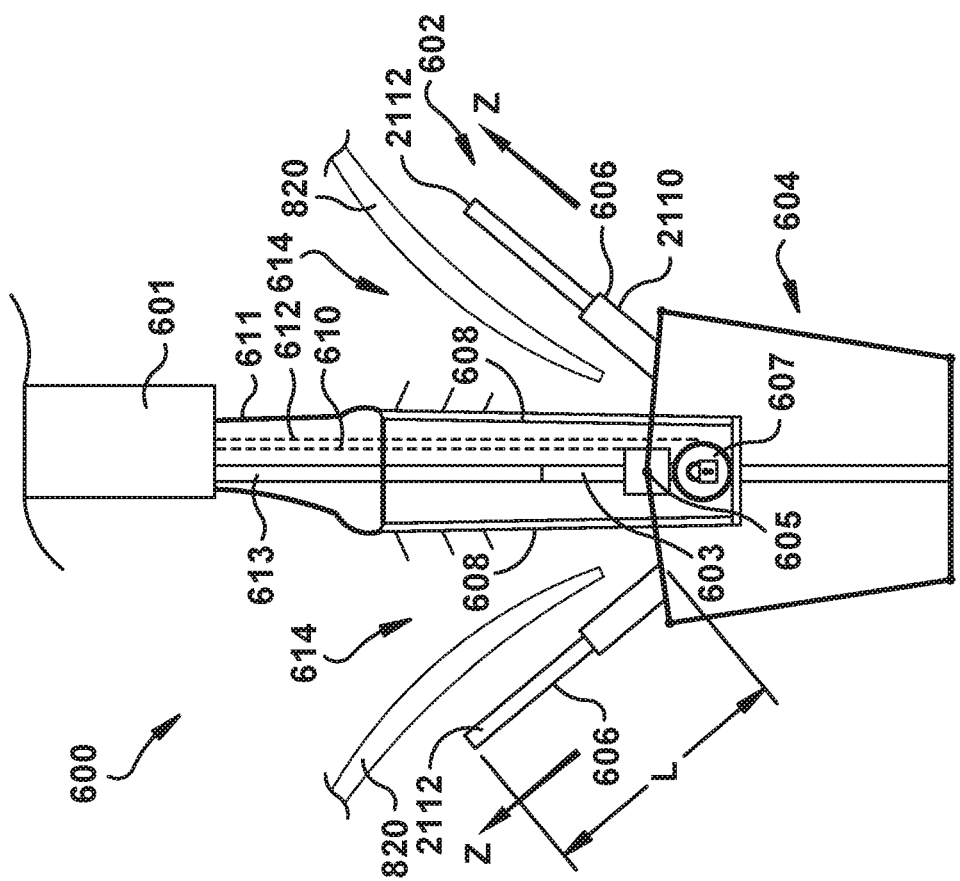
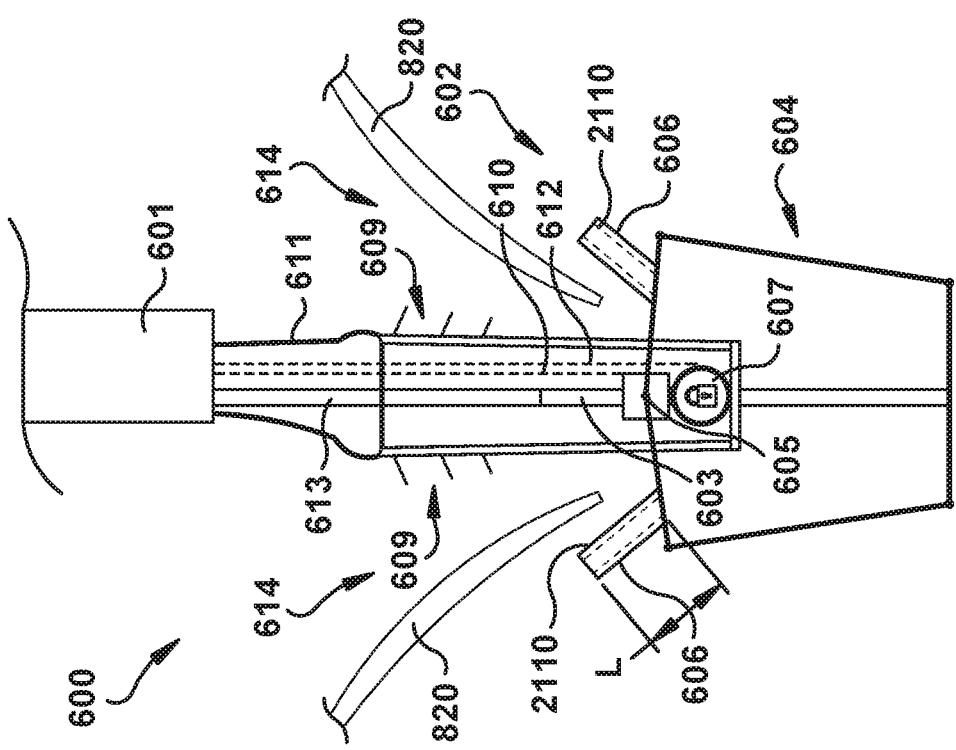

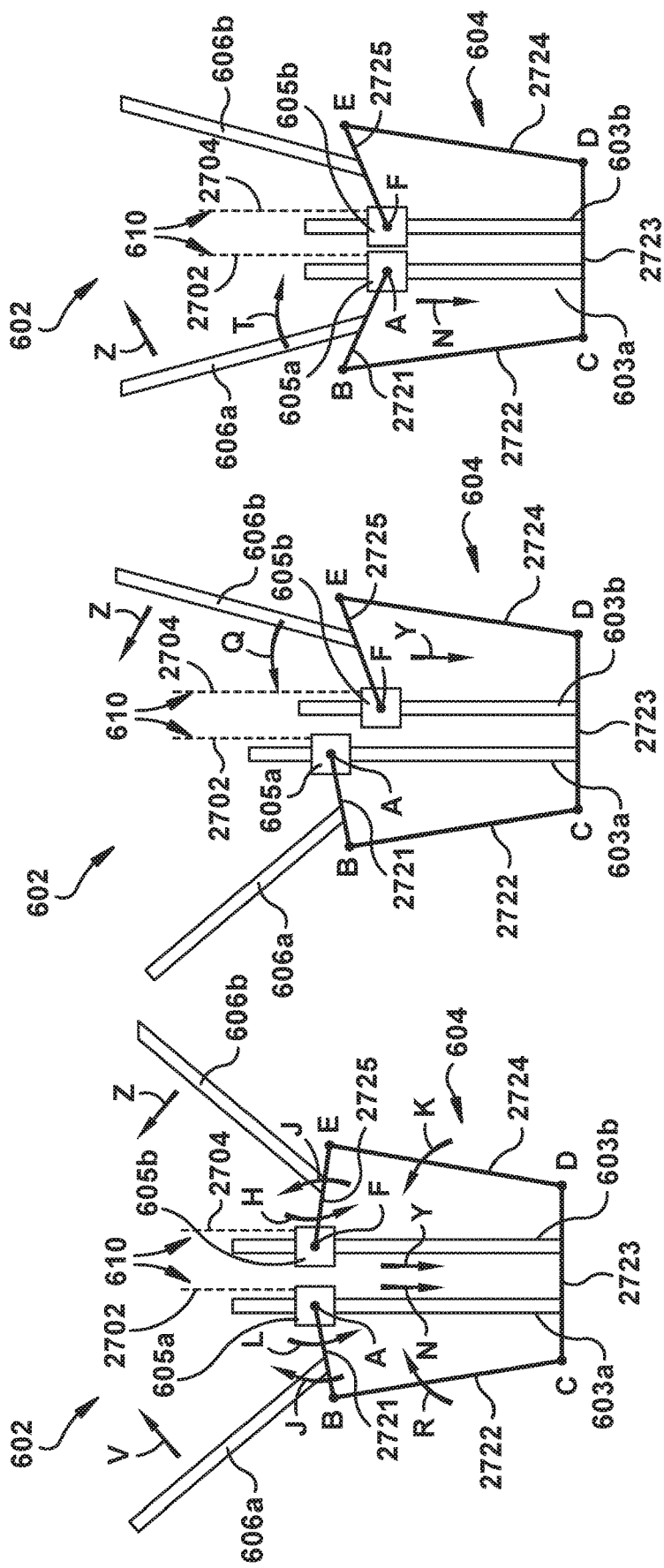

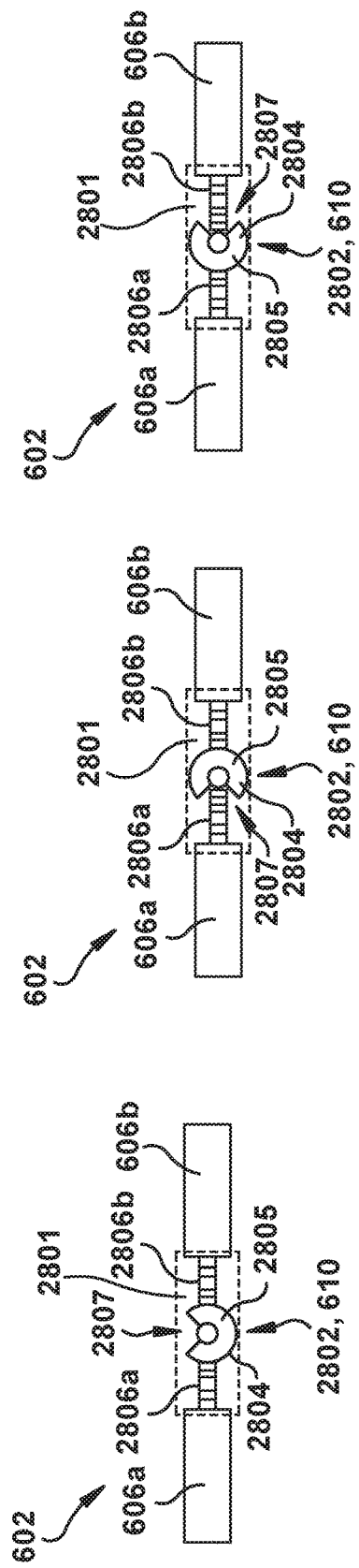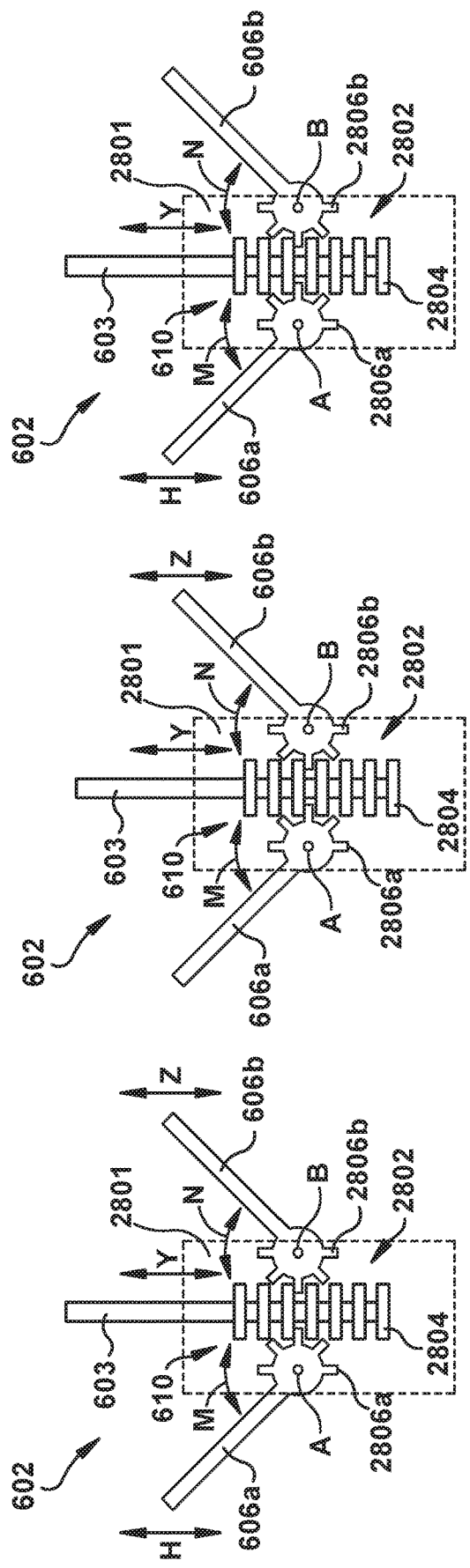

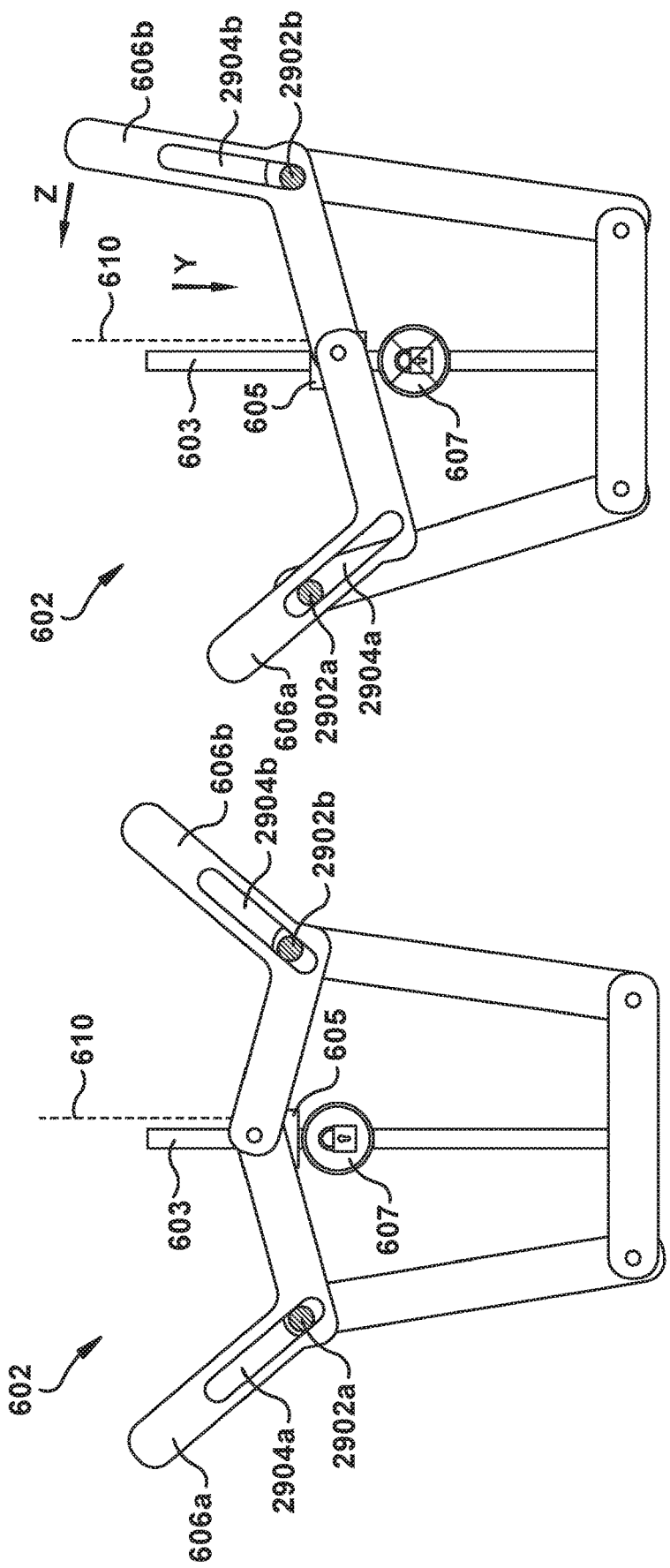

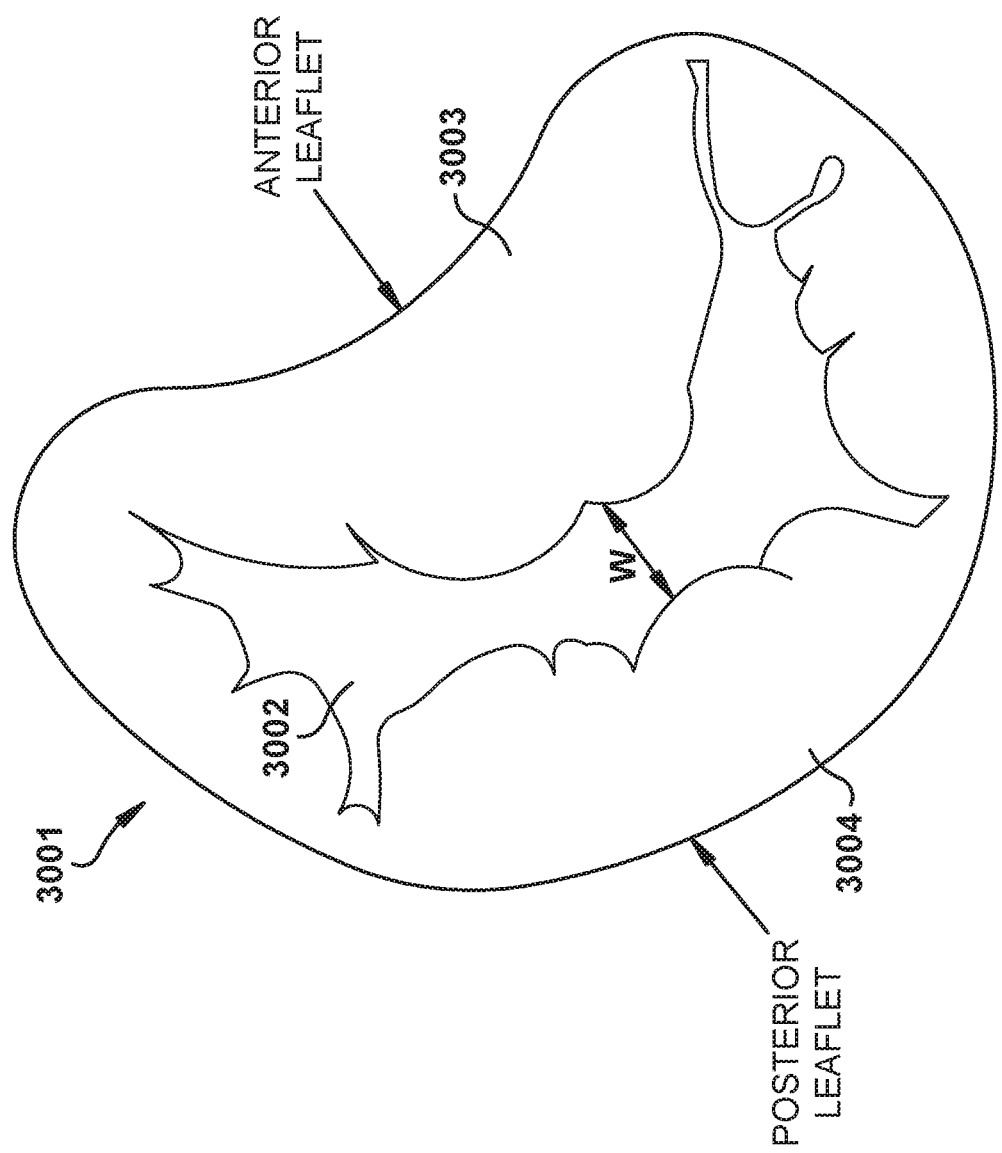

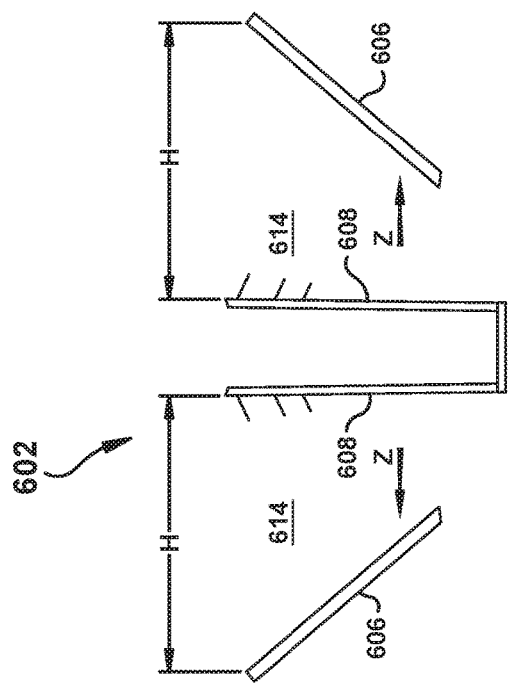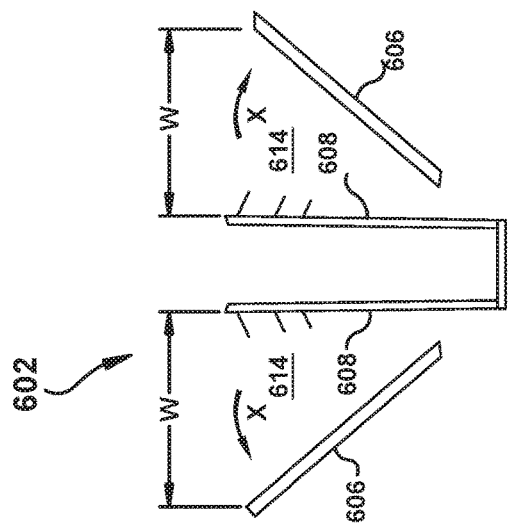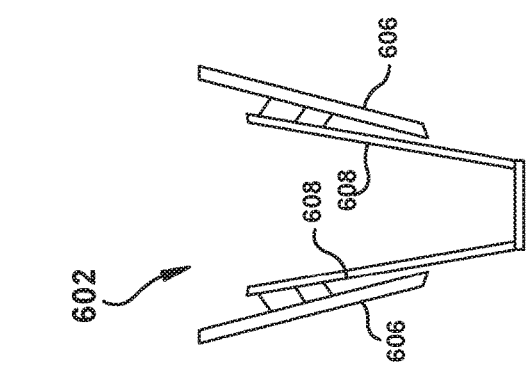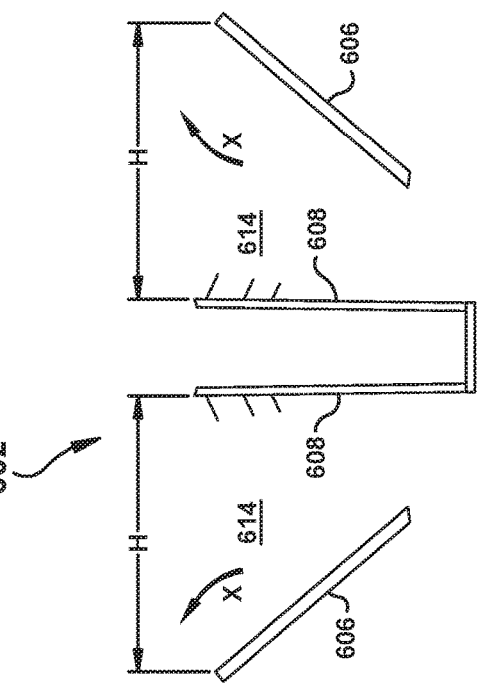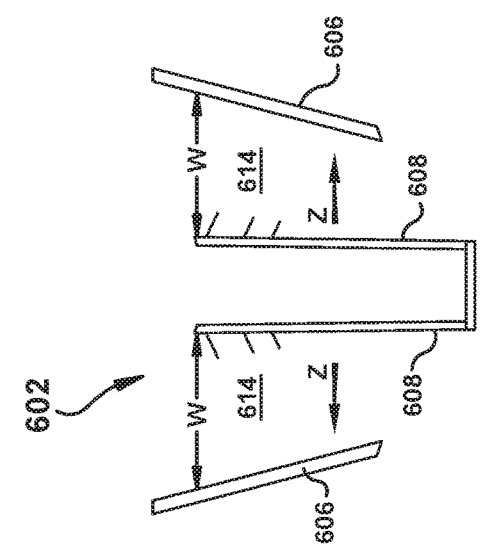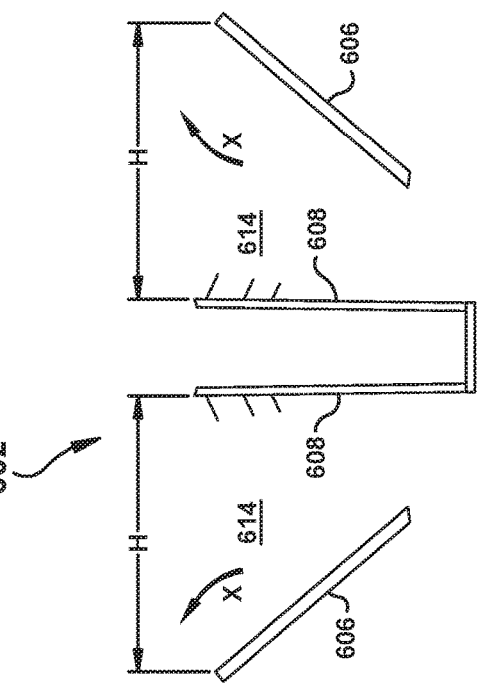

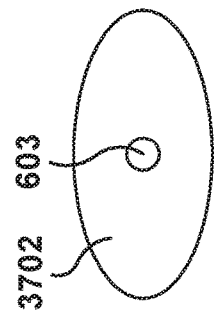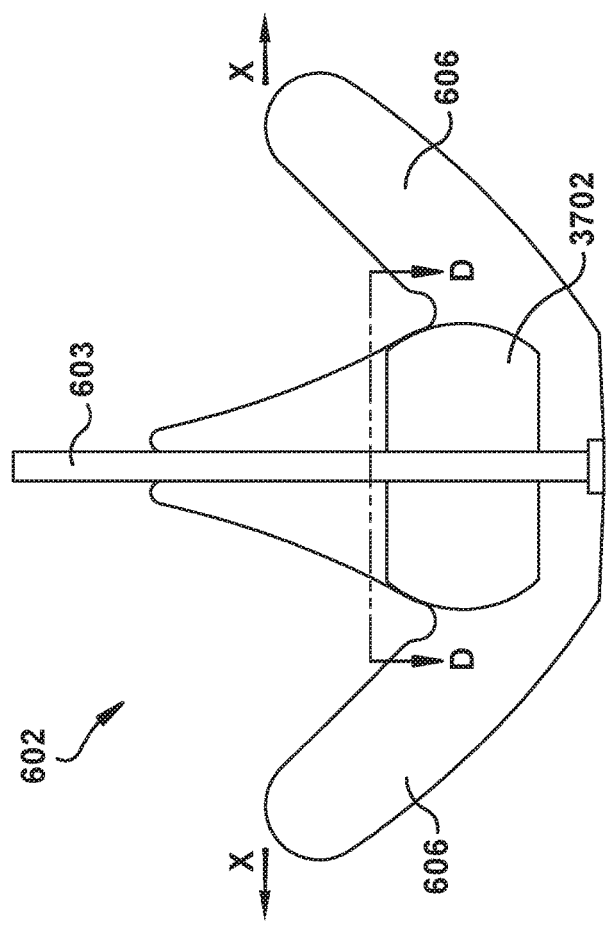
Figure 37B
Figure 37A
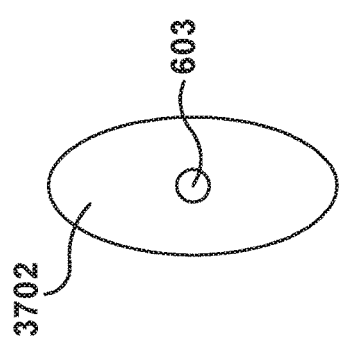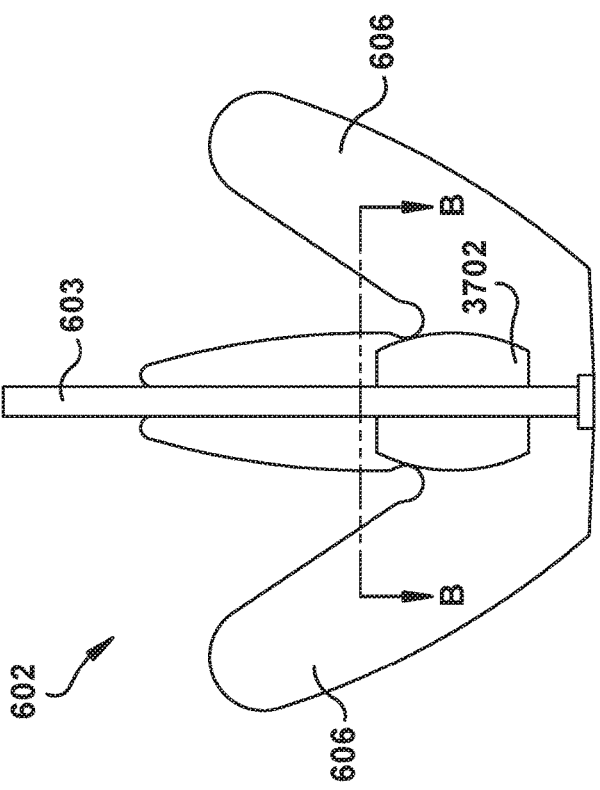
Figure 37D
Figure 37C

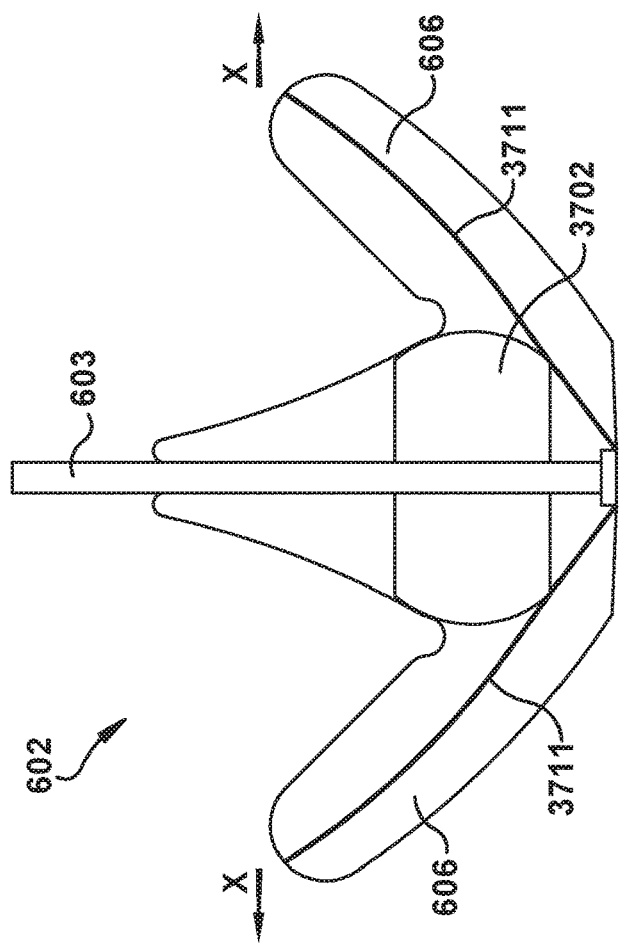
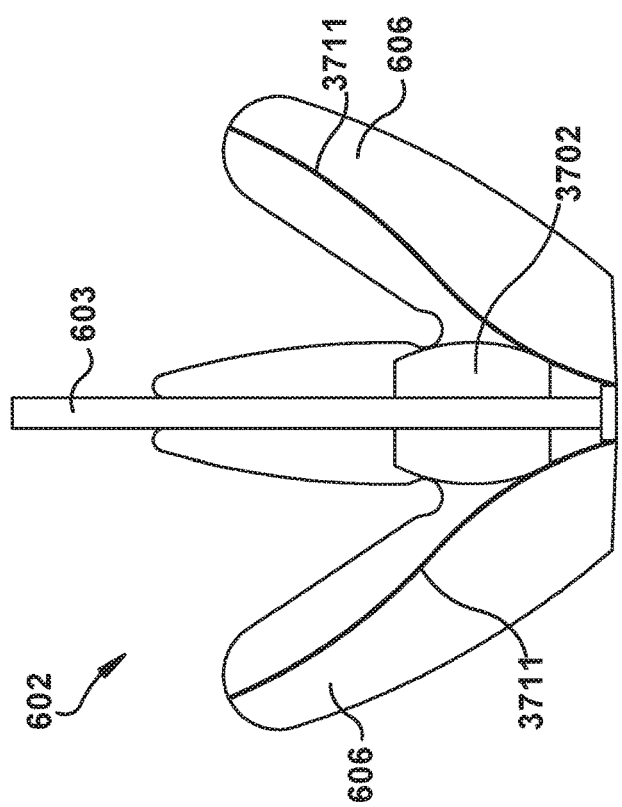
Figure 37F
Figure 37E

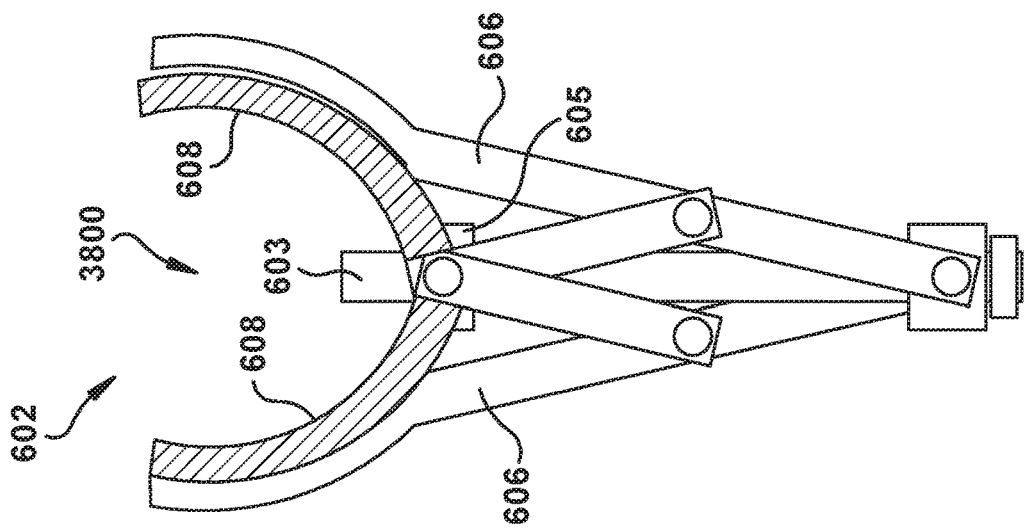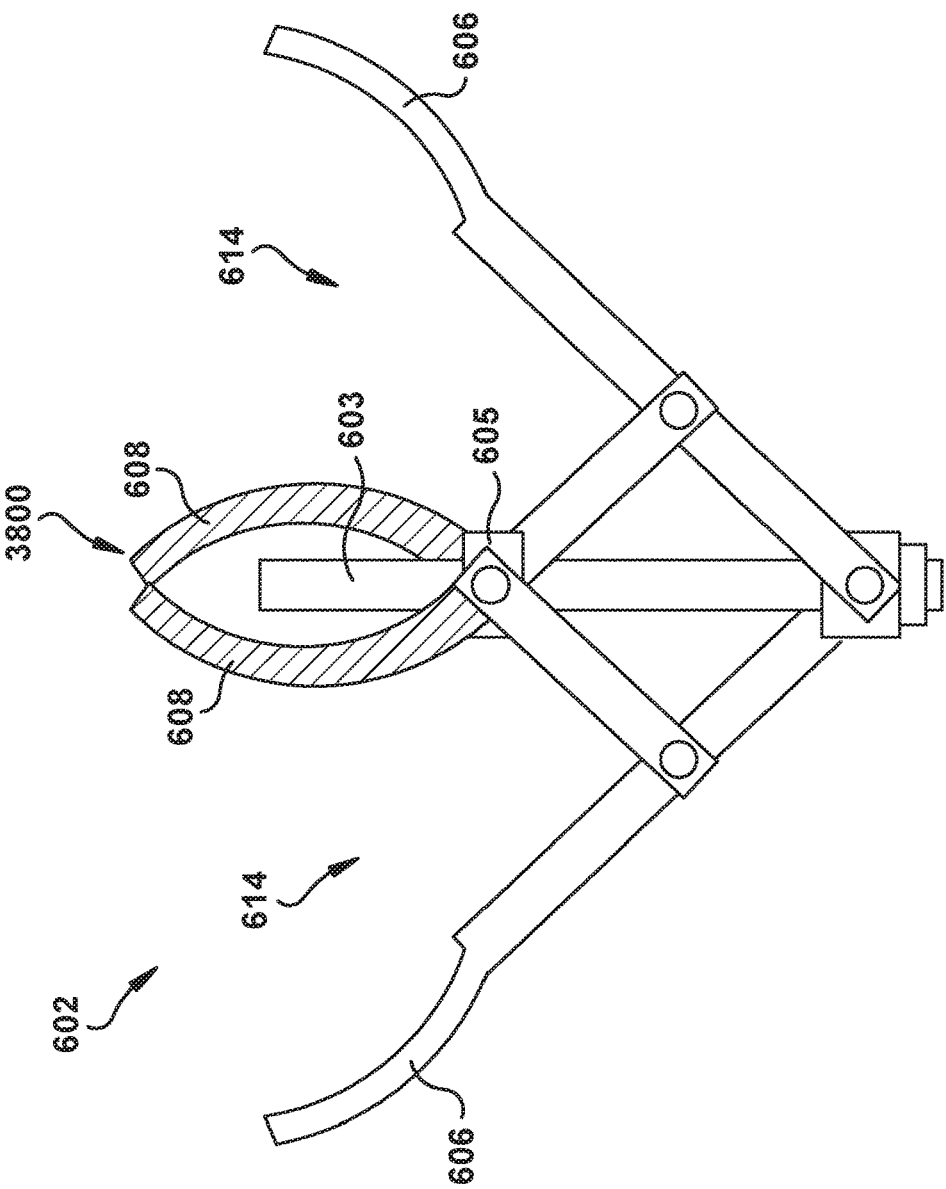
Figure 44B
Figure 44A

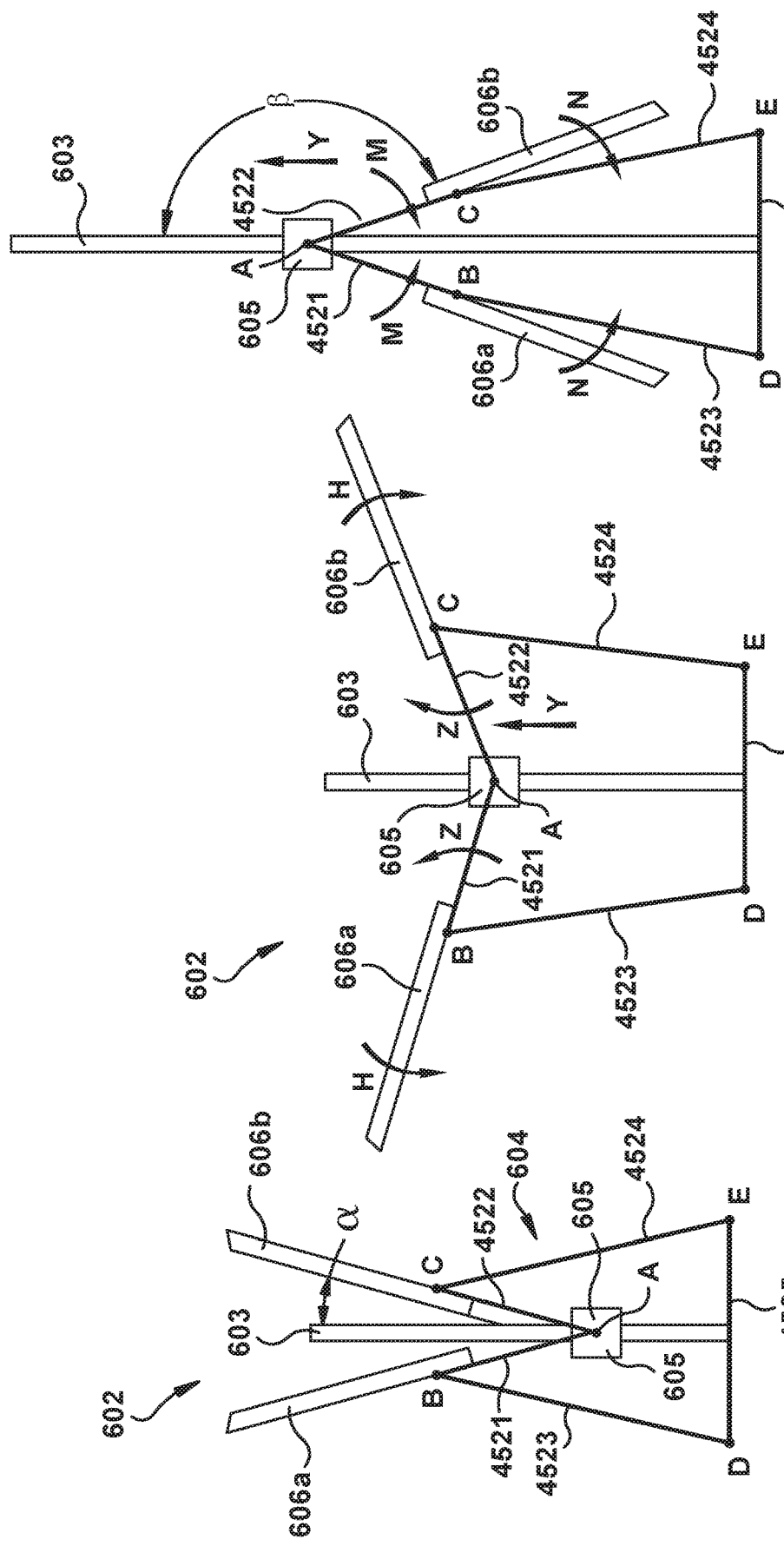

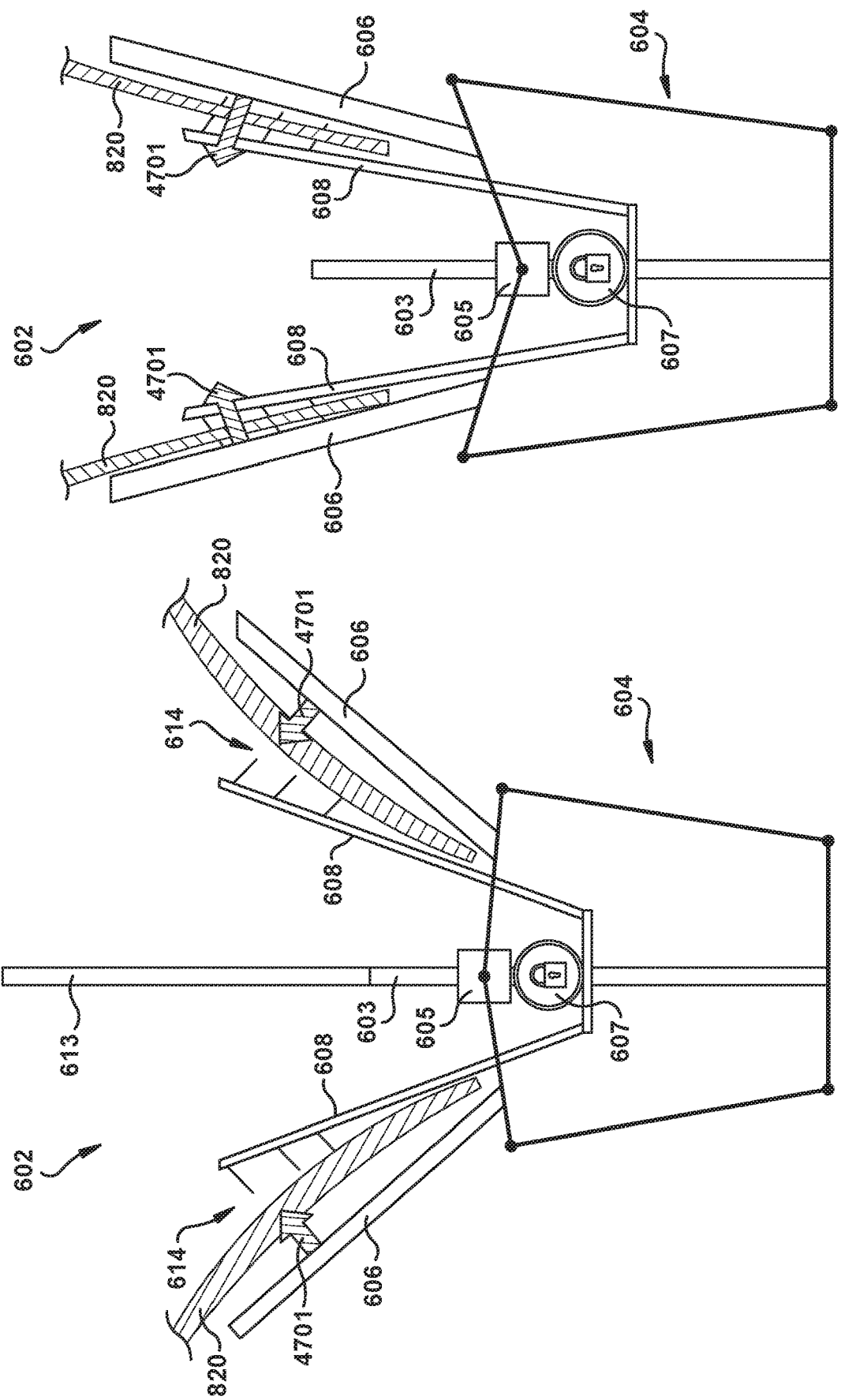

NATIVE VALVE REPAIR DEVICES AND PROCEDURES

CROSS-REFERENCE TO RELATED APPLICATIONS

This application is a continuation of U.S. patent application Ser. No. 16/141,549, filed Sep. 25, 2018, which is a continuation of Ser. No. 15/865,955, filed Jan. 9, 2018, the contents of which are incorporated herein in their entirety for all purposes.

FIELD OF THE INVENTION

The present application relates generally to prosthetic devices and related methods for helping to seal native heart valves and prevent or reduce regurgitation therethrough, as well as devices and related methods for implanting such prosthetic devices.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years the definitive treatment for such damaged valves was surgical repair or replacement of the valve during open heart surgery. However, open heart surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. One particular transvascular technique that is used for accessing the native mitral and aortic valves is the transseptal technique. The trans septal technique comprises inserting a catheter into the right femoral vein, up the inferior vena cava and into the right atrium. The septum is then punctured and the catheter passed into the left atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. For central jet regurgitation, the edges of the leaflets do not meet in the middle. Therefore, the valve does not close and regurgitation is present.

Some prior techniques for treating mitral regurgitation in patients include surgically stitching the edges of the native mitral valve leaflets directly to one another. A catheter delivered clip has been used to attempt to clip the edges of the leaflets together like the surgical stitching method. However, this clip has shortcomings, since it can only be used to clip the middle edges of the leaflets where they overlap by 2 mm or more. Alternately, it has been attempted to use multiple clips on the commisures of the mitral valve, where there may be more overlap. This results in a longer operation time and the patient's leaflets are joined at the sides, restricting blood flow. Both the surgical and clip treatments are thought to create stress on patient leaflets.

Despite these prior techniques, there is a continuing need for improved devices and methods for treating mitral valve regurgitation.

SUMMARY

An exemplary valve repair device for repairing a native valve of a patient includes, a pair of paddles and a pair of gripping members. The paddles are movable between an open position and a closed position. Each of the gripping members has a barbed portion for securing the gripping members to the native valve of a patient. Each gripping member is slidably attached to a corresponding paddle. Each gripping member is moved in a first direction along the paddle before the barbed portion of the gripping member pierces the native valve of the patient. Each gripping member is moved in a direction substantially opposite the first direction after the barbed portion pierces the native valve of the patient such that the gripping members create a tensioning force on the native valve of the patient.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments of the present disclosure will be described and explained with additional specificity and detail through the use of the accompanying drawings.

FIGS. 10A-10B illustrate the movement of the paddles of the valve repair device of FIG. 6 from the open position to a closed position;

FIGS. 15A-15B illustrate another exemplary embodiment of a valve repair device, in which the valve repair device includes paddles that flex along their length to place less stress on valve tissue when the valve repair device is attached to the valve tissue;

FIGS. 21A-21B illustrate another exemplary embodiment of a valve repair device, in which the paddles of the valve repair device are extendable;

FIGS. 27A-27C illustrate another exemplary embodiment of a valve repair device where each paddle of the valve repair device can be independently moved from an open position to a closed position;

FIGS. 28A-28F illustrate another exemplary embodiment of a valve repair device where each paddle of the valve repair device can be independently moved from an open position to a closed position;

FIGS. 29A-29B illustrate another exemplary embodiment of a valve repair device where each paddle of the valve repair device can be independently moved from an open position to a closed position independent of each other;

FIG. 30 illustrates a mitral valve having a wide gap between the posterior leaflet and the anterior leaflet;

FIGS. 32A-32C illustrate another exemplary embodiment of a valve repair device, in which the valve repair device is configured such that paddles of the valve repair device expand by pivoting and spreading apart to create a wide gap for receiving valve tissue;

FIGS. 33A-33C illustrate another exemplary embodiment of a valve repair device, in which the valve repair device is configured such that paddles of the valve repair device expand by spreading apart and pivoting to create a wide gap for receiving valve tissue;

FIGS. 37A-37D illustrate another exemplary embodiment of a valve repair device with mesh paddles and an internal cam for spreading the mesh paddles apart to create a wide gap for spaced apart valve tissues;

FIGS. 37E-37F illustrate another exemplary embodiment of a valve repair device with mesh paddles and an internal cam for spreading the mesh paddles apart to create a wide gap for spaced apart valve tissues;

FIGS. 44A-44B illustrate another exemplary embodiment of a valve repair device with paddles that spread wider and an expanding spacer element;

FIGS. 45A-45C illustrate another exemplary embodiment of a valve repair device with an increased bailout angle for removing the valve repair device;

FIGS. 47A-47B illustrate another exemplary embodiment of a valve repair device with an attachment member for connecting the paddles to the grippers when the valve repair device is in a closed position;

DETAILED DESCRIPTION

The following description refers to the accompanying drawings, which illustrate specific embodiments of the invention. Other embodiments having different structures and operation do not depart from the scope of the present invention.

Exemplary embodiments of the present disclosure are directed to devices and methods for repairing a defective heart valve. It should be noted that various embodiments of native valve reparation devices and systems for delivery are disclosed herein, and any combination of these options can be made unless specifically excluded. In other words, individual components of the disclosed devices and systems can be combined unless mutually exclusive or otherwise physically impossible.

Figure 1:
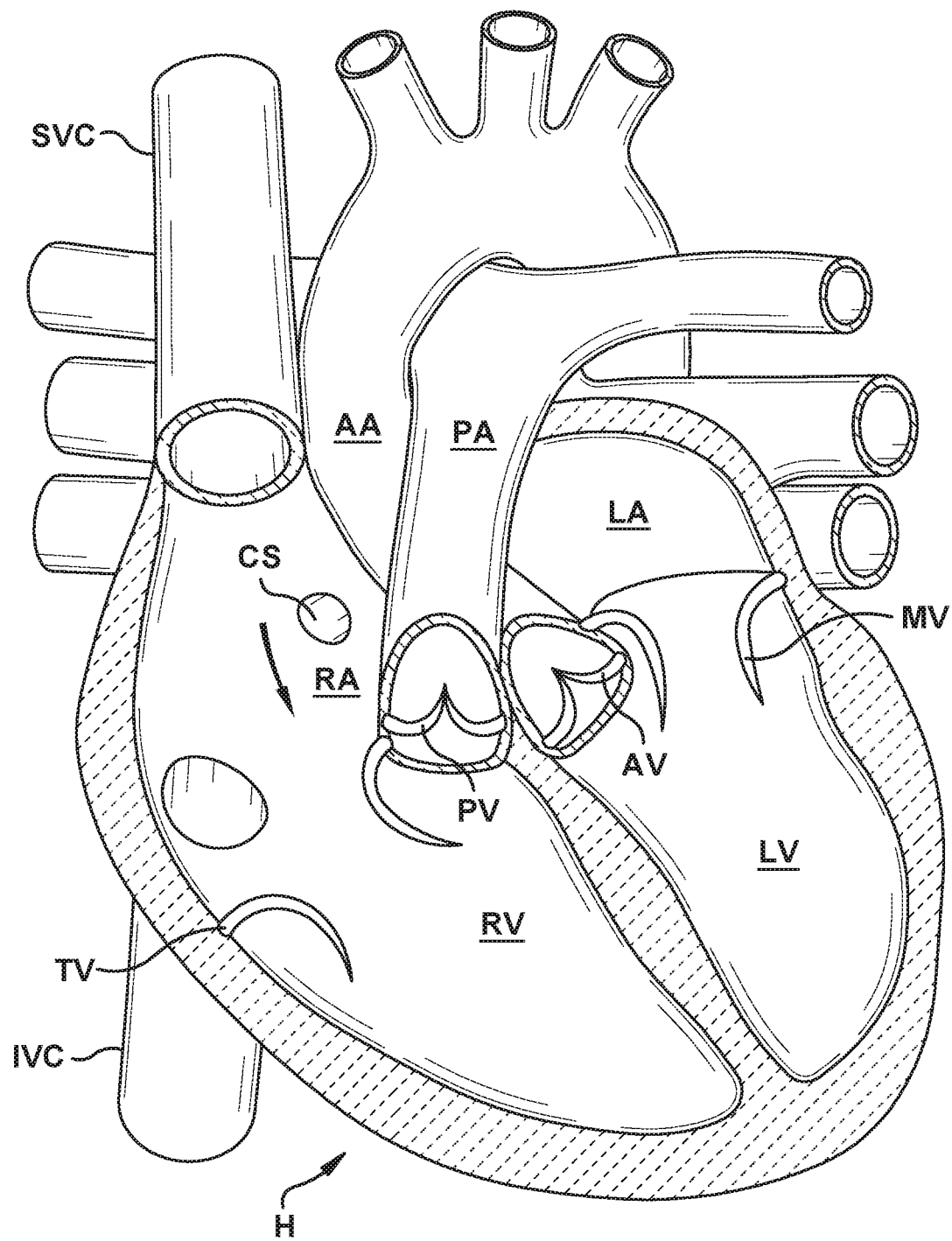
FIG. 1 illustrates a cutaway view of the human heart in a diastolic phase.
Figure 2:
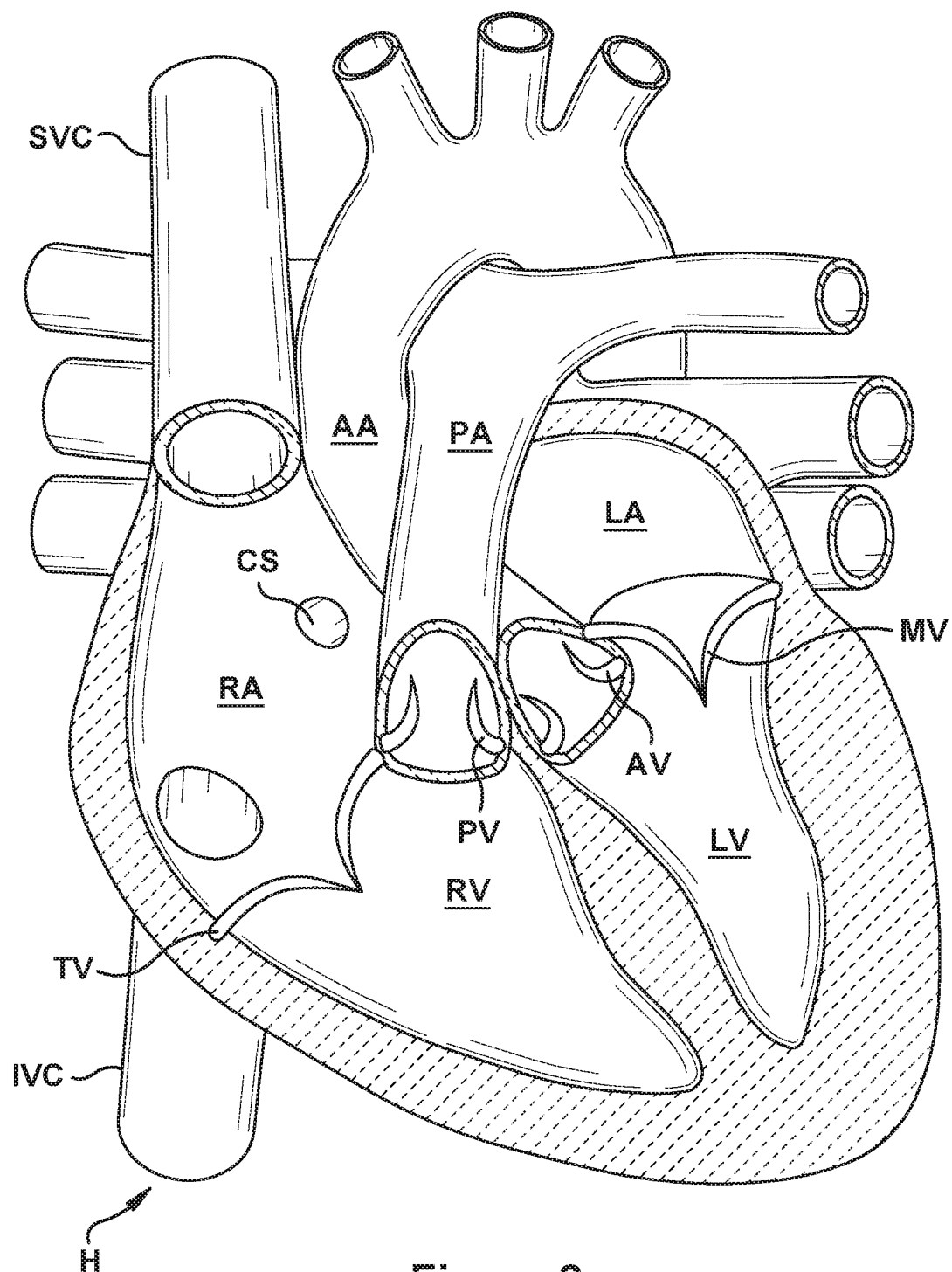
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 302, 304 shown in FIGS. 3 and 4) extending inward across the respective orifices that come together or "coapt" in the flowstream to form the one-way, fluid-occluding surfaces. The native valve repair systems of the present application are described primarily with respect to the mitral valve MV. Therefore, anatomical structures of the left atrium LA and Left ventricle LV will be explained in greater detail. It should be understood that the devices described herein may also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein. In one exemplary embodiment, the devices described by the present application are used to repair the function of a defective mitral valve MV. That is, the devices are configured to help close the leaflets of the mitral valve to prevent blood from regurgitating from the left ventricle LV and back into the left atrium LA.

Figure 3:
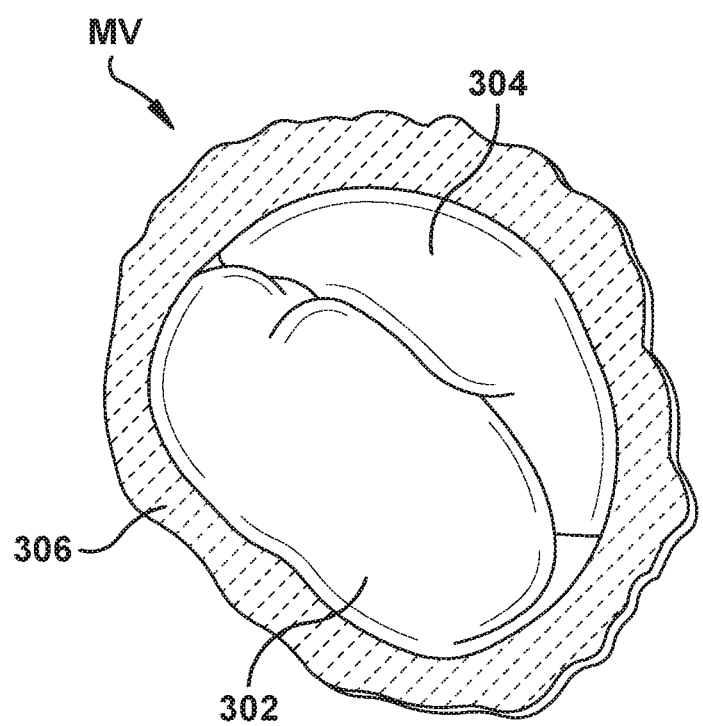
FIG. 3 illustrates a healthy mitral valve with the leaflets closed as viewed from an atrial side of the mitral valve.
Figure 4:
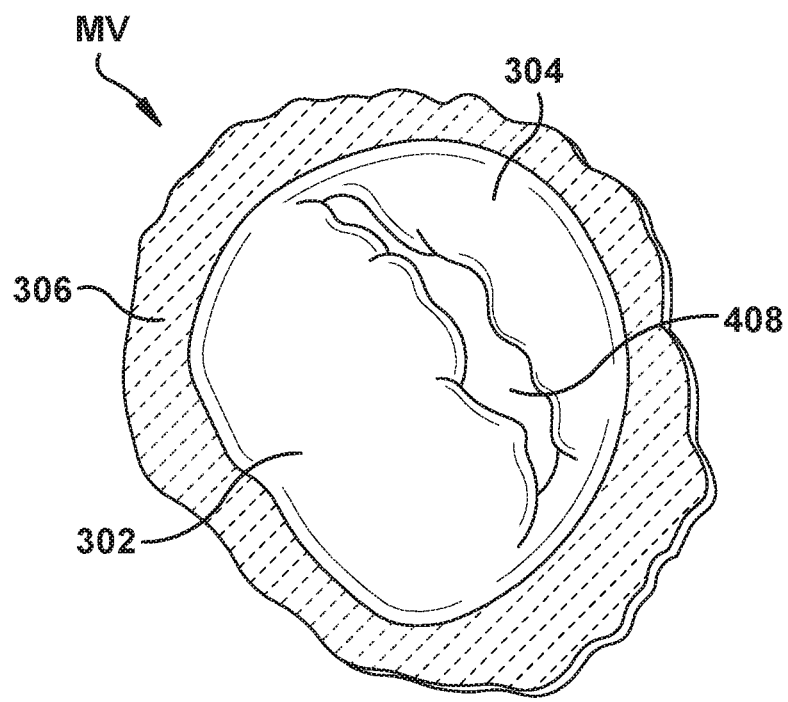
FIG. 4 illustrates a dysfunctional mitral valve with a visible gap between the leaflets as viewed from an atrial side of the mitral valve.
Figure 5:
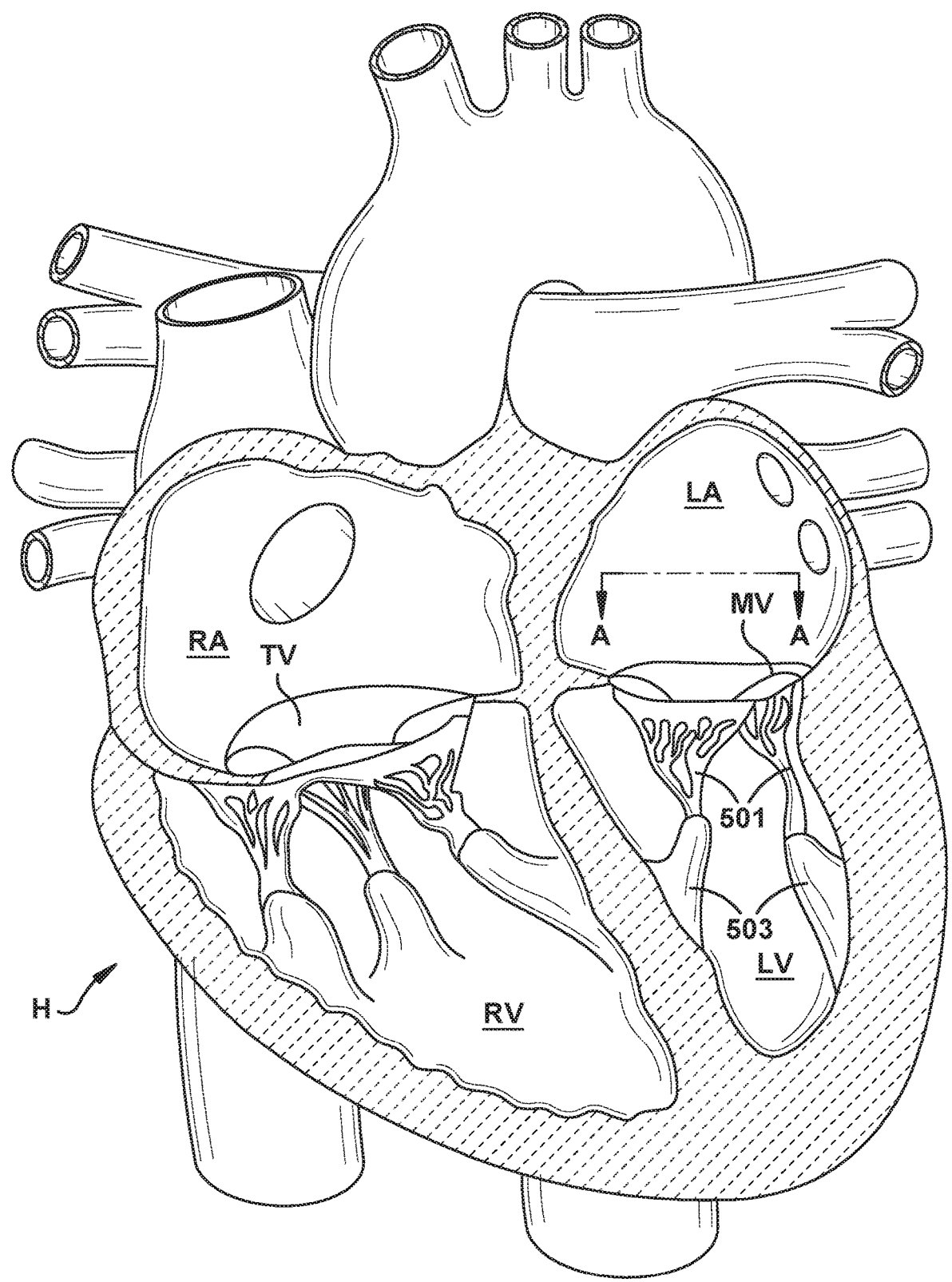
FIG. 5 illustrates a cutaway view of the human heart in a diastolic phase, in which the chordae tendineae are shown attaching the leaflets of the mitral and tricuspid valves to ventricle walls.
Figure 6:
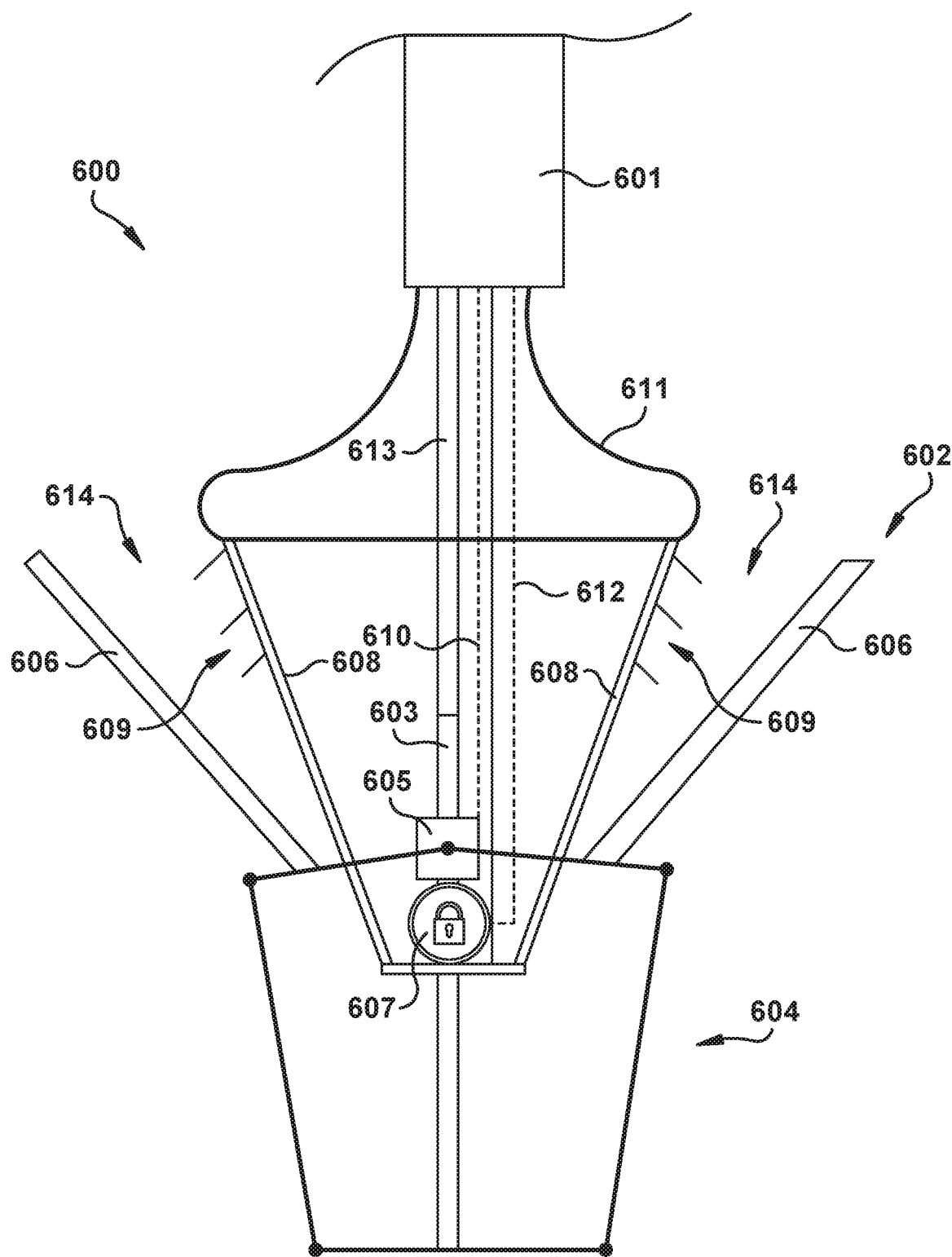
FIG. 6 illustrates a valve repair device with paddles in an open position.

Referring to FIGS. 1-5, the mitral valve MV includes two leaflets, the anterior leaflet 302 and the posterior leaflet 304. The mitral valve MV also includes an annulus 306, which is a variably dense fibrous ring of tissues that encircles the leaflets 302, 304. Referring to FIG. 5, the mitral valve MV is anchored to the wall of the left ventricle LV by chordae tendineae 501. The chordae tendineae 501 are cord-like tendons that connect the papillary muscles 503 (i.e., the muscles located at the base of the chordae tendineae and within the walls of the left ventricle) to the leaflets 302, 304 of the mitral valve MV. The papillary muscles serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflamatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopaty) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 302, 304) of a native valve (e.g., the mitral valve MV), which results in prolapse and regurgitation.

Generally, a native valve may malfunction in two different ways. One possible malfunction is valve stenosis, which occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

Another possible malfunction is valve regurgitation, which occurs when the leaflets of the valve do not close completely thereby causing blood to leak back into the prior chamber (e.g., causing blood to leak from the left ventricle to the left atrium). There are three mechanisms by which a native valve becomes regurgitant or incompetent, which include Carpentier's type I, type II, and type III malfunctions. A Carpentier type 1 malfunction involves the dilation of the annulus such that normally functioning leaflets are distracted from each other and fail to form a tight seal (i.e., do not coapt properly). Included in a type I mechanism malfunction are perforations of the leaflets, as in endocarditis. A Carpentier's type II malfunction involves prolapse of one or more leaflets of a native valve above a plane of coaption. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (Mb).

Referring to FIG. 3, when a healthy mitral valve MV is in a closed position, the anterior leaflet 302 and the posterior leaflet 304 coapt, which prevents blood from leaking from the left ventricle LV to the left atrium LA. Referring to FIG. 4, regurgitation occurs when the anterior leaflet 302 and/or the posterior leaflet 304 of the mitral valve MV is displaced into the left atrium LA during systole. This failure to coapt causes a gap 408 between the anterior leaflet 302 and the posterior leaflet 304, which allows blood to flow back into the left atrium LA from the left ventricle LV during systole. As set forth above, there are several different ways that a leaflet (e.g. leaflets 302, 304 of mitral valve MV) may malfunction, which can thereby lead to regurgitation.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. The mitral valve MV and the tricuspid valve TV are more prone to deformation of leaflets, which, as described above, prevents the mitral valve or tricuspid valve from closing properly and allows for regurgitation or back flow of blood from the ventricle into the atrium (e.g., a deformed mitral valve MV may allow for regurgitation or back flow from the left ventricle LV to the left atrium LA). The regurgitation or back flow of blood from the ventricle to the atrium results in valvular insufficiency. Deformations in the structure or shape of the mitral valve MV or the tricuspid valve TV are often repairable. In addition, regurgitation can occur due to the chordae tendineae 501 becoming dysfunctional (e.g., the chordae tendineae may stretch or rupture), which allows the anterior leaflet 302 and the posterior leaflet 304 to be reverted such that blood is regurgitated into the left atrium LA. The problems occurring due to dysfunctional chordae tendineae 501 can be repaired by repairing the chordae tendineae or the structure of the mitral valve (e.g., by securing the leaflets 302, 304 at the affected portion of the mitral valve).

Figure 4A:
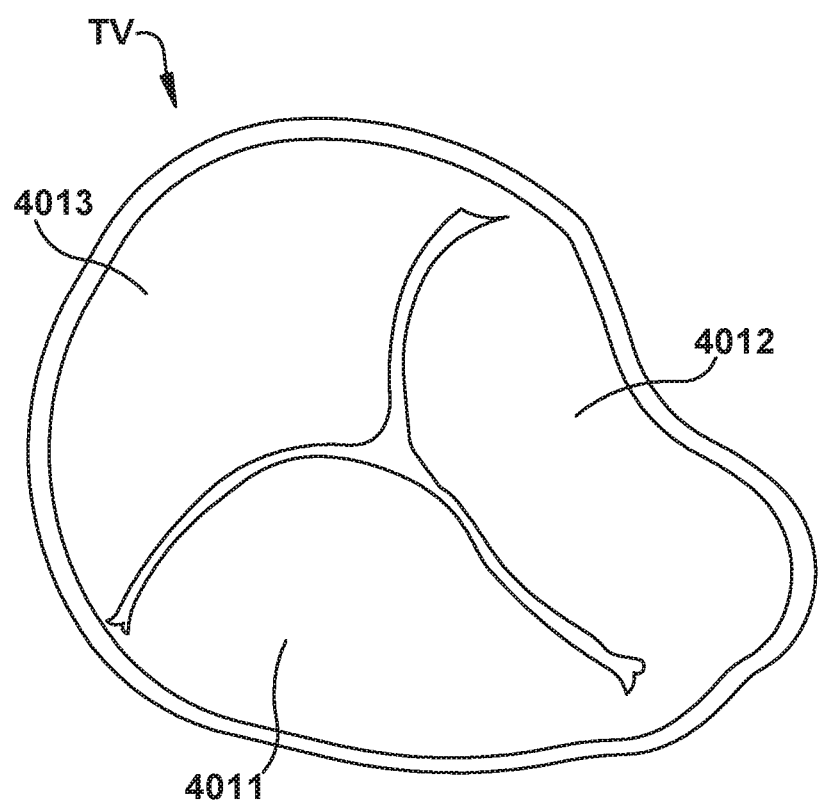
FIG. 4A illustrates tricuspid valve viewed from an atrial side of the tricuspid valve.

The devices and procedures disclosed herein make reference to repairing the structure of a mitral valve. However, it should be understood that the devices and concepts provided herein can be used to repair any native valve, as well as any component of a native valve. Referring to FIG. 4A, any of the devices and concepts provided herein can be used to repair the tricuspid valve TV. For example, any of the devices and concepts provided herein can be used between any two of the anterior leaflet 4011, septal leaflet 4012, and posterior leaflet 4013 to prevent regurgitation of blood from the right ventricle into the right atrium. In addition, any of the devices and concepts provided herein can be used on all three of the leaflets 4011, 4012, 4013 together to prevent regurgitation of blood from the right ventricle to the right atrium. That is, the valve repair devices provided herein can be centrally located between the three leaflets 4011, 4012, 4013.

FIGS. 6-13B illustrate a valve repair system 600 for repairing a native valve of a patient. The valve repair system 600 includes a delivery device 601 and a valve repair device 602, in which delivery device is configured to deliver the valve repair device to the native valve of a patient, and in which the valve repair device is configured to attach to leaflets of a native valve to repair the native valve of the patient. The delivery device 601 can take any suitable form that is capable of delivering the valve repair device 602 to the native valve of a patient. In certain embodiments, the valve repair system 600 is configured to deliver the valve repair device 602 to a native valve of a patient during a non-open-heart procedure. Suitable delivery means for percutaneously delivering the valve repair system 600 in a minimal-invasive procedure, can be delivery sleeves or delivery catheters which may be inserted through small incisions in the skin of a patient and advanced to the implantation site, for example along an endovascular (e.g. transfemoral) path or a transapical path.

The valve repair device 602 includes a base assembly 604, a pair of paddles 606, and a pair of gripping members 608. In one exemplary embodiment, the paddles 606 can be integrally formed with the base assembly. For example, the paddles 606 can be formed as extensions of links of the base assembly. In the illustrated example, the base assembly 604 of the valve repair device 602 has a shaft 603, a coupler 605 configured to move along the shaft, and a lock 607 configured to lock the coupler in a stationary position on the shaft. The coupler 605 is mechanically connected to the paddles 606, such that movement of the coupler 605 along the shaft 603 causes the paddles to move between an open position and a closed position. In this way, the coupler 605 serves as means for mechanically coupling the paddles 606 to the shaft 603 and, when moving along the shaft 603, for causing the paddles 606 to move between their open and closed positions. In certain embodiments, the gripping members 608 are pivotally connected to the base assembly 604 (e.g., the gripping members 608 can be pivotally connected to the shaft 603, or any other suitable member of the base assembly), such that the gripping members can be moved to adjust the width of the opening 614 between the paddles 606 and the gripping members 608. The gripping member 608 can include a barbed portion 609 for attaching the gripping members to valve tissue when the valve repair device 602 is attached to the valve tissue. The gripping member 608 forms a means for gripping the valve tissue (in particular tissue of the valve leaflets) with a sticking means or portion such as the barbed portion 609. When the paddles 606 are in the closed position, the paddles engage the gripping members 608, such that, when valve tissue is attached to the barbed portion 609 of the gripping members, the paddles act as holding or securing means to hold the valve tissue at the gripping members and to secure the valve repair device 602 to the valve tissue. In some embodiments, the gripping members 608 are configured to engage the paddles 606 such that the barbed portion 609 engages the valve tissue member and the paddles 608 to secure the valve repair device 602 to the valve tissue member. For example, in certain situations, it may be advantageous to have the paddles 606 maintain an open position and have the gripping members 608 move outward toward the paddles 606 to engage a valve tissue member and the paddles 606.

While the embodiment shown in FIGS. 6-13B illustrate a pair of paddles 606 and a pair of gripping members 608, it should be understood that the valve repair device 602 can include any suitable number of paddles and gripping members. In certain embodiments, the valve repair system 600 includes a placement shaft 613 that is removably attached to the shaft 603 of the base assembly 604 of the valve repair device 602. After the valve repair device 602 is secured to valve tissue, the placement shaft 613 is removed from the shaft 603 to remove the valve repair device 602 from the remainder of the valve repair system 600, such that the valve repair device 602 can remain attached to the valve tissue, and the delivery device 601 can be removed from a patient's body.

The valve repair system 600 can also include a paddle control mechanism 610, a gripper control mechanism 611, and a lock control mechanism 612. The paddle control mechanism 610 is mechanically attached to the coupler 605 to move the coupler along the shaft, which causes the paddles 606 to move between the open and closed positions. The paddle control mechanism 610 can take any suitable form, such as, for example, a shaft or rod. For example, the paddle control mechanism can comprise a hollow shaft, a catheter tube or a sleeve that fits over the placement shaft 613 and the shaft 603 and is connected to the coupler 605. The gripper control mechanism 611 is configured to move the gripping members 608 such that the width of the opening 614 between the gripping members and the paddles 606 can be altered. The gripper control mechanism 611 can take any suitable form, such as, for example, a line, a suture or wire, a rod, a catheter, etc.

The lock control mechanism 612 is configured to lock and unlock the lock. The lock 607 serves as locking means for locking the coupler 605 in a stationary position with respect to the shaft 603 and can take a wide variety of different forms and the type of lock control mechanism 612 may be dictated by the type of lock used. In one embodiment, the lock 607 takes the form of locks often used in caulk guns. That is, the lock 607 includes a pivotable plate having a hole, in which the shaft 603 of the valve repair device 602 is disposed within the hole of the pivotable plate. In this embodiment, when the pivotable plate is in the tilted position, the pivotable plate engages the shaft 603 to maintain a position on the shaft 603, but, when the pivotable plate is in a substantially non-tilted position, the pivotable plate can be moved along the shaft (which allows the coupler 605 to move along the shaft 603). In other words, the coupler 605 is prevented from moving in the direction Y (as shown in FIG. 10A) along the shaft 603 when pivotable plate of the lock 607 is in a tilted (or locked) position, and the coupler is allowed to move in the direction Y along the shaft 603 when the pivotable plate is in a substantially non-tilted (or unlocked) position. In embodiments in which the lock 607 includes a pivotable plate, the lock control mechanism 612 is configured to engage the pivotable plate to move the plate between the tilted and substantially non-tilted positions. The lock control mechanism 612 can be, for example, a rod, a suture, a wire, or any other member that is capable of moving a pivotable plate of the lock 607 between a tilted and substantially non-tilted position. In certain embodiments, the pivotable plate of the lock 607 is biased in the tilted (or locked) position, and the lock control mechanism 612 is used to move the plate from the titled position to the substantially non-tilted (or unlocked) position. In other embodiments, the pivotable plate of the lock 607 is biased in the substantially non-tilted (or unlocked) position, and the lock control mechanism 612 is used to move the plate from the substantially non-tilted position to the tilted (or locked) position.

FIGS. 10A-10B illustrate the valve repair device 602 moving from an open position (as shown in FIG. 10A) to a closed position (as shown in FIG. 10B). The base assembly 604 includes a first link 1021 extending from point A to point B, a second link 1022 extending from point A to point C, a third link 1023 extending from point B to point D, a fourth link 1024 extending from point C to point E, and a fifth link 1025 extending from point D to point E. The coupler 605 is movably attached to the shaft 603, and the shaft 603 is fixed to the fifth link 1025. The first link 1021 and the second link 1022 are pivotally attached to the coupler 605 at point A, such that movement of the coupler 605 along the shaft 603 moves the location of point A and, consequently, moves the first link 1021 and the second link 1022. The first link 1021 and the third link 1023 are pivotally attached to each other at point B, and the second link 1022 and the fourth link 1024 are pivotally attached to each other at point C. One paddle 606a is attached to first link 1021 such that movement of first link 1021 causes the paddle 606a to move, and the other paddle 606b is attached to the second link 1022 such that movement of the second link 1022 causes the paddle 606b to move. Alternatively, the paddles 606a, 606b can be connected to links 1023, 1024 or be extensions of links 1023, 1024.

In order to move the valve repair device from the open position (as shown in FIG. 10A) to the closed position (as shown in FIG. 10B), the coupler 605 is moved along the shaft 603 in the direction Y, which moves the pivot point A for the first links 1021 and the second link 1022 to a new position. Movement of the coupler 605 (and pivot point A) in the direction Y causes a portion of the first link 1021 near point A to move in the direction H, and the portion of the first link 1021 near point B to move in the direction J. The paddle 606a is attached to the first link 1021 such that movement of the coupler 605 in the direction Y causes the paddle 606a to move in the direction Z. In addition, the third link 1023 is pivotally attached to the first link 1021 at point B such that movement of the coupler 605 in the direction Y causes the third link 1023 to move in the direction K. Similarly, movement of the coupler 605 (and pivot point A) in the direction Y causes a portion of the second link 1022 near point A to move in the direction L, and the portion of the second link 1022 near point C to move in the direction M. The paddle 606b is attached to the second link 1022 such that movement of the coupler 605 in the direction Y causes the paddle 606b to move in the direction V. In addition, the fourth link 1024 is pivotally attached to the second link 1022 at point C such that movement of the coupler 605 in the direction Y causes the fourth link 1024 to move in the direction N. FIG. 10B illustrates the final position of the valve repair device 602 after the coupler 605 is moved as shown in FIG. 10A.

Figure 7:
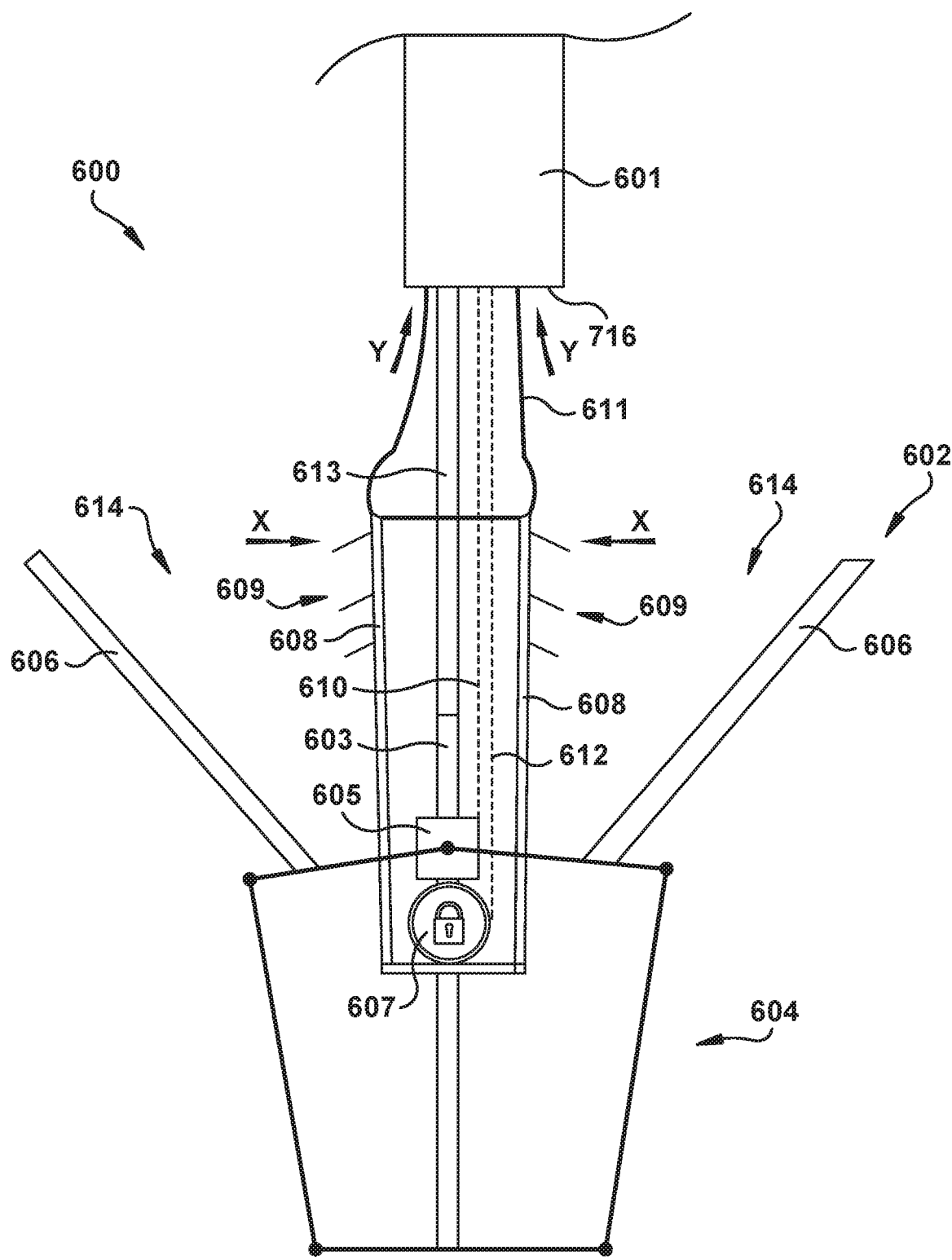
FIG. 7 illustrates the valve repair device of FIG. 6, in which the paddles are in the open position and gripping members are moved to create a wider gap between the gripping members and paddles.

Referring to FIG. 7, the valve repair device 602 is shown in the open position (similar to the position shown in FIG. 10A), and the gripper control mechanism 611 is shown moving the gripping members 608 to provide a wider gap at the opening 614 between the gripping members and the paddles 606. In the illustrated embodiment, the gripper control mechanism 611 includes a line, such as a suture, a wire, etc. that is threaded through an opening in an end of the gripper members 608. Both ends of the line extending through the delivery opening 716 of the delivery device 601. When the line is pulled through the delivery opening 716 in the direction Y, the gripping members 608 move inward in the direction X, which causes the opening 614 between the gripping members and the paddles 606 to become wider.

Figure 8:
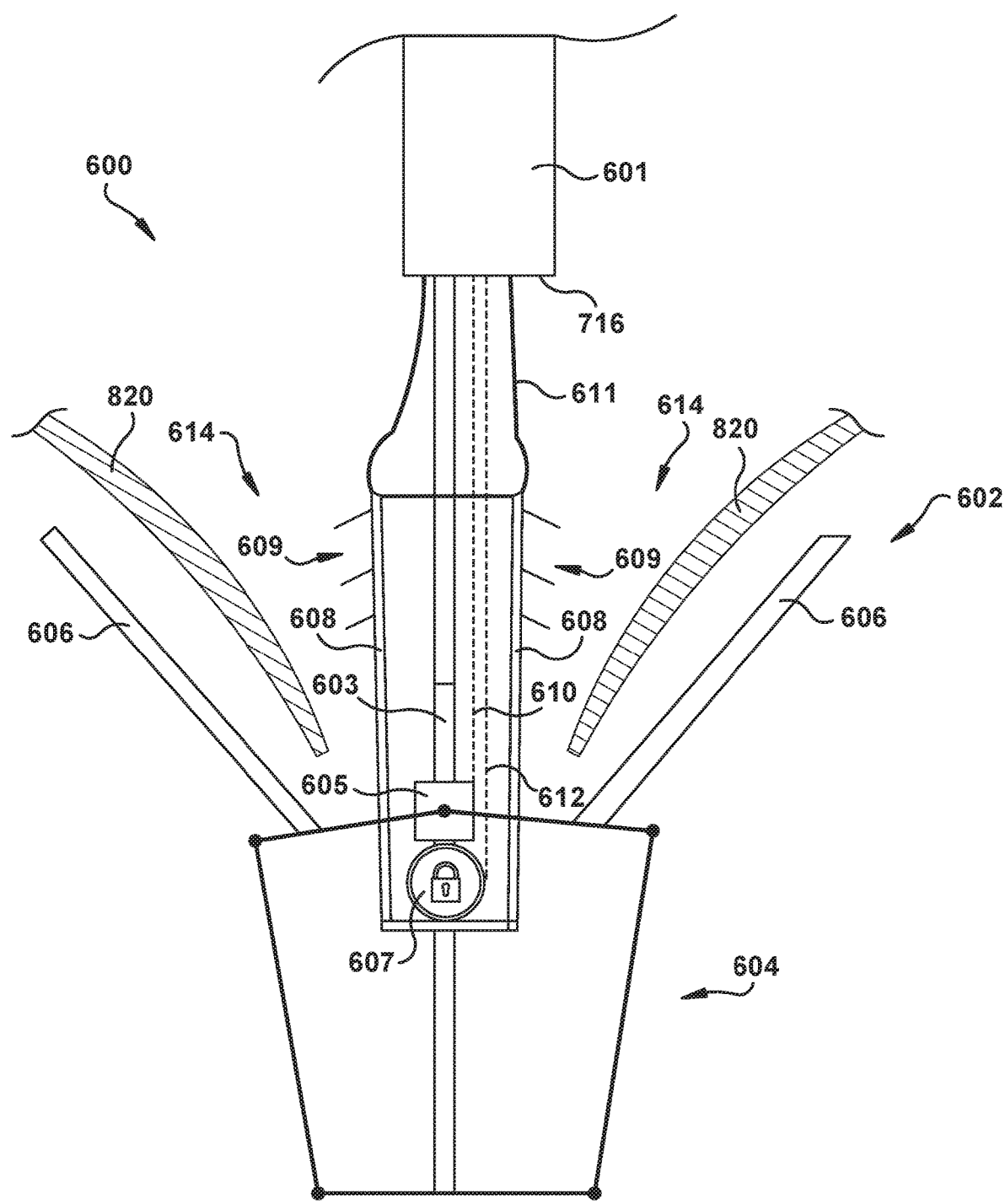
FIG. 8 illustrates the valve repair device of FIG. 6, in which the valve repair device is in the position shown in FIG. 7 with valve tissue placed between the gripping members and the paddles.
Figure 9:
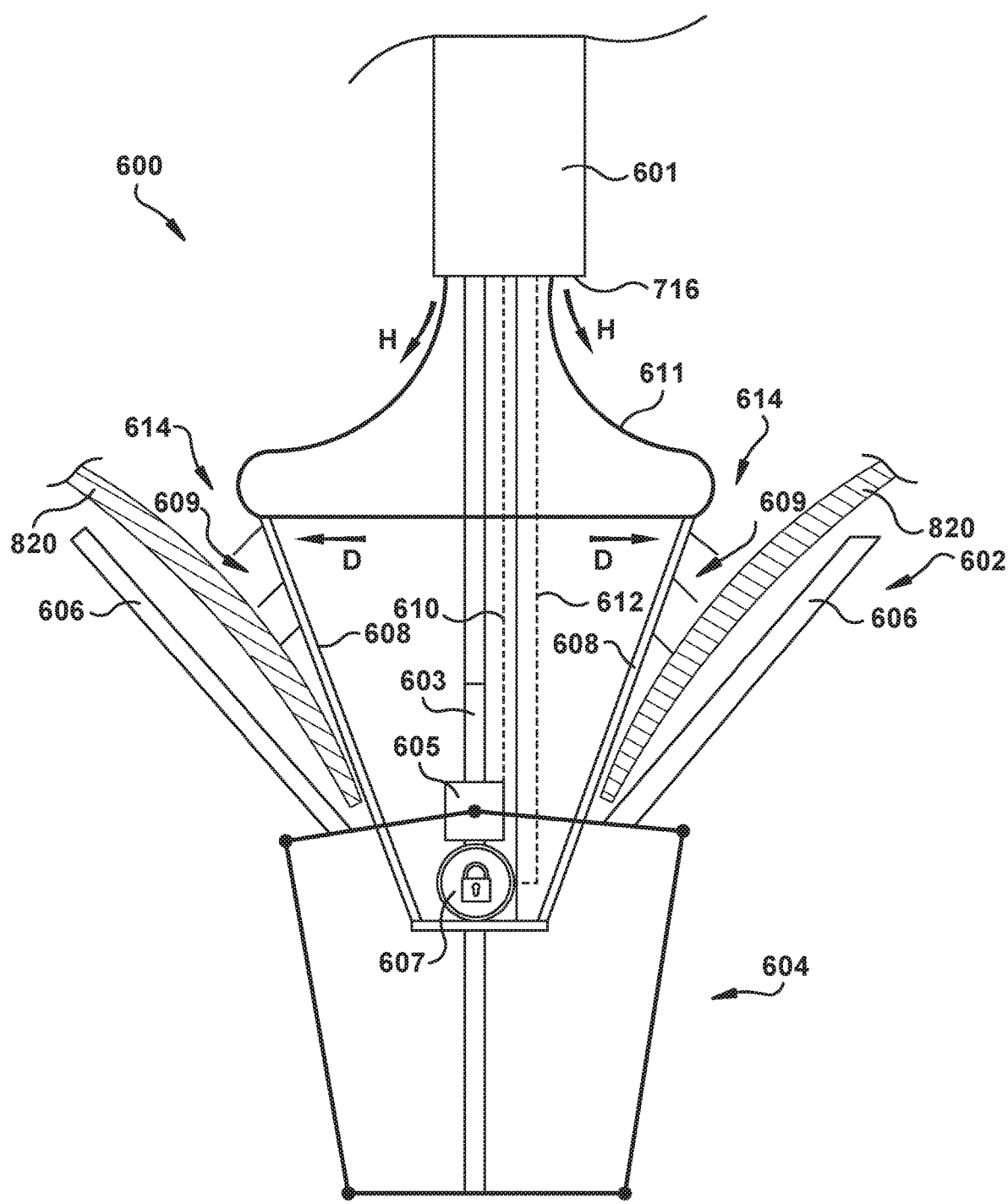
FIG. 9 illustrates the valve repair device of FIG. 6, in which the gripping members are moved to lessen the gap between the gripping members and the paddles.

Referring to FIG. 8, the valve repair device 602 is shown such that valve tissue 820 is disposed in the opening 614 between the gripping members 608 and the paddles 606. Referring to FIG. 9, after the valve tissue 820 is disposed between the gripping members 608 and the paddles 606, the gripper control mechanism 611 is used to lessen the width of the opening 614 between the gripping members and the paddles. That is, in the illustrated embodiment, the line of the gripper control mechanism 611 is released from or pushed out of the opening 716 of the delivery member in the direction H, which allows the gripping members 608 to move in the direction D to lessen the width of the opening 614. While the gripper control mechanism 611 is shown moving the gripping members 608 to increase the width of the opening 614 between the gripping members and the paddles 606 (FIG. 8), it should be understood that the gripping members may not need to be moved in order to position valve tissue in the opening 614. In certain circumstances, however, the opening 614 between the paddles 606 and the gripping members 608 may need to be wider in order to receive the valve tissue.

Figure 11:
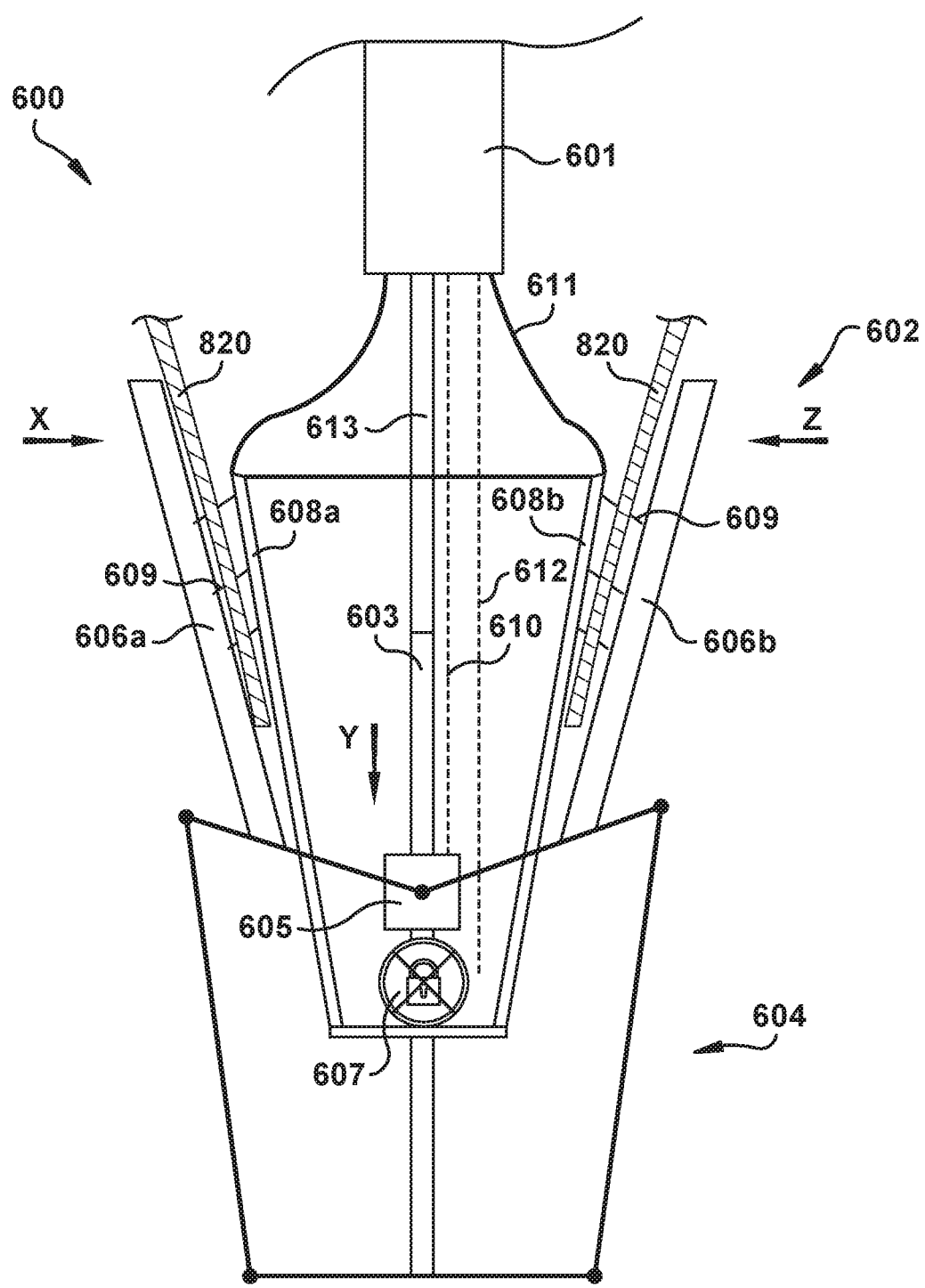
FIG. 11 illustrates the valve repair device of FIG. 6 in a closed position, in which the gripping members are engaging valve tissue.

Referring to FIG. 11, the valve repair device 602 is in the closed position and secured to valve tissue 820. The valve repair device 602 is secured to the valve tissue 820 by the paddles 606a, 606b and the gripping members 608a, 608b. In particular, the valve tissue 820 is attached to the valve repair device 602 by the barbed portion 609 of the gripping members 608a, 608b, and the paddles 606a, 606b engage the gripping members 608 to secure the valve repair device 602 to the valve tissue 820. In order to move the valve repair device 602 from the open position to the closed position, the lock 607 is moved to an unlocked condition (as shown in FIG. 11) by the lock control mechanism 612. Once the lock 607 is in the unlocked condition, the coupler 605 can be moved along the shaft 603 by the paddle control mechanism 610. In the illustrated embodiment, the paddle control mechanism 610 moves the coupler 605 in a direction Y along the shaft, which causes one paddle 606a to move in a direct X and the other paddle 606b to move in a direction Z. The movement of the paddles 606a, 606b in the direction X and the direction Z, causes the paddles to engage the gripping members 608a, 608b and secure the valve repair device 602 to the valve tissue 820.

Figure 12:
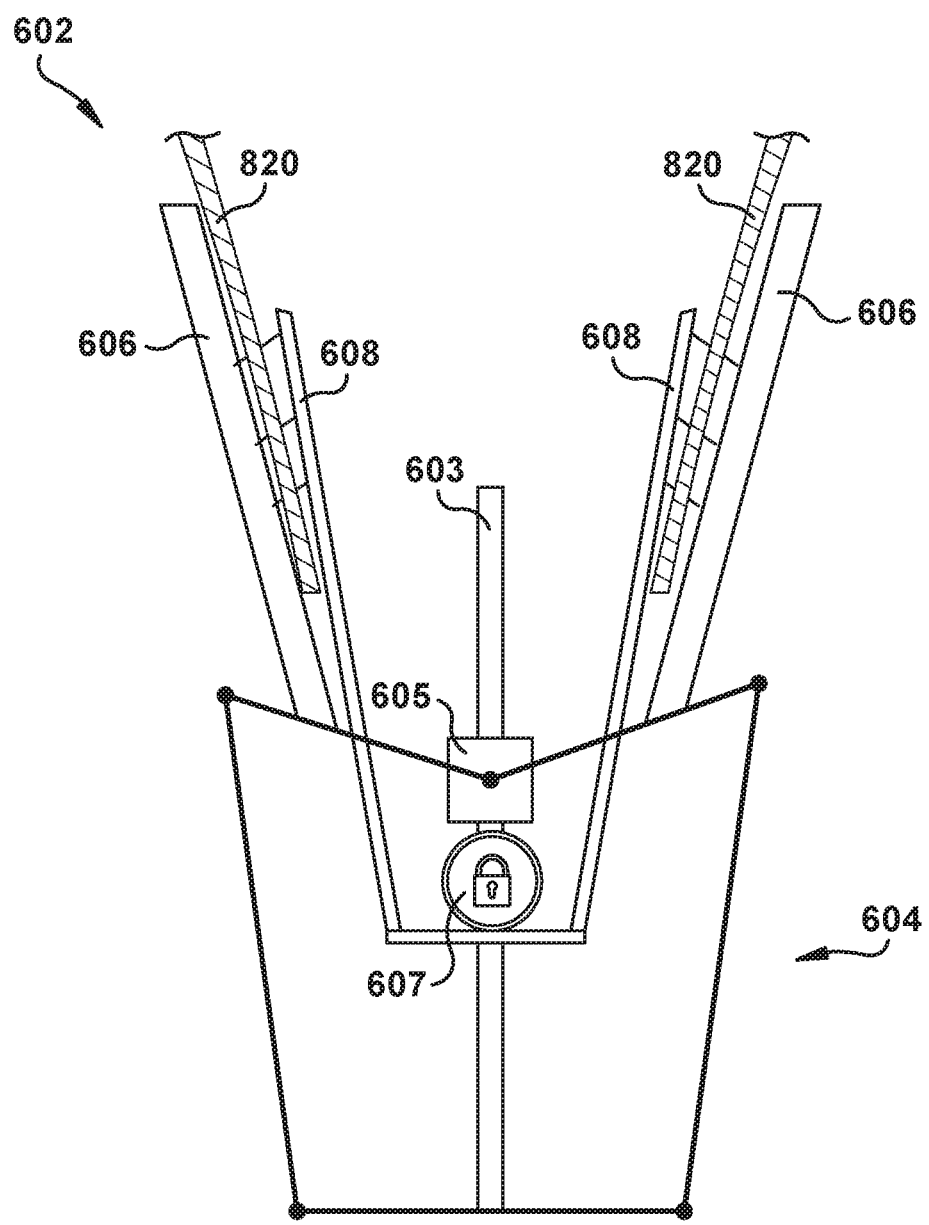
FIG. 12 illustrates the valve repair device of FIG. 6 after being disconnected from a delivery device and attached to valve tissue, in which the valve repair device is in a closed and locked condition.

Referring to FIG. 12, after the paddles 606 are moved to the closed position to secure the valve repair device 602 to the valve tissue 820 (as shown in FIG. 11), the lock 607 is moved to the locked condition by the locking control mechanism 611 (FIG. 11) to maintain the valve repair device 602 in the closed position. After the valve repair device 602 is maintained in the locked condition by the lock 607, the valve repair device 602 is removed from the delivery device 601 by disconnecting the shaft 603 from the placement shaft 613 (FIG. 11). In addition, the valve repair device 602 is disengaged from the paddle control mechanism 610 (FIG. 11), the gripper control mechanism 611 (FIG. 11), and the lock control mechanism 612. Removal of the valve repair device 602 from the delivery device 601 allows the valve repair device to remain secured to valve tissue 820 while the delivery device 601 is removed from a patient.

Figure 13A:
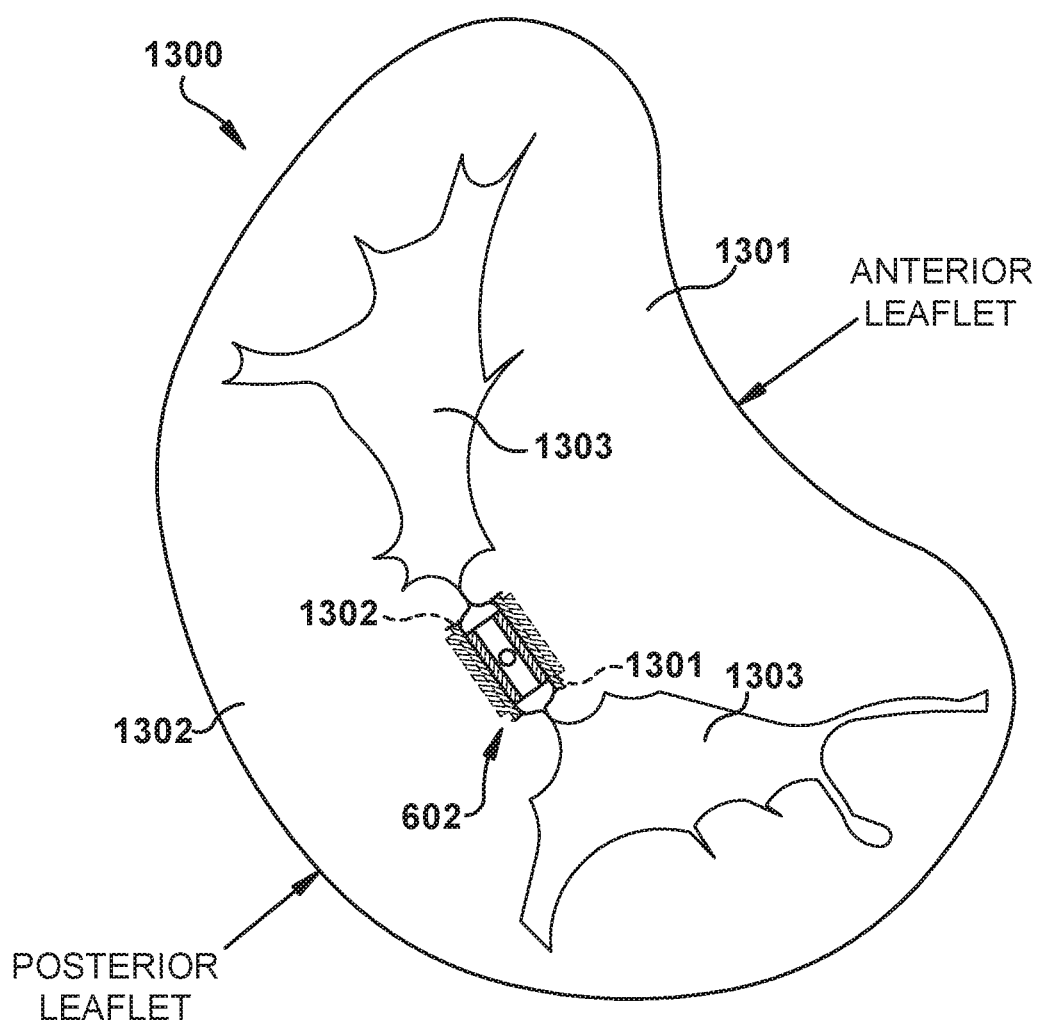
FIG. 13A illustrates an exemplary embodiment of a valve repair device attached to the anterior leaflet and the posterior leaflet of a patient's mitral valve, shown from the left atrium of the patient's heart with the valve repair device and leaflet tissue on the ventricular side shown in hidden lines.
Figure 13B:
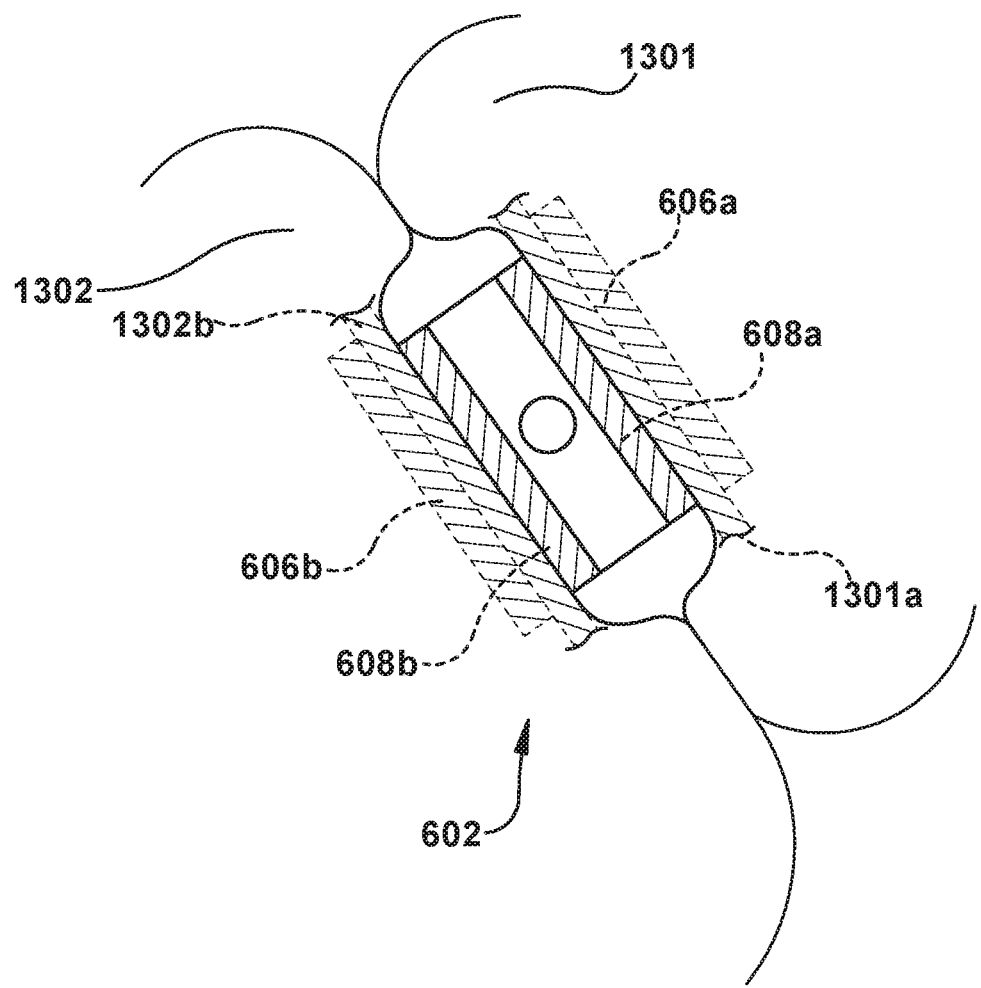
FIG. 13B is an enlarged version of FIG. 13A.

Referring to FIGS. 13A-13B, the mitral valve 1300 of a patient is shown with a valve repair device 602 attached to the anterior leaflet 1301 and the posterior leaflet 1302 of the mitral valve. FIGS. 13A-13B are views from the atrial side of the mitral valve 1300 with portions of the valve repair device 602 and captured mitral valve leaflet tissue on the ventricular side of the mitral valve depicted in hidden lines. During the diastolic phase (as shown in FIG. 1), the blood that collects in the left atrium of the heart enters the mitral valve 1300 by expansion of the left ventricle of the heart. The anterior leaflet 1301 and the posterior leaflet 1302 open to allow blood to travel from the left atrium to the left ventricle. In the systolic phase (as shown in FIG. 2), the left ventricle contracts to force the blood through the aortic valve and the ascending aorta and into the body. During systole, the leaflets of the mitral valve MV close to prevent the blood from regurgitating back into the left atrium LA. As described above, regurgitation of blood from the left ventricle to the left atrium through the mitral valve occurs when the anterior leaflet 1301 and the posterior leaflet 1302 do not close entirely such that a gap exists between the anterior leaflet and the posterior leaflet. In order to repair a mitral valve 1300 to prevent regurgitation of blood through the mitral valve, the valve repair device 602 is connected to the anterior leaflet 1301 and the posterior leaflet 1302 to close the gap.

Referring to FIG. 13A, the mitral valve 1300 is shown from the left atrium of a patient's heart (e.g., from the view indicated by line A-A in FIG. 5). In the illustrated embodiment, the mitral valve 1300 is shown in an open position (i.e., the position the mitral valve takes during the diastolic phase). The valve repair device 602 is attached to the anterior leaflet 1301 and the posterior leaflet 1302 of the mitral valve 1300 in the left ventricle of the patient's heart, and is shown in dotted lines in FIGS. 13A-13B to indicate the location of the valve repair device with respect to the mitral valve. As shown in FIGS. 13A-13B, the valve repair device 602 engages the anterior leaflet 1301 and the posterior leaflet 1302 and causes the anterior leaflet and posterior leaflet to engage each other (i.e., the valve repair device closes a portion of the gap between the anterior leaflet and the posterior leaflet). The valve repair device 602 can be placed in a location in which a gap exists between the anterior leaflet 1301 and the posterior leaflet 1302 when the mitral valve 1301 is in a closed position (i.e., the position of the mitral valve during the systolic phase), such that the valve repair device will prevent the gap from occurring. The illustrated embodiment shows the mitral valve 1300 and valve repair device 602 during the diastolic phase. That is, during the diastolic phase, the valve repair device 602 will cause a portion of the mitral valve to remain closed, but the portions of the mitral valve not engaged by the valve repair device will open such that gaps 1303 are created to allow blood to flow from the left atrium to the left ventricle.

Referring to FIG. 13B, the valve repair device 602 is attached to both the anterior leaflet 1301 and the posterior leaflet 1302. In particular, a portion 1301a of the anterior leaflet 1301 is secured between a paddle 606a and a gripping member 608a of the valve repair device 602, and a portion 1302b of the posterior leaflet 1302 is secured between another paddle 606b and another gripping member 608b of the valve repair device. The valve repair device 602 is secured and locked to the mitral valve 1300, for example, as shown in FIGS. 6-12.

Figure 14A:
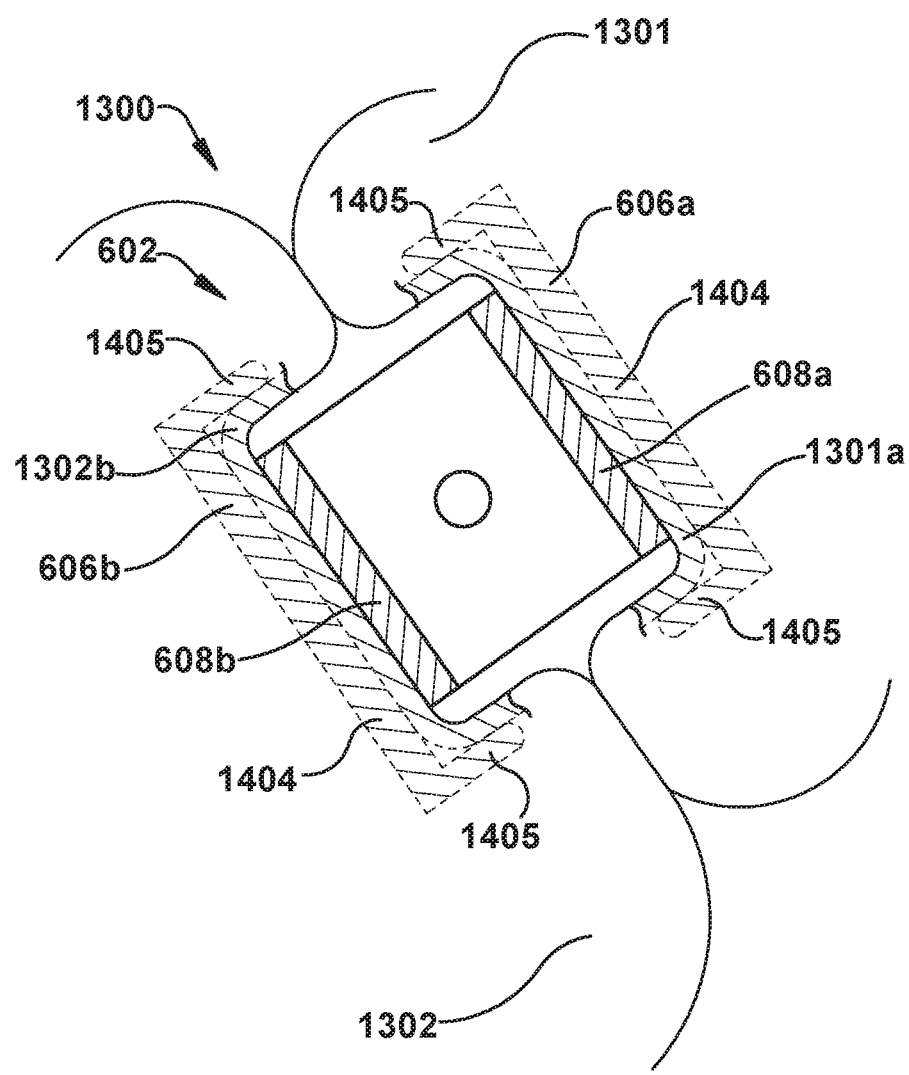
FIG. 14A is another exemplary embodiment of a valve repair device attached to the anterior leaflet and the posterior leaflet of a patient's mitral valve with the valve repair device and leaflet tissue on the ventricular side shown in hidden lines.
Figure 14B:
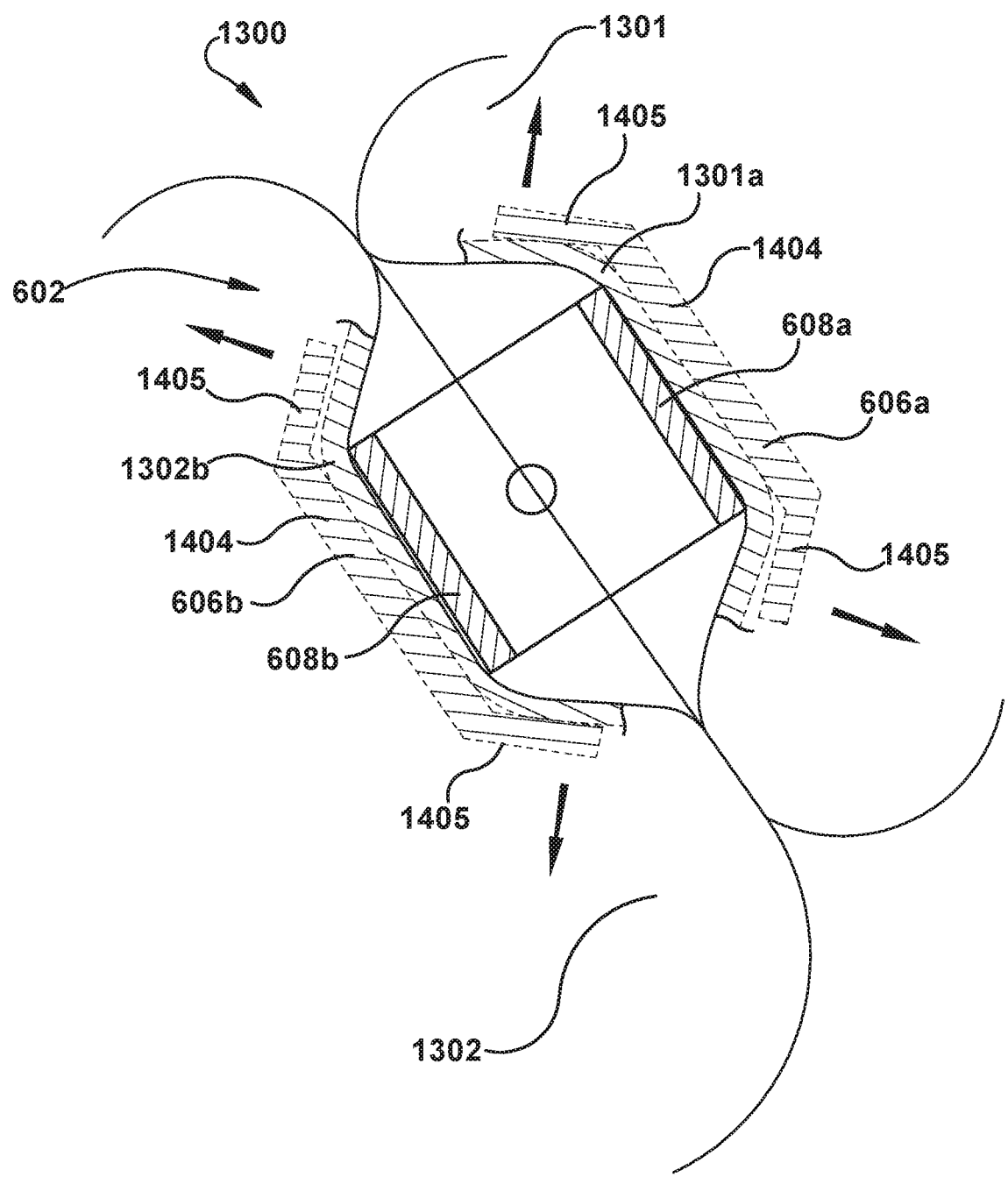
FIG. 14B is another exemplary embodiment of a valve repair device attached to the anterior leaflet and the posterior leaflet of a patient's mitral valve, in which the valve repair device includes paddles that flex to place less stress on the mitral valve tissue with the valve repair device and leaflet tissue on the ventricular side shown in hidden lines.

FIGS. 14A-14B illustrate exemplary embodiments of a valve repair device 602 attached to the anterior leaflet 1301 and posterior leaflet 1302 of a mitral valve 1300. The mitral valve 1300 is shown from the left atrium of a patient's heart (e.g., from the view indicated by line A-A in FIG. 5). Still referring to FIGS. 14A-14B, the valve repair device 602 includes a first paddle 606a, a second paddle 606b, a first gripping member 608a, and a second gripping member 608b. A portion 1301a of the anterior leaflet 1301 is secured between the first paddle 606a and the first gripping member 608a of the valve repair device 602, and a portion 1302b of the posterior leaflet 1302 is secured between the second paddle 606b and the second gripping member 608b of the valve repair device. The first and second paddles 606a, 606b include a main portion 1404 and side portions 1405. Referring to FIG. 14A, the valve repair device 602 is configured such that the portions 1301a, 1302b of the mitral valve 1300 conform to or generally conform to the shape of the paddles 606a, 606b. That is, the valve leaflet portions 1301a, 1302b are pressed into the paddles by the gripping members 608a, 608b, such that the valve leaflet portions 1301a, 1301b are disposed along a main portion 1404 and side portions 1405 of the paddles 606a, 606b. In the embodiment of the valve repair device 602 shown in FIG. 14A, the paddles 606a, 606b can be made of a rigid material, for example, steel, molded plastic, etc.

In the exemplary embodiment illustrated by FIG. 14B, the paddles 606a, 606b of the valve repair device 602 are configured to flex. Because of this flex, when the valve repair device is attached to the mitral valve 1300, the mitral valve tissue portions 1301a, 1302b move the side portions 1405 of the paddles as indicated by arrows 1450, which reduces the stress placed on the mitral valve by the valve repair device as compared to the embodiment illustrated by FIG. 14A. That is, the flexing results in a more gradual contouring of the mitral valve tissue by the paddles, while still securely attaching the valve repair device 602 to the mitral valve tissue. In the embodiment of the valve repair device 602 shown in FIG. 14B, the paddles 606a, 606b can be made of a wide variety of different flexible materials or rigid materials that are cut or otherwise processed to provide flexibility.

FIGS. 15A-15B illustrate another exemplary embodiment of a valve repair device 602. Referring to FIG. 15A, the valve repair device 602 is in the open position and about to engage valve tissue 820 (e.g., the leaflets of a mitral valve). Referring to FIG. 15B, the valve repair device 602 is in the closed position and secured to the valve tissue 820. The valve repair device 602 can take any suitable form, such as, for example, any form described in the present application. The valve repair device 602 can be moved between the open and closed position, and be attached to the valve tissue 820, by a valve repair system, such as, for example, any valve repair system described in the present application. In the illustrated embodiment, the valve repair device 602 includes paddles 606 and gripping members 608. The gripping members 608 include a barbed portion 609 for attaching the gripping members to valve tissue 820. Referring to FIG. 15A, when the valve repair device 602 is in the open position, the paddles 606 maintain an original form. Referring to FIG. 15B, upon engagement with the valve tissue 820, the paddles 606 flex along their length L. That is, a portion of the paddles 606 flex in an inward direction X, and another portion of the paddles extend in an outward direction Z. This flexing of the paddles 606 allows the paddles to conform to the shape of the valve tissue, which places less stress on the valve tissue.

Figure 16B:
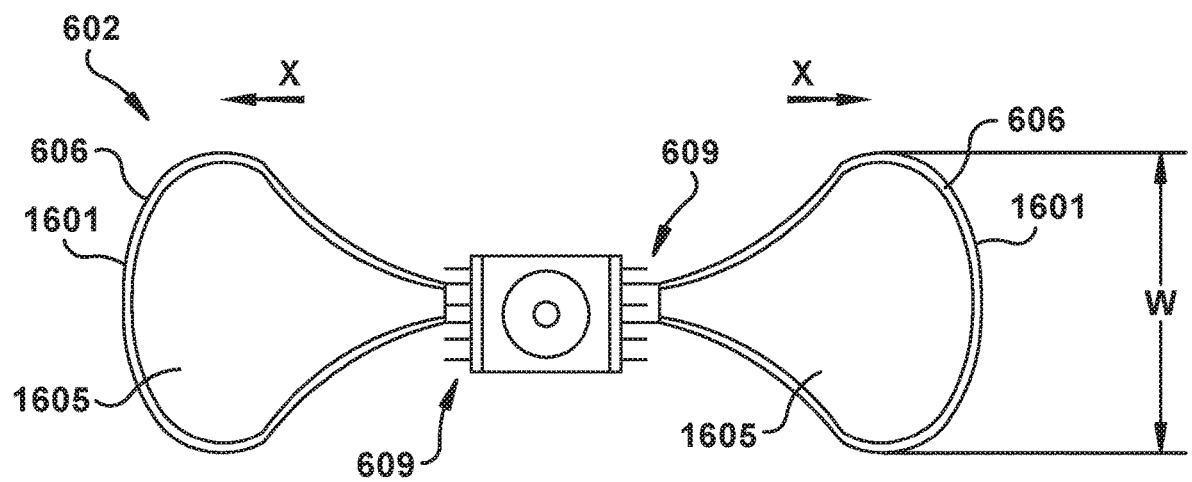
FIGS. 16A-16F illustrate another exemplary embodiment of a valve repair device, in which the valve repair device includes compressible paddles that comprise an exemplary embodiment of a wire loop.
Figure 16A:
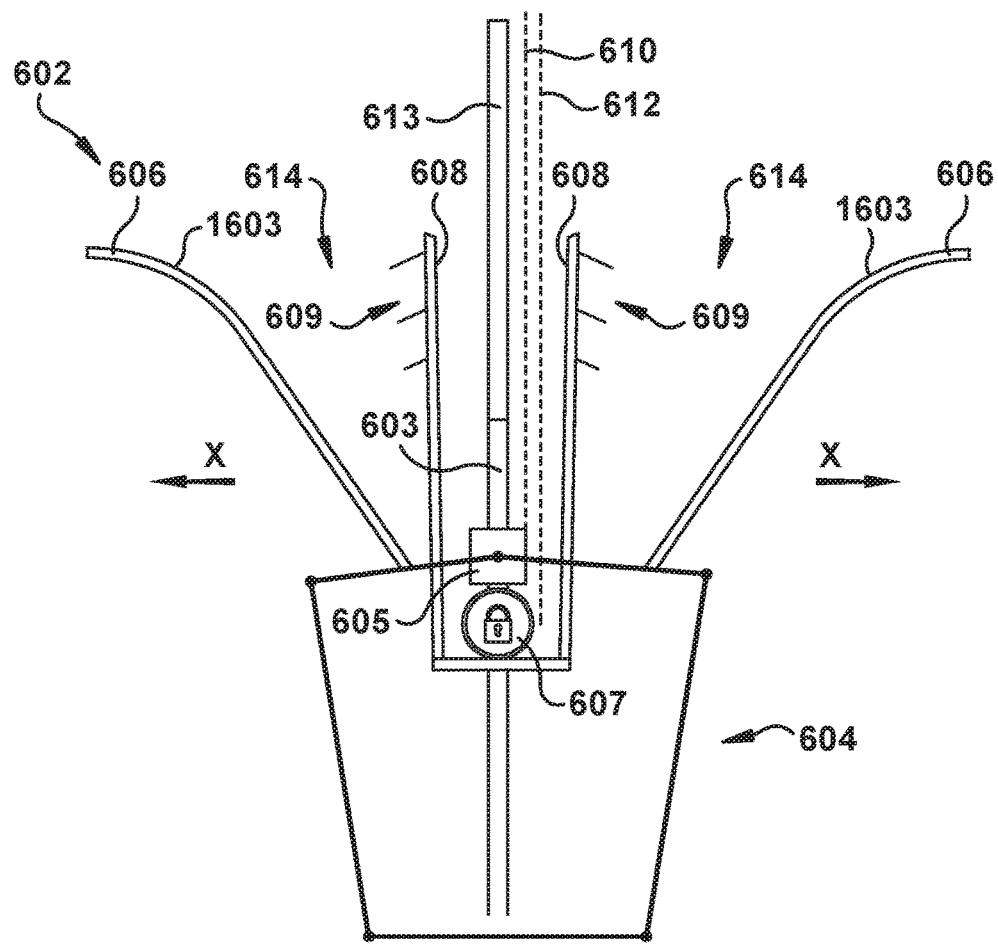
Figure 16D:
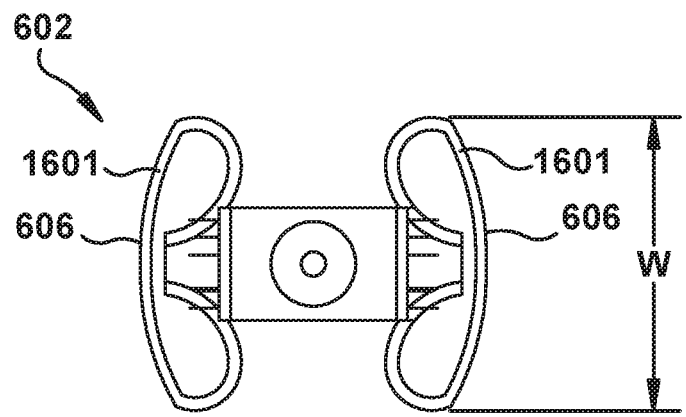
Figure 16C:
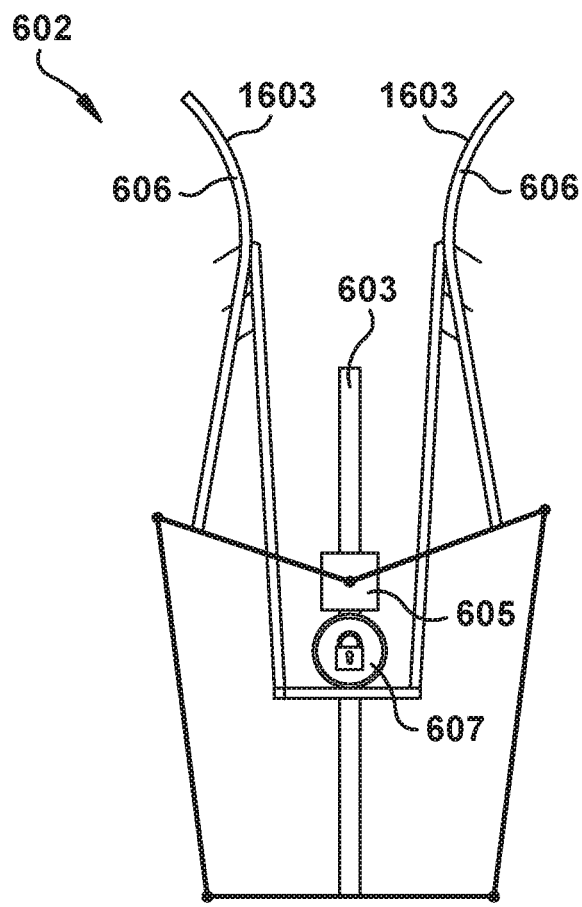
Figure 16F:
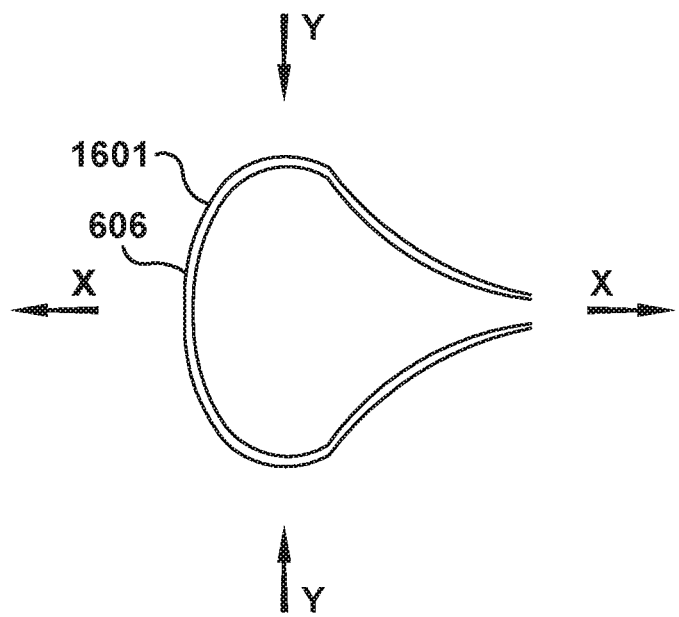
Figure 16E:
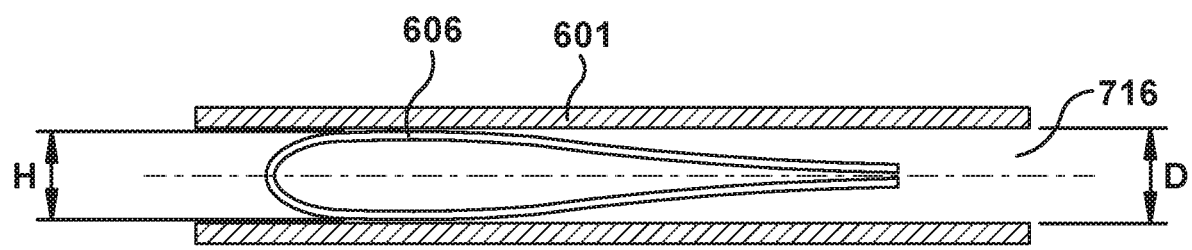

Referring to FIGS. 16A-16F, another exemplary embodiment of a valve repair device 602 includes paddles 606 having a wire loop 1601. The wire loop 1601 can be made of, for example, any suitable metal material, laser cut loops from a sheet of nitinol, a tube of nitinol, or any other suitable material. In some embodiments, the wire loop 1601 can have varying dimensions throughout the length of the wire loop 1601 to optimize the paddle pinch force and the paddle crimp force on a valve tissue when paddle engages the valve tissue. For example, certain sections of the wire loop 1601 can be thinner than other sections of the wire loop 1601. In certain embodiments, the wire loop 1601 of the paddles 606 is compressible, which allows the paddles 606 to be disposed in a delivery device 601 (e.g., a catheter) that has a small diameter (as shown in FIG. 16E) for delivery of the valve repair device 602 to a native valve of a patient, and also allows the paddles 606 to expand (as shown in FIGS. 16A-16D) upon exiting the delivery device 601 such that the paddles 606 have a larger surface area for engaging the native valve of the patient. The valve repair device 602 can take any suitable form, such as, for example, any form described in the present application. The valve repair device 602 can be moved between the open and closed position, and be attached to a native valve, by a valve repair system, such as, for example, any valve repair system described in the present application.

FIGS. 16A-16B illustrate the valve repair device 602 in the open position, and FIGS. 16C-16D illustrate the valve repair device in the closed position. Referring to FIGS. 16A-16B, when the valve repair device 602 is in the expanded and open position, the paddles 606 extend outward to create wide opening 614 between the paddles 606 and gripping members 608 of the valve repair device 602. Referring to FIGS. 16C-16D, when the valve repair device 602 is in the expanded and closed position, the paddles 606 engage the gripping members 608 such that valve tissue can be secured between the paddles and the gripping members. The paddles 606 include a curved surface 1603, which is configured to place less stress on valve tissue when the valve repair device 602 is attached to the valve tissue. When the paddles 606 are in the expanded condition, the paddles have a width W. The width W can be, for example, between about 4 mm and about 21 mm, such as, between about 5 mm and about 20 mm, such as between about 7.5 mm and about 17.5 mm, such as between about 10 mm and about 15 mm. In certain embodiments, the width W can be, for example, 5 mm or more, such as about 7.5 mm or more, such as about 10 mm or more, such as about 15 mm or more, such as about 20 mm or more. In other embodiments, the width W can be less than 5 mm. In certain embodiments, the paddles 606 include a material 1605 disposed over the wire loop 1601 for creating a contact area for the paddles to engage valve tissue. The material 1605 can be any suitable material, such as, for example, a woven material, an electrospun material, or any other material that is capable of promoting tissue ingrowth and protecting liners of the delivery device 601 (FIG. 6) during tracking. In certain embodiments, the material 1605 can be a blood-impermeable cloth, such as a PET cloth or biocompatible covering material such as a fabric that is treated with a coating that is impermeable to blood, polyester, or a processed biological material, such as pericardium.

Referring to FIG. 16E, the paddles 606 are in a compressed condition when the paddles are disposed in a delivery device 601. When the paddles 606 are in the compressed condition, the paddles have a width H. The width H can be, for example between about 4 mm and about 7 mm, such as, between about 5 mm and about 6 mm. In alternative embodiments, the width H can be less than 4 mm or more than 7 mm. In certain embodiments, the width H of the compressed paddles 606 is substantially equal to a width D of the delivery opening 716 of the delivery device 601. The ratio between the width W of the paddles in the expanded condition and the width H of the paddles in the compressed condition can be, for example, about 4 to 1 or less, such as about 3 to 1 or less, such as about 2 to 1 or less, such as about 1.5 to 1, such as about 1.25 to 1, such as about 1 to 1. In alternative embodiments, the ratio between the width W and the width H can be more than 4 to 1. Referring to FIG. 16F, a paddle 606 is moved from the expanded condition to the compressed condition by compressing the paddle in the direction Y and extending a length of the paddle in the direction X.

Figure 16G:
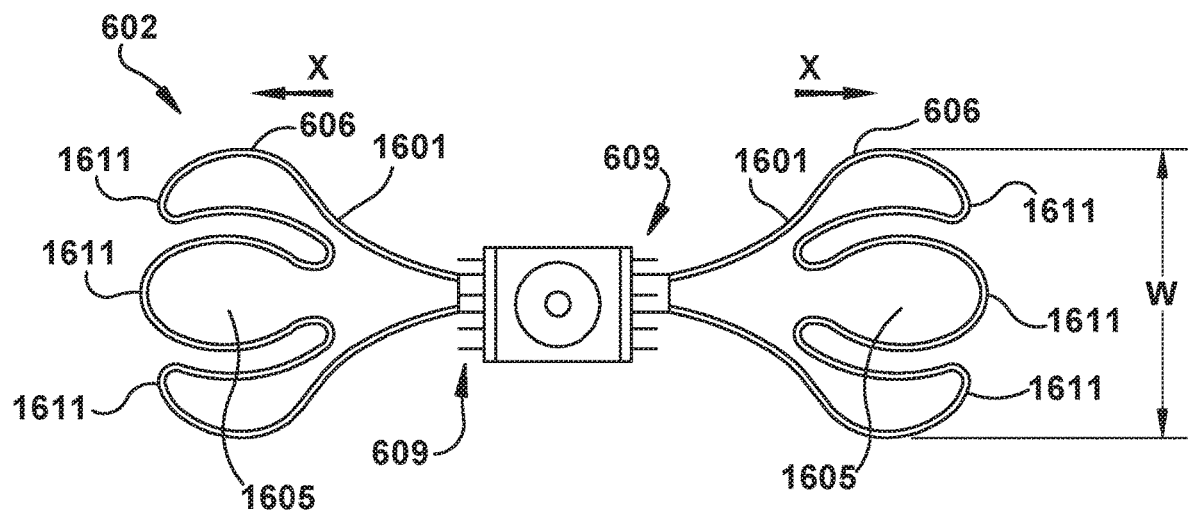
FIGS. 16G-16H illustrate another exemplary embodiment of a valve repair device, in which the valve repair device includes compressible paddles that comprise another exemplary embodiment of a wire loop.
Figure 16H:
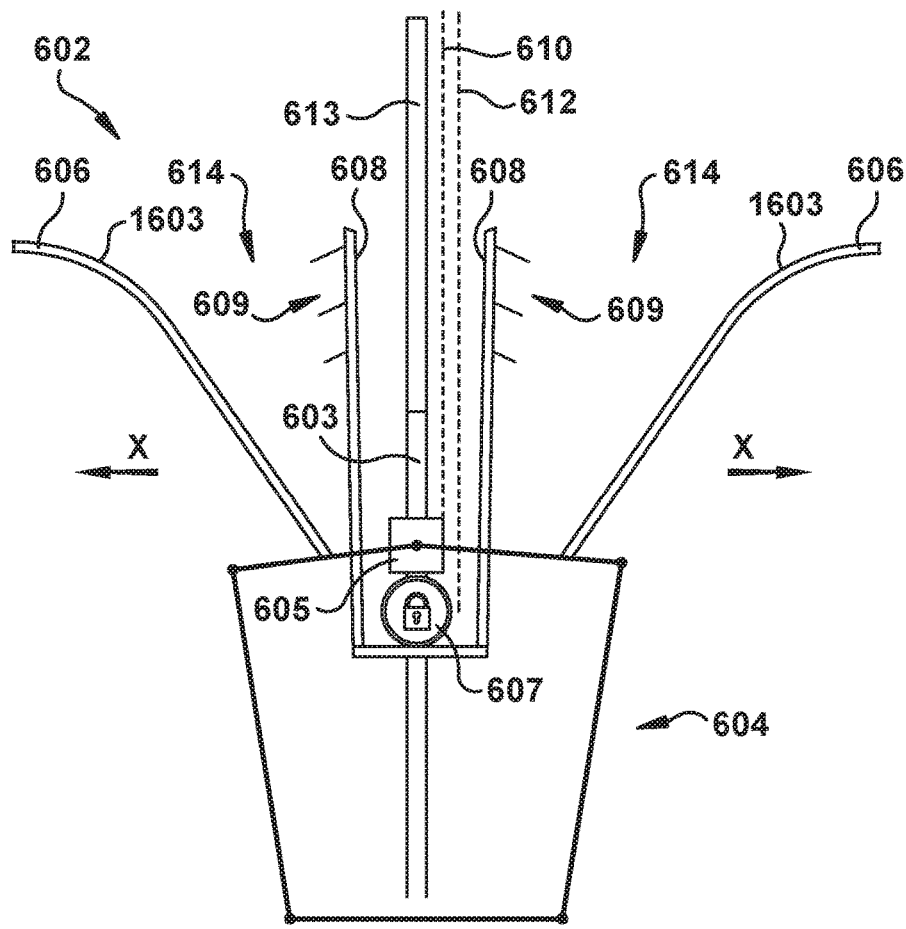
Figure 16I:
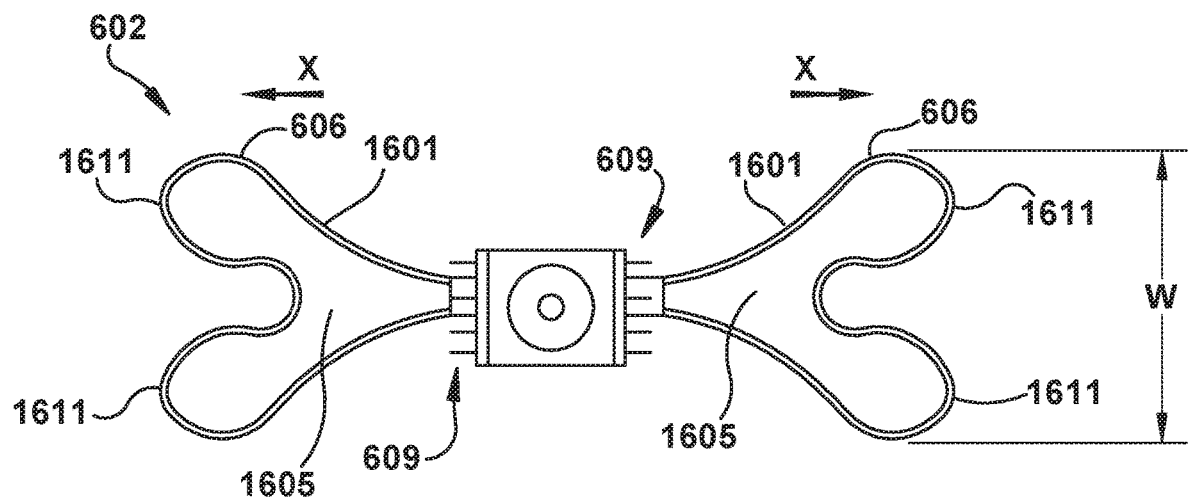
FIGS. 16I-16J illustrate another exemplary embodiment of a valve repair device, in which the valve repair device includes compressible paddles that comprise another exemplary embodiment of a wire loop.
Figure 16J:
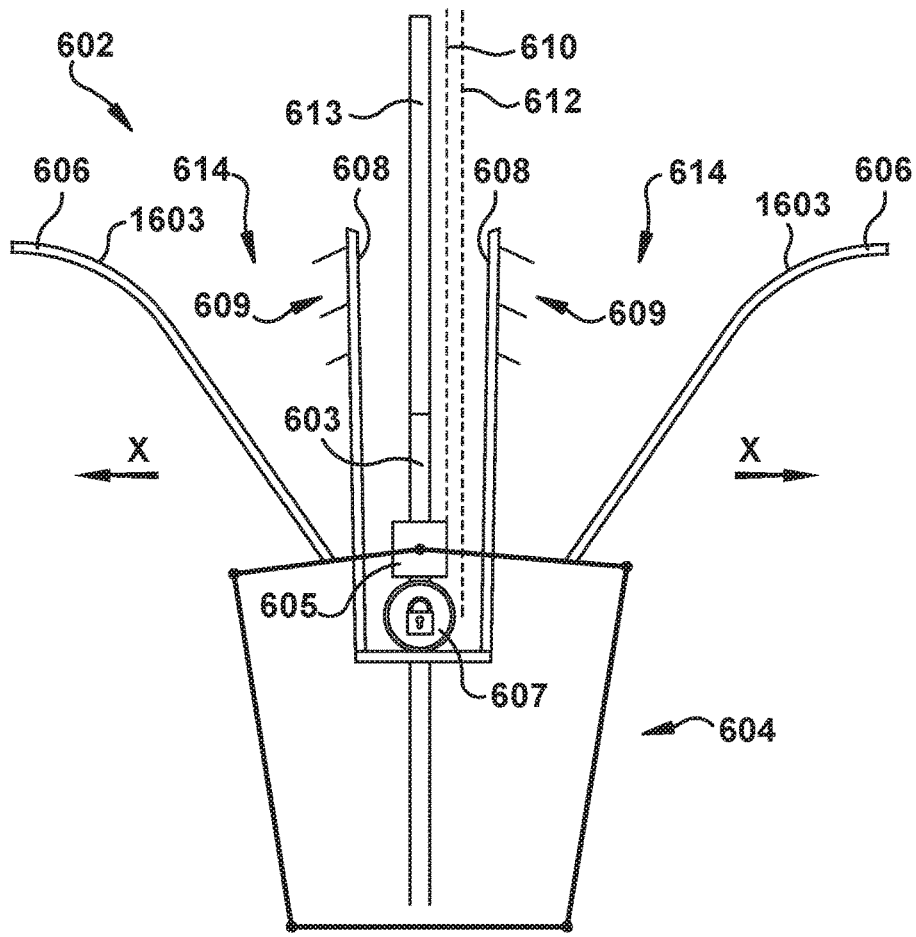

FIGS. 16G-16H illustrate another exemplary embodiment of a valve repair device 602 in the open position, in which the valve repair device includes paddles 606 having a wire loop 1601. In the illustrated embodiment, the paddles 606 are shown having a wire loop 1601 that includes three lobes 1611. Referring to FIGS. 16I-16J, another exemplary embodiment of a valve repair device 602 includes paddles 606 having a wire loop 1601 with two lobes 1611. While the embodiments shown in FIGS. 16G-16H and 16I-16J show the wire loop 1601 of the paddles 606 having three lobes and two lobes, respectively, it should be understood that the valve repair device 602 can include paddles 606 with a wire loop 1601 having any suitable number of lobes 1611, such as, for example, two or more lobes, three or more lobes, four or more lobes, five or more lobes, etc. A paddle 606 having a wire loop 1601 having lobes is advantageous because a paddle having lobes can more easily allow chordae tendinae to assume their natural positions than a single wire loop having no lobes. That is, the chordae tendinae can move into spaces between the multiple of loops.

The embodiments of the valve repair devices 602 shown in FIGS. 16G-16H and 16I-16J can include any of the features described above with reference to FIGS. 16A-16F. For example, the embodiments of the valve repair devices 602 shown in FIGS. 16G-16H and 16I-16J can include a width W, in which the width W can be, for example, between about 4 mm and about 21 mm, such as, between about 5 mm and about 20 mm, such as between about 7.5 mm and about 17.5 mm, such as between about 10 mm and about 15 mm. In certain embodiments, the width W can be, for example, 5 mm or more, such as about 7.5 mm or more, such as about 10 mm or more, such as about 15 mm or more, such as about 20 mm or more. In other embodiments, the width W can be less than 5 mm. The embodiments for the paddles 606 shown in FIGS. 16G-16H and 16I-16J can also include a material disposed over the wire loop 1601 for creating a contact area for the paddles to engage valve tissue. The material can be any suitable material, such as, for example, a woven material, an electrospun material, or any other suitable material that is capable of promoting tissue ingrowth and protecting liners of the delivery device 601 (FIG. 6) during tracking. In certain embodiments, the material 1605 can be a blood-impermeable cloth, such as a PET cloth or biocompatible covering material such as a fabric that is treated with a coating that is impermeable to blood, polyester, or a processed biological material, such as pericardium. The embodiments for the paddles 606 shown in FIGS. 16G-16H and 16I-16J can also be compressed when disposed in a delivery device 601 (e.g., just as shown in FIG. 16E with respect to the embodiment of the paddles 606 shown in FIGS. 16A-16B). The ratio between the width W of the paddles 606 in the expanded condition and the width of the paddles in the compressed condition can be, for example, about 4 to 1 or less, such as about 3 to 1 or less, such as about 2 to 1 or less, such as about 1.5 to 1, such as about 1.25 to 1, such as about 1 to 1. In alternative embodiments, the ratio between the width W and the width H can be more than 4 to 1.

Figure 17B:
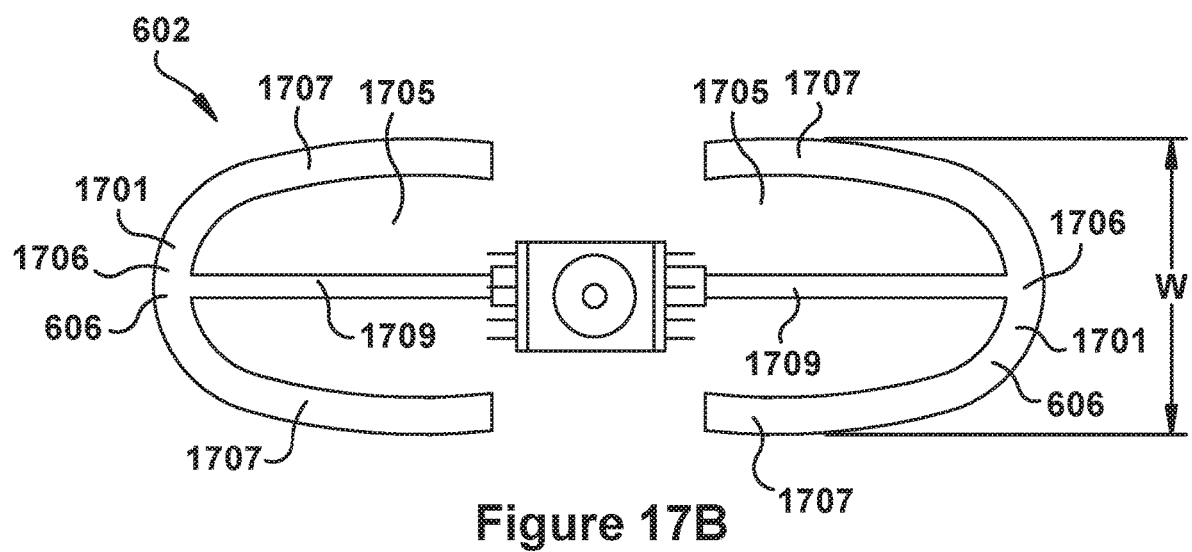
FIGS. 17A-17F illustrate another exemplary embodiment of a valve repair device, in which the valve repair device includes compressible paddles having a horseshoe shape.
Figure 17A:
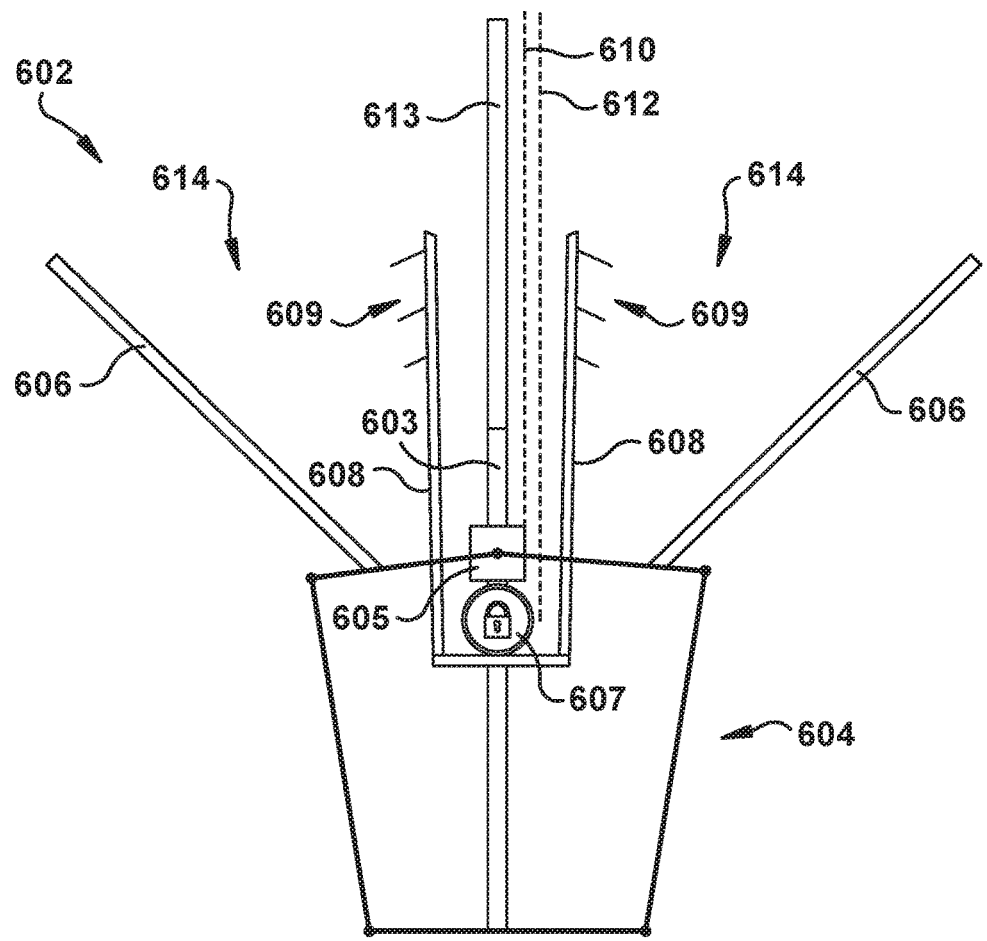
Figure 17C:
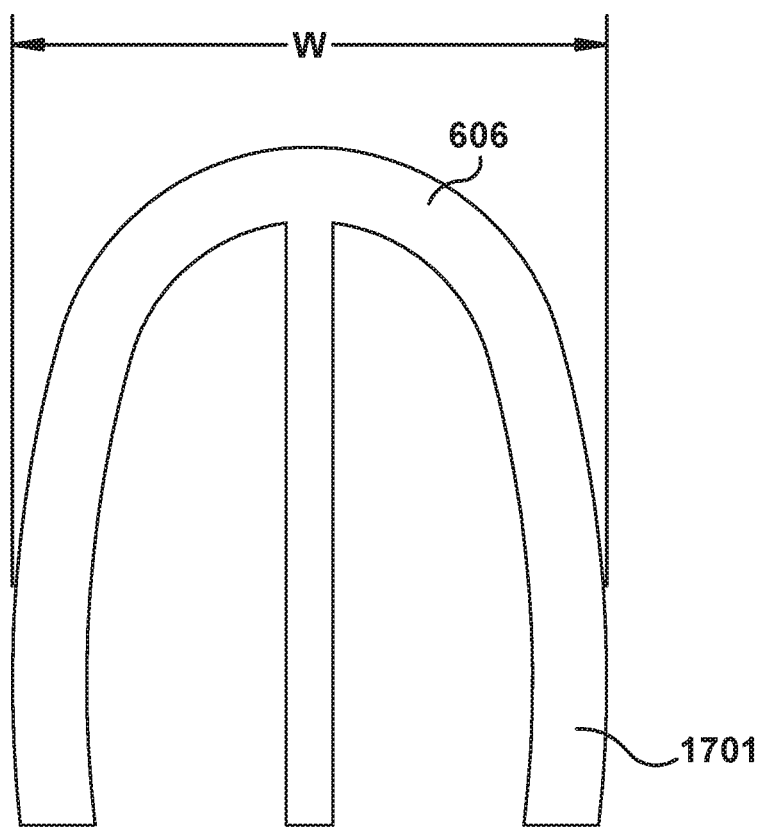
Figure 17D:
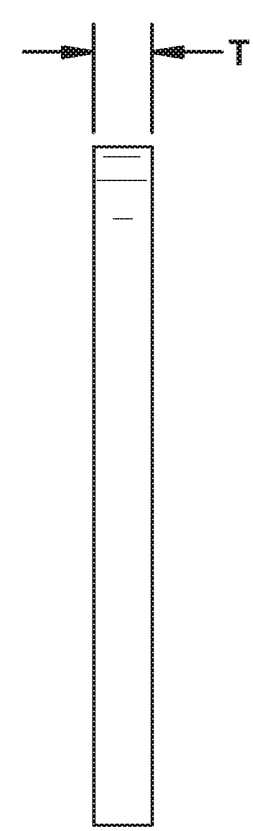
Figure 17F:
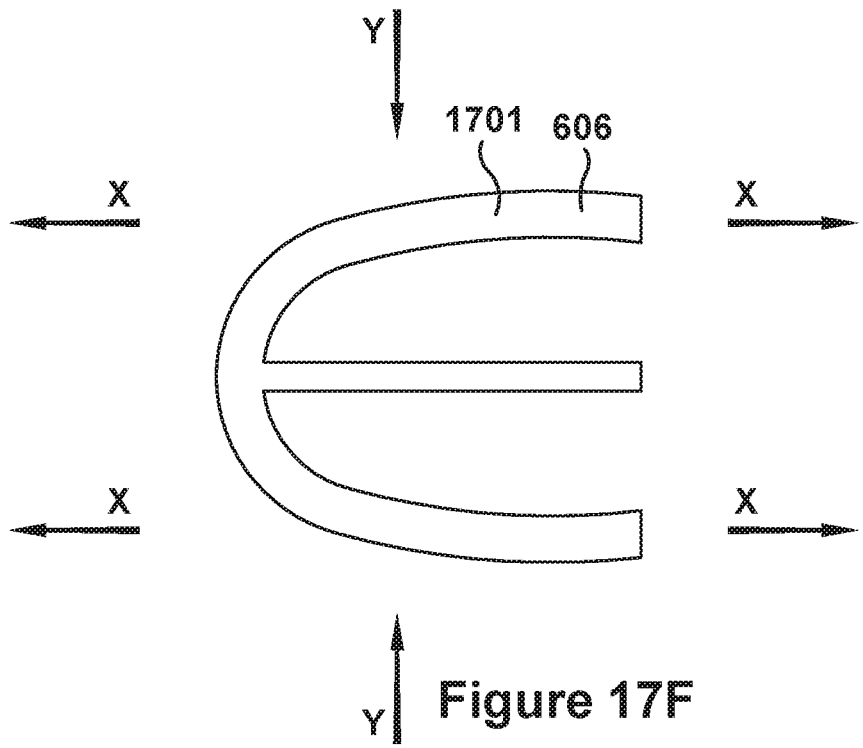

Referring to FIGS. 17A-17F, another exemplary embodiment of a valve repair device 602 includes paddles 606 having a horseshoe shape 1701. In certain embodiments, the horseshoe shape 1701 of the paddles 606 is compressible, which allows the paddles 606 to be disposed in a delivery device 601 (e.g., a catheter) that has a small diameter (as shown in FIG. 17F) for delivery of the valve repair device 602 to a native valve of a patient, and also allows the paddles 606 to expand (as shown in FIGS. 17A-17D) upon exiting the delivery device 601 such that the paddles 606 have a larger surface area for engaging the native valve of the patient. The valve repair device 602 can take any suitable form, such as, for example, any form described in the present application. The valve repair device 602 can be moved between the open and closed position, and be attached to a native valve, by a valve repair system, such as, for example, any valve repair system described in the present application.

FIGS. 17A-17C illustrate the valve repair device 602 in the open position. Referring to FIGS. 17A-17B, when the valve repair device 602 is in the expanded and open position, the paddles 606 extend outward to create wide opening 614 between the paddles 606 and gripping members 608 of the valve repair device 602. In the illustrated embodiment, the horseshoe shape 1701 of the paddles 606 includes side members 1707 that extend from a base 1706 of the paddle 606, and a center member 1709 that extends from the base 1706 and connects to a base assembly 604 of the valve repair device 602, in which the side members 1707 form a horseshoe shape as shown in FIG. 17C, for example. In certain embodiments, the paddles 606 include a material 1705 disposed over the horseshoe shape 1701 for creating a contact area for the paddles to engage valve tissue. The material 1705 can be any suitable material, such as, for example, a woven material, an electrospun material, or any other material that is capable of promoting tissue ingrowth and protecting liners of the delivery device 601 (FIG. 6) during tracking. In certain embodiments, the material 1605 can be a blood-impermeable cloth, such as a PET cloth or biocompatible covering material such as a fabric that is treated with a coating that is impermeable to blood, polyester, or a processed biological material, such as pericardium.

In various embodiments, the paddles 606 are configured to flex to place less stress on valve tissue when the valve repair device 602 is attached to the valve tissue. When the paddles 606 are in the expanded condition, the paddles have a width W. The width W can be, for example, between about 4 mm and about 21 mm, such as, between about 5 mm and about 20 mm, such as between about 7.5 mm and about 17.5 mm, such as between about 10 mm and about 15 mm. In certain embodiments, the width W can be, for example, 5 mm or more, such as about 7.5 mm or more, such as about 10 mm or more, such as about 15 mm or more, such as about 20 mm or more. In other embodiments, the width W can be less than 5 mm. Referring to FIG. 17D, in certain embodiments, the thickness T of the paddle is, for example, between about 0.3 mm and about 0.46 mm, such as between about 0.32 mm and about 0.44 mm, such as between about 0.34 mm and about 0.42 mm, such as between about 0.36 mm and about 0.40 mm, such as about 0.38 mm. In alternative embodiments, the thickness T of the paddle can be less than 0.3 mm or more than 0.46 mm.

Figure 17E:
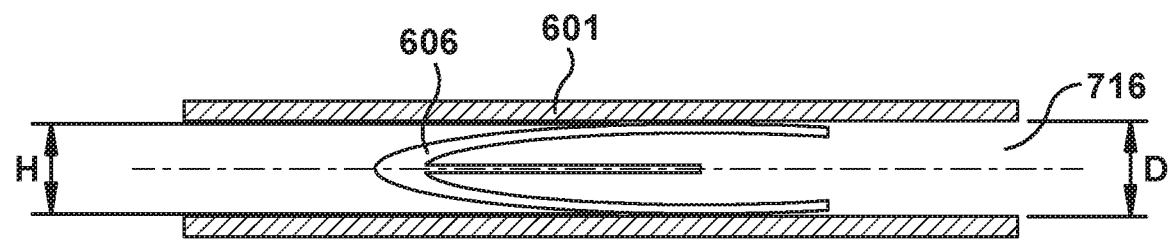

Referring to FIG. 17E, the paddles 606 are in a compressed condition when the paddles are disposed in a delivery device 601. When the paddles 606 are in the compressed condition, the paddles have a width H. The width H can be, for example between about 4 mm and about 7 mm, such as, between about 5 mm and about 6 mm. In alternative embodiments, the width H can be less than 4 mm or more than 7 mm. In certain embodiments, the width H of the compressed paddles 606 is equal to a width D of the delivery opening 716 of the delivery device 601. The ratio between the width W of the paddles in the expanded condition and the width H of the paddles in the compressed condition can be, for example, about 4 to 1 or less, such as about 3 to 1 or less, such as about 2 to 1 or less, such as about 1.5 to 1, such as about 1.25 to 1, such as about 1 to 1. In alternative embodiments, the ratio between the width W and the width H can be more than 4 to 1. Referring to FIG. 17F, a paddle 606 is moved from the expanded condition to the compressed condition by compressing the paddle in the direction Y and extending a length of the paddle in the direction X. In the illustrated embodiment, the length of the side members 1707 of the paddle 606 are extended when the paddle is in the compressed condition, but the length of the center member 1709 maintains the same length.

Figure 18B:
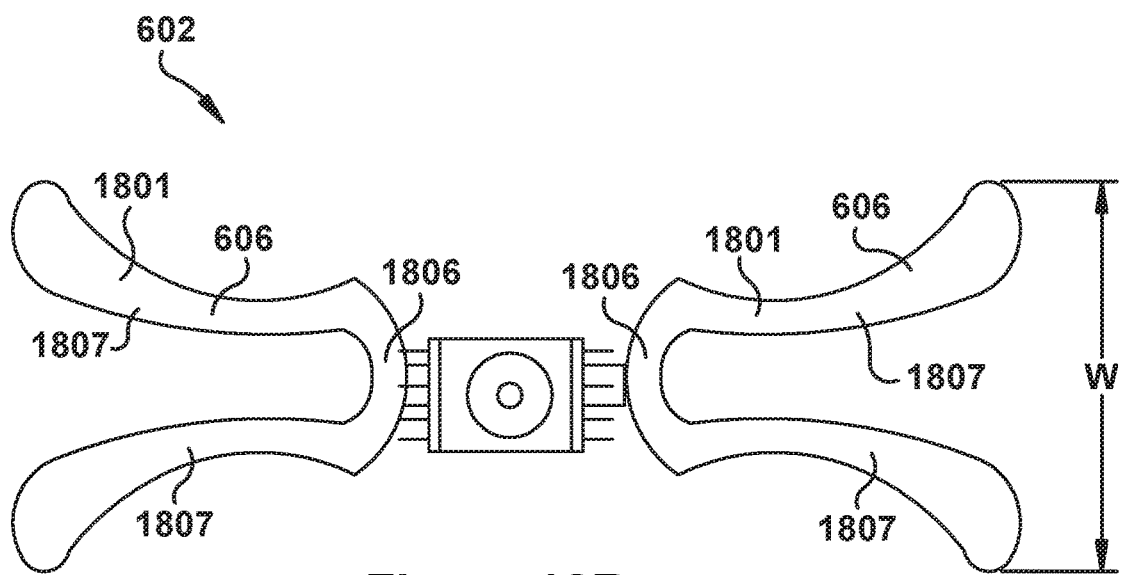
FIGS. 18A-18D illustrate another exemplary embodiment of a valve repair device, in which the valve repair device includes compressible paddles having a horseshoe shape.
Figure 18A:
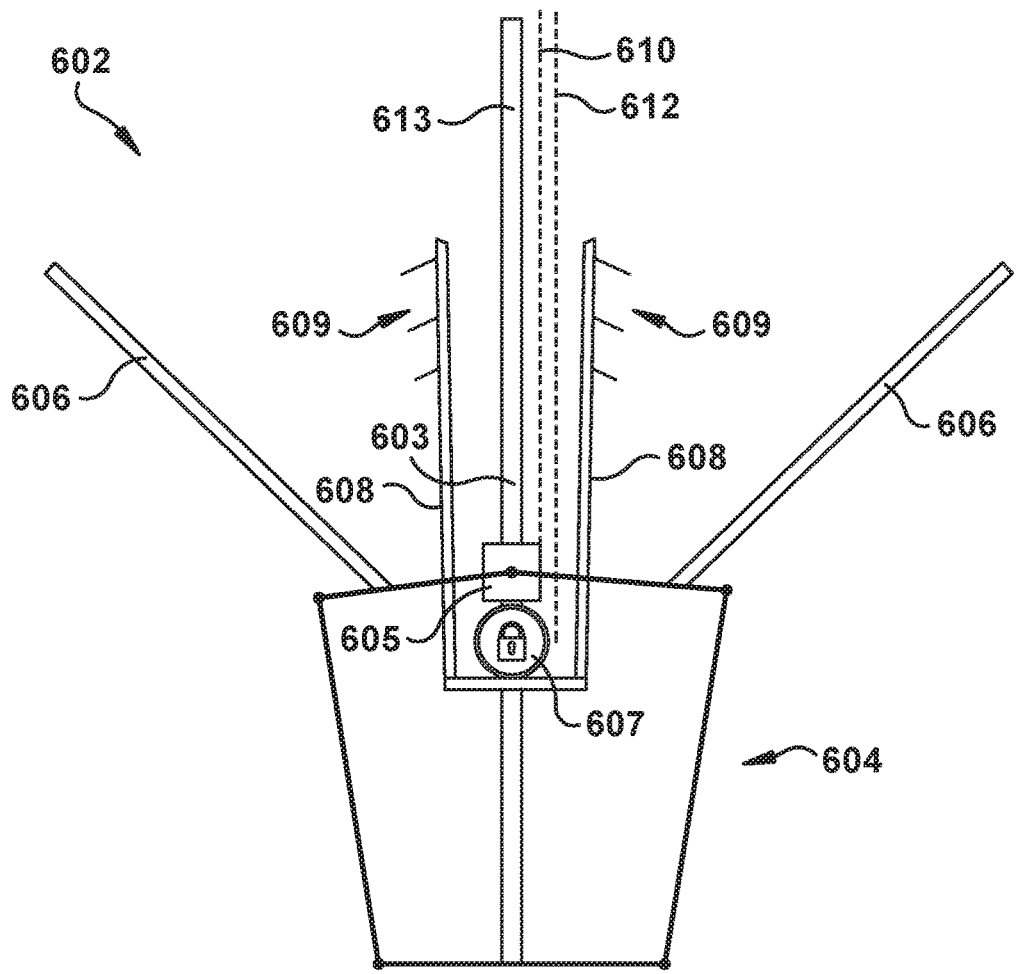
Figure 18D:
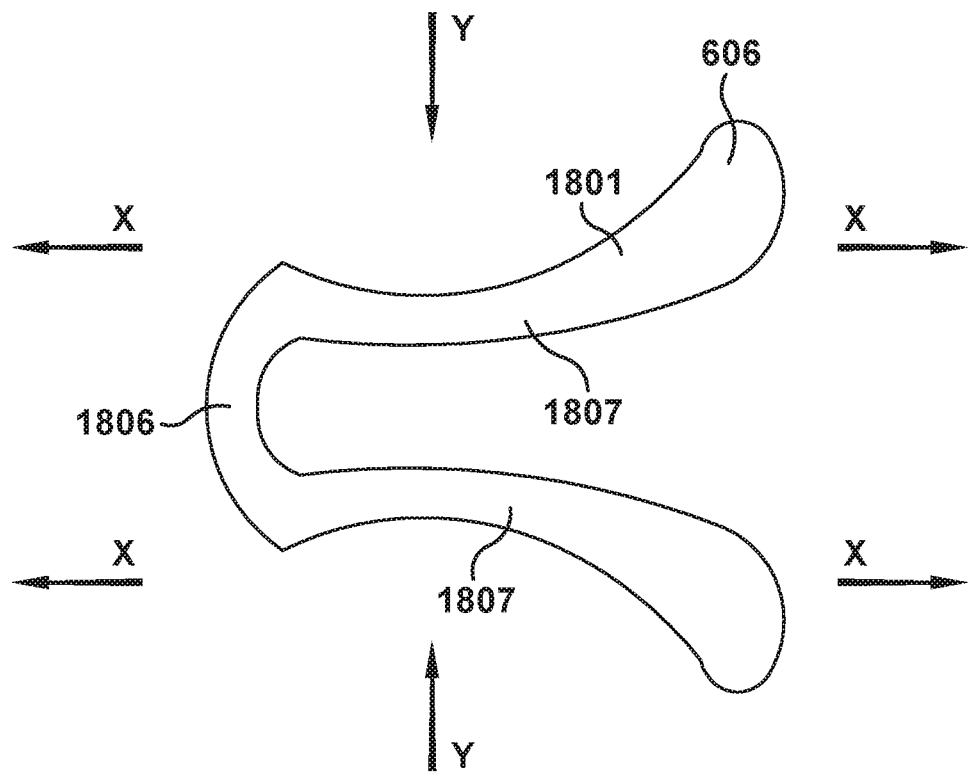
Figure 18C:
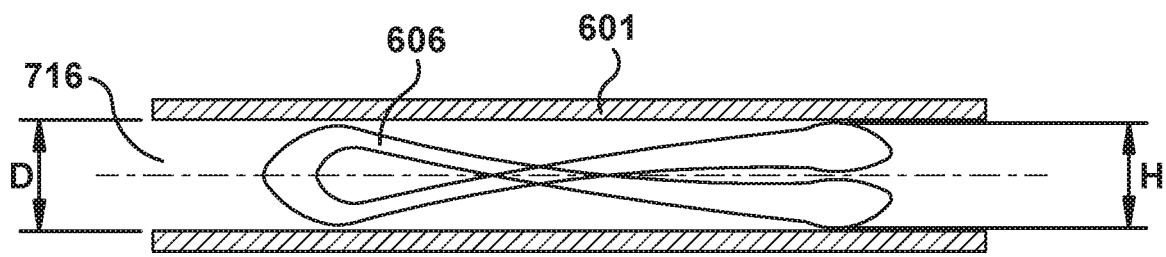
Figure 18F:
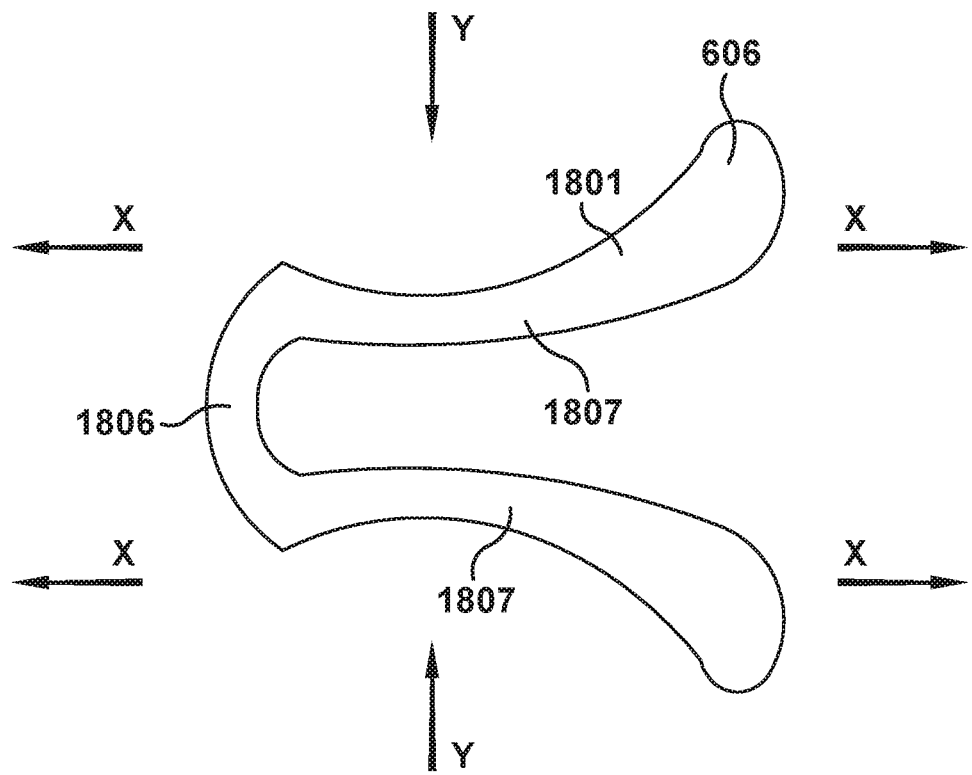
FIGS. 18E and 18F illustrate a compressible paddle that is similar to the compressible paddle shown in FIGS. 18C and 18D, except legs of the paddle do not cross when the paddle is loaded into a catheter.
Figure 18E:
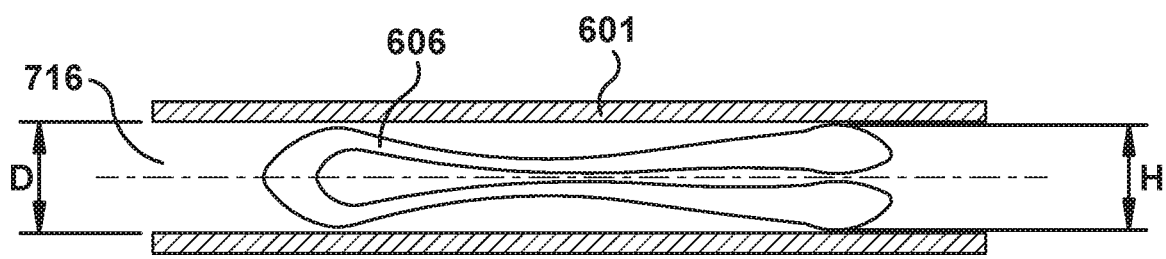

Referring to FIGS. 18A-18D, another exemplary embodiment of a valve repair device 602 includes paddles 606 having another horseshoe shape 1801. In certain embodiments, the horseshoe shape 1801 of the paddles 606 is compressible, which allows the paddles 606 to be disposed in a delivery device 601 (e.g., a catheter) that has a small diameter (as shown in FIG. 18C) for delivery of the valve repair device 602 to a native valve of a patient, and also allows the paddles 606 to expand (as shown in FIGS. 18A-18B) upon exiting the delivery device 601 such that the paddles 606 have a larger surface area for engaging the native valve of the patient. The valve repair device 602 can take any suitable form, such as, for example, any form described in the present application. The valve repair device 602 can be moved between the open and closed position, and be attached to a native valve, by a valve repair system, such as, for example, any valve repair system described in the present application.

FIGS. 18A-18B illustrate the valve repair device 602 in the open position. When the valve repair device 602 is in the open position, the paddles 606 extend outward to create wide opening 614 between the paddles 606 and gripping members 608 of the valve repair device 602. In the illustrated embodiment, the horseshoe shape 1801 of the paddles 606 includes side members 1807 that extend from a base 1806 of the paddle 606, and the base 1806 is attached to the base assembly 604 of the valve repair device 602. In certain embodiments, the paddles 606 include a material 1805 disposed over the horseshoe shape 1801 for creating a contact area for the paddles to engage valve tissue. The material 1805 can be any suitable material, such as, for example, a woven material, an electrospun material, or any other material that is capable of promoting tissue ingrowth and protecting liners of the delivery device 601 (FIG. 6) during tracking. In certain embodiments, the material 1605 can be a blood-impermeable cloth, such as a PET cloth or biocompatible covering material such as a fabric that is treated with a coating that is impermeable to blood, polyester, or a processed biological material, such as pericardium.

In various embodiments, the paddles 606 are configured to flex to place less stress on valve tissue when the valve repair device 602 is attached to the valve tissue. When the paddles 606 are in the expanded condition, the paddles have a width W. The width W can be, for example, between about 4 mm and about 21 mm, such as, between about 5 mm and about 20 mm, such as between about 7.5 mm and about 17.5 mm, such as between about 10 mm and about 15 mm. In certain embodiments, the width W can be, for example, 5 mm or more, such as about 7.5 mm or more, such as about 10 mm or more, such as about 15 mm or more, such as about 20 mm or more. In other embodiments, the width W can be less than 5 mm.

Referring to FIG. 18C, the paddles 606 are in a compressed condition when the paddles are disposed in a delivery device 601. When the paddles 606 are in the compressed condition, the paddles have a width H. The width H can be, for example between about 4 mm and about 7 mm such as, between about 5 mm and about 6 mm. In alternative embodiments, the width H can be less than 4 mm or more than 7 mm. In certain embodiments, the width H of the compressed paddles 606 is equal to a width D of the delivery opening 716 of the delivery device 601. The ratio between the width W of the paddles in the expanded condition and the width H of the paddles in the compressed condition can be, for example, about 4 to 1 or less, such as about 3 to 1 or less, such as about 2 to 1 or less, such as about 1.5 to 1, such as about 1.25 to 1, such as about 1 to 1. In alternative embodiments, the ratio between the width W and the width H can be more than 4 to 1. Referring to FIG. 18D, a paddle 606 is moved from the expanded condition to the compressed condition by compressing the paddle in the direction Y and extending a length of the paddle in the direction X. In the illustrated embodiment, the length of the side members 1807 of the paddle 606 are extended when the paddle is in the compressed condition. Referring to FIG. 18C, in certain embodiments, when the paddles 606 are disposed in the delivery device 601 and in the compressed condition, the side members 1807 of the paddles cross each other.

Figure 19B:
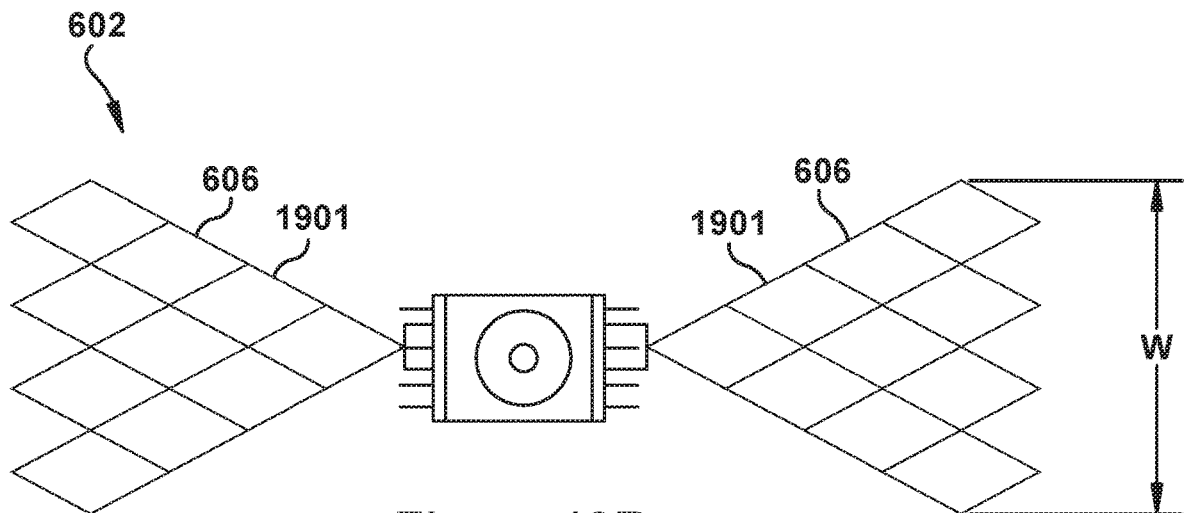
FIGS. 19A-19D illustrate another exemplary embodiment of a valve repair device, in which the valve repair device includes compressible mesh paddles.
Figure 19A:
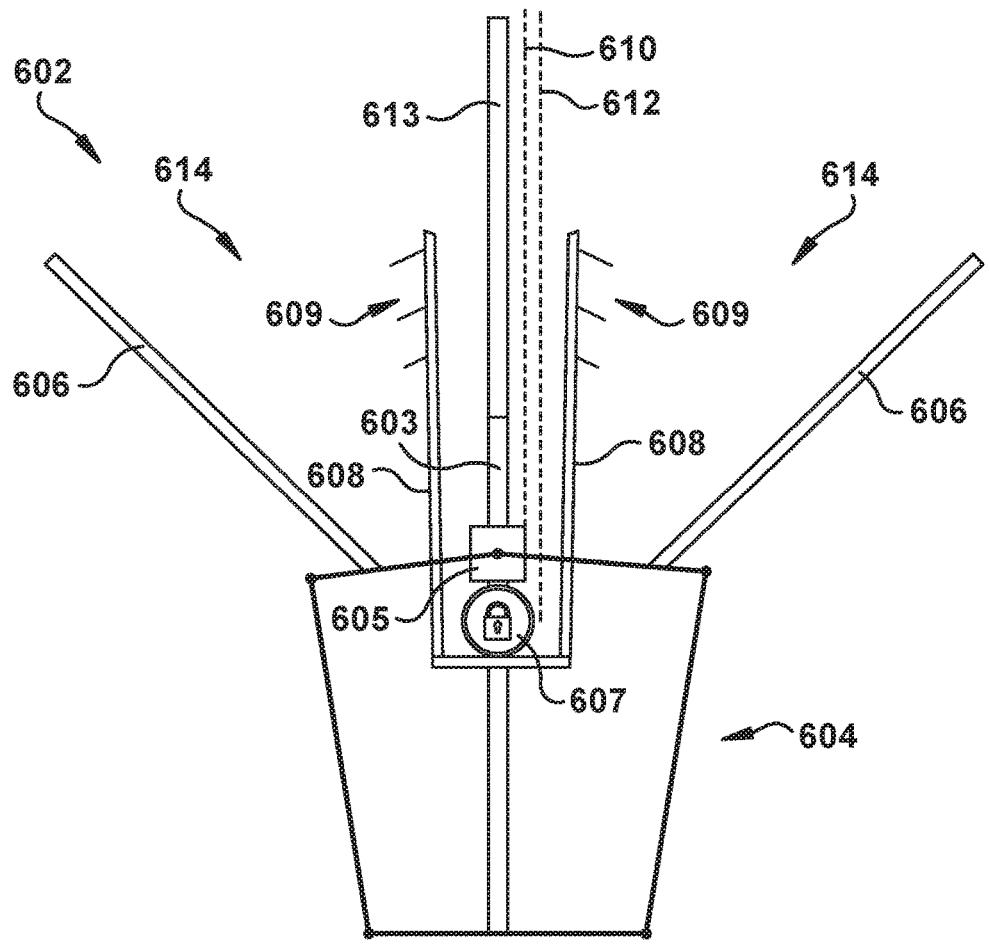
Figure 19D:
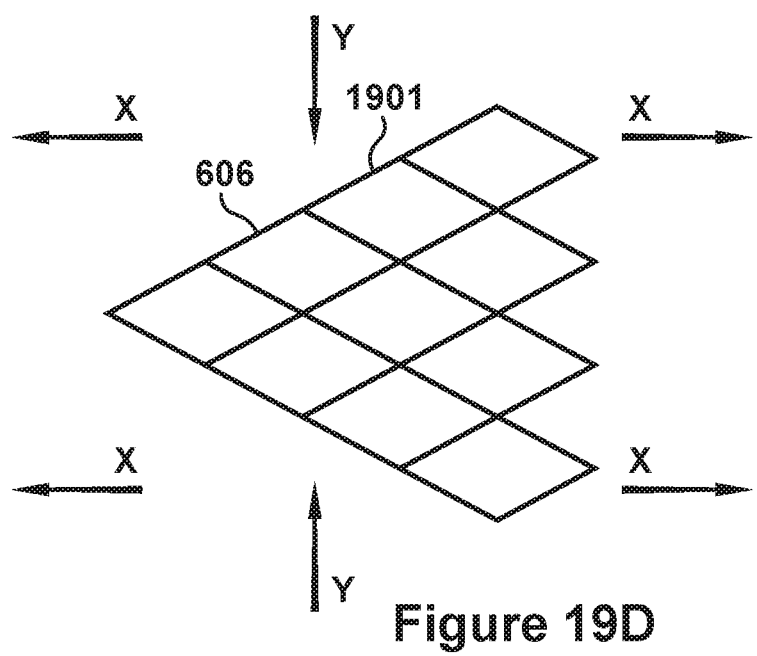
Figure 19C:
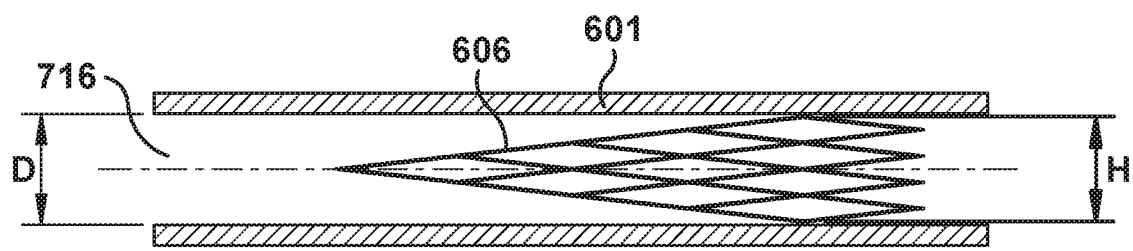

Referring to FIGS. 19A-19D, another exemplary embodiment of a valve repair device 602 includes paddles 606 having a mesh structure 1901. In certain embodiments, the mesh structure 1901 of the paddles 606 is compressible, which allows the paddles 606 to be disposed in a delivery device 601 (e.g., a catheter) that has a small diameter (as shown in FIG. 19C) for delivery of the valve repair device 602 to a native valve of a patient, and also allows the paddles 606 to expand (as shown in FIGS. 19A-19B) upon exiting the delivery device 601 such that the paddles 606 have a larger surface area for engaging the native valve of the patient. The valve repair device 602 can take any suitable form, such as, for example, any form described in the present application. The valve repair device 602 can be moved between the open and closed position, and be attached to a native valve, by a valve repair system, such as, for example, any valve repair system described in the present application.

FIGS. 19A-19B illustrate the valve repair device 602 in the open position. When the valve repair device 602 is in the expanded and open position, the paddles 606 extend outward to create wide opening 614 between the paddles 606 and gripping members 608 of the valve repair device 602. In certain embodiments, the paddles 606 include a material disposed over the mesh structure 1901, such as, for example, a woven material, an electrospun material, or any other material that is capable of promoting tissue ingrowth and protecting liners of the delivery device 601 (FIG. 6) during tracking. In certain embodiments, the material 1605 can be a blood-impermeable cloth, such as a PET cloth or biocompatible covering material such as a fabric that is treated with a coating that is impermeable to blood, polyester, or a processed biological material, such as pericardium.

In various embodiments, the paddles 606 are configured to flex to place less stress on valve tissue when the valve repair device 602 is attached to the valve tissue. When the paddles 606 are in the expanded condition, the paddles have a width W. The width W can be, for example, between about 4 mm and about 21 mm, such as, between about 5 mm and about 20 mm, such as between about 7.5 mm and about 17.5 mm, such as between about 10 mm and about 15 mm. In certain embodiments, the width W can be, for example, 5 mm or more, such as about 7.5 mm or more, such as about 10 mm or more, such as about 15 mm or more, such as about 20 mm or more. In other embodiments, the width W can be less than 5 mm.

Referring to FIG. 19C, the paddles 606 are in a compressed condition when the paddles are disposed in a delivery device 601. When the paddles 606 are in the compressed condition, the paddles have a width H. The width H can be, for example between about 4 mm and about 7 mm, such as, between about 5 mm and about 6 mm. In alternative embodiments, the width H can be less than 4 mm or more than 7 mm. In certain embodiments, the width H of the compressed paddles 606 is equal to a width D of the delivery opening 716 of the delivery device 601. The ratio between the width W of the paddles in the expanded condition and the width H of the paddles in the compressed condition can be, for example, about 4 to 1 or less, such as about 3 to 1 or less, such as about 2 to 1 or less, such as about 1.5 to 1, such as about 1.25 to 1, such as about 1 to 1. In alternative embodiments, the ratio between the width W and the width H can be more than 4 to 1. Referring to FIG. 19D, a paddle 606 is moved from the expanded condition to the compressed condition by compressing the paddle in the direction Y and extending a length of the paddle in the direction X.

Figure 20B:
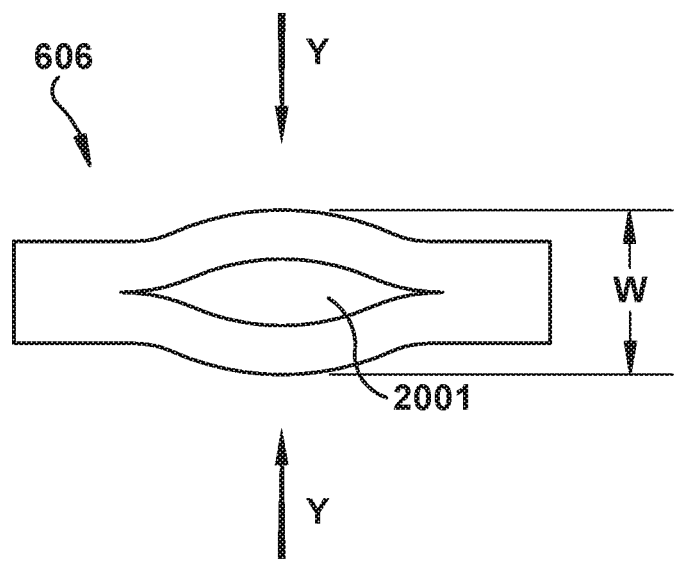
FIGS. 20A-20B illustrate an exemplary embodiment of a paddle for a valve repair device, in which the paddle is compressible.
Figure 20A:
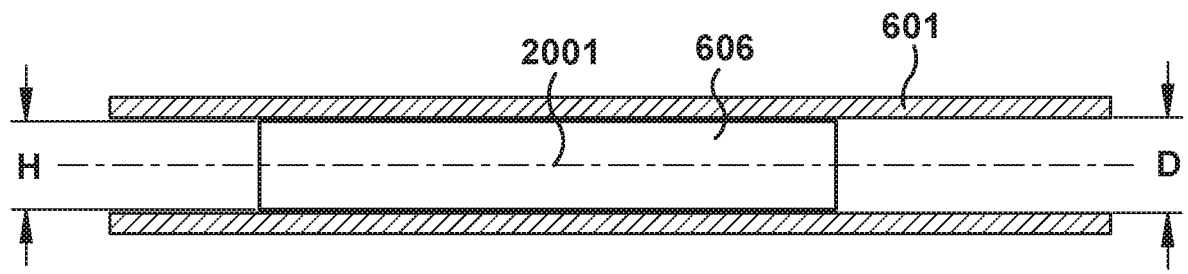

Referring to FIGS. 20A-20B, another exemplary embodiment of a valve repair device includes paddles 606 that are compressible, which allows the paddles 606 to be disposed in a delivery device 601 (e.g., a catheter) that has a small diameter (as shown in FIG. 20A) for delivery of the valve repair device to a native valve of a patient, and also allows the paddles 606 to expand (as shown in FIG. 20B) upon exiting the delivery device 601 such that the paddles 606 have a larger surface area for engaging the native valve of the patient. The paddles 606 can be included on a valve repair device 602 that takes any suitable form, such as, for example, any form described in the present application. The valve repair device (and paddles 606) can be attached to a native valve by a valve repair system, such as, for example, any valve repair system described in the present application.

FIG. 20A illustrates the paddle 606 in a compressed condition inside a delivery device 601. The paddle includes an opening 2001 that allows a portion of the paddle to expand upon being deployed from the delivery device 601. In the compressed condition, the paddle 606, for example, can have a width H between about 4 mm and about 7 mm, such as, between about 5 mm and about 6 mm. In alternative embodiments, the width H can be less than 4 mm or more than 7 mm. In certain embodiments, the width H of the compressed paddles 606 is equal to a width D of the delivery opening 716 of the delivery device 601. FIG. 20B illustrates the paddle 606 in an expanded condition. In the expanded condition, the paddle 606, for example, can have a width W between about 4 mm and about 21 mm, such as, between about 5 mm and about 20 mm, such as between about 7.5 mm and about 17.5 mm, such as between about 10 mm and about 15 mm. In certain embodiments, the width W can be, for example, 5 mm or more, such as about 7.5 mm or more, such as about 10 mm or more, such as about 15 mm or more, such as about 20 mm or more. In other embodiments, the width W can be less than 5 mm. The ratio between the width W of the paddles in the expanded condition and the width H of the paddles in the compressed condition can be, for example, about 4 to 1 or less, such as about 3 to 1 or less, such as about 2 to 1 or less, such as about 1.5 to 1, such as about 1.25 to 1, such as about 1 to 1. In alternative embodiments, the ratio between the width W and the width H can be more than 4 to 1. Referring to FIG. 20B, a paddle 606 is moved from the expanded condition to the compressed condition by compressing the paddle in the direction Y. In various embodiments, the paddles 606 are configured to flex to place less stress on valve tissue when the valve repair device 602 is attached to the valve tissue. In certain embodiments, the paddles 606 include a material disposed over the paddle 606, such as, for example, any material that is capable of promoting tissue ingrowth and protecting liners of the delivery device 601 (FIG. 6) during tracking. In certain embodiments, the material can be a blood-impermeable cloth, such as a PET cloth or biocompatible covering material such as a fabric that is treated with a coating that is impermeable to blood, polyester, or a processed biological material, such as pericardium.

FIGS. 21A-21B illustrate another exemplary embodiment of a valve repair system 600, in which the valve repair system 600 includes a valve repair device 602 having extendable paddles. The valve repair system 600 can take any suitable form, such as, for example, any form described in the present application. In the illustrated embodiment, the valve repair device 602 includes paddles 606 that are telescoping such that a length L of the paddles can be altered. That is, the paddles 606 include a main portion 2110 and an extendable portion 2112. The extendable portion 2112 is able to be housed within the main portion 2110 to create paddles having a shorter length L (as shown in FIG. 21A), and the extendable portion 2112 is able to be extended outside of the main portion to create paddles having a longer length L (as shown in FIG. 21B). The ratio between the shorter length L (as shown in FIG. 21A) and the longer length L (as shown in FIG. 21B) can be, for example, 1.25 to 1 or more, such as 1.5 to 1 or more, such as 2 to 1 or more, such as 2 to 1 or more, such as 4 to 1 or more, such as 5 to 1 or more.

In one embodiment, the main portion 2110 is a hollow conduit having an opening, and the extendable portion 2112 is a rod or conduit configured to be housed in the opening of the hollow member. In certain embodiments, the extendable portion 2112 is spring loaded, such that the extendable portion 2112 is biased toward the extended position, and a latch member is disposed in a locked position to maintain the extendable portion 2112 housed within the main portion 2110 in the non-extended position. Movement of the latch member from the locked position to an unlocked position causes the spring-loaded extendable portion 2112 to move outside the main portion 2110 and into the extended position. In addition, the extendable portion 2112 can be moved back within the main portion 2110 and the latch member can be moved from the unlocked position to the locked position to move the paddles from the extended position to the retracted position. The latch member can be moved between the locked an unlocked position by any suitable means, such as, for example, a rod that engages the latch member to move the latch member between the locked and unlocked positions. In an alternative embodiment, a suture or wire extends through the main portion 2110 and engages the extendable portion 2112 to maintain the extendable portion 2112 in the non-extended position, and removal of the suture or wire allows the spring-loaded extendable portion to move outside the main portion 2110 and into the extended position.

Referring to FIG. 21A, the valve repair device 602 is shown with the paddles 606 in a non-extended position, and the valve repair device is positioned to engage valve tissue 820. Referring to FIG. 21B, after the valve repair device 602 is placed in position to engage the valve tissue 820, the extendable portions 2112 of the paddles 606 are extended such that the paddles have a larger surface area for engaging the valve tissue. After the paddles 606 are extended to a desired length L, the valve repair device 602 is closed to secure the valve repair device to the valve tissue 820, and the valve repair device is removed from the valve repair system 600. In certain embodiments, the valve repair device 602 is configured such that the extendable portions 2112 of the paddles can be extended or retracted after the valve repair device is secured to the valve tissue 820, such that the tension on the valve tissue can be increased or decreased depending on the patient and the procedural circumstances. For example, in embodiments in which the valve tissue 820 is a patient's mitral valve, a valve with excess leaflet material or chordal damage may need more tension to sufficiently seal the mitral valve, or a valve with short non-coapting leaflets may need less tension for a sufficiently seal the mitral valve. The valve repair device can be moved from the open position to a closed position and removed from the valve repair system 600 in any suitable manner, such as, for example, any manner described in the present application.

Referring to FIGS. 22-26, in certain embodiments, the gripper control mechanism 611 is configured to control each of the gripping members 608 independent of each other. Independent control for each of the gripping members 608 is advantageous because the openings 614 between the paddles 606 and the gripping members can be adjusted independently as the valve repair device 602 is being attached to valve tissue (e.g., a mitral valve of a patient). In addition, independent gripper control will also be advantageous in situations in which one gripping member 608 and one paddle 606 sufficiently secure the valve repair device 602 to a first portion of valve tissue, but the other gripping member and the other paddle fail to connect the valve repair device to a second portion of valve tissue. In this situation, the gripper control mechanism 611 can be used to control only the gripping member 608 that is not connected to the valve tissue to create an opening 614 for receiving the second portion of the valve tissue, and, after the second portion of the valve tissue is disposed in the opening, the unattached gripping member and the unattached paddle can be closed to secure the valve repair device 602 to the second portion of the valve tissue.

Still referring to FIGS. 22-26, an exemplary embodiment of a valve repair system 600 includes a delivery device 601 and a valve repair device 602, in which delivery device is configured to deliver the valve repair device to the native valve of a patient, and in which the valve repair device is configured to attach to leaflets of a native valve to repair the native valve of the patient. The delivery device 601 can take any suitable form that is capable of delivering the valve repair device 602 to the native valve of a patient, such as, for example, any form described in the present application. The valve repair device 602 is similar to the previously described valve repair device and includes a base assembly 604, a pair of paddles 606, and a pair of gripping members 608. The base assembly 604 of the valve repair device 602 has a shaft 603, a coupler 605 configured to move along the shaft, and a lock 607 configured to lock the coupler in a stationary position on the shaft. The valve repair device 602 can take any suitable form, such as, for example, any form described in the present application. The valve repair system 600 can also include a paddle control mechanism 610, a gripper control mechanism 611, and a lock control mechanism 612. The paddle control mechanism 610 is mechanically attached to the coupler 605 to move the coupler along the shaft 603, which causes the paddles 606 to move between the open and closed positions. The paddle control mechanism 610 can take any suitable form, such as, for example, any form described in the present application. The lock control mechanism 612 is configured to move the coupler 605 between the locked and unlocked conditions. The lock control mechanism 612 can take any suitable form, such as, for example, any form described in the present application.

Figure 22:
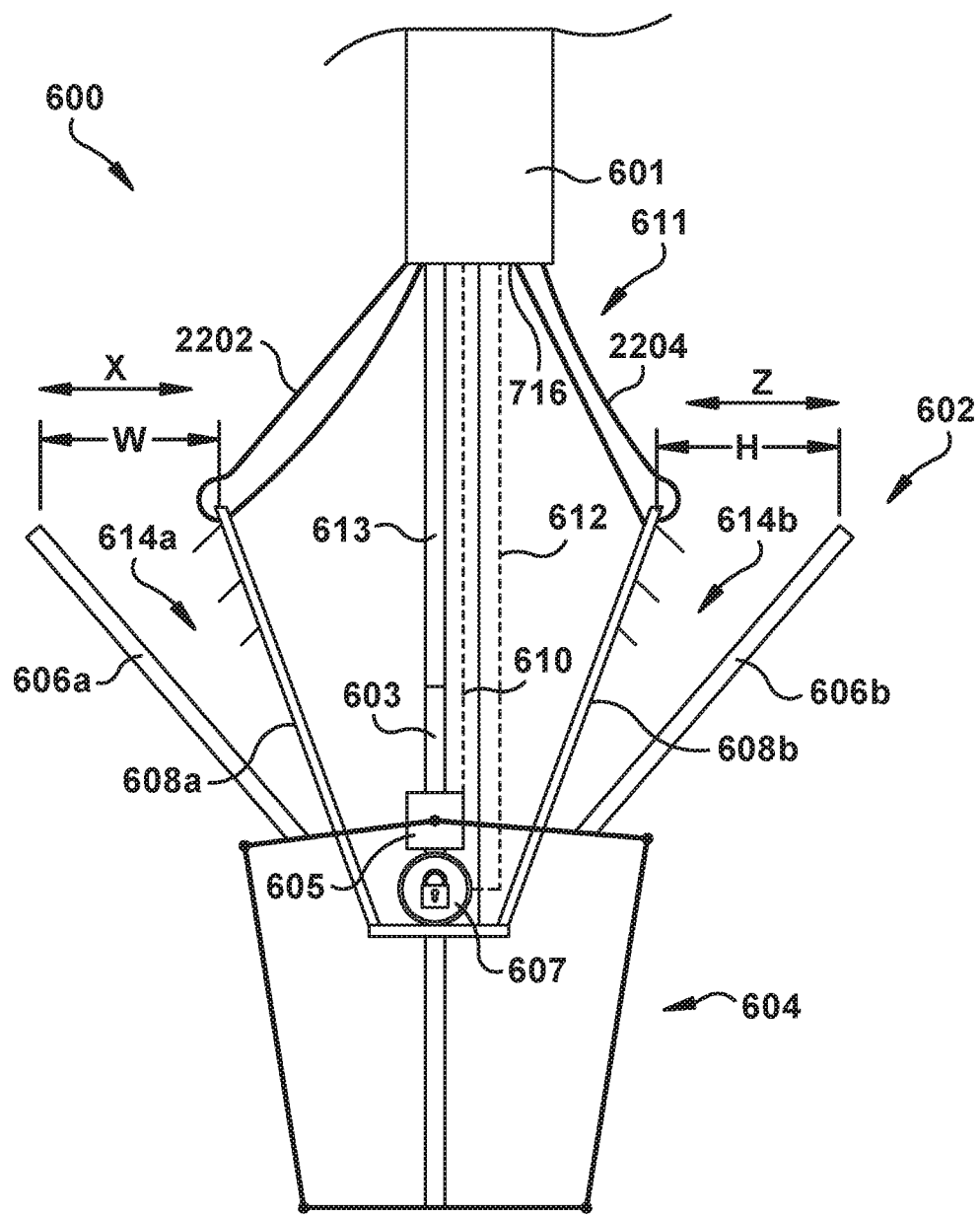
FIG. 22 illustrates another exemplary embodiment of a valve repair assembly where a gripper control mechanism is configured to control each gripper member of a valve repair device independently.

Referring to FIG. 22, an exemplary embodiment of a gripper control mechanism 611 includes a first gripper control member 2202 and a second gripper control member 2204. The first gripper control member 2202 is configured to move the gripping member 608a in the direction X, and the second gripper control member 2204 is configured to move the gripping member 608b in the direction Z. Movement of the gripping member 608a in the direction X will adjust the width W of the opening 614a between the gripping member 608a and the paddle 606a, and movement of the gripping member 608b in the direction Z will adjust the width H of the opening between the gripping member 608b and the paddle 606b. The gripper control members 2202, 2204 can take any suitable form that is capable of independently moving the gripping members 608a, 608b. In the illustrated embodiment, the gripper control members 2202, 2204 are lines, such as sutures, wires, etc. that are removably attached to each of the gripper members 608a, 608b, respectively, with both ends of the line extending through the delivery opening 716 of the delivery device 601. The gripper control members 2202, 2204 can be independently pulled into and cast from the catheter to independently control the positions of the gripping members 608a, 608b.

Figure 22B:
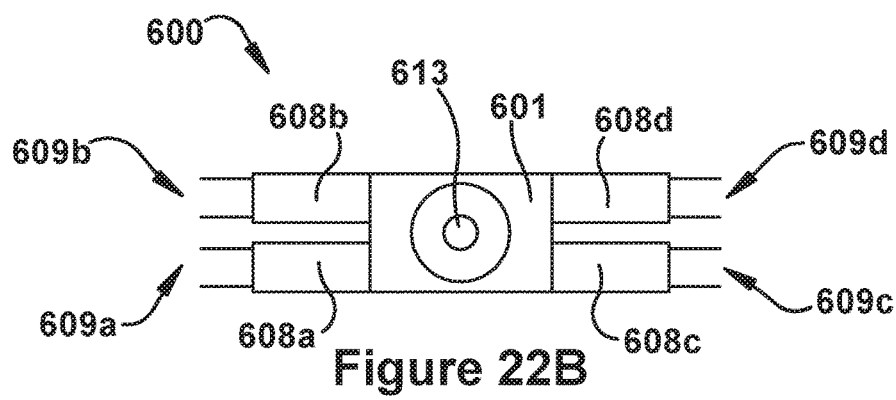
FIGS. 22A-22D illustrate another exemplary embodiment of a valve repair assembly where an exemplary embodiment of gripper control mechanism is configured to control four gripper members of an exemplary embodiment of valve repair device independently of each other.
Figure 22A:
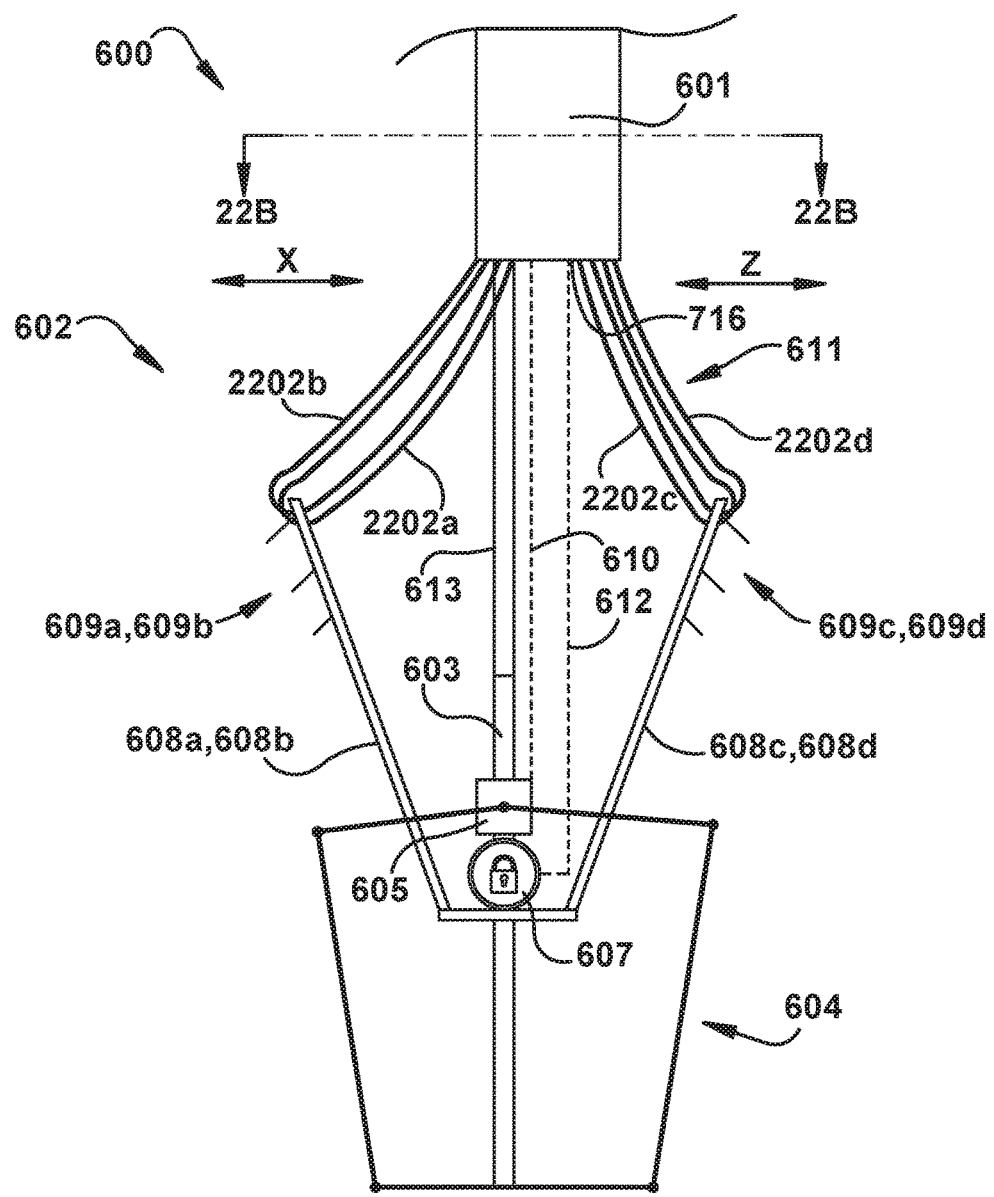
Figure 22D:
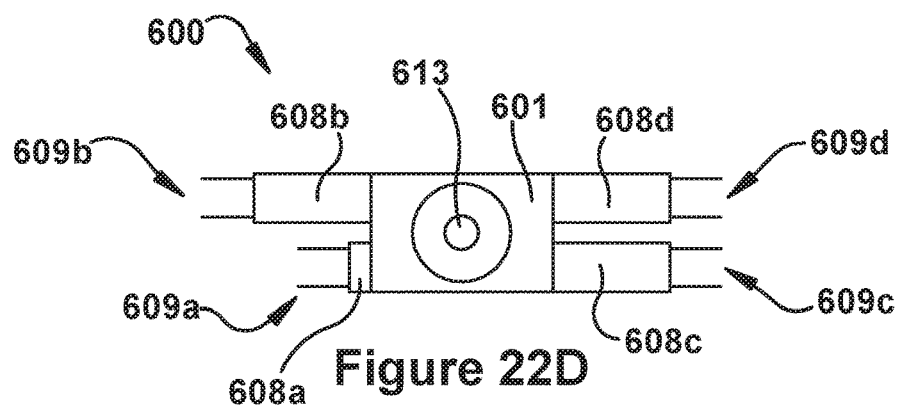
Figure 22C:
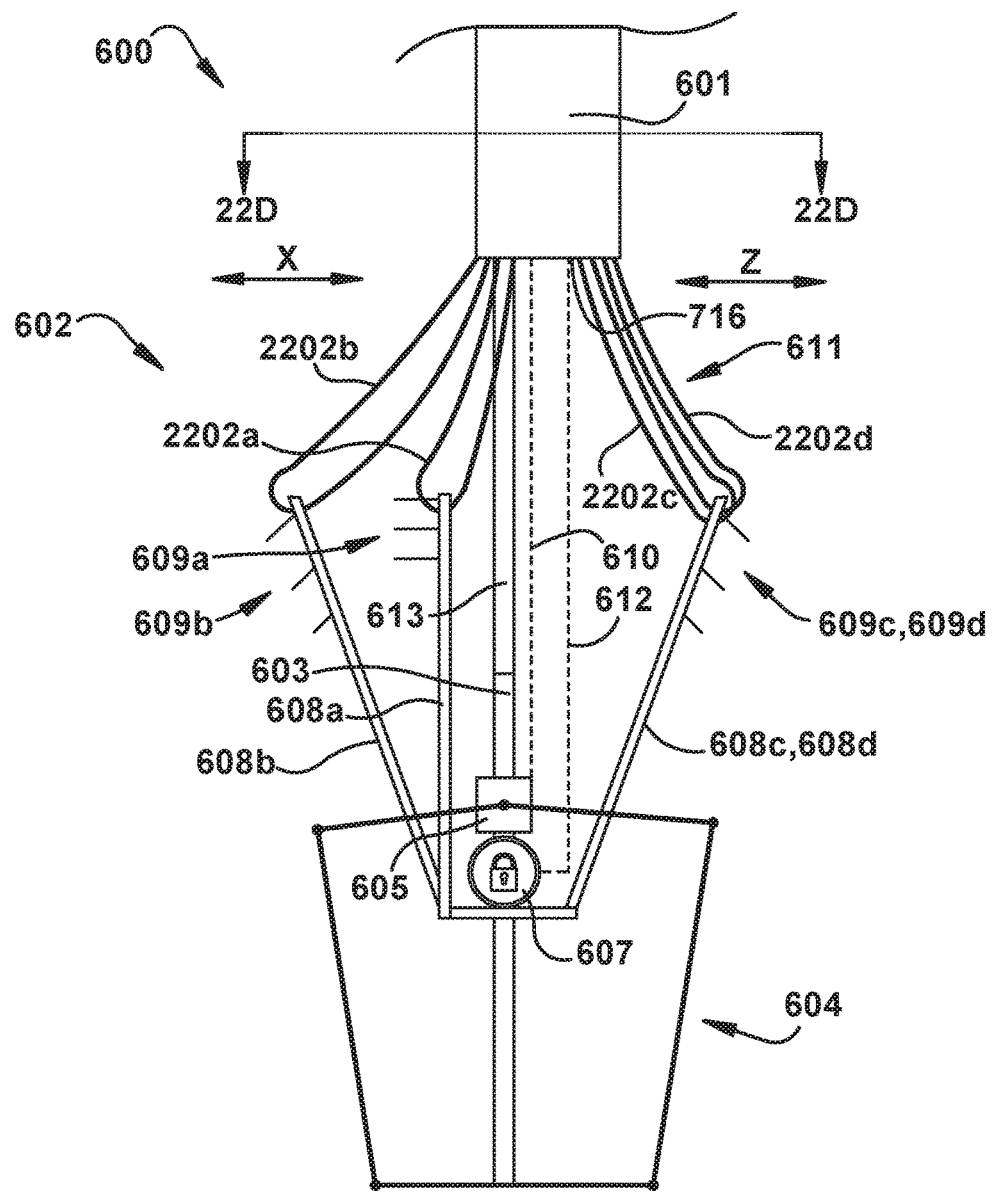

Referring to FIGS. 22A-22D, another exemplary embodiment of valve repair system 600 is shown with another embodiment of a gripper control mechanism 611 used to control the gripping members 608a-d of another exemplary embodiment of a valve repair device 602. For illustrative purposes, the paddles 606 of the valve repair device 602 are not shown on in FIGS. 22A-22D, but it should be noted that the valve repair device 602 also includes paddles 606 that interact with the gripping members 608a-d to secure the valve repair device 602 to valve tissue, and the paddles 606 can take any suitable form, such as, for example, any form described in the present application. FIG. 22A illustrates the valve repair system 600 with the each of the four gripping members 608a-d in a first position, and FIG. 22C illustrates the valve repair system 600 with the one of the gripping members 608a moved to a second position. FIG. 22B is a top view (as indicated by the lines 22B-22B shown in FIG. 22A) of the valve repair system 600 with each of the gripping members 608a-d being disposed in a first position. FIG. 22D is a cross-sectional view (as indicated by the lines C-C shown in FIG. 22C) of the valve repair system 600 with the gripping member 608a disposed the second position. Each of the four gripping members can be independently moved in the same manner as is illustrated by the gripping member 608a.

The valve repair device 602 includes a first gripping member 608a, a second gripping member 608b, a third gripping member 608c, and a fourth gripping member 608d. Each of the gripping members 608a-d include a barbed portion 609a-d for securing the gripping members 608a-d to valve tissue. The gripper control mechanism 611 includes a first gripper control member 2202a configured to control the first gripping member 608a, a second gripper control member 2202b configured to control the second gripping member 608b, a third gripper control member 2202c configured to control the third gripping member 608c, and a fourth gripper control member 2202d configured to control the fourth gripping member 608d. In particular, the first gripper control member 2202a is configured to move the gripping member 608a in the direction X, and the second gripper control member 2202b is configured to move the second gripping member 608b in the direction X. In addition, the third gripper control member 2202c is configured to move the gripping member 608c in the direction Z, and the fourth gripper control member 2202d is configured to move the fourth gripping member 608d in the direction Z. Movement of the gripping members 608a-b in the direction X will adjust the width of the opening between the gripping members 608a-b and the corresponding paddle 606, and movement of the gripping members 608c-d in the direction Z will adjust the width of the opening between the gripping members 608c-d and the corresponding paddle. The gripper control mechanism 611 is configured to move each of the gripping members 608a-d independently of each other. The gripper control members 2202a-d can take any suitable form that is capable of independently moving the gripping members 608a-d. In the illustrated embodiment, the gripper control members 2202a-d are lines, such as sutures, wires, etc. that are removably attached to each of the gripper members 608a-d, respectively, with both ends of the line extending through the delivery opening 716 of the delivery device 601. The gripper control members 2202a-d can be independently pulled into and released from the catheter to independently control the positions of the gripping members 608a-d.

Referring to FIGS. 22A and 22B, each of the gripping members 608a-d are shown in an extended position. Referring to FIGS. 22C and 22D, the first gripping member 608a is shown after the first gripper control member 2202a of the gripper control mechanism was pulled into the catheter causes the first gripping member 608a to move inward toward the shaft 603 in the direction X, and the other gripping members 608b-d remained in the position shown in FIGS. 22A and 22B. In other words, the illustrated embodiment shown in FIGS. 22A-22D show a first gripping member 608a being independently controlled relative to the other gripping members 608b-d. While the illustrated embodiment shows the first gripping member 608a being independently controlled, it should be understood that each of the gripping members 608a-d can be independently controlled by the corresponding gripper control member 2202a-d of the gripper control mechanism 611. In addition, while the illustrated embodiment of FIGS. 22A-22D illustrate a valve repair assembly 600 having four gripping members 608a-d and four gripper control members 2202a-d, it should be understood that any suitable number of gripping members and gripper control members can be utilized, and any number of the gripping members can be independently controlled by the gripper control mechanism. In addition, each of the gripping members 608a-608d can have any of the configurations disclosed in this application and each of the control mechanisms 2202a-2202d can have any of the forms disclosed in this application.

Figure 23:
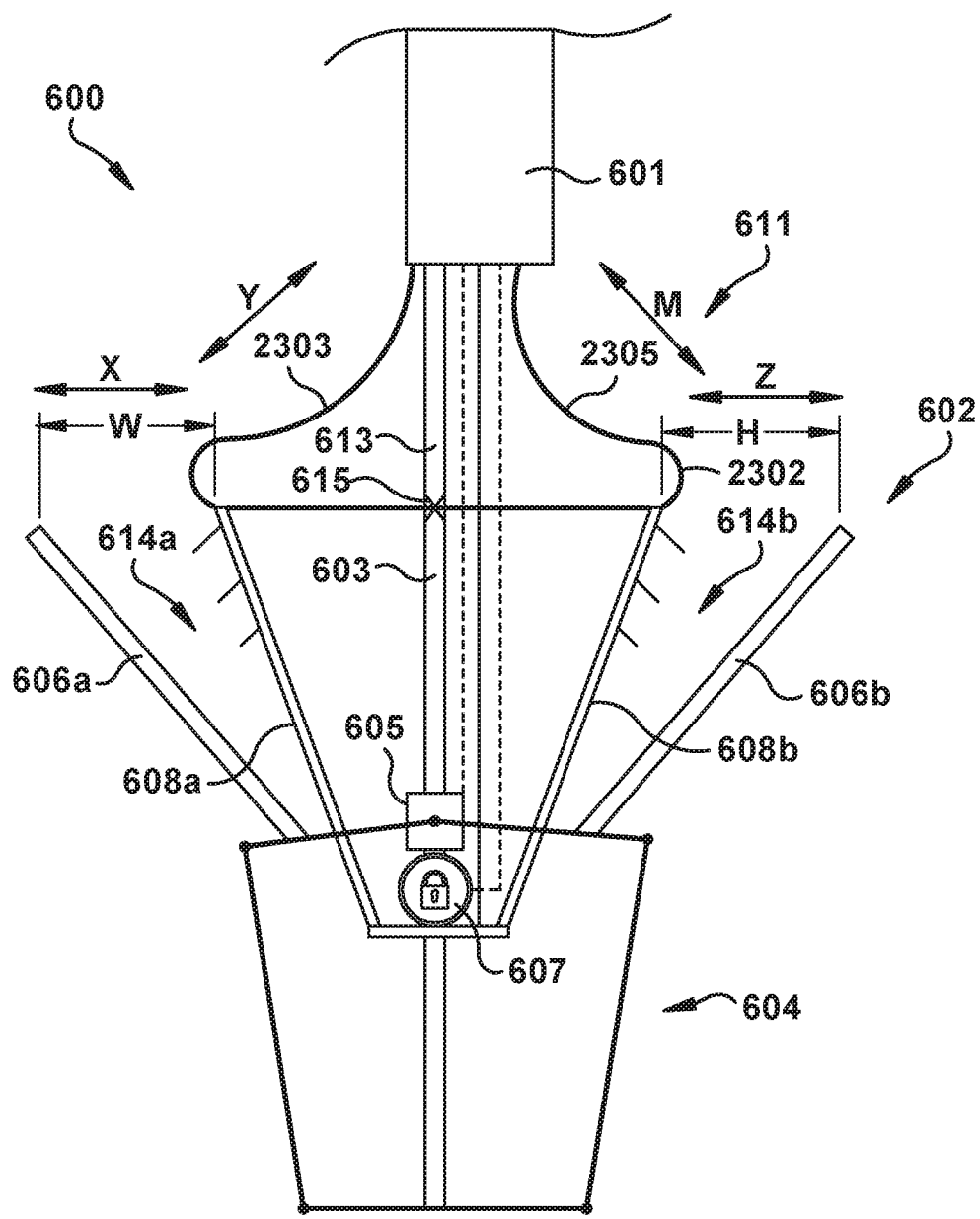
FIG. 23 illustrates another exemplary embodiment of a valve repair assembly where a gripper control mechanism is configured to control each gripper member of a valve repair device independently.

Referring to FIG. 23, another exemplary embodiment of a gripper control mechanism 611 includes a single line 2302, such as a suture or wire, that is removably attached to the gripping members 608a, 608b and removably fixed between a placement shaft 613 and a 603 shaft of the valve repair device. The connection 615 between the placement shaft 613 and a 603 shaft of the valve repair device can be at a wide variety of different positions. In the illustrate example, the connection 615 is aligned or substantially aligned with ends of the gripping members 608a, 608b. However, in other embodiments, the connection 615 can more distal, such as at a most proximal position that the coupler 605 can reach (see for example, the bailout positions of the coupler illustrated by FIGS. 45C and 46D). The single line 2302 is connected between the shaft 613 and the shaft 603, such that the single line 2302 can independently control the gripping members 608a, 608b. That is, movement of a first portion 2303 of the line 2302 in the direction Y will adjust the width W between the gripping member 608a and the paddle 606a, but will not adjust the width H between the gripping member 608b and the paddle 606b. Similarly, movement of a second portion 2305 of the line 2302 in the direction M will adjust the width H between the gripping member 608b and the paddle 606b, but will not adjust the width W between the gripping member 608a and the paddle 606a. After the valve repair device 602 is in the closed position and secured to valve tissue, the placement shaft 613 is detached from the shaft 603 of the valve repair device 602. The detachment of the shaft 603 from the and the shaft 613 causes the line to be released. The line 2302 can then be retracted into the catheter to release the gripping members 608a, 608b by pulling one end of the line 2302 into the catheter. Pulling one end of the line into the catheter pulls the other end of the line through the gripping members 608a, 608b and then into the catheter. Any of the lines described herein can be retracted in this manner.

Figure 24:
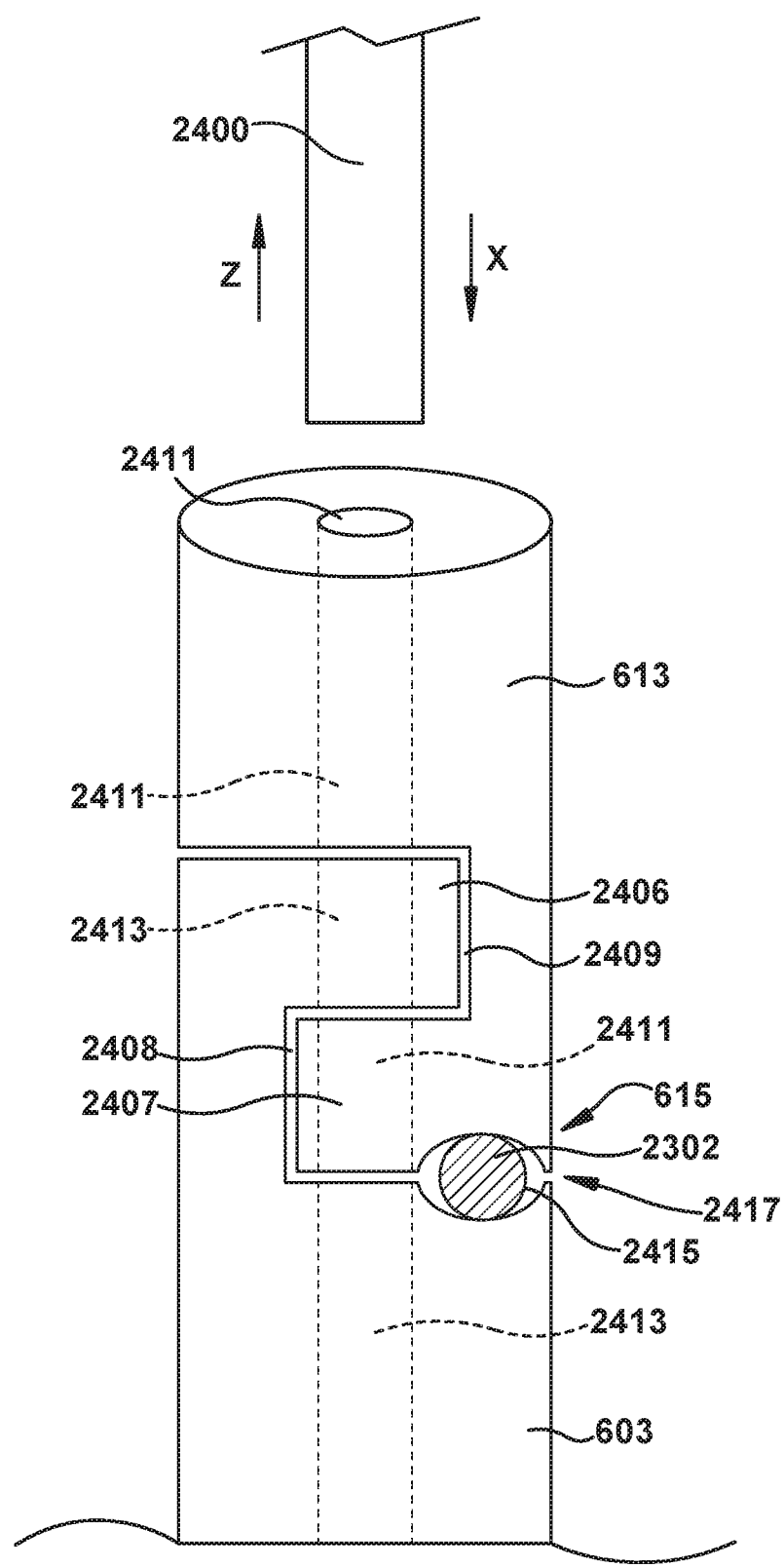
FIG. 24 illustrates an exemplary embodiment of a connection between a placement shaft and a paddle control mechanism shaft of the valve repair device of FIG. 23, in which the gripper control mechanism is attached to the valve repair device at the connection between the placement shaft and the paddle control mechanism shaft.

Referring to FIG. 24, in certain embodiments, the placement shaft 613 and the shaft 603 of the device 602 can be a hollow an fit over a coupling shaft 2400 that holds the shafts 613, 603 together. The shaft 603 of the device 602 can include a protruding portion 2406 and a recessed receiving portion 2408. The positioning shaft 613 can include a protruding portion 2407 and a recessed receiving portion 2409. When the shafts 613, 603 are coupled, the protruding portion 2406 of the shaft 603 is disposed in the receiving portion 2409 of the shaft 613, and the protruding portion 2407 of the shaft 613 is disposed in the receiving portion 2408 of the shaft 603. The shafts 613, 603 can be connected in a wide variety of different ways. For example, the shaft 613 can include a bore or channel 2411 that is aligned with a bore or channel 2413 of the shaft 602 when the protruding portions 2406, 2407 are disposed in the receiving portions 2408, 2409, respectively. When the openings 2411, 2413 are aligned and the retaining shaft 2400 is placed into the openings 2411, 2413 in the direction X, the shafts 613, 603 are retained together. When the placement shaft is removed from the openings 2411, 2413 in the direction Z, protruding portions 2406, 2407 can be removed from the receiving portions 2408, 2409, such that the device 602 is detached from the placement shaft 613.

Still referring to FIG. 24, when the shafts 613, 603 are secured to each other, an aperture 2415 is created at interface 2417 between the shafts 613, 603. The aperture 2415 is configured to secure the line 2302 between the shafts 613, 603 to allow for independent control of the gripping members 608a, 608b. That is, the aperture 2415 is configured such that the line 2302 does not move relative to the aperture 2416 when the shafts 613, 603 are attached. Upon detachment of the shafts 613, 603, the line 2302 is released from the aperture 2415 and can be removed from the valve repair device 602. The line 2302 can then be retracted into the catheter to release the gripping members as described above.

Figure 24A:
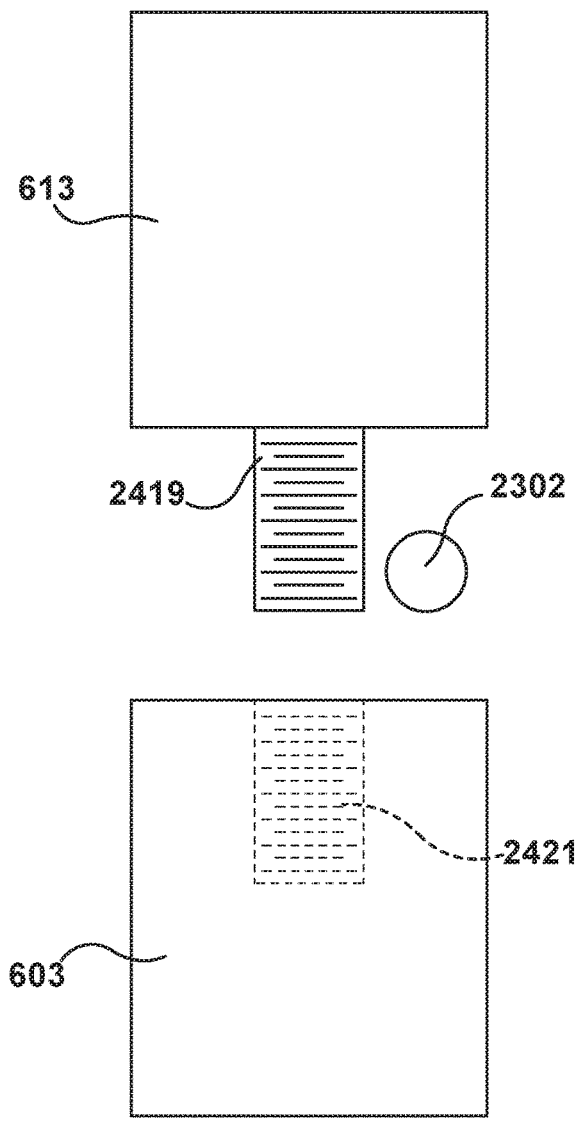
FIGS. 24A-24B illustrate an exemplary embodiment of a connection between a placement shaft and a paddle control mechanism shaft of the valve repair device of FIG. 23, in which the gripper control mechanism is attached to the valve repair device at the connection between the placement shaft and the shaft of the valve repair device.
Figure 24B:
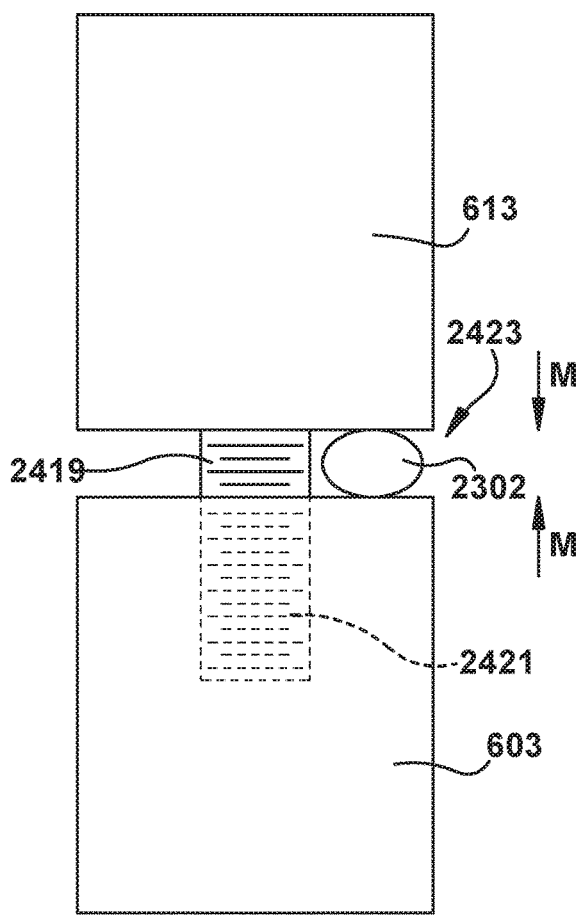

Referring to FIGS. 23 and 24A-24B, in an alternative embodiment, the line 2302 of the gripper control mechanism 610 is secured between the placement shaft 613 and the shaft 603 of by a threaded connection to independently control the gripper members 608a, 608b. Referring to FIG. 24A, the placement shaft 613 includes a male threaded member 2419, and the shaft 603 includes a female threaded member 2421 configured to receive the male threaded member 2419 of the placement shaft 613. However, the male and female threads can be reversed. The placement shaft 613 is secured to the shaft 603 by inserting the male threaded member 2419 into the female threaded member 2421 of the shaft 603. The line 2302 of the gripper control mechanism 611 is disposed between the placement shaft 613 and the shaft 603 such that, when the placement shaft 613 is secured to the shaft 603, the line 2302 is compressed (as shown by reference character M) between the placement shaft 613 and the shaft 603. The compression M of the line 2302 between the placement shaft 613 and the shaft 603 causes the line 2302 to not move relative to the engagement point 2423 between the placement shaft 613, the shaft 603, and the line 2302 when the line 2302 is controlling the gripping members 608a, 608b. As a result, the compression M and resulting retention of the line 2302 allows the line 2302 to independently control the gripping members 608a, 608b.

Figure 25:
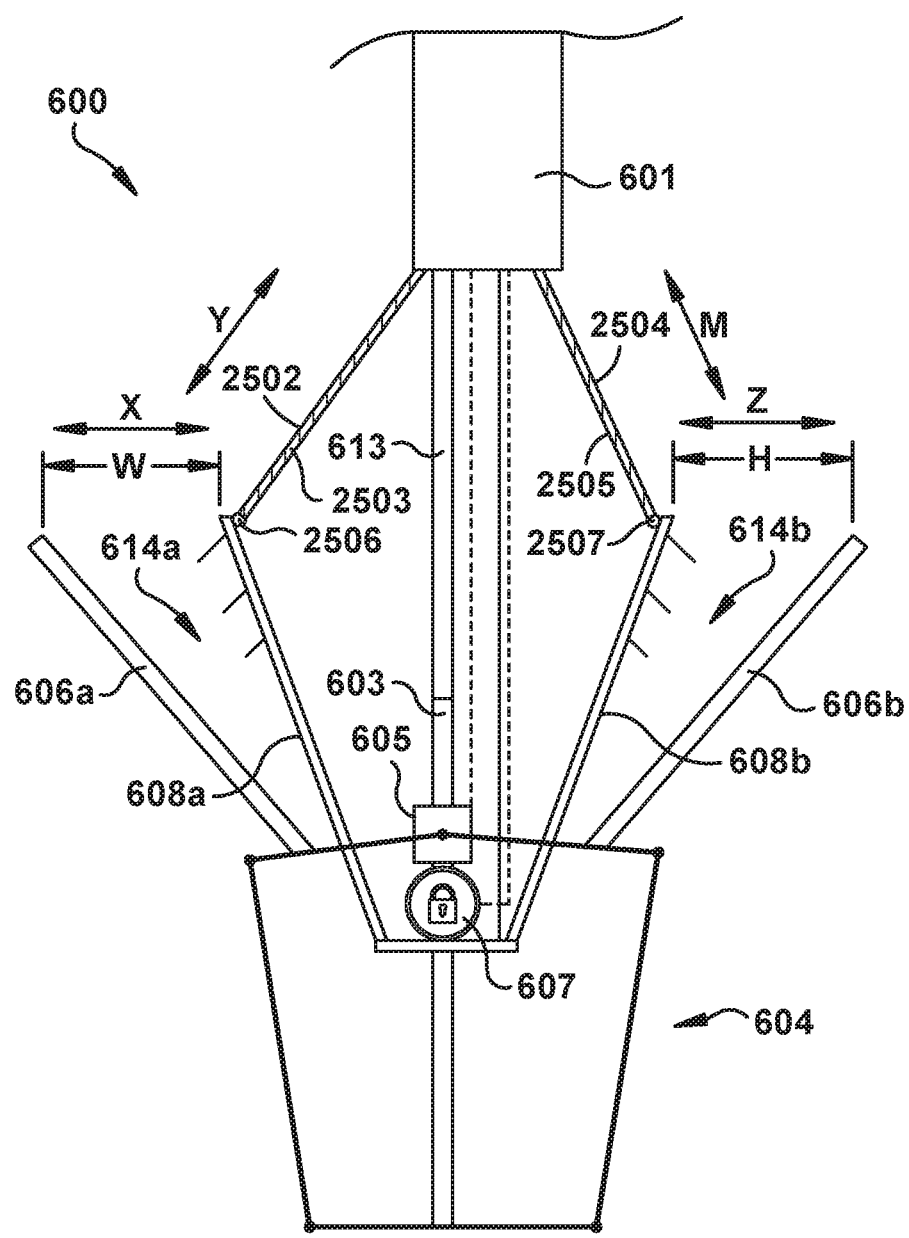
FIG. 25 illustrates another exemplary embodiment of a valve repair assembly in which a gripper control mechanism is configured to control each gripper member of a valve repair device independently of each other.

Referring to FIG. 25, another exemplary embodiment of a gripper control mechanism 611 includes a first gripper control member 2502 and a second gripper control member 2504. The first gripper control member 2502 is configured to move the gripping member 608a bi-directionally in the direction X, and the second gripper control member 2504 is configured to move the gripping member 608b bi-directionally in the direction Z. Movement of the gripping member 608a in the direction X will adjust the width W of the opening 614a between the gripping member 608a and the paddle 606a, and movement of the gripping member 608b in the direction Z will adjust the width H of the opening between the gripping member 608b and the paddle 606b. In the illustrated embodiment, the gripper control members 2202, 2204 include a push/pull link 2503, 2505, such as, for example, a catheter, a flexible rod, or a stiff wire and a coupler 2506, 2507. Each push/pull link 2503, 2505 extends from the delivery device 601 and is removably attached to the corresponding gripping member 608a, 608b by a coupler 2506, 2507. The link 2503 is configured to be pushed and pulled in the direction Y. Movement of the link 2503 in the direction Y causes the gripping member 608a to move in the direction X. Similarly, the link 2505 is configured to be pushed and pulled in the direction M, and movement of the catheter 2505 in the direction M causes the catheter 2505 to move the gripping member 608b in the direction H.

Figure 25A:
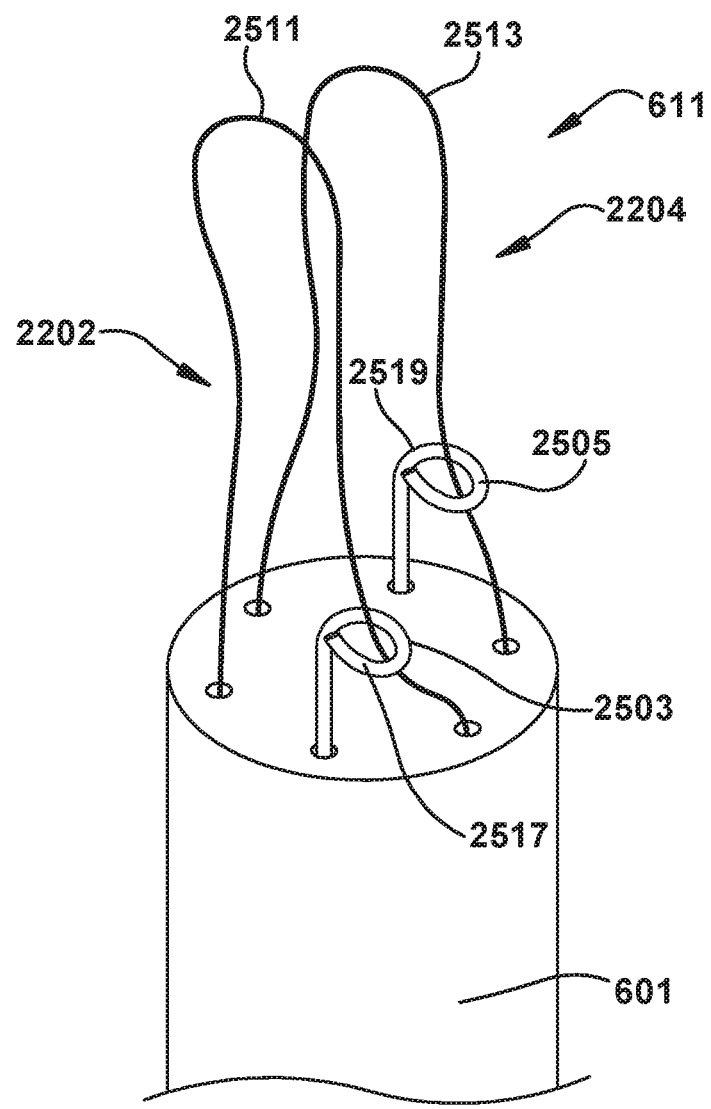
FIG. 25A illustrates another exemplary embodiment of a gripper control mechanism that is configured to control each gripper member of a valve repair device independently of each other.

In another embodiment of a the gripper control mechanism 611 is shown in FIG. 25A. in this embodiment, the gripper control members 2202, 2204 include a suture 2511, 2513 and a flexible wire 2503, 2505. In this embodiment, the first flexible wire 2503 includes a loop 2517 for receiving the first suture 2511 and for engaging a gripping member 608a (FIG. 25), and the second flexible wire 2505 includes a loop 2519 for receiving the second suture 2513 and for engaging the gripping member 608b (FIG. 25). The sutures 2517, 2519 are removably attached to each of the gripper members 608a, 608b, respectively, with both ends of the line extending through the delivery device 601 as described above. Each of the wires 2503, 2505 extends from the delivery device 601 and the loops 2517, 2519 of the respective wires 2503, 2505 are able to move along the corresponding sutures 2511, 2513, such that the loops 2517, 2519 can engage the corresponding gripping member 608a, 608b to move the gripping members (e.g., move the gripping members as described with respect to FIG. 25). The wires 2503, 2505 can be made of, for example, steel, NiTi, or other wire or a plastic material. In certain embodiments, the wires 2503, 2505 can have a diameter of between about 0.1 mm and 0.35 mm, such as between about 0.15 mm and 0.3 mm, such as between about 0.2 mm and 0.25 mm.

Figure 26:
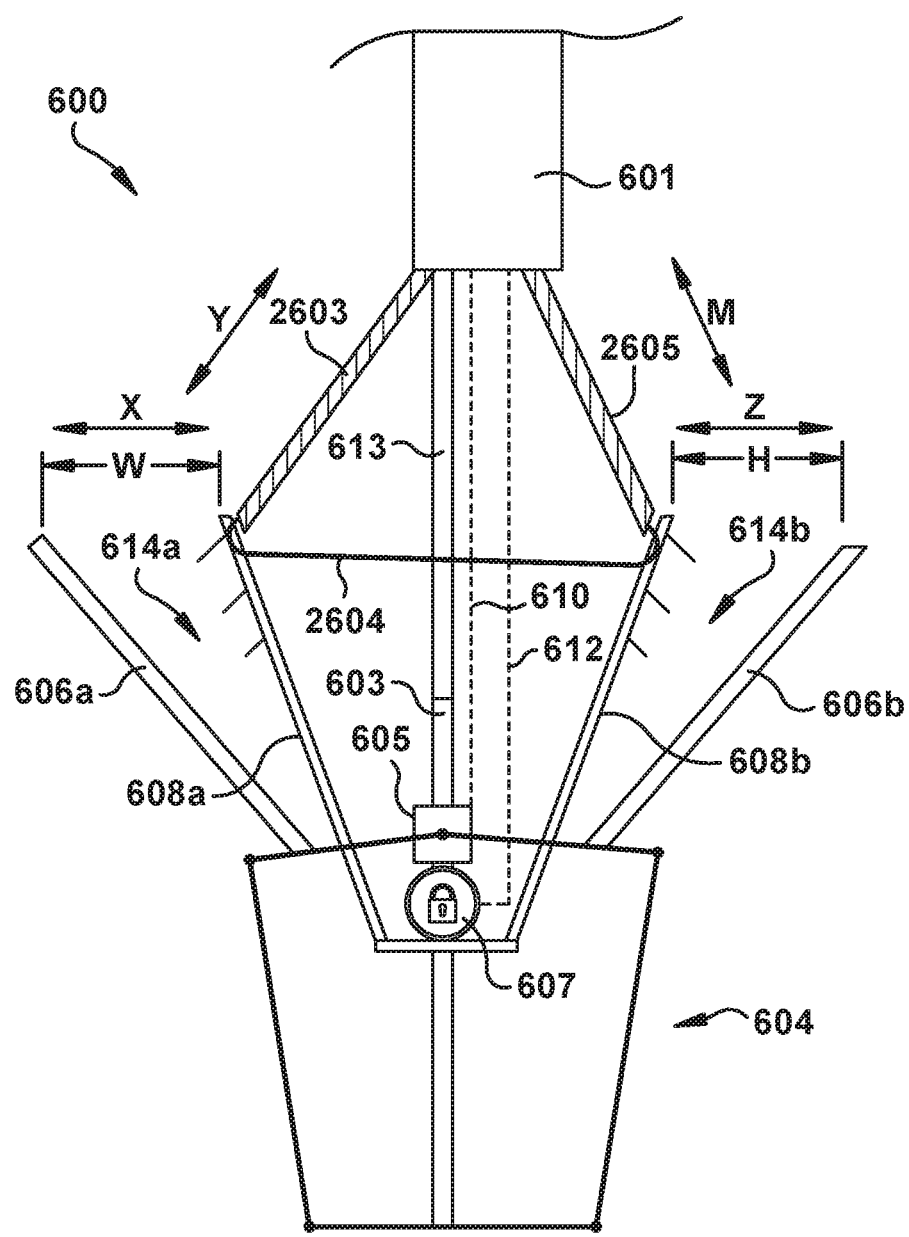
FIG. 26 illustrates another exemplary embodiment of a valve repair assembly in which a gripper control mechanism is configured to control each gripper member of a valve repair device independently of each other.

Referring to FIG. 26, another exemplary embodiment of a gripper control mechanism 611 includes a first catheter 2603, a second catheter 2605, and single line 2604, such as a wire or suture. The first catheter 2603 and line 2604 are configured to move the gripping member 608a in the direction X, and the second catheter 2605 and line 2604 configured to move the gripping member 608b in the direction Z. Movement of the gripping member 608a in the direction X will adjust the width W of the opening 614a between the gripping member 608a and the paddle 606a, and movement of the gripping member 608b in the direction Z will adjust the width H of the opening between the gripping member 608b and the paddle 606b. The line 2604 extends from the delivery device 601 through the catheters 2603, 2605 and is threaded through openings in both gripping member 608a, 608b. Each catheter 2603, 2605 is configured to engage and move the corresponding gripping member 608a, 608b. In particular, the catheter 2603 is configured to be pushed in the direction Y while the line 2604 is payed out of the catheter 2603 or tension in the line is reduced. The catheter 2603 is configured to be pulled in the direction Y while the line 2604 is pulled into the catheter 2603 or tension in the line is increased. Movement of the catheter 2603 in the direction Y causes the catheter 2603 to move the gripping member 608a in the direction X. Similarly, the catheter 2605 is configured to be pushed in the direction M while the line 2604 is payed out of the catheter 2605 or tension in the line is reduced. The catheter 2605 is configured to be pulled in the direction M while the line 2604 is pulled into the catheter 2605 or tension in the line is increased. Movement of the catheter 2505 in the direction M causes the catheter 2505 to move the gripping member 608b in the direction H. In an alternative embodiment, the gripper control mechanism 611 described above with reference to FIG. 26 can include a first flexible wire with a loop (e.g., the flexible wire 2503 with the loop 2517 shown in FIG. 25A) and a second flexible wire with a loop (e.g., the flexible wire 2505 with the hoop 2519 shown in FIG. 25A), and the single line 2604 extends through the hoop 2517, 2519 of each of the wires 2503.

Referring to FIGS. 27A-29B, in certain embodiments, the valve repair device 602 and the paddle control mechanism 610 for a valve repair device 602 are configured such that each of the paddles 606 can be controlled independent of each other. Independent control for each of the paddles 606 is advantageous because the openings 614 between the paddles and the gripping members 608 can be adjusted independently as the valve repair device 602 is being attached to valve tissue (e.g., a mitral valve of a patient). In addition, independent paddle control will also be advantageous in situations in which one gripping member 608 and one paddle 606 sufficiently secure the valve repair device 602 to a first portion of valve tissue, but the other gripping member and the other paddle fail to connect the valve repair device to a second portion of valve tissue. In this situation, the paddle control mechanism 610 can be used to control only the paddle 606 that is not connected to the valve tissue to create an opening 614 for receiving the second portion of the valve tissue, and, after the second portion of the valve tissue is disposed in the opening, the unattached gripping member and the unattached paddle can be closed to secure the valve repair device 602 to the second portion of the valve tissue.

Referring to FIGS. 27A-27C, the base assembly 604 of the valve repair device 602 includes a first shaft 603a, a second shaft 603b, a first coupler 605a, and a second coupler 605b. In addition, the paddle control mechanism 610 includes a first paddle control mechanism 2702 and a second paddle control mechanism 2704. The first paddle control mechanism 2702 is configured to move the first coupler 605a along the shaft 603a, and the second paddle control mechanism 2704 is configured to move the second coupler 605b along the shaft 603b. Movement of the first coupler 605a along the shaft 603a causes the paddle 606a to move between an open position and a closed position, and movement of the second coupler 605b along the shaft 603b causes the paddle 606b to move between an open position and a closed position. In an alternative embodiment, the base assembly 604 can include a single shaft, a first coupler 605a attached to the single shaft, and a second coupler 605b attached to the single shaft. In this alternative embodiment, the paddle control mechanism 610 can include a first paddle control mechanism 2702 configured to move the first coupler 605a along the single shaft to cause the paddle 606a to move between an open position and a closed position, and a second paddle control mechanism 2704 configured to move the second coupler 605b along the single shaft to cause the paddle 606b to move between an open position and a closed position.

FIGS. 27A-27C illustrate the paddles of the valve repair device moving between an open position and a closed position. The base assembly 604 of the valve repair device 602 includes a first link 2721 extending from point A to point B, a second link 2722 extending from point B to point C, a third link 2723 extending from point C to point D, a fourth link 2724 extending from point D to point E, and a fifth link 2725 extending from point E to point F. The coupler 605a is movably attached to the shaft 603a, the coupler 605b is movably attached to the shaft 603b, and the shafts 603a, 603b are fixed to the third link 2723. The first link 2721 is pivotally attached to the coupler 605a at point A, such that movement of the coupler 605a along the shaft 603a moves the location of point A and, consequently, moves the first link 2721. Similarly, the fifth link 2725 is pivotally attached to the coupler 605b at point F, such that movement of the coupler 605b along the shaft 603b moves the location of point F and, consequently moves the fifth link 2725. The first link 2721 and the second link 2722 are pivotally attached to each other at point B, and the fifth link 2725 and the fourth link 2724 are pivotally attached to each other at point E. One paddle 606a is attached to the first link 2721 such that movement of the first link 2721 causes the paddle 606a to move, and the other paddle 606b is attached to the fifth link 2725 such that movement of the fifth link 2725 causes the paddle 606b to move.

Referring to FIG. 27A, the paddles 606a, 606b are in the open position. Referring to FIGS. 27A and 27B, the paddle 606b is moved from the open position (as shown in FIG. 27A) to the closed position (as shown in FIG. 27B) when the second paddle control mechanism 2704 moves the second coupler 605b along the shaft 603b in the direction Y, which causes a portion of the fifth link 2725 near point F to move in the direction H, and a portion of the fifth link 2725 near point E to move in the direction J. The paddle 606b is attached to the fifth link 2725 such that movement of the second coupler 605b in the direction Y causes the paddle 606b to move in the direction Z. In addition, the fourth link 2724 is pivotally attached to the fifth link 2725 at point E such that movement of the second coupler 605b in the direction Y causes the fourth link 2724 to move in the direction K. Referring to FIG. 27B, the paddle 606b moves in the direction Q when moving from the open position to the closed position. In an alternative embodiment in which the pivotal connection at point E between the fourth link 2724 and the fifth link 2725 is significantly lower than pivotal connection at point F between the fifth link 2725 and the second coupler 605b, movement of the paddle 606b from the open position to the closed position will act as shown in the embodiment shown in FIG. 27A except that the fourth link 2724 will initially move in the direction substantially opposite to the direction K as the paddle 606b is being closed. In any of the above-mentioned embodiments, the second paddle control mechanism 2704 can take any suitable form for moving the second coupler 605b along the shaft 603b, such as, for example, any form of a paddle control mechanism described in the present application.

Referring to FIGS. 27A and 27C, the paddle 606a is moved from the open position (as shown in FIG. 27A) to the closed position (as shown in FIG. 27C) when the first paddle control mechanism 2702 moves the first coupler 605a along the shaft 603a in the direction N, which causes a portion of the first link 2721 near point A to move in the direction L, and a portion of the first link 2721 near point B to move in the direction I. The paddle 606a is attached to the first link 2721 such that movement of the first coupler 605a in the direction N causes the paddle 606a to move in the direction V. In addition, the second link 2722 is pivotally attached to the first link 2721 at point B such that movement of the first coupler 605a in the direction N causes the second link 2722 to move in the direction R. Referring to FIG. 27C, the paddle 606a moves in the direction T when moving from the open position to the closed position. In an alternative embodiment in which the pivotal connection at point B between the first link 2721 and the second link 2722 is significantly lower than pivotal connection at point A between the first link 2721 and the first coupler 605a, movement of the paddle 606a from the open position to the closed position will act as shown in the embodiment shown in FIG. 27A except that the second link 2722 will initially move in the direction substantially opposite to the direction R as the paddle 606b is being closed. In any of the above-mentioned embodiments, the first paddle control mechanism 2702 can take any suitable form for moving the first coupler 605a along the shaft 603a, such as, for example, any form of a paddle control mechanism described in the present application.

Referring to FIGS. 28A-28C, in certain embodiments, the paddle control mechanism 610 includes a rack and pinion mechanism 2802 that is configured to selectively couple and decouple the paddles 606a, 606b from the shaft 603. The rack and pinion mechanism 2802 includes a first member 2804 attached to the shaft 603 and a toothed member 2806a, 2806b attached to each of the paddles 606a, 606b and pivotally connected to a base member 2801 at connections points A, B. The first member 2804 is configured such that the paddles 606a, 606b can be moved between the open and closed positions independent of each other. In the illustrated embodiment, the first member 2804 has ribbed portion 2805 and an open portion 2807. When the toothed member(s) 2806a, 2806b is aligned with the ribbed portion 2805 of the first member 2804, the toothed member(s) 2806a, 2806b are configured to engage the ribbed portion 2805 such that movement of the shaft in the direction Y relative to the base member 2801 causes the toothed member 2806a to pivot about connection point A in the direction M to move the paddle 606a between an open position and a closed position in the direction H, and causes the toothed member 2806b to pivot about connection point B in the direction N to move the paddle 606b between an open position and a closed position in the direction Z. When the open portion 2807 of the first member 2804 is aligned with either of the toothed members 2806a or 2806b, the tooth member that is aligned with the open portion 2807 is not engaged by the ribbed portion 2805 of the paddle 606a or 606b. As a result, movement of the shaft 603 in the direction Y does not affect the position of the paddle 606a or 606b.

FIGS. 28A-28B illustrate the corkscrew mechanism 2802 in a first position. In the first position, the toothed members 2806a, 2806b for both paddles 606a, 606b are aligned with the ribbed portion 2805 of the first member 2804. Referring to FIG. 28A, when the shaft 603 is moved in the direction Y, the toothed members 2806a, 2806b both engage the ribbed portion 2805 of the first member, which causes both paddles 606a, 606b to be moved between the open and closed positions. FIGS. 28C-28D illustrate the corkscrew mechanism 2802 in a second position. In the second position, the toothed member 2806a is aligned with the open portion 2807 of the first member 2804, and the toothed member 2806b is aligned with the ribbed portion 2806 of the first member 2804. Referring to FIG. 28C, when the shaft 603 is moved in the direction Y, the toothed member 2806b engages the ribbed portion 2805 of the first member 2804, which causes the paddle 606b to be moved between the open and closed positions, and the toothed member 2806a does not engage the first member, which causes the paddle 606a to remain in a current position. FIGS. 28E-28F illustrate the corkscrew mechanism 2802 in a third position. In the third position, the toothed member 2806b is aligned with the open portion 2807 of the first member 2804, and the toothed member 2806a is aligned with the ribbed portion 2806 of the first member 2804. Referring to FIG. 28E, when the shaft 603 is moved in the direction Y, the toothed member 2806a engages the ribbed portion 2805 of the first member 2804, which causes the paddle 606a to be moved between the open and closed positions, and the toothed member 2806b does not engage the first member, which causes the paddle 606b to remain in a current position. In certain embodiments, the rack and pinion mechanism 2802 is moved between the positions shown in FIGS. 28A-28F by rotating the shaft 603. In various embodiments, the rack and pinion mechanism 2802 includes a mechanism configured to maintain the paddles 606a, 606b in a desired position when the paddles are aligned with the open portion 2807 of the first member 2804, but is also configured to allow the paddles to move when the paddles are aligned with the ribbed portion 2805 of the first member 2804. The mechanism can take any suitable form, such as, for example, a clutch mechanism, a biasing member, a friction element, etc.

Referring to FIGS. 29A-29B, the paddle control mechanism 610 is configured to move a coupler 605 along a shaft 603 to move the paddles 606a, 606b between the open and closed positions (similar to the embodiment shown in FIGS. 6-12), and a locking mechanism 207 is configured to lock the coupler 605 on the shaft 603 to maintain the paddles 606a, 606b in a desired position. In certain embodiments, as shown in FIGS. 29A-29B, each of the paddles 606a, 606b include a pin 2902a, 2902b and a slot 2904a, 2904b. The pin 2902a is configured to move in slot 2904a, and the pin 2902b is configured to move in slot 2904b. The pins 2902a, 2902b are also configured to be locked in the slots 2904a, 2904b. When a pin 2902a, 2902b is unlocked in a slot 2904a, 2904b, the corresponding paddle 606a, 606b remains in a current position when the paddle control mechanism 610 moves the coupler 605 along the shaft 603. When a pin 2902a, 2902b is locked in a slot 2904a, 2904b, the corresponding paddle 606a, 606b moves between an open and closed position when the paddle control mechanism 610 moves the coupler 605 along the shaft 603.

FIG. 29A illustrates the valve repair device 602 with the paddles 606a, 606b in an open position. FIG. 29B illustrates the valve repair device 602 with the pin 2902a unlocked in slot 2904a, and pin 2902b locked in slot 2904b. Referring to FIG. 29B, the lock 607 is in an unlocked condition such that the coupler 605 can be moved along the shaft 603. Movement of the coupler 605 along the shaft 603 in the direction Y causes the paddle 606b to pivot about the locked pin 2902b such that the paddle 606b moves in the direction Z to a closed position. In addition, movement of the coupler 605 in the direction Y does not cause the paddle 606a to move because the pin 2902a is in an unlocked condition in the slot 2904a. Instead, movement of the coupler 605 in the direction Y causes the pin 2902a to move in the slot 2904a. Alternatively, the pin 2902a could be locked in slot 2904a and the pin 2902b could be unlocked in slot 2904b, such that movement of the coupler 605 in the direction Y would cause the paddle 606a to move to a closed position, and the paddle 606b to remain in the open position (by the pin 2902b moving in the slot 2904b). In addition, the pin 2902a could be locked in slot 2904a and the pin 2902b could be locked in slot 2904b, such that movement of the coupler 605 in the direction Y would cause both paddles 606a, 606b to move to the closed position. The pins 2902a, 2902b can be locked in the slot 2904a, 2904b by any suitable means, such as, for example, any means described herein with reference to lock 607.

Referring to FIG. 30, in certain situations, the mitral valve 3001 of a patient can have a wide gap 3002 between the anterior leaflet 3003 and the posterior leaflet 3004 when the mitral valve is in a closed position (i.e., during the systolic phase). For example, the gap 3002 can have a width W between about 2.5 mm and about 17.5 mm, such as between about 5 mm and about 15 mm, such as between about 7.5 mm and about 12.5 mm, such as about 10 mm. In some situations, the gap 3002 can have a width W greater than 15 mm. In any of the above-mentioned situations, a valve repair device is desired that is capable of engaging the anterior leaflet 3003 and the posterior leaflet 3004 to close the gap 3002 and prevent regurgitation of blood through the mitral valve 3001.

Figure 31A:
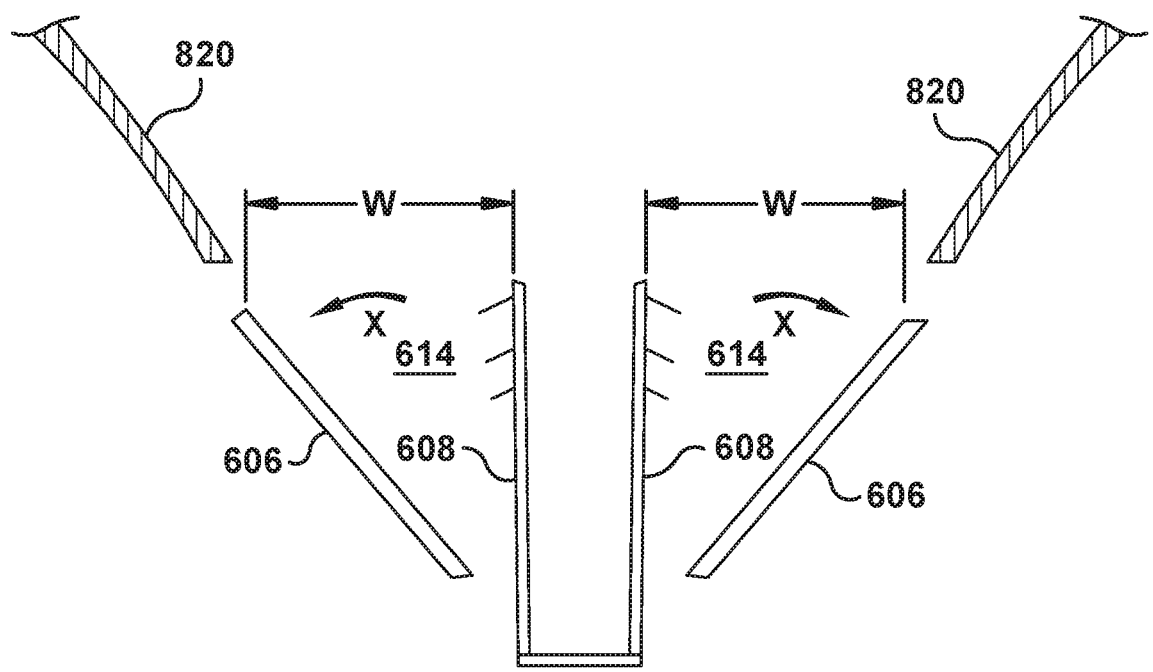
FIGS. 31A-31B illustrate another exemplary embodiment of a valve repair device, in which the paddles of the valve repair device expand to create a wide gap for receiving valve tissue.
Figure 31B:
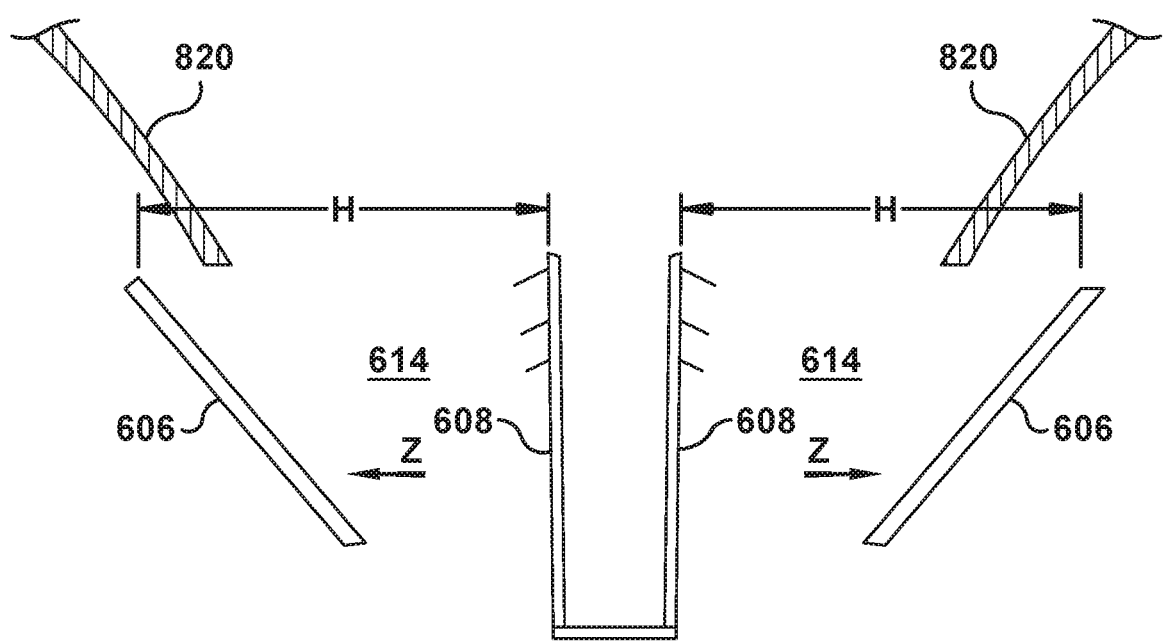

FIGS. 31A-37D provide various embodiments of valve repair devices 602 that are configured to close a wide gap 3002 (FIG. 30) between the anterior leaflet 3003 and posterior leaflet 3004 of a mitral valve 3001. Referring to FIGS. 31A-31B, an exemplary embodiment of a valve repair device 602 includes paddles 606 and gripping members 608. In addition, the valve repair device 602 can include any other features for a valve repair device discussed in the present application, and the valve repair device 602 can be positioned to engage valve tissue 820 as part of any suitable valve repair system (e.g., any valve repair system disclosed in the present application). Referring to FIG. 31A, the paddles 606 of the valve repair device 602 are pivoted outward in the direction X to create an opening 614 between the paddles 606 and the gripping members 608 having a width W. The width W can be, for example, between about 5 mm and about 15 mm, such as between 7.5 mm and about 12.5 mm, such as about 10 mm. In alternative embodiments, the width W can be less than 5 mm or greater than 15 mm. Referring to FIG. 31B, the paddles 606 of the valve repair device 602 are moved outward in the direction Z such that the opening 614 has a width H. The width H can be, for example, between about 10 mm and about 25 mm, such as between about 10 mm and about 20 mm, such as between about 12.5 mm and about 17.5 mm, such as about 15 mm. In alternative embodiments, the width H can be less than 10 mm or more than 25 mm. In certain embodiments, the ratio between the width H and the width W can be about 5 to 1 or less, such as about 4 to 1 or less such as about 3 to 1 or less, such as about 2 to 1 or less, such as about 1.5 to 1 or less, such as about 1.25 to 1 or less, such as about 1 to 1. The valve repair device 602 can be configured such that the paddles 606 are pivoted outward in the direction X and then moved outward in the direction Z to create the opening 614 having a width H between the paddles 606 and the gripping members 608. Alternatively, the valve repair device 602 can be configured such that the paddles are moved outward in the direction Z and then pivoted outward in the direction X to create width H between the paddles 606 and gripping members 608. In addition, the valve repair device 602 can be configured such that the paddles 606 are pivoted outward in the direction X and moved outward in the direction Z simultaneously to create the width H between the paddles 606 and the gripping members 608.

FIGS. 32A-32C illustrate a valve repair device 602 in which the paddles 606 are pivoted outward in the direction X, and, subsequently, moved outward in the direction Z to create a wider opening 614. FIG. 32A illustrates the valve repair device 602 in a closed position, such that the paddles 606 are engaging the gripping members 608. Referring to FIG. 32B, the paddles 606 are pivoted outward in the direction X to create an opening 614 having a width W for receiving valve tissue. Referring to FIG. 32C, after the paddles 606 are pivoted outward in the direction X, the paddles 606 are moved outward in the direction Z such that the opening 614 has a width H. After valve tissue is received in the openings 614 between the paddles 606 and the gripping members 608, the valve repair device is moved back to the closed position (as shown in FIG. 32A) to secure the valve repair device 602 to the valve tissue. The valve repair device 602 can include any other features for a valve repair device discussed in the present application, and the valve repair device 602 can be positioned to engage valve tissue 820 as part of any suitable valve repair system (e.g., any valve repair system disclosed in the present application).

FIGS. 33A-33C illustrate a valve repair device 602 in which the paddles 606 are moved outward in the direction Z, and, subsequently, pivoted outward in the direction X to create a wider opening 614. FIG. 33A illustrates the valve repair device 602 in a closed position, such that the paddles 606 are engaging the gripping members 608. Referring to FIG. 33B, the paddles 606 are moved outward in the direction Z to create an opening 614 having a width W for receiving valve tissue. Referring to FIG. 33C, after the paddles 606 are moved outward in the direction Z, the paddles 606 are pivoted outward in the direction X such that the opening 614 has a width H. After valve tissue is received in the openings 614 between the paddles 606 and the gripping members 608, the valve repair device is moved back to the closed position (as shown in FIG. 33A) to secure the valve repair device 602 to the valve tissue. The valve repair device 602 can include any other features for a valve repair device discussed in the present application, and the valve repair device 602 can be positioned to engage valve tissue 820 as part of any suitable valve repair system (e.g., any valve repair system disclosed in the present application).

While FIGS. 32A-32C illustrate a valve repair device 602 in which the paddles 606 are pivoted and then spread apart, and FIGS. 33A-33C illustrate a valve repair device 602 in which the paddles 606 are spread apart and then pivoted, it alternative embodiments, a valve repair device 602 can include paddles 606 that can be spread apart and pivoted simultaneously. In addition, in certain embodiments, the paddles 606 can be spread apart and pivoted independently of each other. That is, in the embodiments for the valve repair device 602 shown in FIGS. 32A-32C and 33A-33C, as well as the embodiment in which the spreading apart and pivoting of each paddle 606 is completed simultaneously, the paddles 606 can be controlled independently of each other.

Figure 34A:
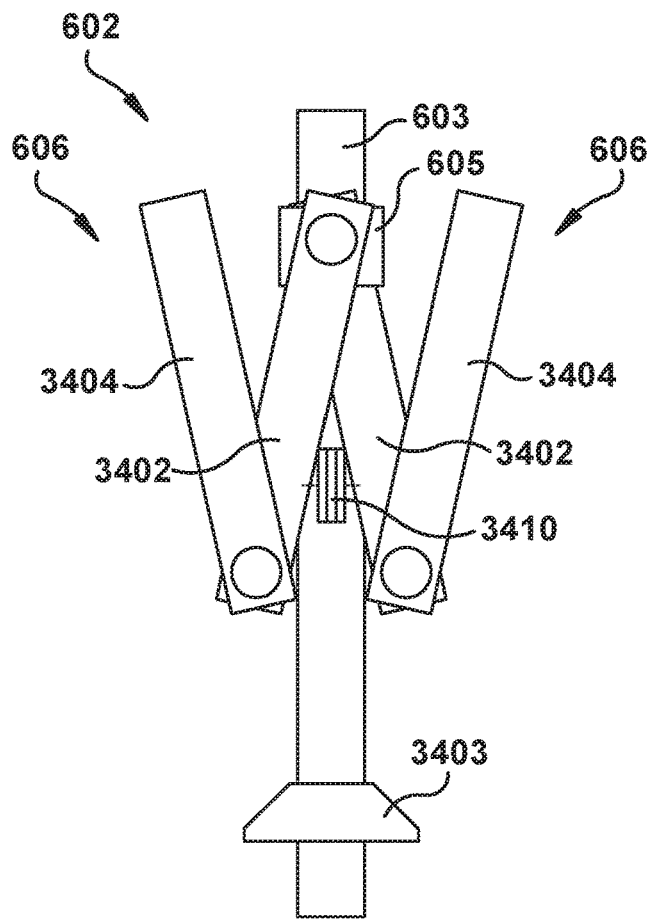
FIGS. 34A-34B illustrate another exemplary embodiment of a valve repair device, in which a "W"-shaped mechanism expands the paddles of the valve repair device to create a wide gap.
Figure 34B:
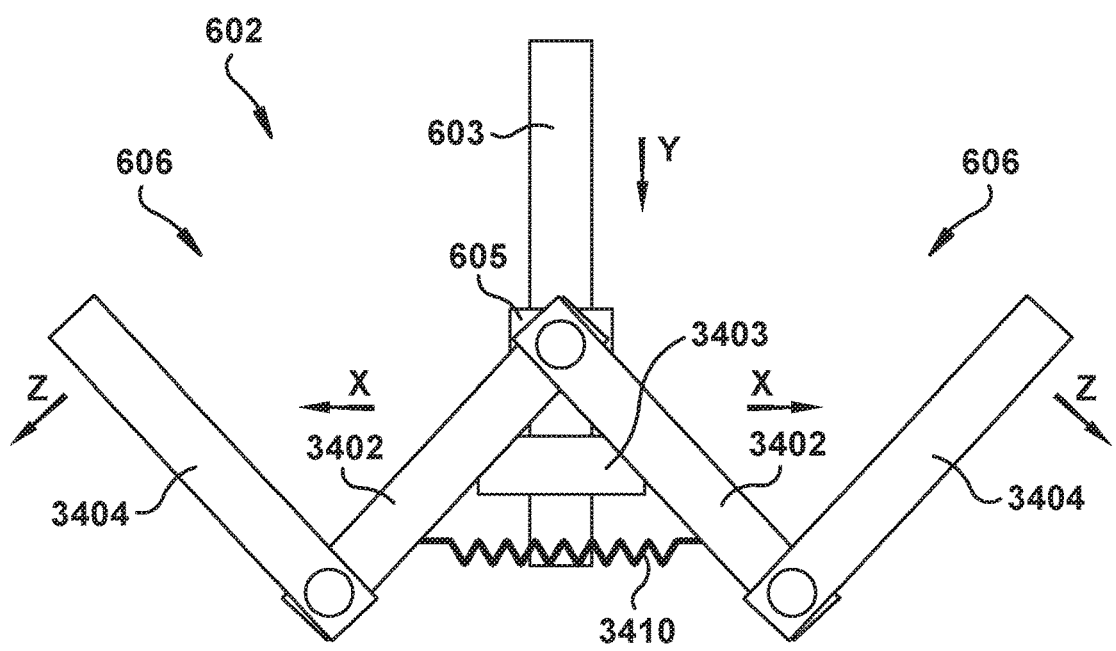

Referring to FIGS. 34A-34B, another exemplary embodiment of a valve repair device 602 configured to close a wide gap 3002 (FIG. 30) between the anterior leaflet 3003 and the posterior leaflet 3004 includes a W-shaped mechanism. In particular, the valve repair device 602 includes a coupler 605 configured to move along a shaft 603 and paddles 606 pivotally attached to the coupler 605. The paddles 606 include an inner link 3402 and an outer link 3404. The inner link 3402 of each paddle 606 is pivotally attached to coupler 605, and the outer link 3404 of each paddle 606 is pivotally attached to the corresponding inner link 3402. Referring to FIG. 34A, the valve repair device 602 is shown in a closed position. Referring to FIG. 34B, movement of the coupler 605 in the direction Y causes the inner links 3402 of the paddles 606 to extend in an outward direction X. In the illustrated example, the inner links 3402 engage a cam member 3403, which forces the inner links 3402 to open in the X direction. Although the illustrated embodiment shows a valve repair device 602 having generally linear links 3402, 3404 that create a W-shaped mechanism, it should be understood that the links 3402, 3404 may take any suitable form that allows the valve repair device 602 to function as shown in FIGS. 34A-34B. In embodiments in which the links 3402, 3404 take non-linear forms (e.g., a curved form), the valve repair device may not have a W-shaped mechanism, however, the valve repair device can include similar connections such that the valve repair device will function as shown in FIGS. 34A-34B.

The outer links 3404 can be moved to the illustrated more open position in the direction Z in a variety of different ways. For example, the outer links cam be moved using any of the clasp control arrangements described herein. For example, movement of the outer links 3404 can be controlled using any of the clasp control arrangements shown in FIGS. 22-26 and/or any of the paddle control arrangements described herein. In one embodiment, referring to FIGS. 34C-34D, a link 3411 is attached to the pivotal connection between the inner link 3402 and the coupler 605 and the pivotal connection between the inner link 3402 and the outer link 3404, such that movement of the coupler 605 in the direction Y causes a first end 3413 of the link 3411 to rotate in the direction M with the pivotal connection 3475, which causes a second end 3415 of the link 3411 to rotate in the direction N with the pivotal connection 3477. The rotation of the second end 3415 of the link 3411 in the direction N causes the outer link 3404 to move to an open position in the direction Z.

Figure 34C:
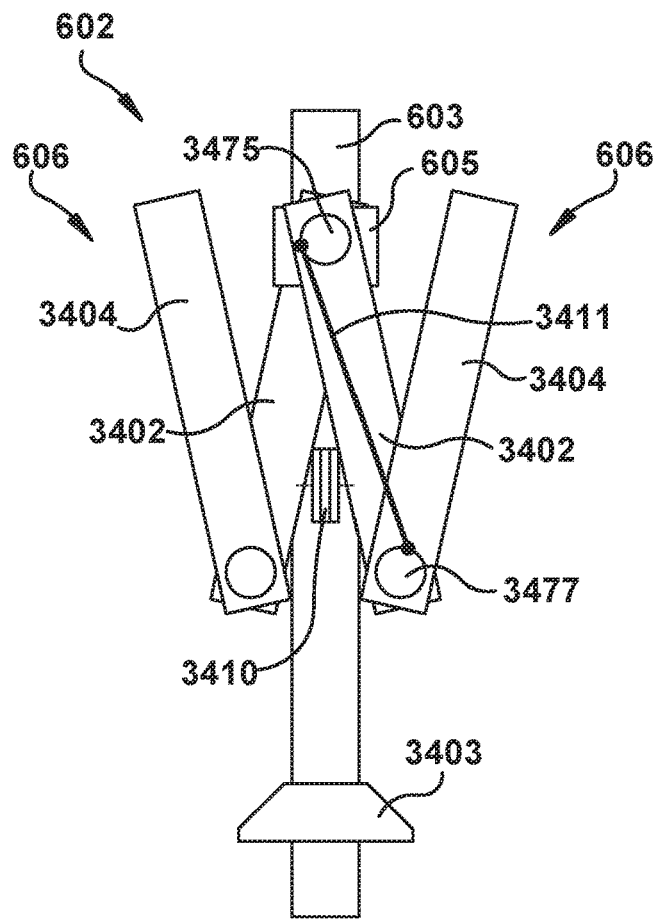
FIGS. 34C-34D illustrate another exemplary embodiment of a valve repair device, in which a "W"-shaped mechanism expands the paddles of the valve repair device to create a wide gap.
Figure 34D:
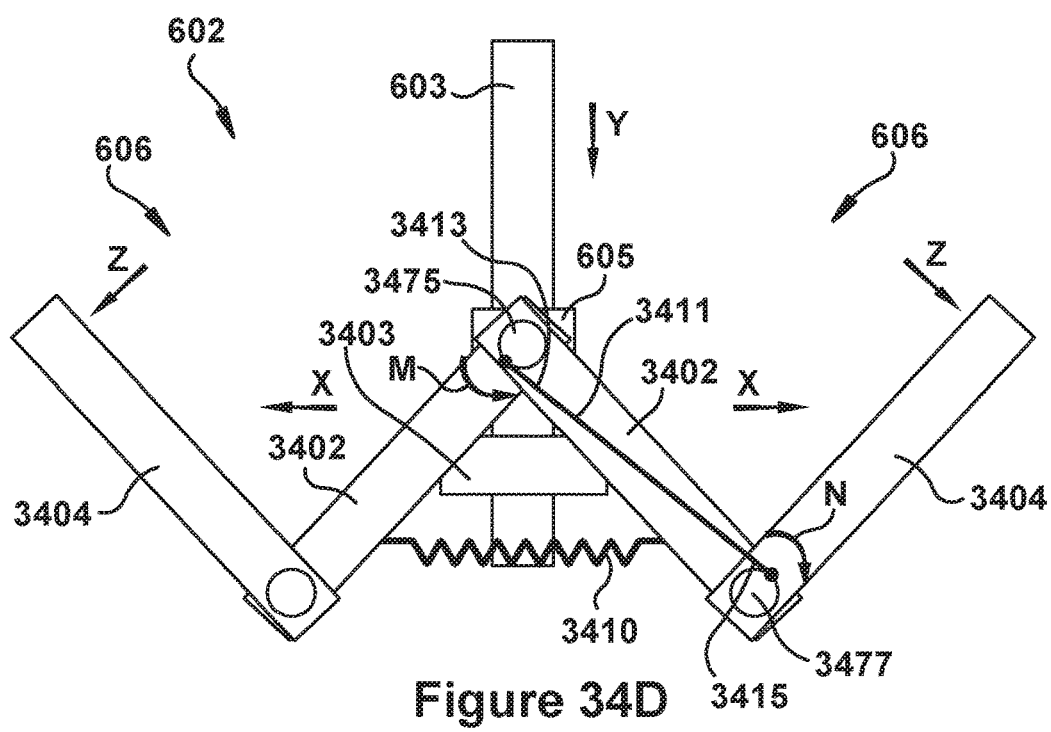

For illustrative purposes, the embodiment shown in FIGS. 34C-34D show a link 3411 for one of the paddles 606, however, it should be understood that another link 3411 interacts with the other paddle in the same manner described above to cause the outer link 3404 of the other paddle to move to an open position in the direction Z. In an alternative embodiment, a four-bar linkage can be used to move the paddles 606 to an open position. In another alternative embodiment, a suture can be removably attached to the outer links 3404 of the paddles 606, and the suture can be controlled to move the outer links 3404 of the paddles 606 to an open position in the direction Z.

In certain embodiments, the valve repair device 602 includes a biasing member 3410 (e.g., a spring) that attaches the inner links 3402 of the paddles 606 to each other. The biasing member 3410 maintains the inner links 3402 in a closed position (as shown in FIGS. 34A and 34C), until the inner links 3402 engage the cam member 3403 (as shown in FIGS. 34B and 34D). The valve repair device 602 can include any other features for a valve repair device discussed in the present application, and the valve repair device 602 can be positioned to engage valve tissue 820 as part of any suitable valve repair system (e.g., any valve repair system disclosed in the present application).

Figure 35B:
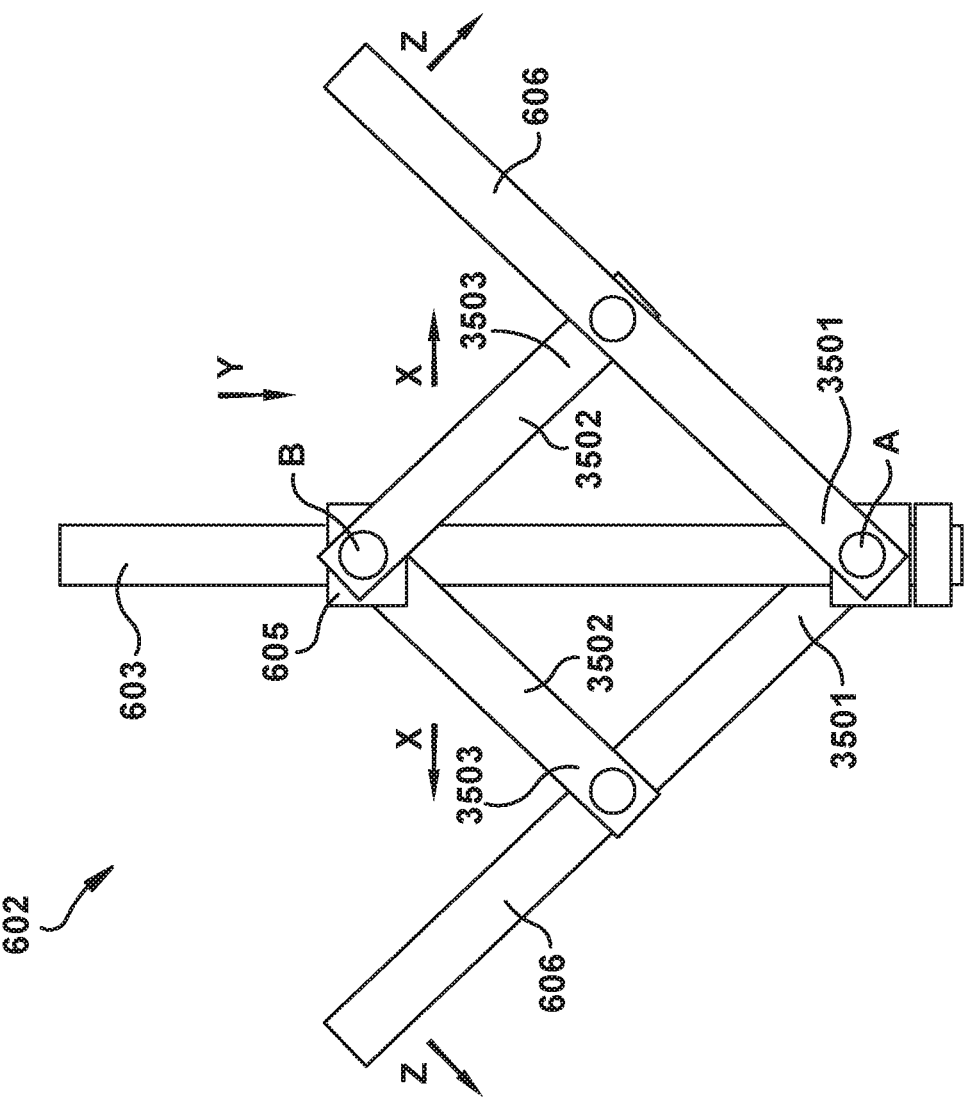
FIGS. 35A-35B illustrate another exemplary embodiment of a valve repair device, in which a "W"-shaped mechanism expands paddles of the valve repair device to create a wide gap for receiving valve tissue.
Figure 35A:
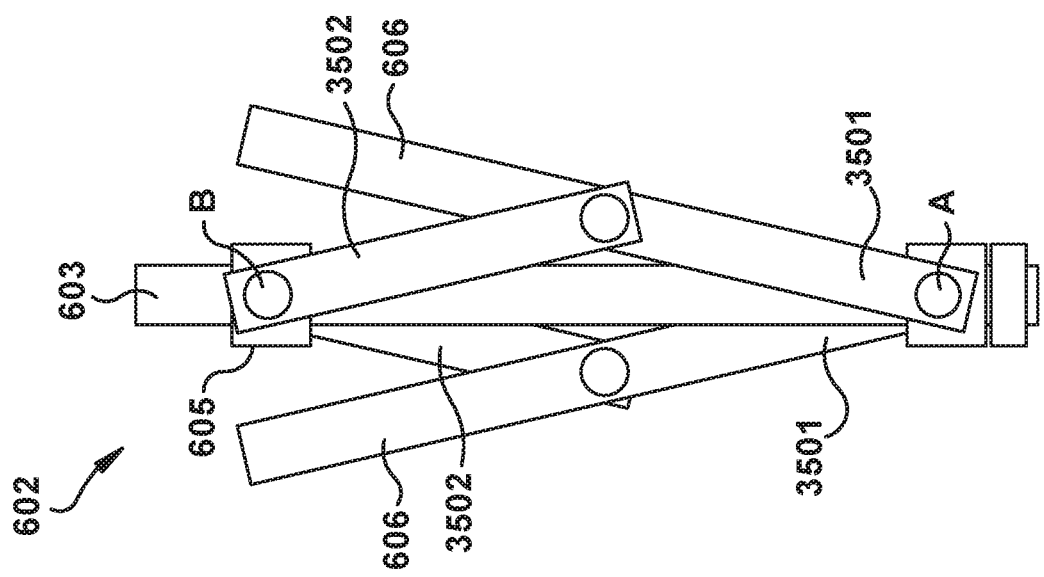

Referring to FIGS. 35A-35B, another exemplary embodiment of a valve repair device 602 configured to close a wide gap 3002 (FIG. 30) between the anterior leaflet 3003 and the posterior leaflet 3004 includes a W-shaped mechanism. In particular, the valve repair device 602 includes a coupler 605 configured to be moved along a shaft 603 and paddles 606 pivotally attached to the shaft and to the coupler 605. The lower ends 3501 of each paddle 606 of the valve repair device 602 are pivotally connected to the shaft at point A. Each of the paddles 606 include an intermediate member 3502 that pivotally attach the paddles to the coupler 605 at pivot point B. Referring to FIG. 35A, the valve repair device 602 is shown in a closed position. Referring to FIG. 35B, movement of the coupler 605 in the direction Y causes the intermediate members 3502 of the paddles 606 to pivot such that a lower end 3503 of the intermediate members 3502 extend in an outward direction X, which causes the paddles 606 to move to an open position in the direction Z. The valve repair device 602 can include any other features for a valve repair device discussed in the present application, and the valve repair device 602 can be positioned to engage valve tissue 820 as part of any suitable valve repair system (e.g., any valve repair system disclosed in the present application).

Figure 36A:
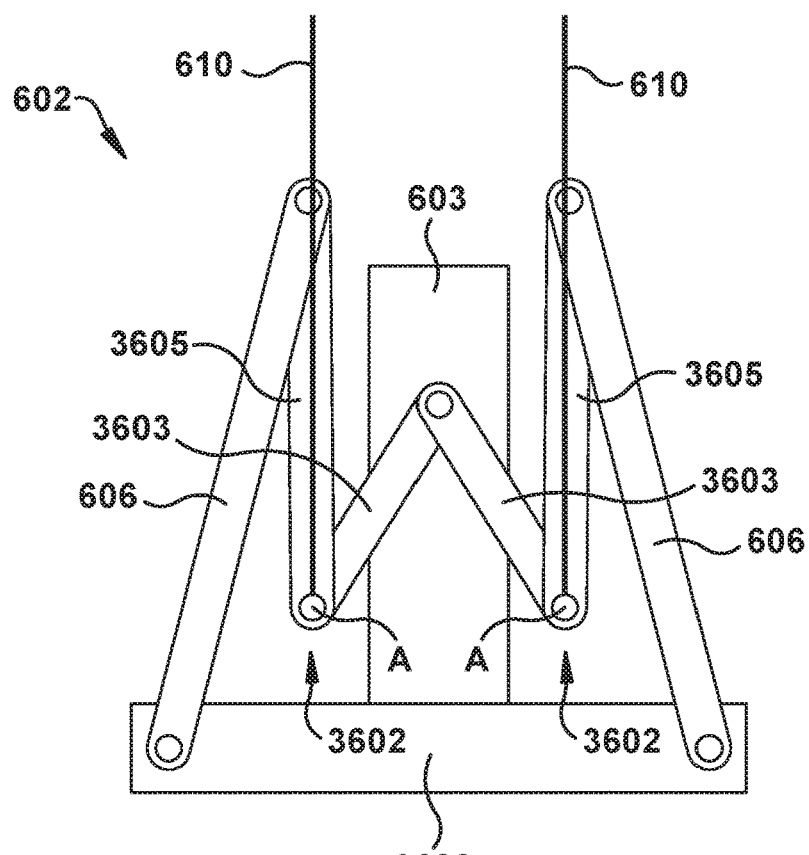
FIGS. 36A-36B illustrate another exemplary embodiment of a valve repair device, in which a "W"-shaped mechanism expands paddles of the valve repair device to create a wide gap.
Figure 36B:
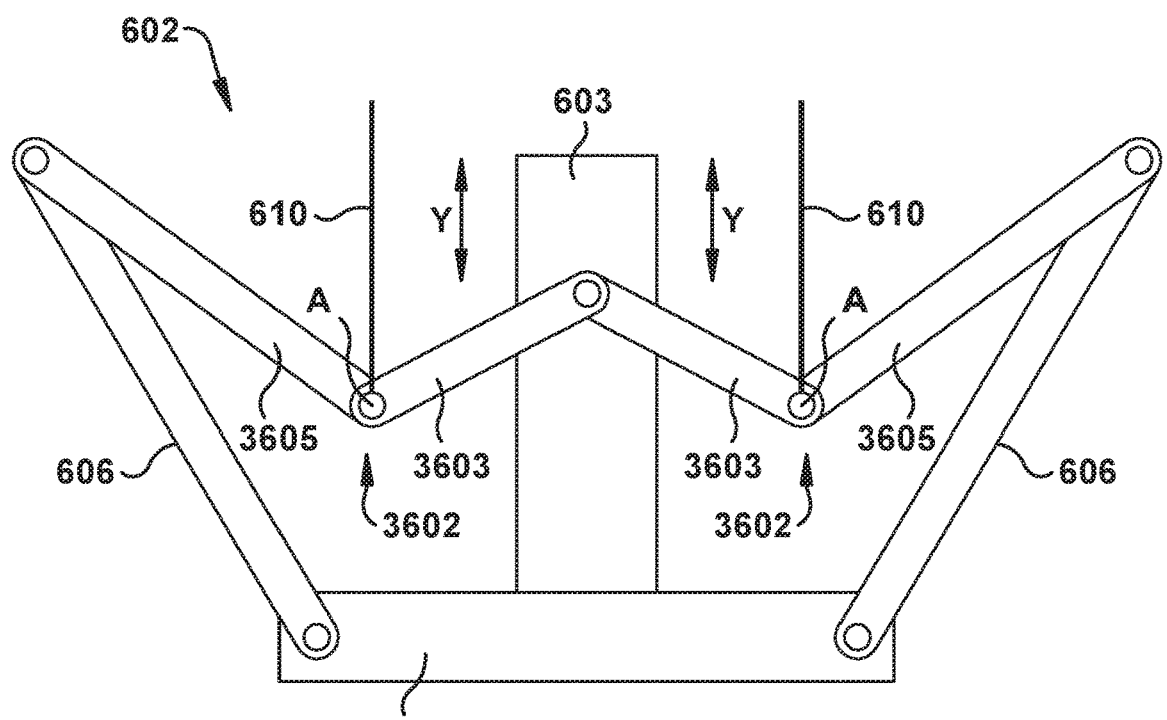

Referring to FIGS. 36A-36B, another exemplary embodiment of a valve repair device 602 configured to close a wide gap 3002 (FIG. 30) between the anterior leaflet 3003 and the posterior leaflet 3004 includes a W-shaped mechanism. In particular, the valve repair device 602 includes paddles 606 having a linkage 3602 pivotally attaching the paddles 606 to a shaft 603 of the valve repair device 602. The linkage 3602 includes an inner link 3603 and an outer link 3605. The inner link 3603 is pivotally attached to the shaft 603 and pivotally attached to the outer link 3605. The outer link 3605 is pivotally attached to the inner link 3603 and pivotally attached to the paddle 606. The paddles 606 are also attached to a link 3608 of the valve repair device 602. A paddle control mechanism 610 is configured to move the pivotal connection at point A between the inner link 3603 and the outer link 3605 of the linkage 3602 in the direction Y, which causes the paddles 606 to move between an open position (as shown in FIG. 36B) and a closed position (as shown in FIG. 36A).

Still referring to FIGS. 36A and 36B, although the paddle control mechanism is shown attached at the pivotal connection point A, it should be understood that the paddle control mechanism 610 can be attached to one or more of any of the links of the valve repair device 602. For example, the paddle control mechanism 610 can be coupled to the paddle 606, the link 3605, and/or the link 3603. The paddle control mechanism 610 can take any suitable form, such as, for example, a control wire or any other form described in the present application. For example, the paddle control device 610 can take the form of any of the gripper control devices shown in FIGS. 6-8 and 22-26. The valve repair device 602 can include any other features for a valve repair device discussed in the present application.

Figure 36C:
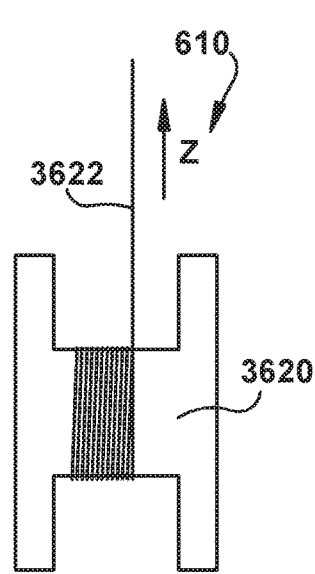
FIG. 36C illustrate an exemplary embodiment of a paddle control mechanism for the valve repair device of FIGS. 36A-36B.

Referring to FIG. 36C, the paddle control mechanism 610 of the embodiment illustrated by FIGS. 36A and 36B can include a spool 3620 and a line 3622 (e.g., a suture, a wire, etc.), and the line is attached to and wrapped around the spool. In this embodiment, creating a force on the line 3622 in the direction Z causes the spool 3620 to turn and line 3622 to be unwrapped from the spool. In this embodiment, the rotation of the spool 3620 causes the paddle control mechanism 610 to move in the direction Y and the valve repair device 602 to move to the open position (as shown in FIG. 36B).

Figure 36D:
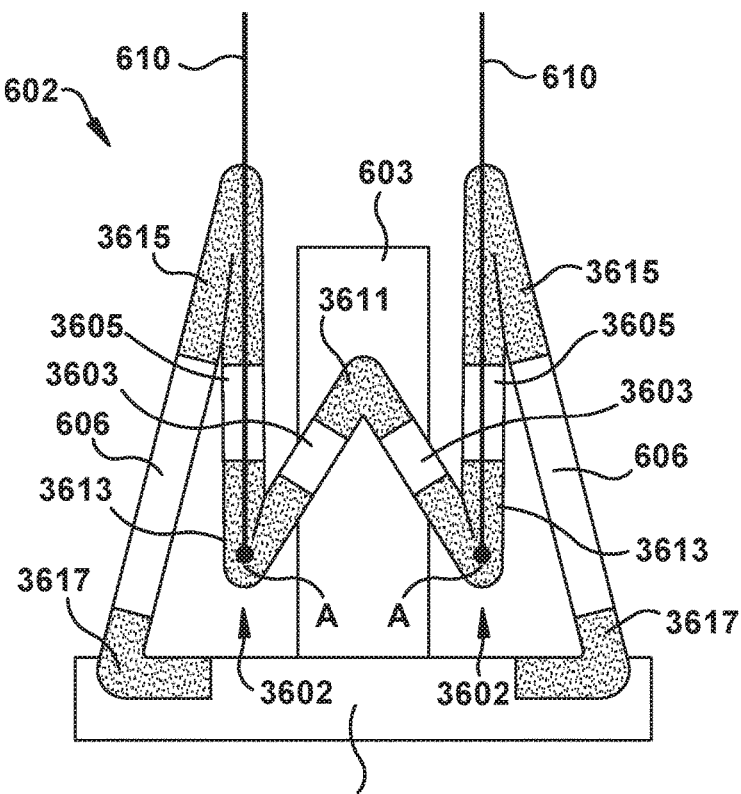
FIGS. 36D-36E illustrate another exemplary embodiment of a valve repair device, in which a "W"-shaped mechanism expands paddles of the valve repair device to create a wide gap.
Figure 36E:
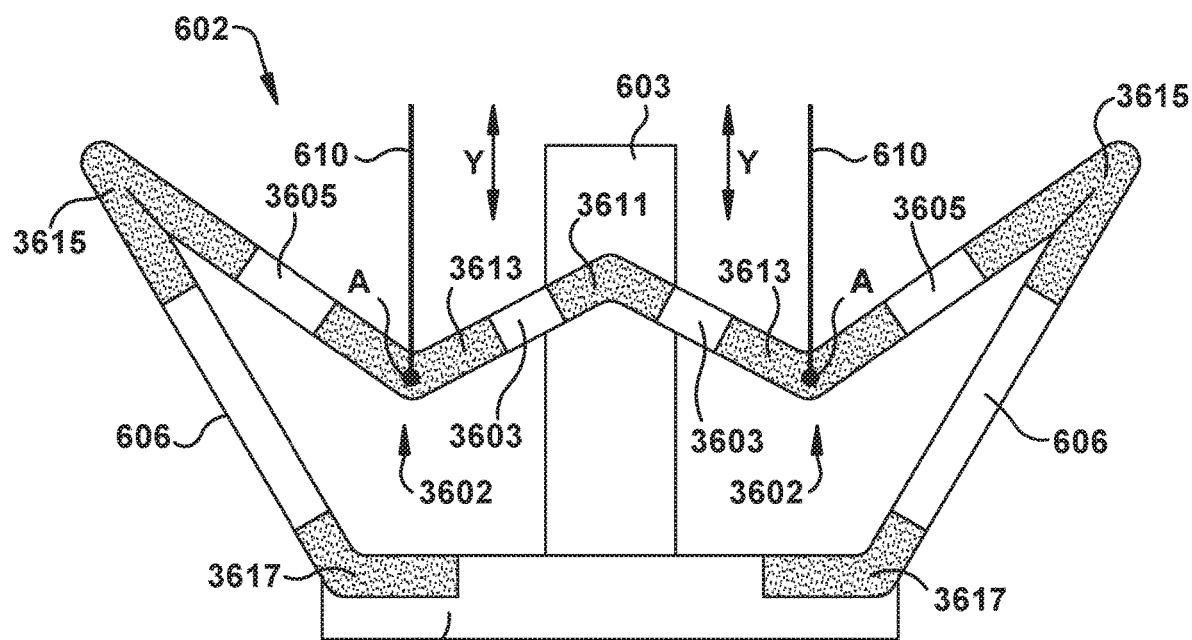

Referring to FIGS. 36D-36E, another exemplary embodiment of a valve repair device 602 configured to close a wide gap 3002 (FIG. 30) between the anterior leaflet 3003 and the posterior leaflet 3004 includes a semi-rigid W-shaped mechanism. In particular, the valve repair device 602 has a linkage 3602 that flexibly attaches the paddles 606 to a shaft 603 of the valve repair device 602. The linkage 3602 includes a rigid inner link 3603 and an outer rigid link 3605. The inner rigid link 3603 is flexibly attached to the shaft 603 by a flexible member or portion 3613 and flexibly attached to the outer rigid link 3605 by a flexible member or portion 3611, and the outer rigid link 3506 is flexibly attached to the paddle 606 by a flexible member or portion 3615. The paddles 606 are also flexibly attached to a link 3608 of the valve repair device 602 by a flexible member or portion 3617. The rigid links 3603, 3605 can be made of, for example, steel or nitinol. The flexible members 3611, 3613, 3615, 3617 can be made of, for example, nitinol. A paddle control mechanism 610 is configured to move the pivotal connection at point A between the inner link 3603 and the outer link 3605 of the linkage 3602 in the direction Y, which causes the paddles 606 to move between an open position (as shown in FIG. 36D) and a closed position (as shown in FIG. 36C). However, the paddle control mechanism 610 can be attached to one or more of any of the links of the valve repair device. For example, the paddle control mechanism 610 can be coupled to the paddle 606, the link 3605, and/or the link 3603. The paddle control mechanism 610 can take any suitable form, such as, for example, a control wire or any other form described in the present application. For example, the paddle control device 610 can take the form of any of the gripper control devices shown in FIGS. 6-8 and 22-26. The valve repair device 602 can include any other features for a valve repair device discussed in the present application.

Referring to FIGS. 37A-37D, another exemplary embodiment of a valve repair device 602 configured to close a wide gap 3002 (FIG. 30) between the anterior leaflet 3003 and the posterior leaflet 3004 includes wire mesh paddles 606 and an internal cam 3702 configured to push the mesh paddles 606 apart. The internal cam 3702 is rotatably attached to the shaft 603 such that the cam can be moved between a first position (as shown in FIGS. 37A-37B) and a second position (as shown in FIGS. 37C-37D). FIG. 37B is a top view illustrating the internal cam 3702 in the first position, shown along the lines B-B in FIG. 37A. FIG. 37D is a top view illustrating the internal cam 3702 in the second position, shown along the lines D-D in FIG. 37C.

Referring to FIGS. 37A and 37B, when the internal cam 3702 is in the first position, the internal cam does not engage the paddles 606, and the valve repair device is maintained in a closed position. Referring to FIGS. 37C and 37D, when the internal cam 3702 is in the second position, the internal cam engages the paddles 606 to move the paddles to move the paddles in an outward direction X to an open position. The valve repair device 602 is moved from the open position to the closed position by moving the internal cam 3702 from the second position to the first position.

In some embodiments, referring to FIGS. 37E-37F, the paddles 606 of the valve repair device can include a flexible member or portion 3711 that bias the paddles into the closed position or the open position. The flexible member or portion 3711 can be configured to flex upon being engaged by the cam 3702 to allow the paddles 606 to move to the open position. The flexible member or portion 3711 is also configured to widen the reach of the paddles 606 when the paddles are in the open position. Any other suitable mechanisms can be used to bias the paddles in the closed position and/or widen the reach of the paddles 606 when the paddles are in the open position, such as, for example, a spring-loaded mechanism. The valve repair device 602 can include any other features for a valve repair device discussed in the present application, and the valve repair device 602 can be positioned to engage valve tissue 820 as part of any suitable valve repair system (e.g., any valve repair system disclosed in the present application). The mesh paddles 606 can be made out of any suitable material that can be expanded by the internal cam 3702, such as, for example, nitinol, stainless steel, or any braided or electrospun material.

Figure 38:
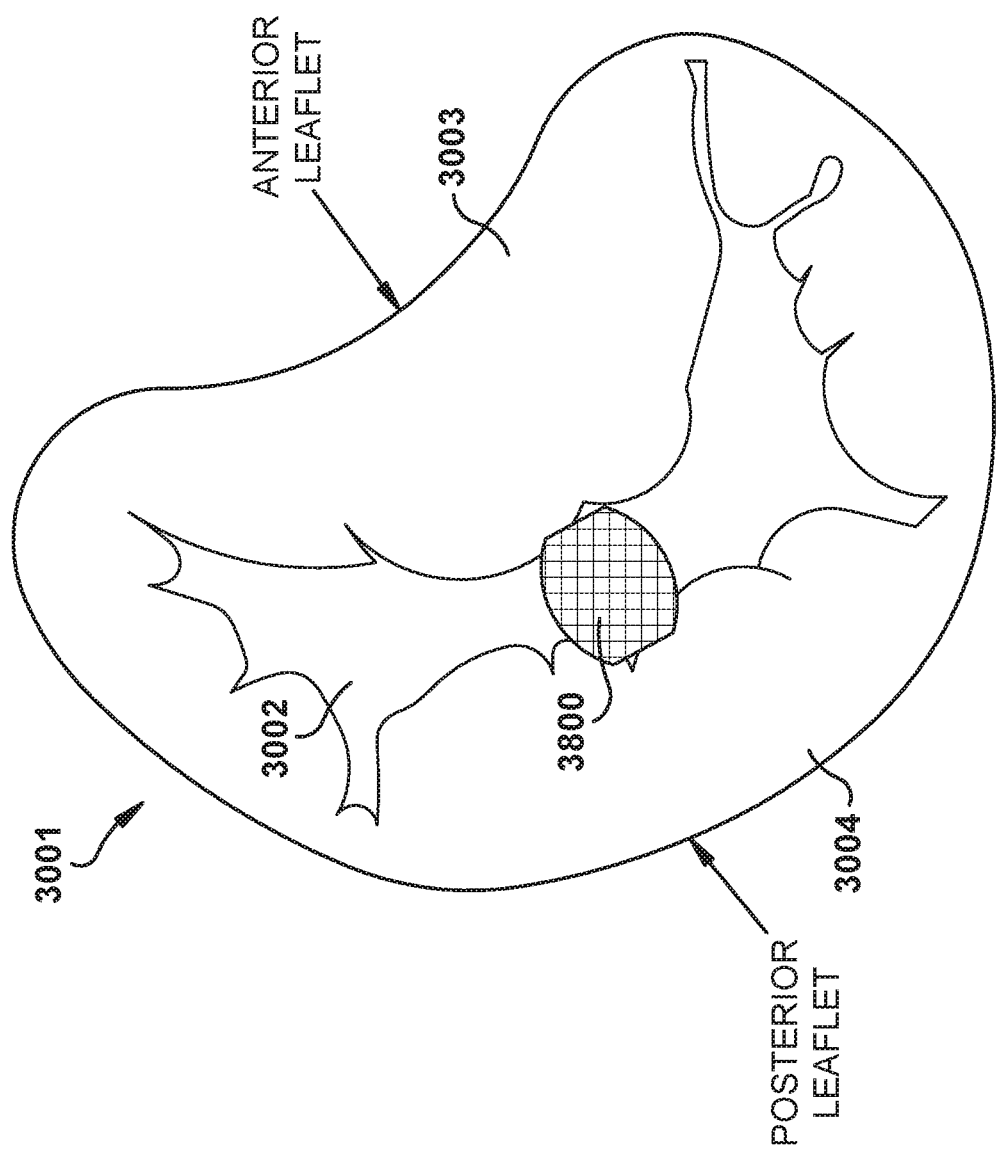
FIG. 38 illustrates an exemplary embodiment of a valve repair device that includes an exemplary embodiment of a spacer element, in which the valve repair device is attached to a mitral valve.
Figure 39:
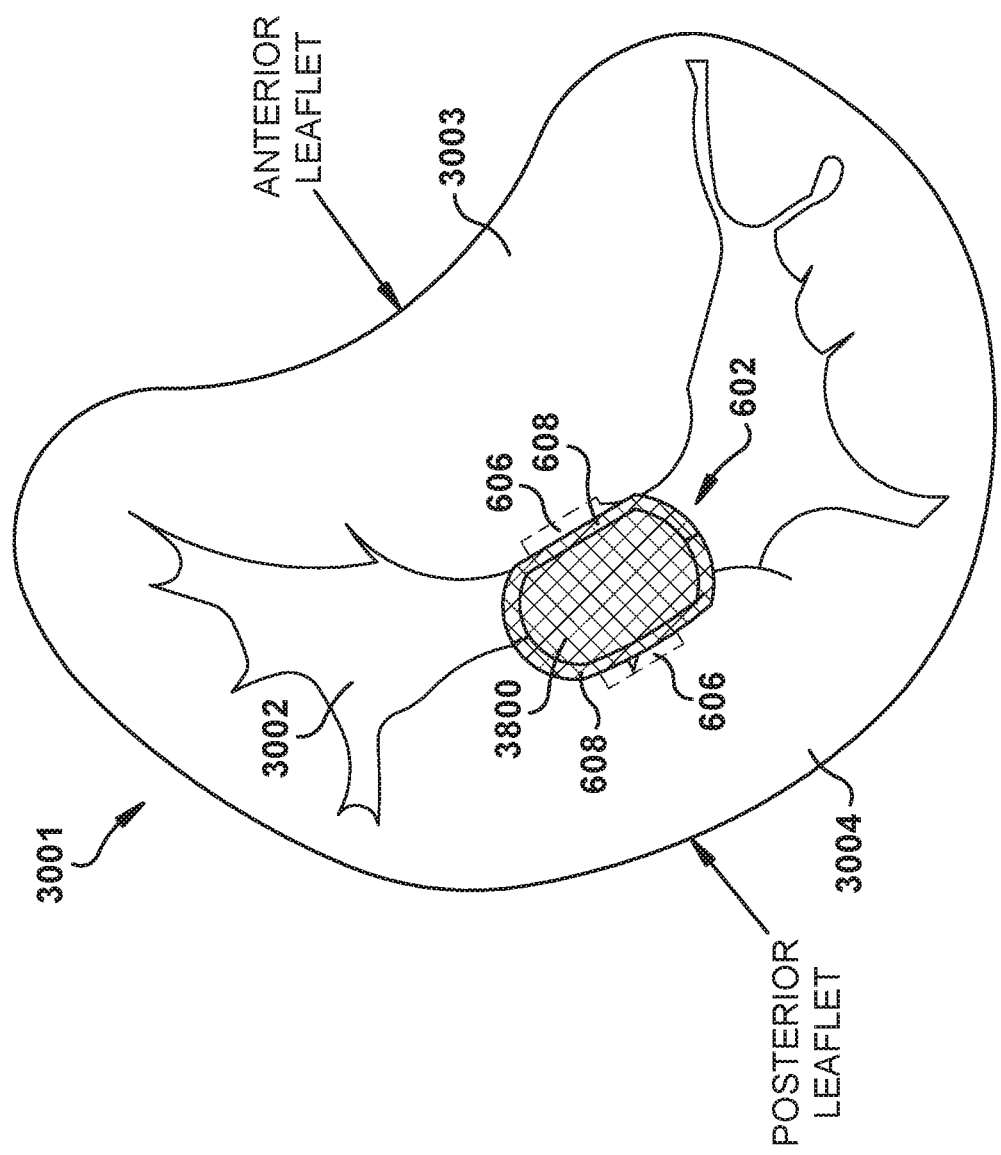
FIG. 39 illustrates another exemplary embodiment of a valve repair device that includes an exemplary embodiment of a spacer element, and in which the valve repair device is attached to a mitral valve.

Referring to FIGS. 38-39, in certain situations, the mitral valve 3001 of a patient can have a wide gap 3002 between the anterior leaflet 3003 and the posterior leaflet 3004 when the mitral valve is in a closed position (i.e., during the systolic phase). For example, the gap 3002 can have a width W between about 2.5 mm and about 17.5 mm, such as between about 5 mm and about 15 mm, such as between about 7.5 mm and about 12.5 mm, such as about 10 mm. In some situations, the gap 3002 can have a width W greater than 15 mm. In any of the above-mentioned situations, a valve repair device is desired that fills a sufficient volume to allow the gap 3002 to be closed or filled without placing a large amount of strain on the leaflets 3003, 3004. For example, the valve repair device can include a spacer element 3800.

Referring to FIG. 39, in certain embodiments, the spacer element 3800 is attached to the valve repair device 602, such that, when the paddles 606 and gripping members 608 secure the valve repair device 602 to the mitral valve 3001, the spacer element 3800 is disposed in the gap 3002 between the anterior leaflet 3003 and the posterior leaflet 3004. The spacer element 3800 can be made of any suitable material, such as, for example, braided mesh, fabric, biocompatible material, foam, pericardial tissue, any material disclosed herein, etc.

Figure 40B:
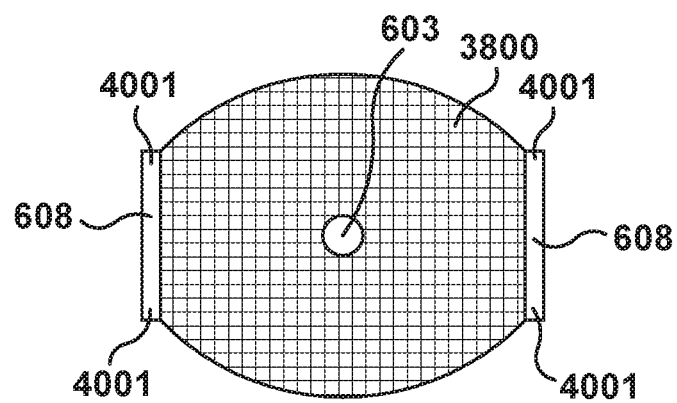
FIGS. 40A-40B illustrate another exemplary embodiment of a valve repair device that includes an exemplary embodiment of a spacer element, in which the spacer element is attached to a shaft of the valve repair device.
Figure 40A:
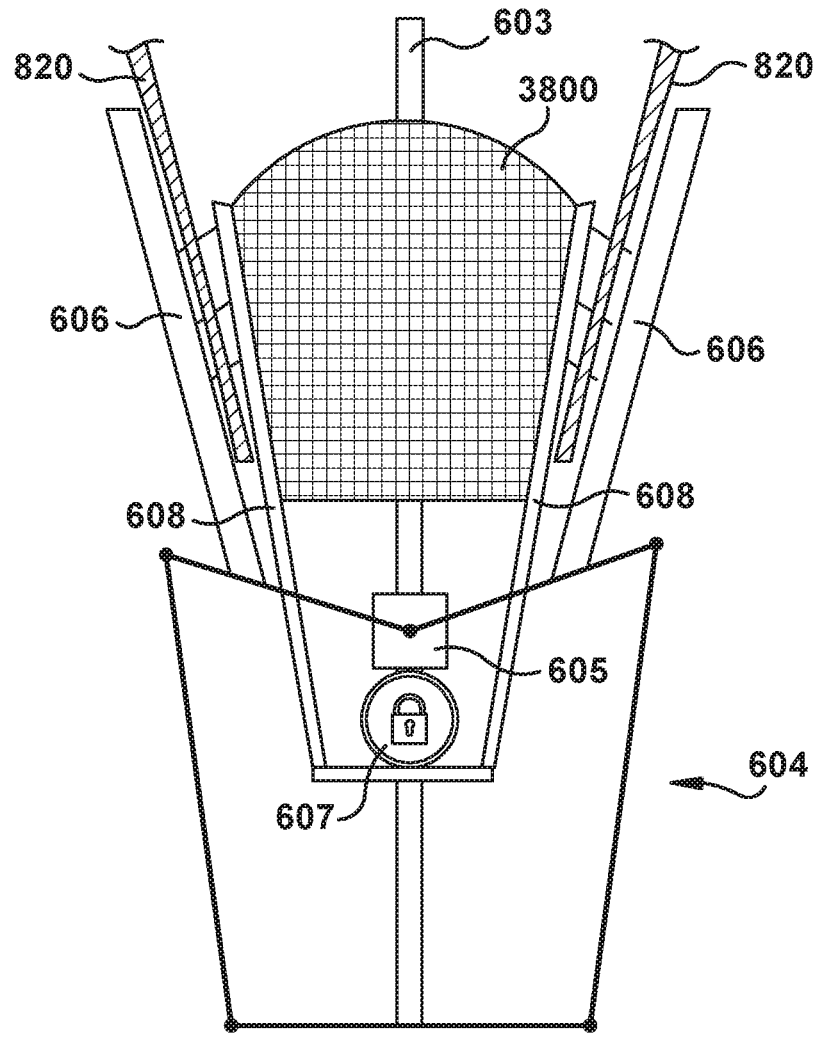

Referring to FIGS. 40A-40B, an exemplary embodiment of a valve repair device 602 has a spacer element 3800 attached to the shaft 603 of the valve repair device. The spacer element 3800 can extend past the outer edges 4001 of the gripping members 3800 as illustrated for providing additional surface area for closing the gap 3002 (FIGS. 38-39) of a mitral valve 301. In an alternative embodiment, the coupler member 605 can take the form of the spacer element 3800. That is, a single element can be used as the coupler member 605 that causes the paddles 606 to move between the open and closed positions and the spacer element 3800 that closes the gap between the leaflets 3003, 3004 when the valve repair device 602 is attached to the leaflets. The valve repair device 602 can include any other features for a valve repair device discussed in the present application, and the valve repair device 602 can be positioned to engage valve tissue 820 as part of any suitable valve repair system (e.g., any valve repair system disclosed in the present application).

Figure 42A:
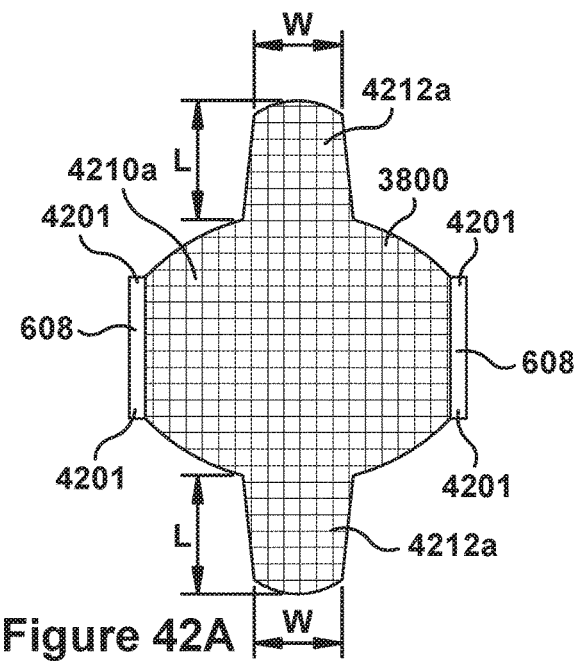
FIGS. 42A-42C illustrate the valve repair device of FIGS. 40A-40B with the spacer element having various shapes.
Figure 42B:
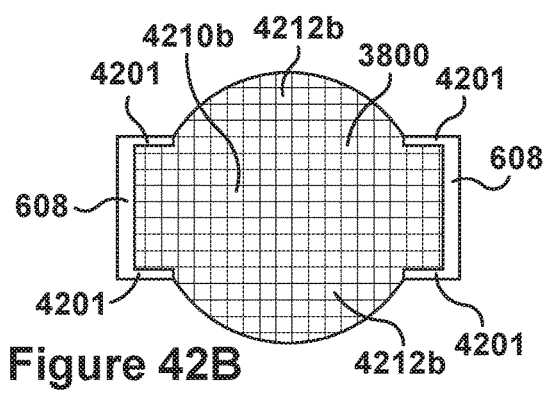
Figure 42C:
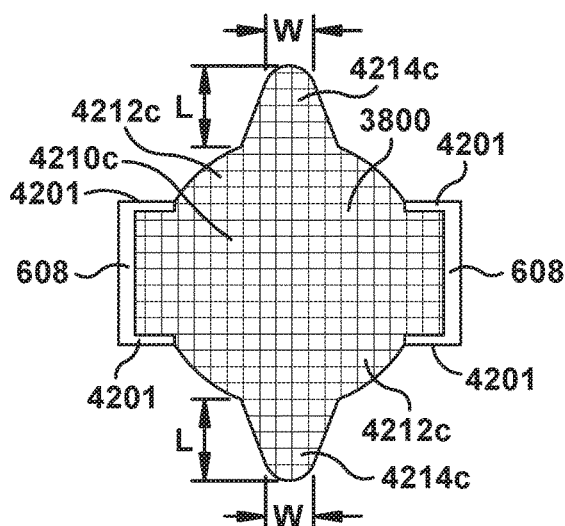

Referring to FIGS. 42A-42C, the spacer element 3800 shown in FIGS. 40A-40B can take a variety of different shapes. Referring to FIG. 42A, an exemplary embodiment of a spacer element 3800 includes a main body 4210*a* extending between the gripping members 608 and past the edges 4201 of the gripping members, and extended portions 4212*a* that extend from the main body 4210*a*. The extended portions 4212*a* allow portions of the gap 3002 (FIGS. 38-39) of the mitral valve between the anterior leaflet 3003 and posterior leaflet 3004 and adjacent to the valve repair device 602 to be filled when the valve repair device is in a closed position. That is, when a valve repair device 602 is attached to a mitral valve to prevent regurgitation of blood through the mitral valve, the portions of the mitral valve next to the valve repair device may include openings from the tissue of the mitral valve extending around the valve repair device. The extended portions 4212*a* are configured to fill or plug the openings adjacent to the valve repair device 602. In the illustrated embodiment, the length L of the extended portions 4212*a* are greater than the width W of the extended portions.

Referring to FIG. 42B, another exemplary embodiment of a spacer element 3800 includes a main body 4210*b* extending between the gripping members 608 and extended portions 4212*b* that extend from the main body 4210*b*. In the illustrated embodiment, the extended portions 4212*b* have a semicircular shape. The extended portions 4212*b* are configured to fill the openings adjacent to the valve repair device 602 due to tissue of the mitral valve extending around the valve repair device.

Referring to FIG. 42C, another exemplary embodiment of a spacer element 3800 includes a main base assembly 4210*c* extending between the gripping members 608, first extending portions 4212*c* that extend from the main body 4210*c*, and second extending portions 4214*c* that extend from the first extending portions 4212*c*. In the illustrated embodiment, the first extended portions 4212*c* have a semicircular shape, and the second extended portions 4214*c* have a length L that is greater than its width W. The extended portions 4212*b* are configured to fill the openings adjacent to the valve repair device 602 due to tissue of the mitral valve extending around the valve repair device.

Figure 41B:
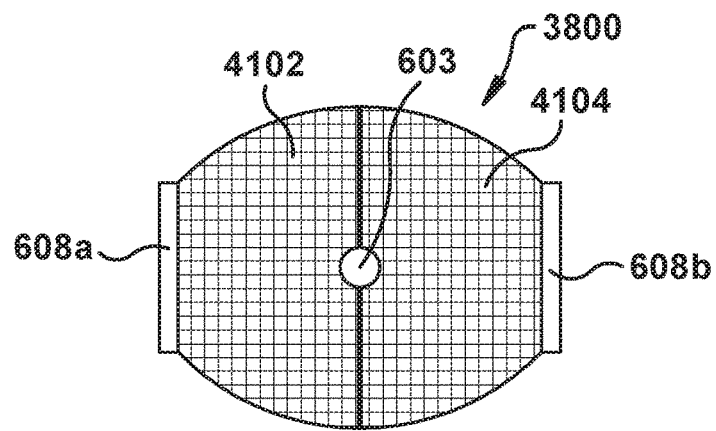
FIGS. 41A-41D illustrate another exemplary embodiment of a valve repair device that includes an exemplary embodiment of a spacer element with a first portion attached to a first gripping member of the valve repair device and a second portion attached to a second gripping member of the valve repair device.
Figure 41A:
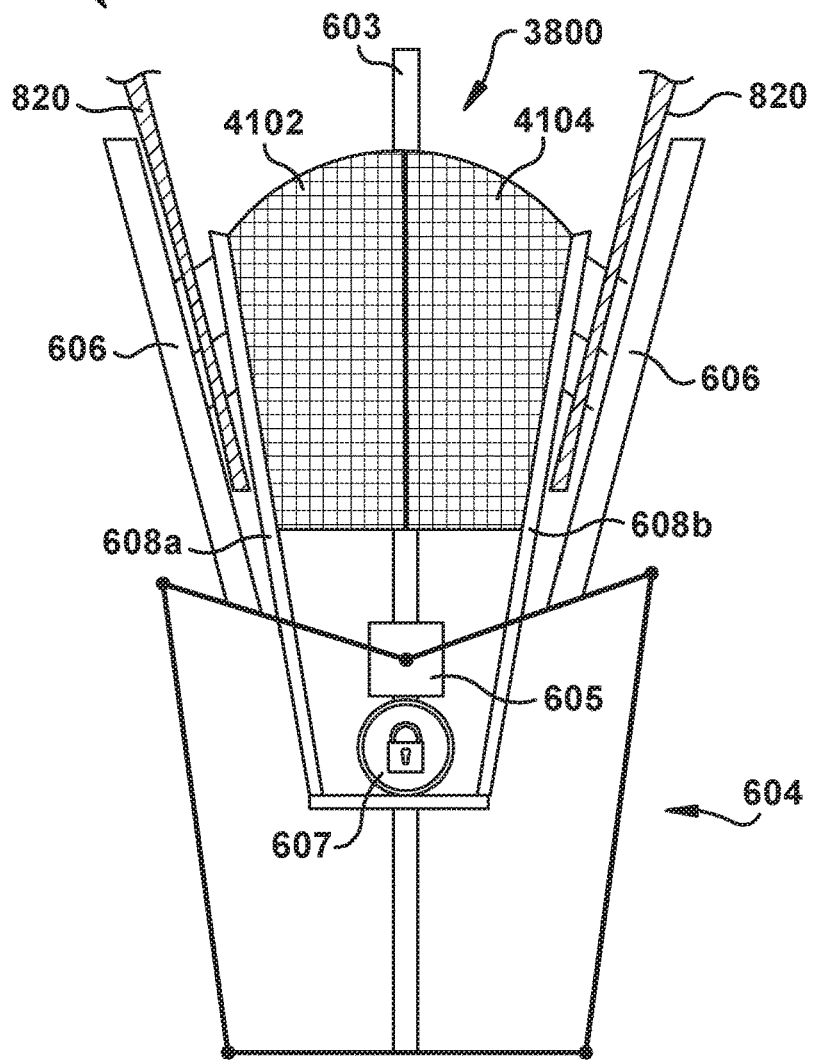
Figure 41D:
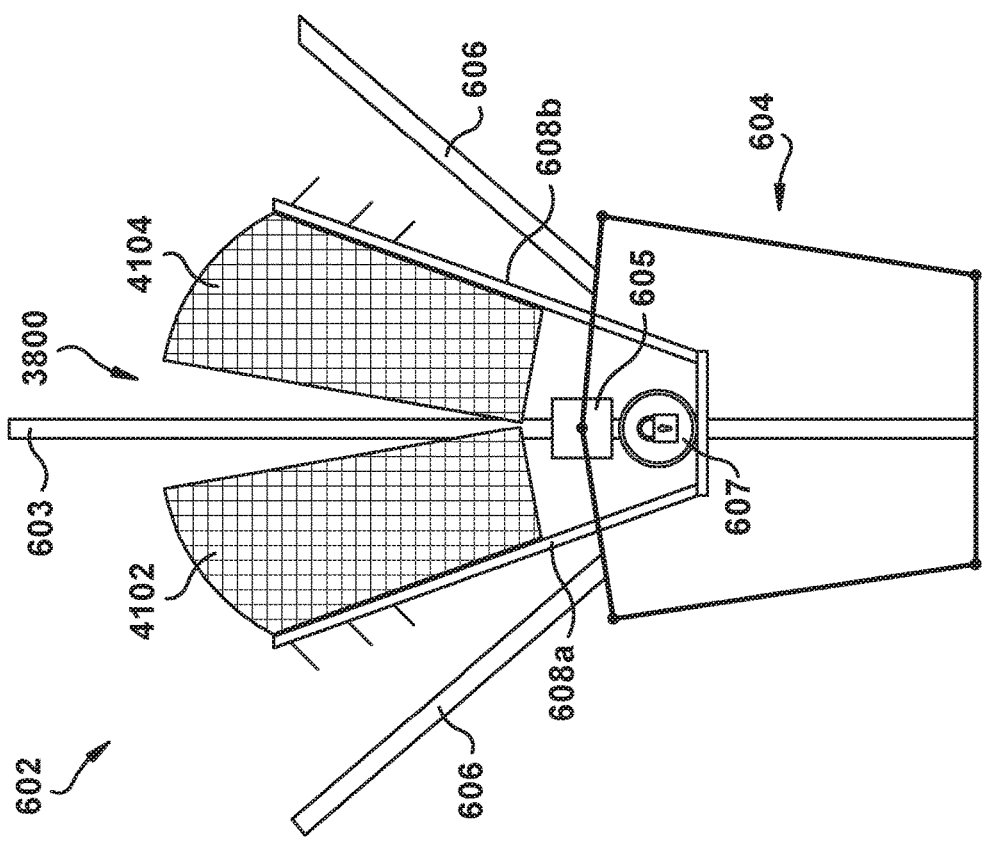
Figure 41C:
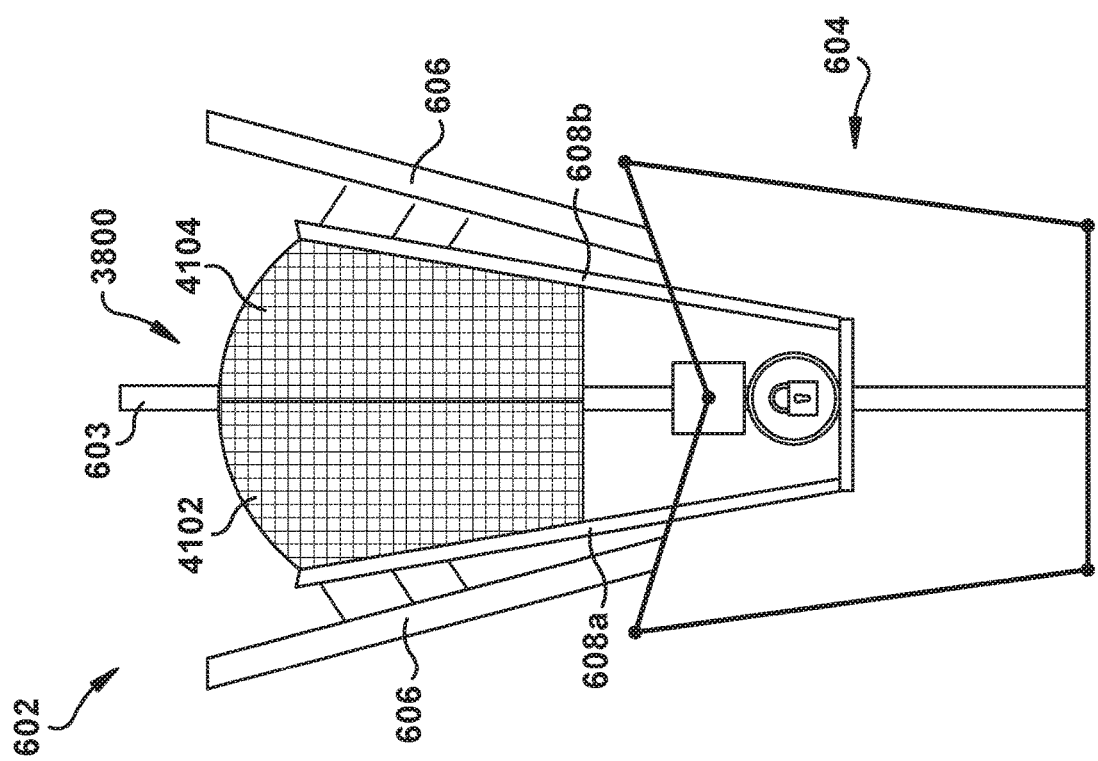

Referring to FIGS. 41A-41D, another exemplary embodiment of a valve repair device 602 has a spacer element 3800 attached to the gripping members 608*a*, 608*b* of the valve repair device. The spacer element 3800 includes a first portion 4102 attached to one gripping member 608*a* and a second portion 4104 attached to the other gripping member 608*b*. Referring to FIG. 41C, the valve repair device 602 is shown in the closed position. When the valve repair device 602 is in the closed position, the first portion 4102 of the spacer element 3800 and the second portion 4104 of the spacer element 3800 engage each other and surround the shaft 603 (as shown in FIG. 41B). Referring to FIG. 41D, the valve repair device 602 is shown in the open position, the first portion 4102 of the spacer element 3800 moves with the gripping member 608*a*, and the second portion 4104 of the spacer element 3800 moves with the gripping member 608*b*. A spacer element 3800 having multiple portions 4102, 4104 allows the gripping members 608*a*, 608*b* to be moved to adjust the width of the opening between the paddles 606 and the gripping members, which is advantageous in attaching the valve repair device 602 to valve tissue 820. Referring to FIG. 41B, the spacer element 3800 extends past the outer edges 4001 of the gripping members 3800 for providing additional surface area for filling the gap 3002 (FIGS. 38-39) of a mitral valve 301. The valve repair device 602 can include any other features for a valve repair device discussed in the present application, and the valve repair device 602 can be positioned to engage valve tissue 820 as part of any suitable valve repair system (e.g., any valve repair system disclosed in the present application).

Figure 43A:
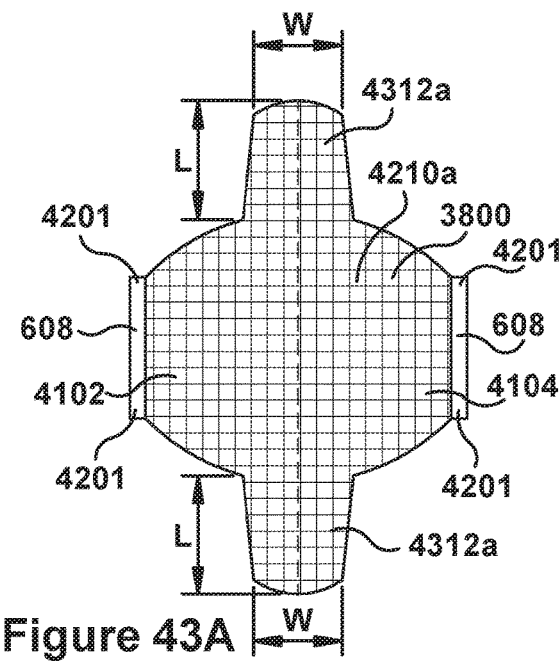
FIGS. 43A-43C illustrate the valve repair device of FIGS. 41A-41B with the spacer element having various shapes.
Figure 43B:
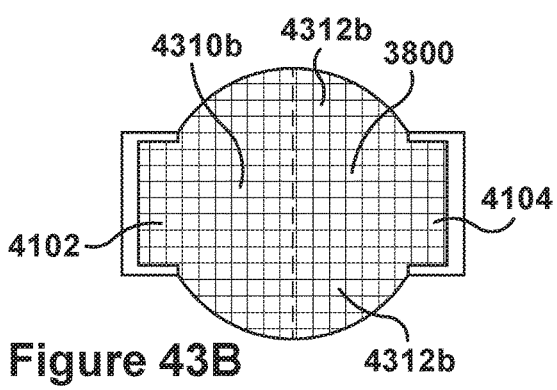
Figure 43C:
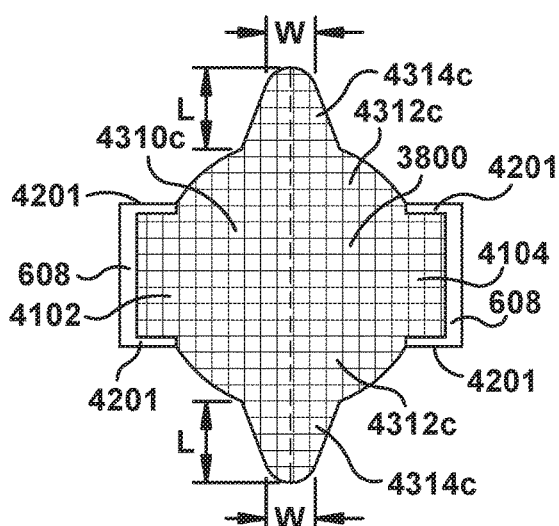

Referring to FIGS. 43A-43C, the spacer element 3800 shown in FIGS. 41A-41D can take a variety of different shapes. Referring to FIG. 43A, an exemplary embodiment of a spacer element 3800 in the closed position includes a main body 4310a extending between the gripping members 608 and past the edges 4201 of the gripping members, and extended portions 4312a that extend from the main body 4310a. The extended portions 4312a allow portions of the gap 3002 (FIGS. 38-39) of the mitral valve between the anterior leaflet 3003 and posterior leaflet 3004 and adjacent to the valve repair device 602 to be filled when the valve repair device is in a closed position. That is, when a valve repair device 602 is attached to a mitral valve to prevent regurgitation of blood through the mitral valve, the portions of the mitral valve next to the valve repair device may include openings from the tissue of the mitral valve extending around the valve repair device. The extended portions 4312a are configured to fill the openings adjacent to the valve repair device 602. In the illustrated embodiment, the length L of the extended portions 4312a are greater than the width W of the extended portions.

Referring to FIG. 43B, another exemplary embodiment of a spacer element 3800 in the closed position includes a main body 4310b extending between the gripping members 608 and extended portions 4312b that extend from the main body 4310b. In the illustrated embodiment, the extended portions 4312b have a semicircular shape. The extended portions 4312b are configured to fill the openings adjacent to the valve repair device 602 due to tissue of the mitral valve extending around the valve repair device.

Referring to FIG. 43C, another exemplary embodiment of a spacer element 3800 includes a main base assembly 4310c extending between the gripping members 608, first extending portions 4312c that extend from the main body 4310c, and second extending portions 4314c that extend from the first extending portions 4312c. In the illustrated embodiment, the first extended portions 4312c have a semicircular shape, and the second extended portions 4314c have a length L that is greater than its width W. The extended portions 4312b are configured to fill the openings adjacent to the valve repair device 602 due to tissue of the mitral valve extending around the valve repair device.

Referring to FIGS. 44A-44B, in certain embodiments, an expanding spacer element 3800 is integral with the valve repair device 602. The expanding spacer element 3800 is configured to expand as the paddles 606 close (as shown in FIG. 44B). Referring to FIG. 44A, the valve repair device 602 is in an open position such that valve tissue can be received in the opening 614 between the expanding spacer element 3800 and the paddles 606. Referring to FIG. 44B, the valve repair device 602 is in the closed position, in which the paddles 606 and the expanded spacer element 3800 are engaged to secure the valve repair device to valve tissue. When the spacer elements 3800 and the paddles 606 are engaged, the spacer element 3800 expands to provide a larger surface area for closing a gap 3002 (FIG. 38) between the anterior leaflet 3003 and posterior leaflet 3004 of a mitral valve 3001. In the illustrated embodiment, the valve repair device 602 takes the form of the valve repair device 602 in FIGS. 35A-35B. However, any valve repair device 602 described in the present application can include an expanding spacer element 3800. The valve repair device 602 can include any other features for a valve repair device discussed in the present application, and the valve repair device 602 can be positioned to engage valve tissue 820 as part of any suitable valve repair system (e.g., any valve repair system disclosed in the present application).

Referring to FIGS. 45A-46D, in certain situations, the valve repair device 602 needs to be detached from a native valve and removed from the patient. In these situations, it is advantageous to have a valve repair device that can be narrowed and rearranged (to a bailout position) such that the valve repair device will be easier to remove from the patient without disturbing any valve tissue of the patient's heart. Referring to FIGS. 45A-45C, the base assembly 604 of an exemplary embodiment of a valve repair device 602 includes a first link 4521 extending from point A to point B, a second link 4522 extending from point A to point C, a third link 4523 extending from point B to point D, a fourth link 4524 extending from point C to point E, and a fifth link 4525 extending from point D to point E. A coupler 605 is movably attached to a shaft 603, and the shaft 603 is fixed to the fifth link 4525. The first link 4521 and the second link 4522 are pivotally attached to the coupler 605 at point A, such that movement of the coupler 605 along the shaft 603 moves the location of point A and, consequently, moves the first link 4521 and the second link 4522. The first link 4521 and the third link 4523 are pivotally attached to each other at point B, and the second link 4522 and the fourth link 4524 are pivotally attached to each other at point C. One paddle 606a is attached to first link 4521 such that movement of first link 4521 causes the paddle 606a to move, and the other paddle 606b is attached to the second link 4522 such that movement of the second link 4522 causes the paddle 606b to move.

In order to move the valve repair device 602 from the closed position (as shown in FIG. 45A) to the bailout position (as shown in FIG. 45C), the coupler 605 is moved along the shaft 603 in the direction Y, which moves the pivot point A for the first link 4521 and the second link 4522 to a new position. Referring to FIG. 45A, the valve repair device 602 is shown in a closed position with an angle α between the paddle 606 and the shaft 603. The angle α can be, for example, between about 0 degrees and about 45 degrees, such as between about 5 degrees and about 40 degrees, such as between about 15 degrees and about 30 degrees, such as between about 20 degrees and about 25 degrees. Referring to FIG. 45B, the valve repair device 602 is moved to the open position by moving the coupler 605 along the shaft 603 in the direction Y. Movement of the coupler 605 in the direction Y causes the first link 4521 to pivot about point A such that the first link 4521 and the second link 4522 move outward in the direction Z, which causes the paddles 606a, 606b to move downward and outward in the direction H. Referring to FIG. 45C, the valve repair device 602 is moved to the bailout position by continuing to move the coupler 605 along the shaft 603 in the direction Y. The continued movement of the coupler 605 in the direction Y causes the first link 4521 and the second link 4522 to move inward in the direction M, which causes the paddles 606a, 606b to move downward and inward in the direction N. Still referring to FIG. 45C, in the bailout position, the valve repair device 602 has an angle β between the paddles 606 and the shaft 603. The angle β can be, for example, greater than or equal to 120 degrees, such as greater than or equal to 130 degrees, such as greater than or equal to 140 degrees, such as greater than or equal to 150 degrees, such as greater than or equal to 160 degrees.

Referring to FIGS. 46A-46D, the base assembly 604 of another exemplary embodiment of a valve repair device 602 includes a first link 4621 extending from point A to point B, a second link 4622 extending from point A to point C, a third link 4623 extending from point B to point D, a fourth link 4624 extending from point C to point E, a fifth link 4625 extending from point D to point F, and a sixth link 4626 extending from point E to point F. A coupler 605 is movably attached to a shaft 603, and the shaft 603 is attached to the fifth link 4625 and the sixth link 4626 at point F. The first link 4621 and the second link 4622 are pivotally attached to the coupler 605 at point A, such that movement of the coupler 605 along the shaft 603 moves the location of point A and, consequently, moves the first link 4621 and the second link 4622. The fifth link 4625 and the sixth link 4626 are pivotally attached to the shaft at point F, such that movement of the shaft moves the location of point F and, consequently, moves the fifth link 4625 and the sixth link 4626. A locking element 4631 is configured to selectively lock the fifth link 4625 and the sixth link 4626 to the shaft at point F, such that the fifth link 4625 and the sixth link 4626 cannot pivot relative to the shaft 603 when the locking element 4631 is in the locked position. However, when the locking element 4631 is in the unlocked position, the fifth link 4625 and the sixth link 4626 can pivot about the shaft 603 when the shaft moves the location of point F (as described above). The first link 4621 and the third link 4623 are pivotally attached to each other at point B, and the second link 4622 and the fourth link 4624 are pivotally attached to each other at point C. One paddle 606a is attached to first link 4621 such that movement of first link 4621 causes the paddle 606a to move, and the other paddle 606b is attached to the second link 4622 such that movement of the second link 4622 causes the paddle 606b to move.

Figure 46D:
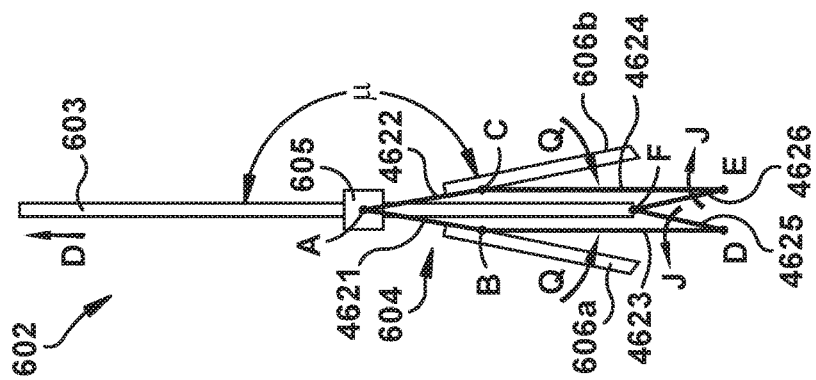
FIGS. 46A-46D illustrate another exemplary embodiment of a valve repair device with an increased bailout angle for removing the valve repair device.
Figure 46C:
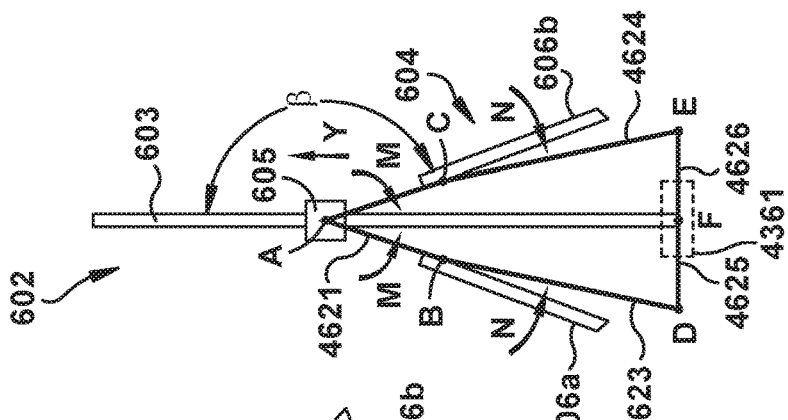
Figure 46B:
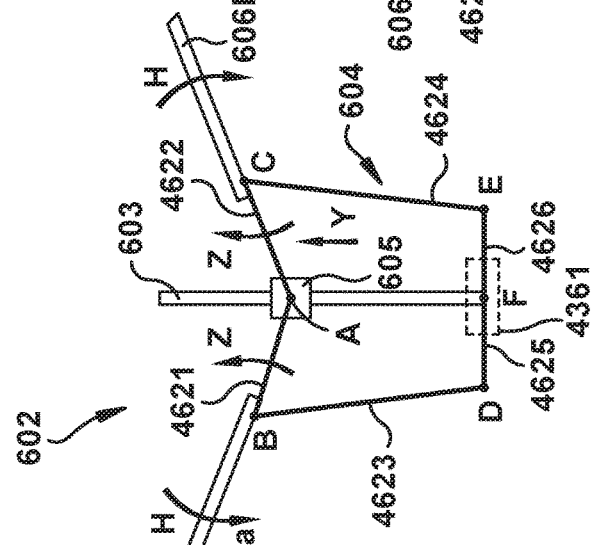
Figure 46A:
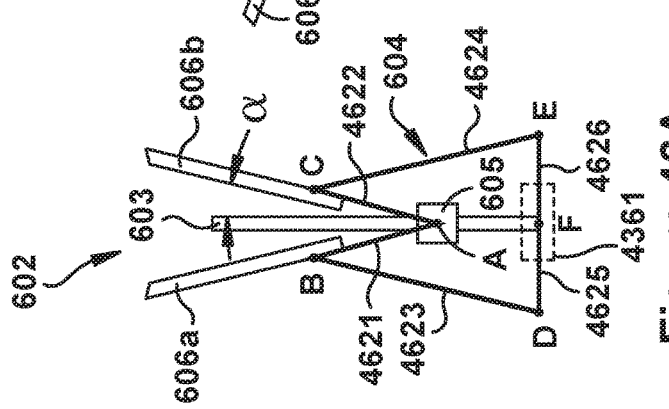

In order to move the valve repair device 602 from the closed position (as shown in FIG. 46A) to a bailout position (as shown in FIG. 46C), the locking element 4631 is maintained in a locked position, and the coupler 605 is moved along the shaft 603 in the direction Y, which moves the pivot point A for the first link 4621 and the second link 4622 to a new position. In order to move the valve repair device 602 from the bailout position to the collapsed bailout position (as shown in FIG. 46D), the locking element 4631 is moved to an unlocked position, and the shaft 603 is moved in the direction D, which moves the pivot point F for the fifth link 4625 and the sixth link 4626 to a new position, which causes the fifth link 4625 and the sixth link 4626 to pivot about the shaft 603.

Referring to FIG. 46A, the valve repair device 602 is shown in a closed position with an angle α between the paddle 606 and the shaft 603. The angle α can be, for example, between about 0 degrees and about 45 degrees, such as between about 5 degrees and about 40 degrees, such as between about 15 degrees and about 30 degrees, such as between about 20 degrees and about 25 degrees. Referring to FIG. 46B, the valve repair device 602 is moved to the open position by moving the coupler 605 along the shaft 603 in the direction Y. Movement of the coupler 605 in the direction Y causes the first link 4621 and the second link 4622 to move outward in the direction Z, which causes the paddles 606a, 606b to move downward and outward in the direction H. The locking element 4631 is maintained in the locked position when the valve repair device 602 is moved from the closed position (as shown in FIG. 46A) to the open position (as shown in FIG. 46B).

Referring to FIG. 46C, the valve repair device 602 is moved to the bailout position by continuing to move the coupler 605 along the shaft 603 in the direction Y. The continued movement of the coupler 605 in the direction Y causes the first link 4621 and the second link 4622 to move inward in the direction M, which causes the paddles 606a, 606b to move downward and inward in the direction N. Still referring to FIG. 45C, in the bailout position, the valve repair device 602 has an angle β between the paddles 606 and the shaft 603. The angle β can be, for example, greater than or equal to 120 degrees, such as greater than or equal to 130 degrees, such as greater than or equal to 140 degrees, such as greater than or equal to 150 degrees, such as greater than or equal to 160 degrees. The locking element 4631 is maintained in the locked position when the valve repair device 602 is moved from the open position (as shown in FIG. 46B) to the bailout position (as shown in FIG. 46C).

Referring to FIG. 46D, the valve repair device 602 is moved from the bailout position to the collapsed position by moving the locking element 4631 to an unlocked position and moving the shaft 603 in the direction D, which causes the fifth link 4625 and the sixth link 4626 to pivot about connection point F and move upward in a direction J, which causes the third link 4623 and the fourth link 4624 to move inward and downward in the direction Q, which causes the paddles 606a, 606b to move downward and inward in the direction Q. Still referring to FIG. 46D, in the collapsed bailout position, the valve repair device 602 has an angle μ between the paddles 606 and the shaft 603. The angle μ can be, for example, greater than or equal to 120 degrees, such as greater than or equal to 130 degrees, such as greater than or equal to 140 degrees, such as greater than or equal to 150 degrees, such as greater than or equal to 160 degrees, such as greater than or equal to 170 degrees.

It is advantageous to have a valve repair device that includes features to ensure that the valve repair device remains in a closed position after the valve repair device is attached to the native valve of a patient. In other words, it is advantageous to have a valve repair device that includes features to prevent the valve repair device from becoming detached from the native valve of a patient after placement of the valve repair device inside of the patient, which could cause problems (e.g., regurgitation of blood through the mitral valve). Examples of additional features for preventing a valve repair device from becoming detached from a native valve are shown in FIGS. 47A-49.

Referring to FIGS. 47A-47B, an exemplary embodiment of a valve repair device 602 includes a latch member 4701 attached to the paddles 606, in which the latch member 4701 is configured to attach the paddles 606 to the gripping members 608 when the valve repair device is in the closed position. The valve repair device 602 can include any other features for a valve repair device discussed in the present application, and the valve repair device 602 can be positioned to engage valve tissue 820 as part of any suitable valve repair system (e.g., any valve repair system disclosed in the present application). In the illustrated embodiment, the valve repair device 602 includes an optional lock 607 configured to keep a coupler 605 in a locked condition on the shaft 603. If the optional lock 607 fails, however, the coupler 605 could move on the shaft 603 and cause the valve repair device to move to an open position. The latch member 4701 is configured to keep the valve repair device 602 in the closed position if the lock 607 fails.

Referring to FIG. 47A, the valve repair device 602 is in an open position with valve tissue 820 disposed in the opening 614 between the paddles 606 and the gripping members 608. Referring to FIG. 47B, the valve repair device 602 is moved to the closed position such that the valve tissue 820 is secured between the paddles 606 and the gripping members 608 of the valve repair device. The valve repair device 602 can be moved to the closed position by any suitable manner, such as, for example, any manner described in the present application. When the valve repair device 602 is moved to the closed position, the latch member 4701 punctures the valve tissue 820 and the gripping member 608 to secure the paddle to the gripping member. The latch member 4701 can take any suitable form that is capable of securing the paddles 606 to the gripping members 608, such as, for example, metals, plastics, etc.

Figure 48:
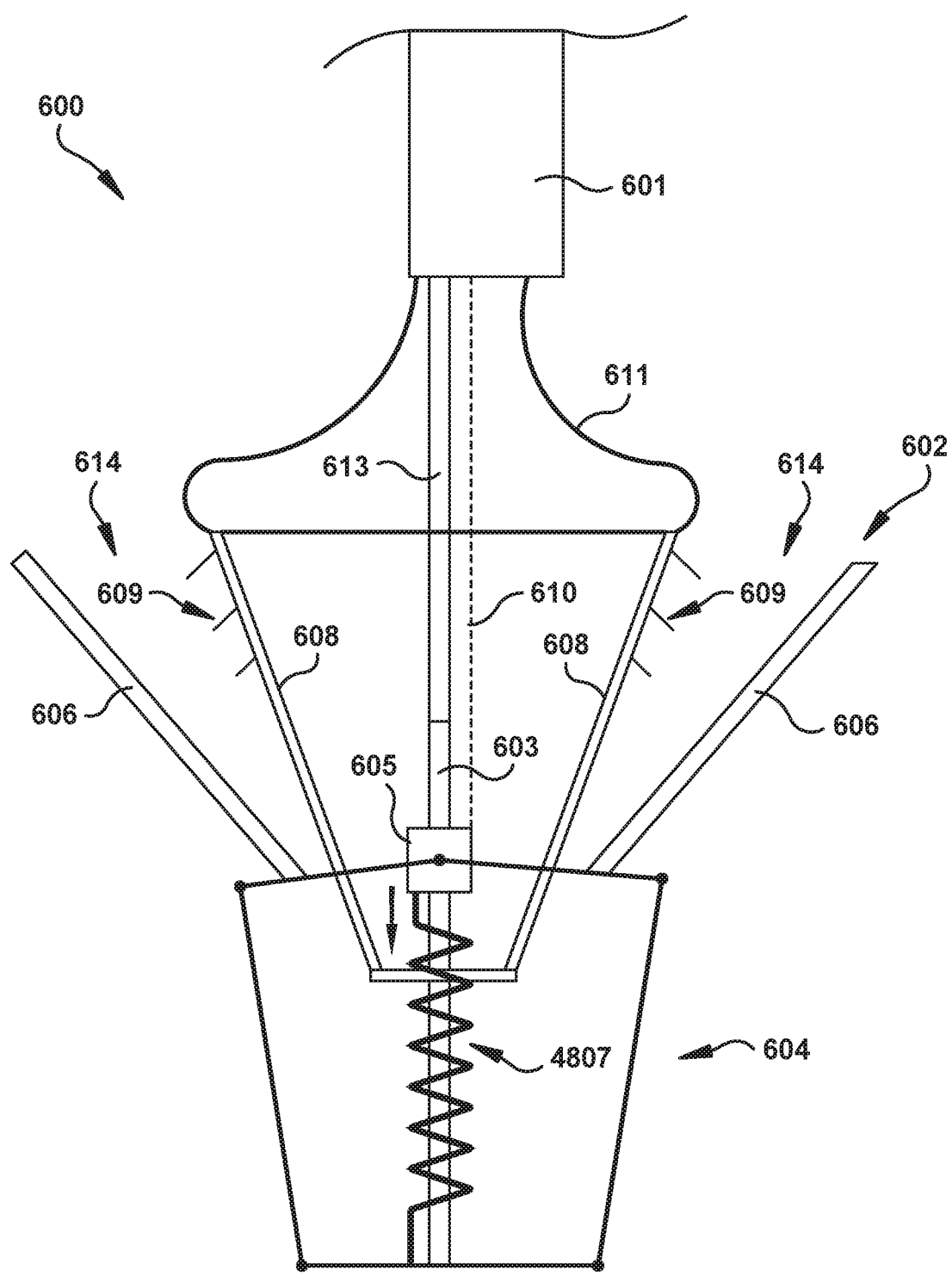
FIG. 48 illustrates another exemplary embodiment of a valve repair device having a spring member that is configured to bias the paddles of the valve repair device to a closed position.

Referring to FIG. 48, another exemplary embodiment of a valve repair system 600 includes a delivery device 601 and a valve repair device 602, in which is delivery device is configured to deliver the valve repair device to the native valve of a patient, and in which the valve repair device is configured to attach to leaflets of a native valve to repair the native valve of the patient. The delivery device 601 can take any suitable form that is capable of delivering the valve repair device 602 to the native valve of a patient, such as, for example, any form described in the present application. The valve repair device 602 includes a base assembly 604, a pair of paddles 606, and a pair of gripping members 608. The base assembly 604 of the valve repair device 602 has a shaft 603 and a coupler 605 configured to move along the shaft. The coupler 605 is mechanically connected to the paddles such that movement of the coupler along the shaft 603 causes the paddles to move between an open position and a closed position. In the closed position, the paddles 606 and the gripping members 608 engage valve tissue and each other to secure the valve repair device 602 to the valve tissue. The valve repair device 602 also includes a biasing member 4807 (e.g., a spring) configured to bias the coupler 605 on the shaft such that the valve repair device 602 is in a closed position.

In certain embodiments, the valve repair system 600 includes a placement shaft 613 that is removably attached to the shaft 603 of the base assembly 604 of the valve repair device 602. After the valve repair device 602 is secured to valve tissue, the placement shaft 613 is removed from the shaft 603 to remove the valve repair device 602 from the valve repair system 600, such that the valve repair device 602 can remain attached to the valve tissue, and the delivery device 601 can be removed from a patient's body. After the valve repair device 602 is attached to the valve tissue, and the valve repair system 600 is removed from the patient's body, the biasing member 4807 maintains the valve repair device in a closed position to prevent detachment of the valve repair device from the valve tissue. The valve repair device 602 can include any other features for a valve repair device discussed in the present application, and the valve repair device 602 can be positioned to engage valve tissue 820 as part of any suitable valve repair system (e.g., any valve repair system disclosed in the present application).

Figure 49:
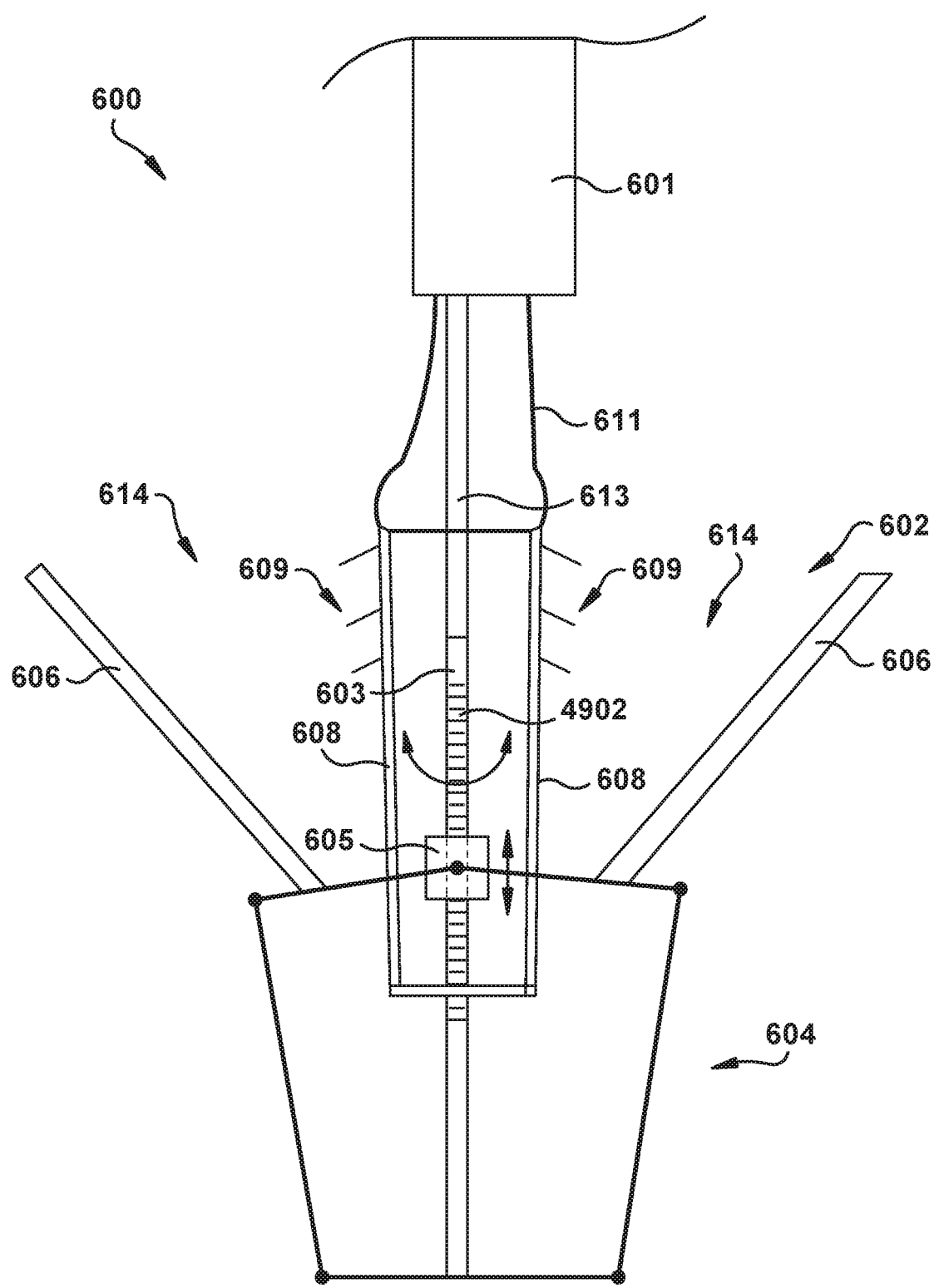
FIG. 49 illustrates another exemplary embodiment of a valve repair device having a threaded mechanism for moving the valve repair device between the open position and the closed position.

Referring to FIG. 49, another exemplary embodiment of a valve repair system 600 includes a delivery device 601 and a valve repair device 602, in which the delivery device is configured to deliver the valve repair device to the native valve of a patient, and in which the valve repair device is configured to attach to leaflets of a native valve to repair the native valve of the patient. The delivery device 601 can take any suitable form that is capable of delivering the valve repair device 602 to the native valve of a patient, such as, for example, any form described in the present application. The valve repair device 602 includes a base assembly 604, a pair of paddles 606, and a pair of gripping members 608. The base assembly 604 of the valve repair device 602 has a shaft 603 and a coupler 605 configured to move along the shaft. In the illustrated embodiment, the shaft 603 includes a threaded portion 4902, and the coupler 605 is configured to move along the threaded portion 4902 of the shaft. That is, rotating the shaft 603 causes the coupler 605 to move up and down the shaft 603. The coupler 605 is mechanically connected to the paddles such that movement of the coupler along the shaft 603 causes the paddles to move between an open position and a closed position. In the closed position, the paddles 606 and the gripping members 608 engage valve tissue and each other to secure the valve repair device 602 to the valve tissue.

In certain embodiments, the valve repair system 600 includes a placement shaft 613 that is removably attached to the shaft 603 of the base assembly 604 of the valve repair device 602. After the valve repair device 602 is secured to valve tissue, the placement shaft 613 is removed from the shaft 603 to remove the valve repair device 602 from the valve repair system 600, such that the valve repair device 602 can remain attached to the valve tissue, and the delivery device 601 can be removed from a patient's body. After the valve repair device 602 is attached to the valve tissue, and the valve repair system 600 is removed from the patient's body, the valve repair device is prevented from detaching from the valve tissue, because the coupler can only be moved by rotating the shaft 603. The valve repair device 602 can include any other features for a valve repair device discussed in the present application, and the valve repair device 602 can be positioned to engage valve tissue 820 as part of any suitable valve repair system (e.g., any valve repair system disclosed in the present application).

Figure 52:
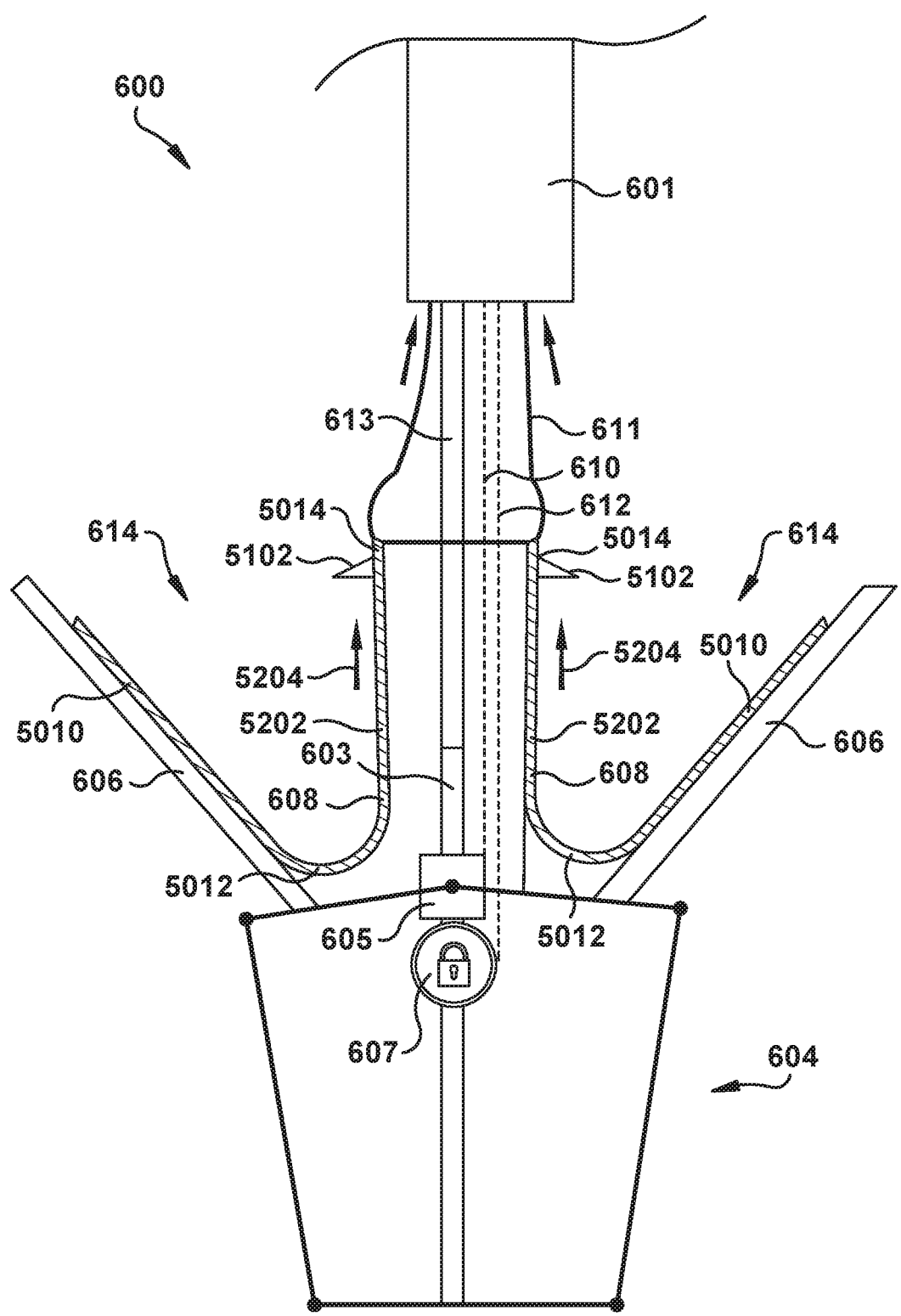
FIG. 52 illustrates another exemplary embodiment of a valve repair device having gripping members that are extendable in length.
Figure 53A:
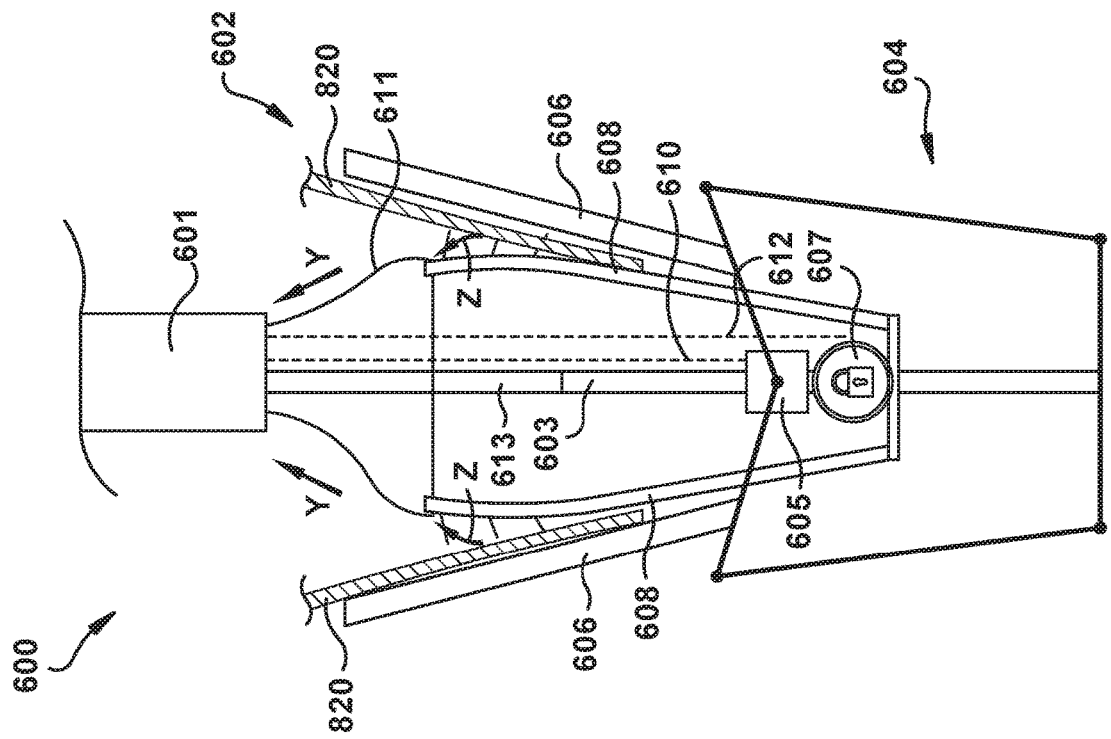
FIGS. 53A-53B illustrate another exemplary embodiment of a valve repair device having gripping members that are flexible.
Figure 53B:
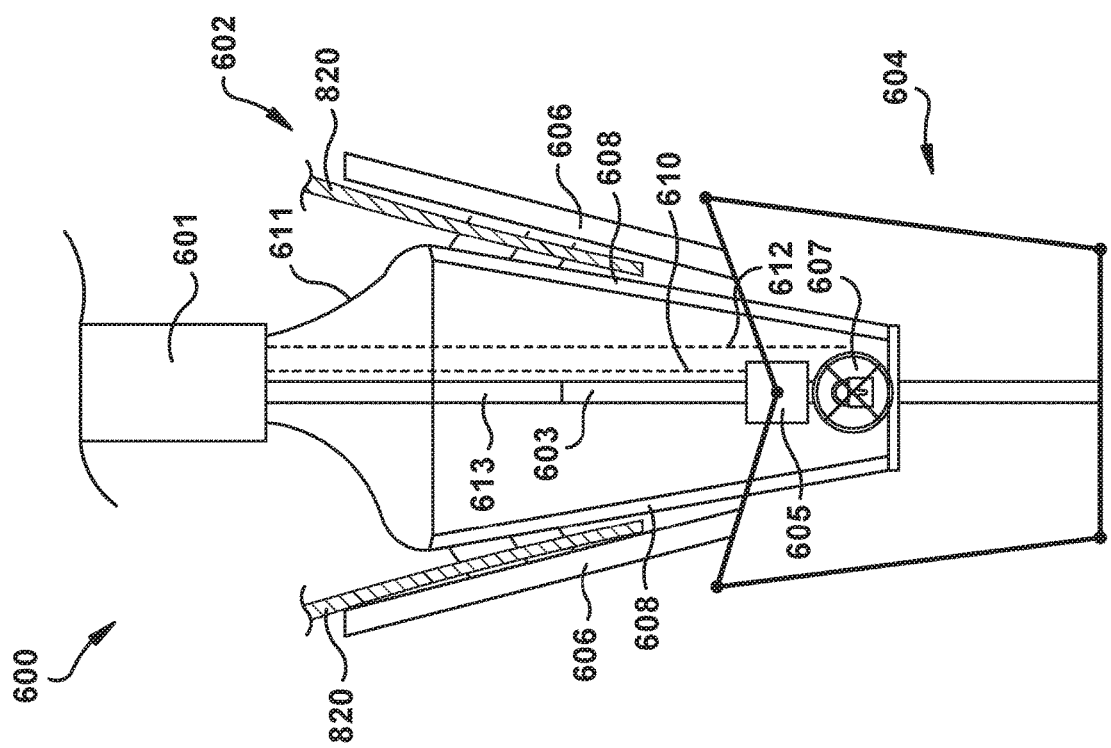
Figure 54:
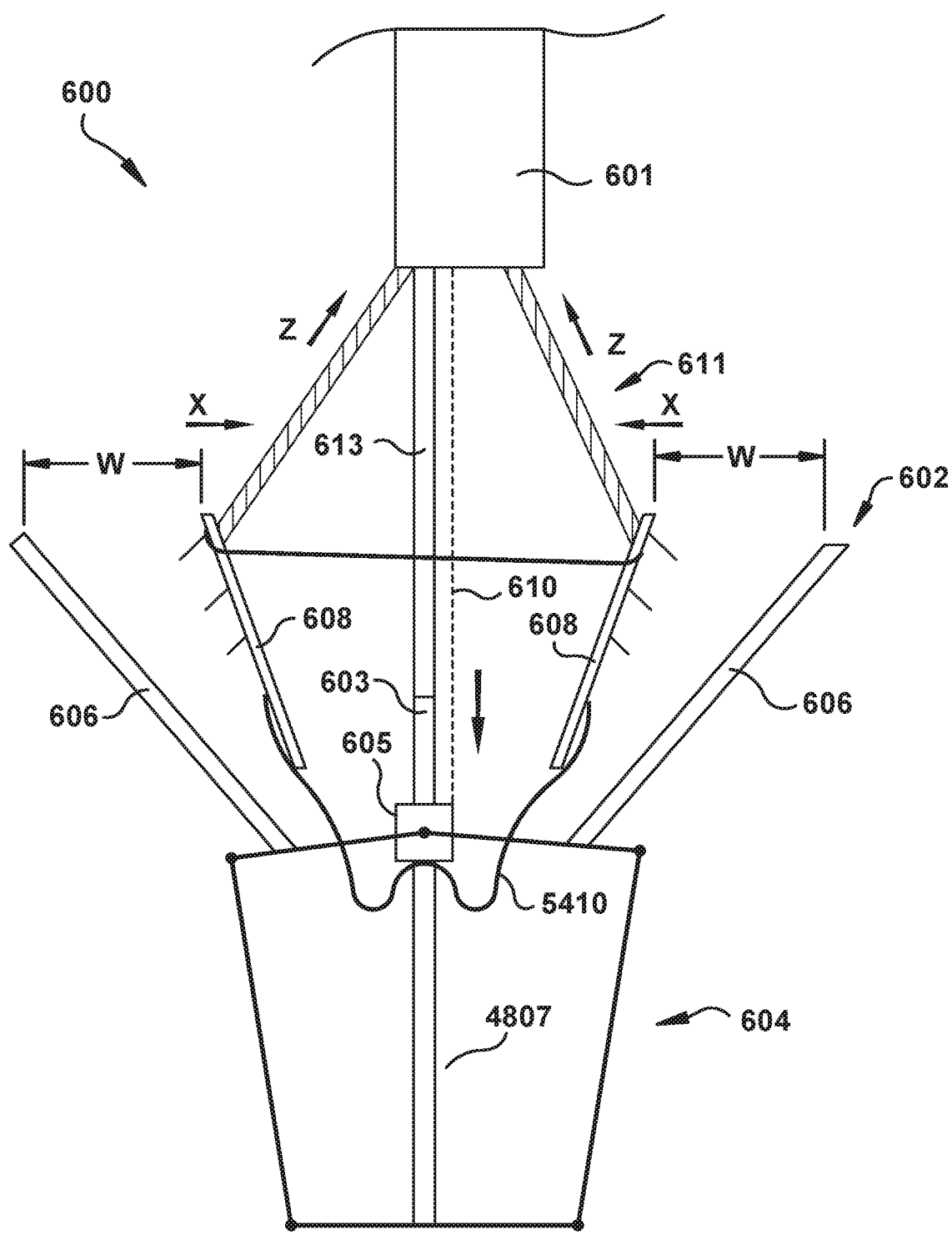
FIG. 54 illustrate another exemplary embodiment of a valve repair device, in which gripping members are attached to a separate spring member.

Referring to FIGS. 50-54, embodiments of valve repair systems 600 include a delivery device 601 and a valve repair device 602, in which the delivery device is configured to deliver the valve repair device to the native valve of a patient, and in which the valve repair device is configured to attach to leaflets of a native valve to repair the native valve of the patient. The delivery device 601 can take any suitable form that is capable of delivering the valve repair device 602 to the native valve of a patient, such as, for example, any form described in the present application. The valve repair device 602 is similar to the valve repair devices described above and includes a base assembly 604, a pair of paddles 606, and a pair of gripping members 608. The base assembly 604 of the valve repair device 602 has a shaft 603 and a coupler 605 configured to move along the shaft. The coupler 605 is mechanically connected to the paddles such that movement of the coupler along the shaft 603 causes the paddles to move between an open position and a closed position. In some embodiments, the valve repair device 602 includes a lock 607 configured to lock the coupler 605 in a desired position on the shaft (as shown in FIGS. 50-53B). In alternative embodiments, the valve repair device 602 includes a biasing member 4807 configured to maintain the coupler 605 in a desired position on the shaft 603 (as shown in FIG. 54). In the closed position, the paddles 606 and the gripping members 608 engage valve tissue and each other to secure the valve repair device 602 to the valve tissue. In certain embodiments, the valve repair system 600 includes a placement shaft 613 that is removably attached to the shaft 603 of the base assembly 604 of the valve repair device 602. After the valve repair device 602 is secured to valve tissue, the placement shaft 613 is removed from the shaft 603 to remove the valve repair device 602 from the valve repair system 600, such that the valve repair device 602 can remain attached to the valve tissue, and the delivery device 601 can be removed from a patient's body. The valve repair device 602 can include any other features for a valve repair device discussed in the present application, and the valve repair device 602 can be positioned to engage valve tissue 820 as part of any suitable valve repair system (e.g., any valve repair system disclosed in the present application).

Figure 50:
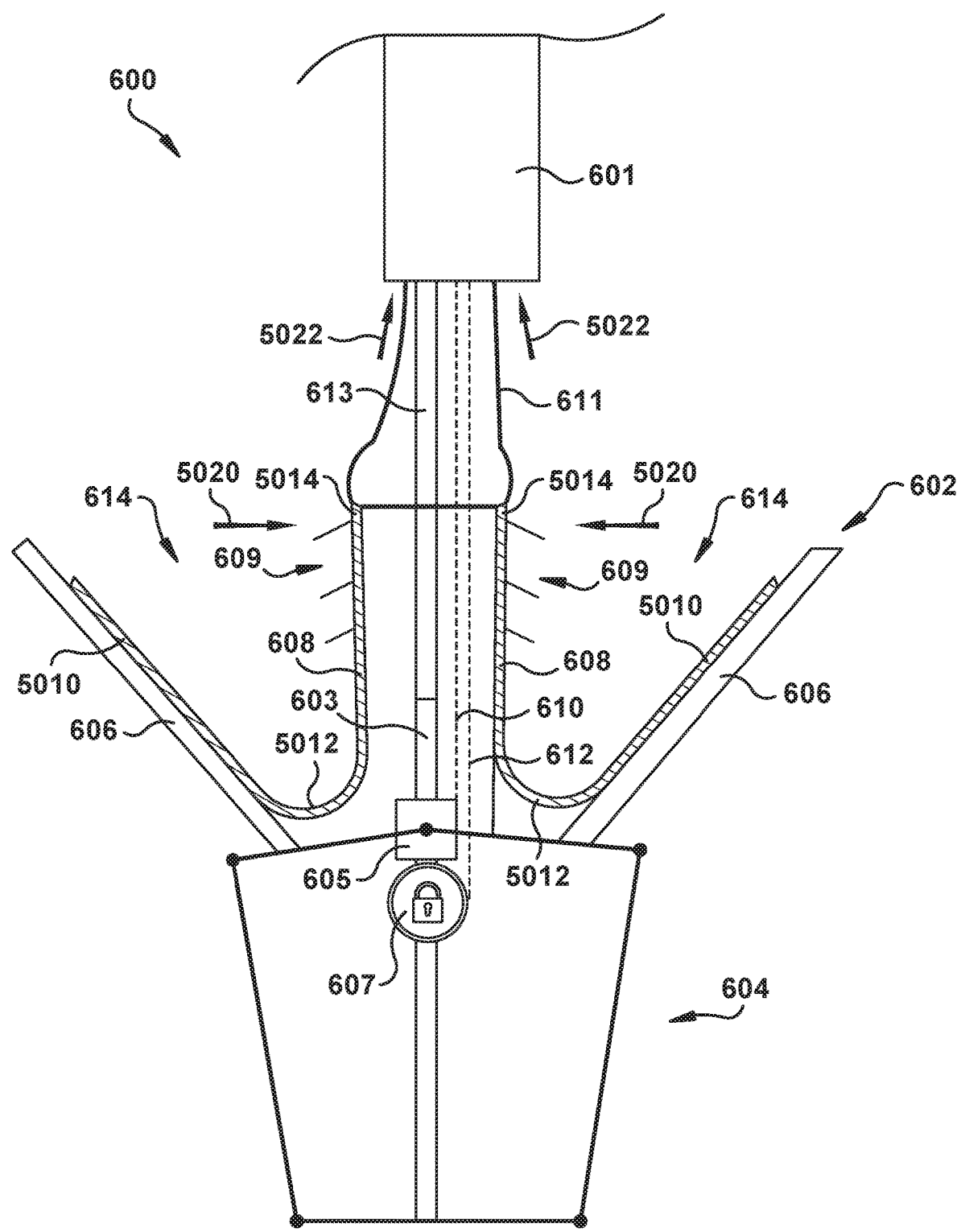
FIG. 50 illustrates another exemplary embodiment of a valve repair device having gripping members attached to the paddles.

Referring to FIG. 50, in some embodiments, the gripping members 608 are attached to the paddles 606. In the example illustrated by FIG. 50, the gripping members 608 include an attachment portion 5010, a hinge or flex portion 5012, and a gripping or barbed portion 5014. The attachment portion 5010 can take any form that allows the gripping member to be attached to the paddle 606. The hinge or flex portion 5012 can take a variety of different forms. For example, the hinge or flex portion can be configured to bias the gripping or barbed portion 5014 toward the attachment portion 5010. In one exemplary embodiment, the hinge or flex portion 5012 biases the gripping or barbed portion 5014 to a fully closed position where the gripping or barbed portion engages the attachment portion 5010 and/or the paddle 606. When valve tissue is positioned between the paddle 606 and the gripping portion 5014, the hinge or flex portion biases the gripping portion 5014 to clamp the valve tissue between the gripping or barbed portion 5014 and the paddle. The gripping member 608 illustrated by FIG. 50 moves with the paddle 606. The hinge or flex portion 5012 allows the gripping portion 5014 to move in the direction indicated by arrows 5020 and can allow the gripping portion to be pulled in the direction indicated by arrows 5022.

Figure 51:
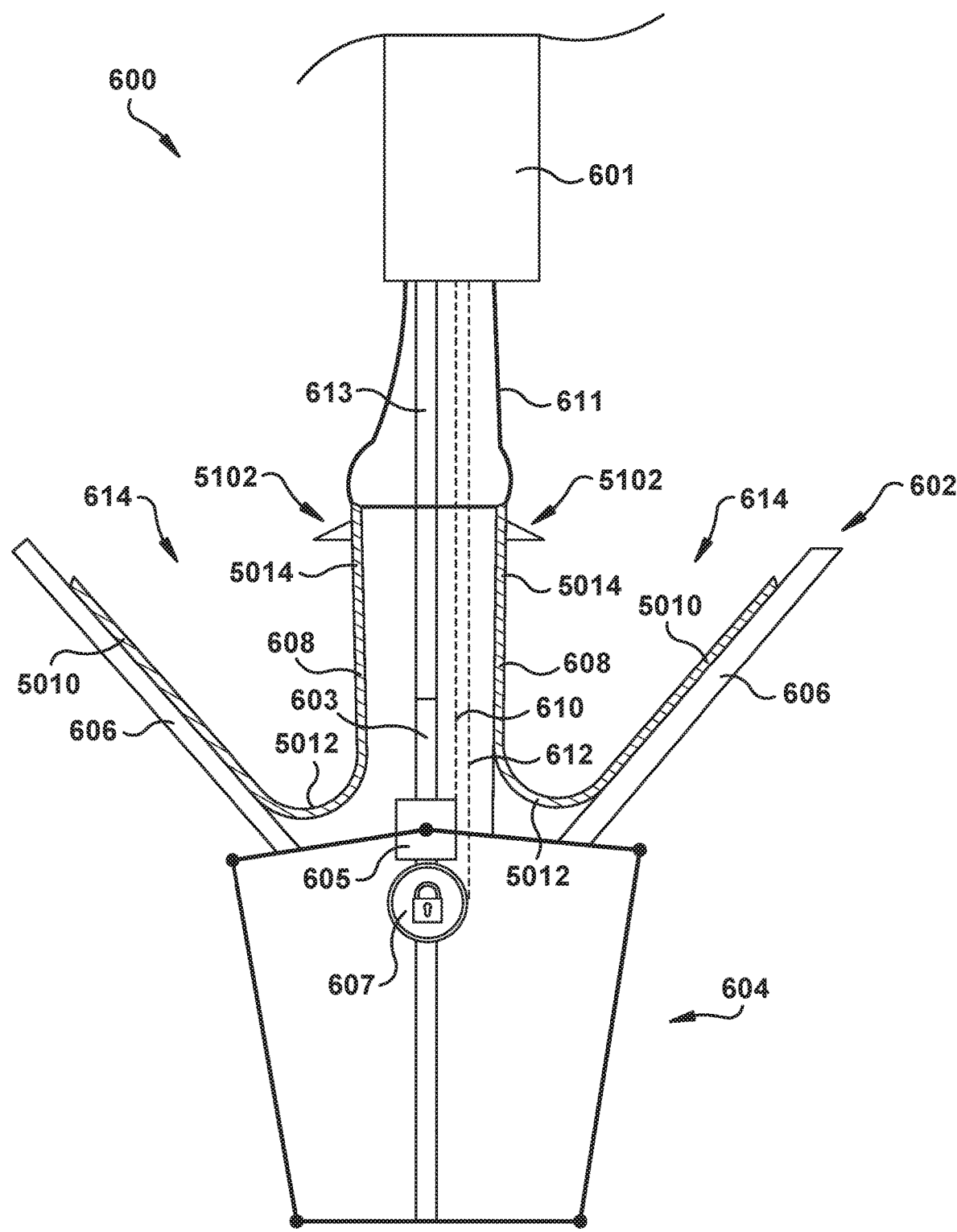
FIG. 51 illustrates another exemplary embodiment of a valve repair device having gripping members with a single row of barbs.

In certain embodiments, it is advantageous for the barbed portion 609 to be disposed toward a proximal end of the gripping members 608 because it will provide for an easier release of the gripping members 608 from valve tissue. Referring to FIG. 51, in one embodiment, the gripping members 608 comprise a single row of barbs 5102 configured to engage the valve tissue and the paddles 606 to secure the valve repair device to the valve tissue. The single row of barbs 5102 makes it easier for the gripping portion 5014 to release from the valve tissue. In an alternative embodiment, the gripping members 608 can comprise two or more rows of barbs 5102 disposed at a proximal end of the gripping members 608. In additional embodiments, the barbs 5102 can be disposed at a proximal end of the gripping members 608 in any other suitable configuration that provides for an easier release of the gripping members 608 from valve tissue.

Figure 51A:
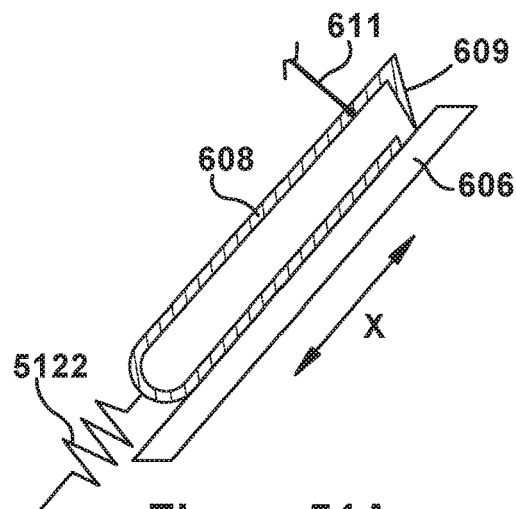
FIGS. 51A-51E illustrate another exemplary embodiment of a valve repair system having a valve repair assembly with a valve repair device having gripping members configured to place a tensioning force on valve tissue when the valve repair device is attached to the valve tissue.
Figure 51B:
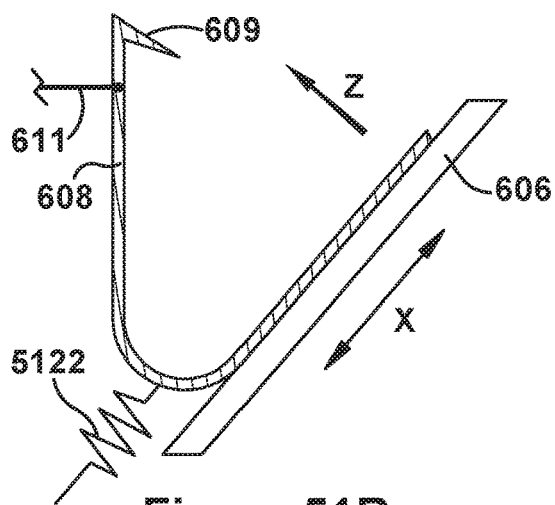

In some embodiments, as shown in FIGS. 51A-51E, the gripping member 608 is configured to place a tensioning force on the valve tissue when the valve repair device (e.g., any valve repair device 602 described in the present application) is attached to the valve tissue. The gripping member 608 is slidably connected to the paddle 606, such that the gripping member 608 can be moved along the paddle in the direction X. For example, a gripper control mechanism 611 can be used to move the gripping member 608 along the paddle 606 in the direction X, and the gripper control mechanism 611 can also be used to move the gripping member 608 between the closed position (as shown in FIG. 51A) and the open position (as shown in FIG. 51B). The gripper control mechanism 611 can take any form described in the present application. In certain embodiments, the valve repair device 602 includes an optional biasing member 5122 (e.g., a spring) configured to maintain the gripping member 608 in a desired position along the paddle 606 (e.g., the position shown in FIGS. 51A and 51E). In the illustrated embodiment, the gripping member 608 includes a single row of barbs 609 at a proximal end of the gripping members (e.g. as shown in the embodiment of the valve repair device 602 shown in FIG. 51), however, it should be understood that the features described herein regarding FIGS. 51A-51E can be used with any of the embodiments of the valve repair device described in the present application.

Figure 51C:
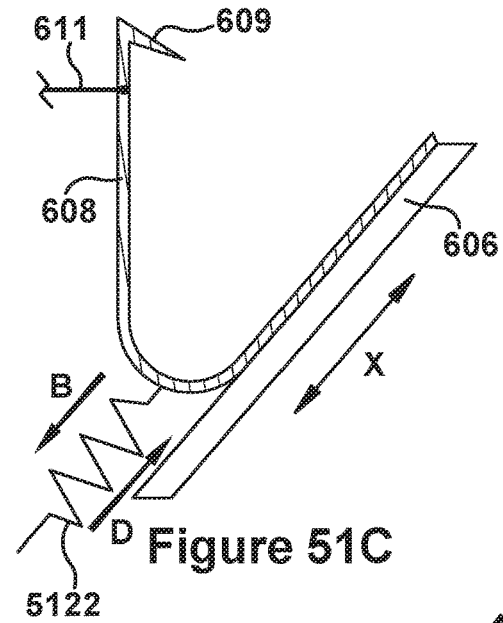
Figure 51D:
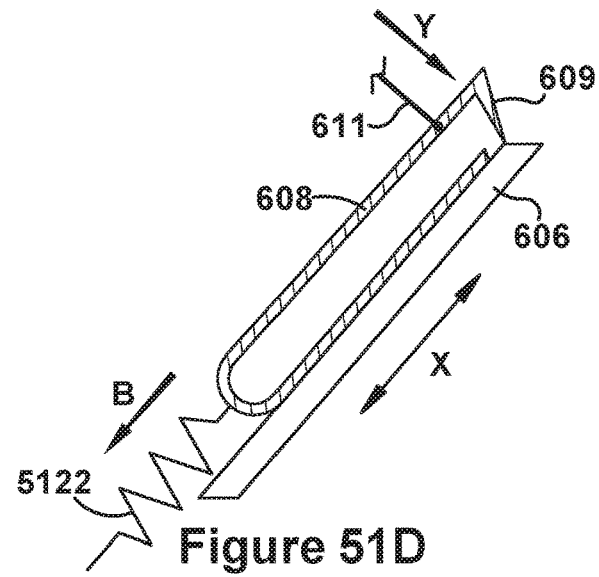
Figure 51E:
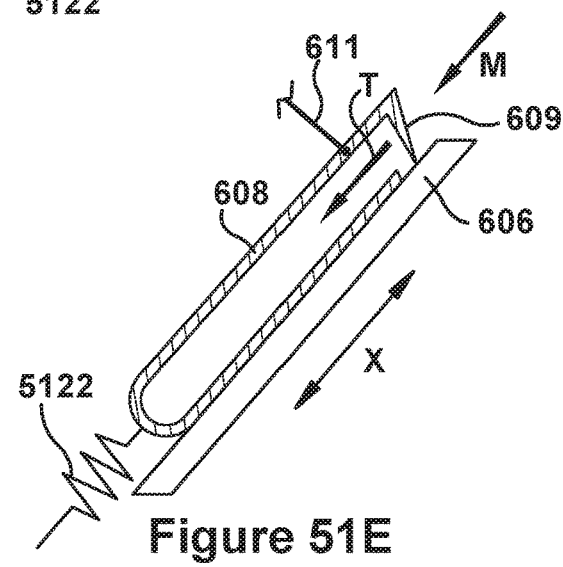

Referring to FIG. 51A, the gripping member 608 is shown in a first position on the paddle 606 and in a closed position. Referring to FIG. 51B, the gripping member 608 is shown after it has been moved in the direction Z to an open position by the gripper control mechanism 611. Referring to FIG. 51C, the gripping member 608 is shown after it has been moved along the paddle 606 in the direction D to a second position. In certain embodiments, the gripping member 608 is moved along the paddle in the direction D by the gripper control mechanism 611 or a separate mechanism. In embodiments that include the biasing member 5122, enough force needs to be applied on the gripping member 608 to move the gripping member in the direction D, which will cause the biasing member to expand and create a tensioning force on the gripping member 608 in the direction B. While the illustrated embodiment shows the gripping member 608 being moved to an open position (as shown in FIG. 51B) prior to the gripping member 608 being moved along the paddle 606 in the direction D to the second position (as shown in FIG. 51C), it should be understood that gripping member 608 can be moved in the direction D to the second position prior to the gripping member 608 being moved in the direction Z to an open position or the movements can be simultaneous. Referring to FIG. 51D, the gripping member 608 is moved to a closed position in the direction Y by the gripper control mechanism 611 to secure the barbed portion 609 of the gripping member 608 to valve tissue (not shown). In the position shown in FIG. 51D, the biasing member 5122 is being maintained in an extended position (e.g., as a result of the force applied to the gripping member 608 by the gripper control mechanism (or another mechanism) to keep the gripping member in the second position), which means the biasing member 5122 is placing a tensioning force on the gripping member 608 in the direction B. Referring to FIG. 51E, after the barbed portion 609 of the gripping member 608 is secured to the valve tissue, the force maintaining the gripping member 608 in the second position is released, which causes the tensioning force applied by the biasing member 5122 to move the gripping member 608 along the paddle 606 in the direction M. The movement of the gripping member 608 in the direction M causes the barbed portion 609 to create a tensioning force on the valve tissue in the direction T. This tensioning force on the valve tissue allows the valve repair device 602 to maintain a secure connection to the valve tissue.

Figure 51H:
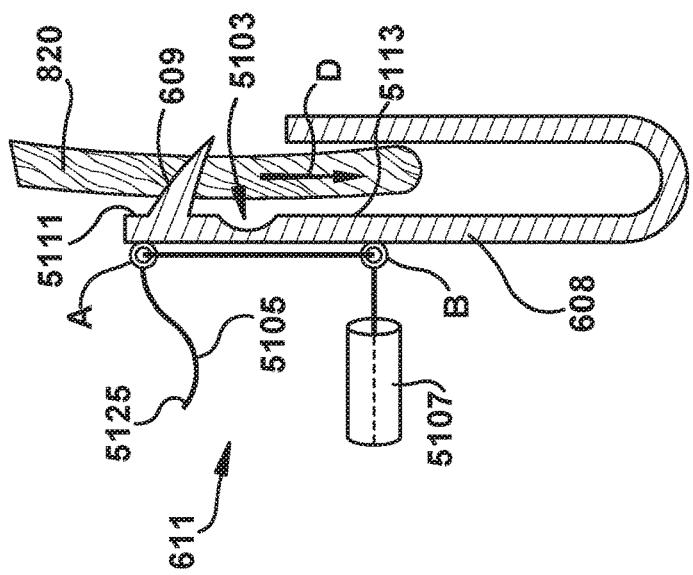
FIGS. 51F-51H illustrate another exemplary embodiment of a valve repair assembly having gripping members configured to place a tensioning force on valve tissue when the valve repair device is attached to the valve tissue.
Figure 51G:
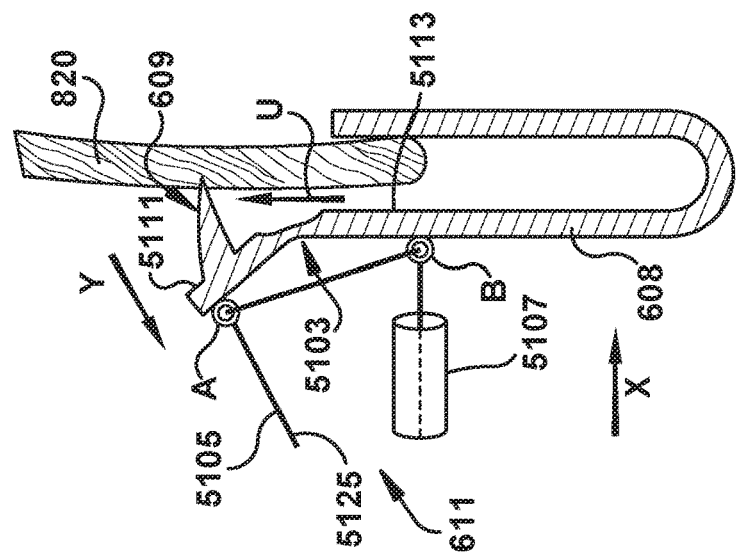
Figure 51F:
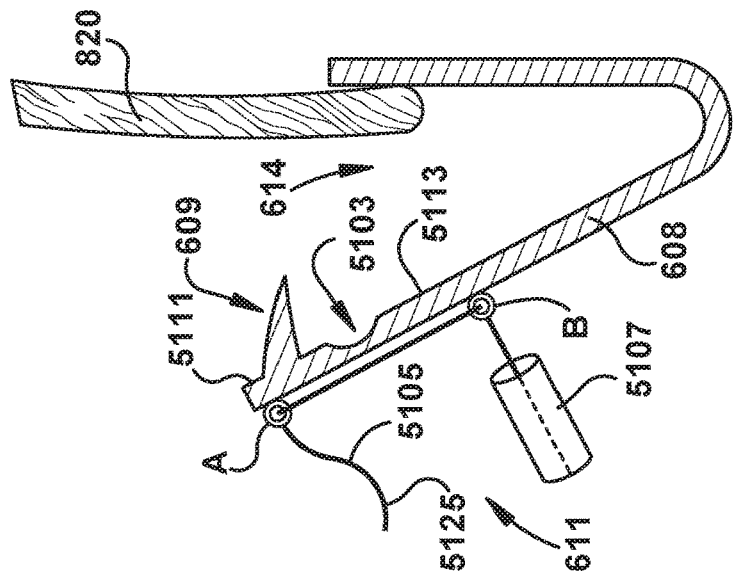

In another embodiment, as shown in FIGS. 51F-51G, the gripping member 608 includes a barbed portion 609 and a weakened or flexing portion 5103. The barbed portion 609 is disposed on a first side 5111 of the weakened or flexing portion 5103. In the illustrated embodiment, the barbed portion 609 includes a single row of barbs, but it should be understood that any suitable configuration of the barbs can be used, such as, for example, any configuration described in the present application. The weakened portion or flexing 5103 can be, for example, a cutout in the gripping member, a different material as compared to the remainder of the gripping member 608, or can take any other suitable form that allows the weakened or flexing portion 5103 to be weaker and/or more flexible than a remained of the gripping member 608. However, in other embodiments, the weaker and flexible portion 5103 is omitted and the link 5107 and line 5105 described below are still able to flex the barbed portion as illustrated by FIGS. 51F-51H.

Referring to FIGS. 51F-51H, the gripper control mechanism 611 includes a line 5105 (e.g., a suture) and a push/pull link 5107 configured to receive the line 5105. For example, the push/pull link 5107 can be a catheter, a wire with a loop (as shown FIG. 25A), or any other link that is capable of receiving the line 5105 and pushing/pulling the gripping member 608. A first end 5125 of the line 5105 extends from a delivery device (e.g., any delivery device 601 described in the present application) and is removably attached to the gripping member 608 on a first side 5111 of the weakened or flexible portion 5103 at a first connection point A. The line 5105 also extends from the connection point A and is removably attached to the gripping member 608 on a second side 5113 of the weakened or flexible portion 5103 at a second connection point B. In addition, the line 5105 extends from the second connection point B and through push/pull link 5107.

Referring to FIG. 51F, the gripping member 608 is shown in an open position with a valve tissue member 820 disposed in an opening 614 between the gripping member 608 and a paddle (not shown). The gripping member can be moved to the open position by pulling on the line 5105. Referring to FIG. 51G, the link 5107 and line 5105 of the gripper control mechanism 611 is used to move the gripping member 608 in the direction X to the closed position and flex the portion 609 in the direction Y. The first end 5125 of the line 5105 is pulled in a direction Y, such that the first side 5111 of the gripping member 608 pivots or flexes about the weakened portion 5103. This flexing causes the barbed portion 609 to move in directions U and Y to a flexed position. Still referring to FIG. 51G, the link 5107 and the line 5105 are moved such that the barbed portion 609 pierces the valve tissue 820 while the barbed portion is in the flexed position.

Referring to FIG. 51H, the line 5105 is released, which causes the first end 5111 of the gripping member 608 to pivot about the weakened or flexible portion 5103. This causes the barbed portion 609 to move through the valve tissue 820 in a direction D, which causes the barbed portion 609 the valve repair device to create a tensioning force on the valve tissue 820 in the direction D. After the gripping member 608 is secured to the valve tissue 820 (as shown in FIG. 51H), the link 5107 and the line 5105 are removed from the gripping member 608.

Referring to FIG. 52, in various embodiments, the gripping members 608 include a stretchable portion 5202 to allow for movement in the direction 5204. The movement in the direction 5204 allows for clean disengagement from the valve tissue. In some embodiments, the stretchable portion 5202 is configured to be moved such that the barbs 5102 exit the valve tissue in a direction substantially opposite the direction in which the barbs entered the valve tissue. Alternatively, the gripping members 608 can be otherwise extendable to allow for disengagement from the valve tissue without tearing the valve tissue. For example, as mentioned above, the hinge portions 5012 can be configured to allow the gripping portions 5014 of the gripping members 608 to be pulled in the direction 5204.

Referring to FIGS. 53A-53B, in certain embodiments, the gripping members 608 are made of flexible material. Referring to FIG. 53A, the valve repair device 602 is shown in a closed position and secured to valve tissue 820. Referring to FIG. 53B, the gripping members 608 are shown being moved by the gripper control mechanism 611 to remove the gripping members 608 from the valve tissue 820. In particular, movement of the gripper control mechanism 611 in the direction Y causes the gripping members 608 to peel back off of the valve tissue in the direction Z. The flexible material of the gripping members 608 allows for the peeling back of the gripping members 608 when removing the gripping members from the valve tissue 820. The peeling back of the gripping members 608 is advantageous because it helps the gripping members to pull out of the valve tissue 820 without damaging the valve tissue. In certain embodiments, the flexible gripping members 608 allows for the barbed portion 609 of the gripping members 608 to be removed from valve tissue in a direction substantially opposite the direction in which the barbs entered the valve tissue.

Referring to FIG. 54, in certain embodiments, the gripping members 608 are connected to each other by a separate biasing member 5410 (e.g., a spring) that is configured to maintain the gripping members in a desired position, such that, when the paddles 606 are in an open position, a width W exists between the paddles and the gripping members. The width W can be adjusted by engaging the gripping members 608 with the gripper control mechanism 611. That is, movement of the gripper control mechanism 611 into the delivery device in the direction Z will cause the biasing member 5410 to flex and the paddles to move in an inward direction X. Disengagement of the gripping members by the gripper control mechanism 611 will cause the biasing member 5410 to move the desired position (as shown in FIG. 54). The gripper control mechanism 611 can take any suitable form for controlling the gripping members 608, such as, for example, any form described in the present application. In addition, when the paddles 606 are moved to the closed position, the paddles will engage the gripping members 608, which will cause the biasing member to flex and the gripping members to move in an inward direction X. The paddles 608 can be moved from the open position to the closed position in any suitable manner, such as, for example, any manner described in the present application. While the various devices described in the present application refer to engaging and repairing the mitral valve, it should be understood that these devices can be used in repairing any other native valves (e.g., the tricuspid valve, the pulmonary valve, the aortic valve) or any other portion of the heart. In addition, it should be understood that various features of the various embodiments for the devices described herein can be used in combination with each other.

While the foregoing is a complete description of the preferred embodiments of the invention, various alternatives, modifications, and equivalents can be used. Moreover, it will be obvious that certain other modifications can be practiced within the scope of the appended claims.

The invention claimed is:

1. A valve repair system for repairing a native valve of a patient, the valve repair system comprising:
   a delivery catheter;
   a gripper control that extends through the delivery catheter;
   a paddle control that extends through the delivery catheter;
   a valve repair device disposed inside the delivery catheter, wherein the valve repair device comprises:
      a pair of paddles coupled to the paddle control;
      wherein movement of the paddle control in the catheter moves the paddles between an open position and a closed position;
      a pair of gripping members coupled to the gripper control;
      wherein movement of the gripper control in the catheter moves the pair of grippers relative to the pair of paddles;
      wherein the gripper control and the paddle control are useable to secure a pair of native valve leaflets with the pair of paddles and the pair of gripping members;

wherein the pair of paddles are compressed inside the delivery catheter; and wherein each paddle of the pair of paddles is configured to expand upon exiting the delivery catheter to increase the surface area of each paddle.

2. The valve repair system of claim 1 wherein a ratio of a width of each paddle expanded outside the delivery catheter to a width of each paddle compressed inside the delivery catheter is in the range of ratios from about 4/1 and about 1.25/1.

3. The valve repair system of claim 1 wherein each paddle is compressed to between 4 mm and 7 mm in the delivery catheter.

4. The valve repair system of claim 1 further comprising a blood impermeable cloth over each of the paddles.

5. The valve repair system of claim 4 wherein a ratio of a width of each paddle expanded outside the delivery catheter to a width of each paddle compressed inside the delivery catheter is in the range of ratios from about 4/1 and about 1.25/1.

6. The valve repair system of claim 1 wherein each paddle includes a pair of side members and a center member and each side member of the pair of side members is compressed laterally toward the center member when the pair of paddles are compressed inside the delivery catheter.

7. The valve repair system of claim 1 wherein each paddle includes a pair of side members and a center member and wherein the center member is unflexed and each side member of the pair of side members is flexed toward the center member when the pair of paddles are compressed inside the delivery catheter.

8. A valve repair system for repairing a native valve of a patient, the valve repair system comprising:
a delivery catheter;
a gripper control that extends through the delivery catheter;
a paddle control that extends through the delivery catheter;
a valve repair device disposed inside the delivery catheter, wherein the valve repair device comprises:
a pair of paddles coupled to the paddle control;
wherein each paddle comprises a center portion and a pair of outer portions;
wherein movement of the paddle control in the catheter moves the paddles between an open position and a closed position;
a pair of gripping members coupled to the gripper control;
wherein movement of the gripper control in the catheter moves the pair of grippers relative to the pair of paddles;
wherein the gripper control and the paddle control are useable to secure a pair of native valve leaflets with the pair of paddles and the pair of gripping members;
wherein the pair of paddles are compressed inside the delivery catheter such that the outer portions are compressed toward the center portion; and
wherein each paddle of the pair of paddles is configured to expand such that each outer portion expands away from the center portion upon exiting the delivery catheter to increase the surface area of each paddle.

9. The valve repair system of claim 8 wherein a ratio a width of each paddle expanded outside the delivery catheter to a width of each paddle compressed inside the delivery catheter is in the range of ratios from about 4/1 and about 1.25/1.

10. The valve repair system of claim 8 wherein each paddle is compressed to between 4 mm and 7 mm in the delivery catheter.

11. The valve repair system of claim 8 further comprising a blood impermeable cloth over each of the paddles.

12. The valve repair system of claim 11 wherein a ratio a width of each paddle expanded outside the delivery catheter to a width of each paddle compressed inside the delivery catheter is in the range of ratios from about 4/1 and about 1.25/1.

13. The valve repair system of claim 8 wherein each side member is compressed laterally toward the center member when the pair of paddles are compressed inside the delivery catheter.

14. The valve repair system of claim 8 wherein the center member is unflexed and each side member is flexed toward the center member when the pair of paddles are compressed inside the delivery catheter.

15. A valve repair system for repairing a native valve of a patient, the valve repair system comprising:
a delivery catheter;
a valve repair device disposed inside the delivery catheter, wherein the valve repair device comprises:
a pair of paddles that are movable between an open position and a closed position;
wherein each paddle comprises a center portion and a pair of outer portions;
wherein each outer portion of the pair of outer portions is covered with cloth; and
a pair of gripping members;
wherein the pair of paddles and the pair of gripping members are configured to secure the valve repair device to leaflets of the native valve of the patient;
wherein the cloth covered outer portions of the paddles are compressed inside the delivery catheter; and
wherein the cloth covered outer portions of the paddles are configured to expand upon exiting the delivery catheter to increase the surface area of each paddle.

16. The valve repair system of claim 15 wherein a ratio of a width of each paddle expanded outside the delivery catheter to a width of each paddle compressed inside the delivery catheter is in the range of ratios from about 4/1 and about 1.25/1.

17. The valve repair system of claim 15 wherein each paddle is compressed to between 4 mm and 7 mm in the delivery catheter.

18. The valve repair system of claim 15 wherein the center member is unflexed.

19. A valve repair system for repairing a native valve of a patient, the valve repair system comprising:
a delivery catheter;
a valve repair device disposed inside the delivery catheter, wherein the valve repair device comprises:
a pair of paddles that are movable between an open position and a closed position;
a pair of gripping members;
wherein the pair of paddles and the pair of gripping members are configured to secure the valve repair device to leaflets of the native valve of the patient;
wherein the pair of paddles are compressed inside the delivery catheter;
wherein each paddle of the pair of paddles is configured to expand upon exiting the delivery catheter to increase the surface area of each paddle; and
wherein a ratio of a width of each paddle expanded outside the delivery catheter to a width of each paddle compressed inside the delivery catheter is in the range of ratios from about 4/1 and about 1.25/1.

20. The valve repair system of claim 19 wherein each paddle is compressed to between 4 mm and 7 mm in the delivery catheter.

21. A valve repair system for repairing a native valve of a patient, the valve repair system comprising:
a delivery catheter;
a valve repair device disposed inside the delivery catheter, wherein the valve repair device comprises:
a pair of paddles that are movable between an open position and a closed position; and
a pair of gripping members;
wherein the pair of paddles and the pair of gripping members are configured to secure the valve repair device to leaflets of the native valve of the patient;
wherein the pair of paddles are compressed inside the delivery catheter;
wherein each paddle of the pair of paddles is configured to expand upon exiting the delivery catheter to increase the surface area of each paddle; and
wherein each paddle includes a pair of side members and a center member.

22. The valve repair system of claim 21 wherein each side member of the pair of side members is laterally compressed toward the center member when the pair of paddles are compressed inside the delivery catheter.

23. The valve repair system of claim 21 wherein the center member is unflexed and each side member of the pair of side members is compressed toward the center member when the pair of paddles are compressed inside the delivery catheter.

24. A valve repair system for repairing a native valve of a patient, the valve repair system comprising:
a delivery catheter;
a valve repair device disposed inside the delivery catheter, wherein the valve repair device comprises:
a pair of paddles that are movable between an open position and a closed position; and
a pair of gripping members;
wherein the pair of paddles and the pair of gripping members are configured to secure the valve repair device to leaflets of the native valve of the patient;
wherein the pair of paddles are compressed inside the delivery catheter;
wherein each paddle of the pair of paddles is configured to expand upon exiting the delivery catheter to increase the surface area of each paddle; and
a paddle control mechanism usable to control movement of the pair of paddles and a gripper control mechanism usable to control movement of the pair of gripping members.

25. The valve repair system of claim 24 wherein a ratio a width of each paddle expanded outside the delivery catheter to a width of each paddle compressed inside the delivery catheter is in the range of ratios from about 4/1 and about 1.25/1.

26. The valve repair system of claim 24 wherein each paddle is compressed to between 4 mm and about 7 mm in the delivery catheter.

27. The valve repair system of claim 24 further comprising a blood impermeable cloth over each of the paddles.

* * * * *